US011459308B2

(12) United States Patent
Bowlin et al.

(10) Patent No.: US 11,459,308 B2
(45) Date of Patent: Oct. 4, 2022

(54) BROAD SPECTRUM INHIBITORS OF FILOVIRUSES

(71) Applicants: Microbiotix, Inc., Worcester, MA (US); Albert Einstein College Of Medicine, Inc., Bronx, NY (US); The Government Of The United States As Represented By The Secretary Of The Army, Fort Detrick, MD (US)

(72) Inventors: Terry L. Bowlin, Maineville, OH (US); Donald T. Moir, Concord, MA (US); Kartik Chandran, Brooklyn, NY (US); John M. Dye, Jr., Frederick, MD (US); John D. Williams, Fulton, MD (US); Zachary D. Aron, Acton, MA (US); Jay P. Barbor, Worcester, MA (US); Kelly N. Lively, Holliston, MA (US); Peter J. Nash, Newton, MA (US); Debra M. Mills, Francestown, NH (US); Arnab Basu, Acton, MA (US)

(73) Assignees: Microbiotix, Inc., Worcester, MA (US); Albert Einstein College of Medicine, Bronx, NY (US); The Government of the United States as Represented by the Secretary of the Army, Washington, DC (US)

(*) Notice: Subject to any disclaimer, the term of this patent is extended or adjusted under 35 U.S.C. 154(b) by 0 days.

(21) Appl. No.: 16/348,033

(22) PCT Filed: Dec. 5, 2017

(86) PCT No.: PCT/US2017/064675
§ 371 (c)(1),
(2) Date: May 7, 2019

(87) PCT Pub. No.: WO2018/106667
PCT Pub. Date: Jun. 14, 2018

(65) Prior Publication Data

US 2019/0292165 A1 Sep. 26, 2019

Related U.S. Application Data

(60) Provisional application No. 62/430,205, filed on Dec. 5, 2016.

(51) Int. Cl.

| | |
|---|---|
| *C07D 401/04* | (2006.01) |
| *A61P 31/14* | (2006.01) |
| *C07D 401/14* | (2006.01) |
| *C07D 403/04* | (2006.01) |
| *A61K 31/54* | (2006.01) |
| *A61K 31/437* | (2006.01) |
| *A61K 31/4184* | (2006.01) |
| *A61K 9/00* | (2006.01) |
| *A61K 31/551* | (2006.01) |
| *A61K 45/06* | (2006.01) |
| *A61K 31/4375* | (2006.01) |
| *A61K 31/5375* | (2006.01) |
| *A61K 31/454* | (2006.01) |
| *A61K 31/496* | (2006.01) |

(52) U.S. Cl.
CPC .............. *C07D 401/04* (2013.01); *A61K 9/00* (2013.01); *A61K 31/4184* (2013.01); *A61K 31/437* (2013.01); *A61K 31/4375* (2013.01); *A61K 31/454* (2013.01); *A61K 31/496* (2013.01); *A61K 31/5375* (2013.01); *A61K 31/54* (2013.01); *A61K 31/551* (2013.01); *A61K 45/06* (2013.01); *A61P 31/14* (2018.01); *C07D 401/14* (2013.01); *C07D 403/04* (2013.01); *A61K 9/0014* (2013.01); *A61K 9/0029* (2013.01); *A61K 9/0053* (2013.01)

(58) Field of Classification Search
CPC .................................................... C07D 401/04
See application file for complete search history.

(56) References Cited

U.S. PATENT DOCUMENTS

| | | |
|---|---|---|
| 6,020,336 A | 2/2000 | Lavielle et al. |
| 2011/0065691 A1 | 3/2011 | Kaplan et al. |

(Continued)

FOREIGN PATENT DOCUMENTS

| | | |
|---|---|---|
| EP | 1 676 842 | 7/2006 |
| WO | WO 2006/069807 | 7/2006 |

(Continued)

OTHER PUBLICATIONS

Aitken et al., "Pharmacokinetics and Safety of Intravesicular Cidofovir in Allogeneic HSCT Recipients.", J. Antimicrob. Chemother., 71(3): 727-730 (2016).
Barrette et al., "Current perspectives on the phylogeny of Filoviridae", Infect. Genet. Evol., S1567-1348 (2011).
Bornholdt et al., "Host-Primed Ebola Virus GP Exposes a Hydrophobic NPC1 Receptor-Binding Pocket, Revealing a Target for Broadly Neutralizing Antibodies" MBio, 7(1): e02154-15 (2016).

(Continued)

*Primary Examiner* — Paul V Ward
(74) *Attorney, Agent, or Firm* — David G. O'Brien, Esq.

(57) ABSTRACT

The present invention is related to the development of therapeutics and prophylactics for the treatment and/or prevention of filovirus infection in humans and other mammals. A new class of small molecules is disclosed that inhibits the interaction of naturally processed (i.e., proteolytically cleaved) filovirus glycoprotein ($GP_{CL}$) with its host receptor Niemann-Pick C1 (NPC1) protein and thus block infection of host cells by filoviruses. Also disclosed are methods of using the small molecule inhibitors in the treatment/prevention of filovirus infection.

41 Claims, 7 Drawing Sheets

(56) References Cited

U.S. PATENT DOCUMENTS

| | | | |
|---|---|---|---|
| 2011/0144107 A1* | 6/2011 | Chatterjee | C07D 211/58 514/235.5 |
| 2012/0189614 A1* | 7/2012 | Basu | A61P 37/04 424/130.1 |
| 2014/0121195 A1 | 5/2014 | Leleti et al. | |

FOREIGN PATENT DOCUMENTS

| | | |
|---|---|---|
| WO | WO 2006/081332 | 8/2006 |
| WO | WO 2010/025375 | 3/2010 |
| WO | WO 2011/000566 | 1/2011 |
| WO | WO 2012/047538 | 4/2012 |
| WO | WO 2013/074965 | 3/2013 |
| WO | WO 2013/082490 | 6/2013 |
| WO | WO 2015/022332 | 2/2015 |

OTHER PUBLICATIONS

Bray et al., "A Mouse Model for Evaluation of Prophylaxis and Therapy of Ebola Hemorrhagic Fever." J. Infect. Dis., 178: 651-661 (1998).

Carette et al., "Ebola Virus Entry Requires the Cholesterol Transporter Niemann-Pick C1.", Nature, 477: 340-343 (2011).

Chughtai et al., "Persistence of Ebola Virus in Various Body Fluids During Convalescence: Evidence and Implications for Disease Transmission and Control.", Epidemiol. Infect., 144(8): 1652-1660 (2016).

Cote et al., "Small Molecule Inhibitors Reveal Niemann-Pick C1 is Essential for Ebola Virus Infection.", Nature, 477: 344-348(2011).

Deffieu et al., "Niemann—Pick Type C 1 Function Requires Lumenal Domain Residues that Mediate Cholesterol-Dependent NPC2 Binding", Proc. Natl. Acad. Sci. USA, 108: 18932-18936 (2011).

DeLa Vega et al., "Ebolavirus Evolution: Past and Present", PLoS Pathog., 11:e1005221(2015).

Geisbert et al., "Development of a New Vaccine for the Prevention of Lassa Fever", PLoS Med., 2e183 (2005).

Herbert et al., "Niemann-Pick C1 Is Essential for Ebolavirus Replication and Pathogenesis In Vivo", MBio., 6: e00565-15 (2015).

Jahrling et al., "Evaluation of Immune Globulin and Recombinant Interferon-a2b for Treatment of Experimental Ebola Virus Infections", J. Infect. Dis., 179 Suppl 1: S224-234 (1999).

Kuhn et al., "Proposal for a Revised Taxonomy of the Family Filoviridae: Classification, Names of Taxa and Viruses, and Virus Abbreviations", Arch. Virol., 155 2083-2103 (2010).

Leonard et al., "Development of a Novel High-Concentration Galantamine Formulation Suitable for Intranasal Delivery", J. Pharm. Sci., 94: 1736-1746 (2005).

Madelain et al., "Ebola Virus Infection: A Review on the Pharmacokinetic and Pharmacodynamic Properties of Drugs Considered for Testing in Human Efficacy Trials", Clin. Pharmacokinet., 55(8): 907-923 (2016).

Maruyama et al., "Ebola Virus Can Be Effectively Neutralized by Antibody Produced in Natural Human Infection", J. Virol., 73: 6024-6030 (1999).

Matsubara et al., "Improvement of Nasal Bioavailability of Luteinizing Hormone-Releasing Hormone Agonist, Buserelin, by Cyclodextrin Derivatives in Rats", J. Pharm. Sci., 84: 1295-1300 (1995).

Miller et al., "Ebola Virus Entry Requires the Host-Programmed Recognition of an Intracellular Receptor", EMBO J., 31: 1947-1960 (2012).

Ngdungo et al., "A Single Residue in Ebola Virus Receptor NPC1 Influences Cellular Host Range in Reptiles.", mSphere, 1(2) pii:e00007-16 (2016).

Ng et al., "Cell Entry by a Novel European Filovirus Requires Host Endosomal Cysteine Proteases and Niemann-Pick C1.", Virology, 468-470: 637-646 (2014).

Ng et al., "Filovirus Receptor NPC1 Contributes to Species-Specific Patterns of Ebolavirus Susceptibility in Bats", Elife, 4:e11785 (2015).

Rajewski et al., "Pharmaceutical Applications of Cyclodextrins. 2. In Vivo Drug Delivery", J. Pharm. Sci., 85: 1142-1169 (1996.

Schornberg et al., "Role of Endosomal Cathepsins in Entry Mediated by the Ebola Virus Glycoprotein.", J. Virol., 80: 4174-4178 (2006).

Sridhar S., "Clinical Development of Ebola Vaccines", Ther. Adv. Vaccines., 3: 125-138 (2015).

Swenson et al., "Generation of Marburg virus-like particles by co-expression of glycoprotein and matrix protein1", FEMS Immunol. Med. Microbiol., 40: 27-37 (2004).

Towner et al., "Newly Discovered Ebola Virus Associated with Hemorrhagic Fever Outbreak in Uganda", PLoS Pathog., 4(11): e1000212 (2008).

Wang et al., "Ebola Viral Glycoprotein Bound to Its Endosomal Receptor Niemann-Pick C1.", Cell, 164: 258-268 (2016).

Wong et al., "A Forward Genetic Strategy Reveals Destabilizing Mutations in the Ebolavirus Glycoprotein that Alter its Protease Dependence During Cell Entry.", J. Virol., 84: 163-175 (2010).

Zhao et al., "Structure of Glycosylated NPC1 Luminal Domain C Reveals Insights into NPC2 and Ebola Virus Interactions", FEBS Lett., 590(5): 605-312 (2016).

Basu et al., "Identification of a Small-Molecule Entry Inhibitor for Filoviruses", Journal of Virology, 85(7): 3106-3119 (2011).

Mohamed et al., Development of 2-Substituted-N-(naphth-1-ylmethyl) and N-Benzhydrylpyrimidin-4-amines as Dual Cholinesterase and A-aggregation Inhibitors: Synthesis and Biological Evaluation, Bioorganic & Medicinal Chemistry Letters, 21(19): 5881-5887 (2011).

Picazo et al., "Small Molecule Inhibitors of Ebola Virus Infection", Drug Discovery Today, 20(2): 277-289 (2015).

\* cited by examiner

Fig. 5

BROAD SPECTRUM INHIBITORS OF FILOVIRUSES

STATEMENT REGARDING FEDERALLY SPONSORED RESEARCH

This invention was made with government support under NIH grants R21/R33 AI102240 and JSTO CBD DTRA SEED project and Defense Threat Reduction Agency (DTRA) grant CB3873. The United States Government has certain rights in the invention.

FIELD OF THE INVENTION

This invention is in the field of therapeutic and prophylactic drugs to treat filovirus infections and disease. In particular, the invention provides organic compounds that inhibit the interaction of naturally processed (i.e., proteolytically cleaved) filovirus glycoprotein ($GP_{CL}$) with its host receptor Niemann-Pick C1 (NPC1) protein and thus block infection of host cells by filoviruses.

BACKGROUND OF THE INVENTION

The family Filoviridae of enveloped RNA viruses consists of five recognized ebolaviruses (Ebola virus: EBOV, Sudan virus: SUDV, Reston virus: RESTV, Bundibugyo virus: BDBV, and Taï Forest virus: TAFV) and two marburgviruses (Marburg virus: MARV and Ravn virus: RAVV), and one cuevavirus (Lloviu virus: LLOV) (Kuhn et al., *Arch. Virol.*, 155: 2083-2103 (2010); Barrette et al., *Infect. Genet. Evol.*, S1567-1348 (2011)). The filoviruses Ebola virus (EBOV), Sudan virus (SUDV), and Marburg virus (MARV) cause periodic outbreaks of severe viral hemorrhagic fever with mortality rates that can approach 90%, as demonstrated dramatically by the recent epidemic in West Africa (de La Vega et al., *PLoS Pathog.*, 11:e1005221 (2015)). Currently, there are no FDA-approved vaccines or drugs effective against filovirus infections. The most advanced candidates for anti-filovirus therapy, with proven efficacy in non-human primates (NHPs), utilize RNA interference (RNAi), mixtures of monoclonal antibodies, or repurposed influenza, herpes, respiratory syncytial (RSV), or hepatitis C (HCV) virus inhibitors (Madelain et al., *Clin. Pharmacokinet.*, 55(8): 907-923 (2016)). Although they represent important advances, these approaches are not tailored to filovirus pathogenicity and are as yet unproven. Moreover, the biologic approaches (antibodies, RNAi) are expensive, challenging to deploy in the field, and act in a viral species-specific manner, requiring that multiple therapeutics be stockpiled to cover all known virulent filoviruses, or limiting their utility in outbreaks caused by new viral species. Recently a vectored rVSV vaccine in which the VSV surface G protein was deleted and replaced with EBOV GP has shown some efficacy (5 Sridhar S., *Ther. Adv. Vaccines.*, 3:125-138 (2015)). However, broad-spectrum small molecule therapeutic and prophylactic approaches will be vital to protect populations in emergencies even if an effective vaccine is developed. In addition, small molecule therapeutics may be able to penetrate tissues and eliminate reservoirs of EBOV as detected following antibody treatments (Chughtai et al., *Epidemiol. Infect.*, 144(8): 1652-1660 (2016)). Therefore, there is an acute need for broad-spectrum, small molecule-based therapeutics to treat filovirus infections.

The endosomal cholesterol transport protein, Niemann-Pick C1 (NPC1) is a critical receptor for infection by all known filoviruses, and it is absolutely required for viral pathogenesis in human and non-human primate cells, and in mouse models of filovirus infection (Carette et al., Nature, 477: 340-343 (2011); Miller et al., *EMBO J.*, 31: 1947-1960 (2012)). Our results demonstrate that a single luminal segment (domain C) in NPC1 mediates filovirus entry by binding specifically and directly to filovirus GP, which has been naturally proteolytically processed to $GP_{CL}$ (Miller et al., *EMBO J.*, 31: 1947-1960 (2012)). Therefore, the GP-NPC1 interaction represents a new and unique molecular target for developing broadly active anti-filovirus therapeutics.

We have identified a potent drug-like small molecule series that targets the filoviral $GP_{CL}$ interaction with its endosomal receptor, NPC1, at sub-µM potency. This new chemical entity, a phenyl piperazine (PPZ) series, provides potent and broad protection against authentic filovirus infection in cell culture. Further, it is novel since no similar compounds have been described previously as inhibitors of filovirus infection. This chemotype is highly attractive for drug development, and it appears to act by specifically blocking or disrupting the crucial NPC1/$GP_{CL}$ interaction. Unlike a previously described NPC1/$GP_{CL}$ inhibitor with a different scaffold, compound 3.47 (Cote et al., *Nature*, 477: 344-348 (2011)), members of the PPZ series provide broad-spectrum protection against authentic filovirus infection. Furthermore, members of the PPZ series are selective for filoviruses, exhibiting no significant activity against the arenavirus Lassavirus (LASV), consistent with their specificity for NPC1, which is dispensable for LASV entry (Cote et al., *Nature*, 477: 344-348 (2011)). Furthermore, the PPZ and CSM series are also not lysosomotropic and do not inhibit filovirus infection by raising endo/lysosomal pH in cells.

Chemical optimization generated analogs with improved potency, metabolic stability, and murine PK/PD properties [i.e., soluble to 100 mg/mL in isotonic saline; stable in serum; stable in the presence of liver microsomes (91% remaining after 1 h in the presence of NADPH); minimal inhibition of binding by a 30-member Eurofins/Panlabs receptor panel; murine elimination phase $t_{1/2}$>3 h; maximum tolerated dose of 100 mg/kg by intraperitoneal administration]. An optimized PPZ analog demonstrated protection of mice from EBOV infection, providing in vivo proof of principle for this series. Recent structural and functional studies have revealed that specific residues on NPC1 lumenal domain C (NPC1-C) interact with a cavity in thermolysin-cleaved EBOV glycoprotein ($GP_{CL}$) (Miller et al., *EMBO J.*, 31: 1947-1960 (2012); Wang et al., *Cell*, 164: 258-268 (2016); Ng et al., *Elife* 4:e11785 (2015); Bornholdt et al., *M Bio*, 7(1): e02154-15 (2016)). Recently, NPC1-domain C was successfully crystallized alone [(Zhao et al., *FEBS Lett.*, 590(5): 605-612 (2016)) 2.45 Å resolution)] and in complex with cleaved GP [(Wang et al., *Cell*, 164: 258-268 (2016)) 2.3 Å resolution]. The resulting NPC1-C/$GP_{CL}$ structure revealed two loops protruding from NPC1-C and interacting with a cavity in $GP_{CL}$ (Wang et al., *Cell*, 164: 258-268 (2016)). While loop 1 contacts the side of the cavity and includes some hydrophilic interactions, the majority of the binding energy is provided by hydrophobic interactions between loop 2 and $GP_{CL}$; residues F503, F504, and Y506 of NPC1 are the major contributors to the binding energy. Consistent with these findings, sequence variations in NPC1-C at residues 502 and 503 account for species-specific differences in the host susceptibility of filoviruses (Ng et al., *Elife* 4:e11785 (2015); Ndungo et al., *mSphere*, 1(2) pii: e00007-16 (2016)). Wang et al. (*Cell*, 164: 258-268

(2016)) also demonstrated using a surface plasmon resonance (SPR) binding assay that the Kd of the NPC1-C/$GP_{CL}$ interaction is about 150 µM, much weaker than antibody/$GP_{CL}$ interactions (typically single digit nM). It is unclear whether the weak NPC1-C/$GP_{CL}$ interaction measured here is due to the use of a portion of domain C isolated from the full length NPC1 or whether this crucial interaction is inherently weak. The small molecule inhibitors of his invention may interact with NPC1-C loops or $GP_{CL}$ cavities, and may not need to bind them extremely avidly to block EBOV entry.

The present invention is directed to the identification, isolation, and characterization of small molecule inhibitors of filovirus infections for use in the treatment and/or prevention of filovirus infections in mammals, and in particular the treatment and/or prevention of filovirus infections in humans.

SUMMARY OF THE INVENTION

The present invention is related to the discovery of novel broad-spectrum small molecule inhibitors of filovirus entry into a host cell. The inhibitors described herein are suitable for the treatment and/or prevention of filovirus infections in mammals. More particularly, the inhibitors described herein are suitable for the treatment and/or prevention of filovirus infections in humans.

In another embodiment, the present invention is directed to a composition for treating or preventing filovirus infection, the composition comprising a novel broad-spectrum small molecule inhibitor of filovirus entry into a host cell. The compositions described herein are suitable for the treatment or prevention of filovirus infections in mammals, and in particular, humans.

In another embodiment, the present invention is directed to a method for treating or preventing filovirus infections in a mammal by administration of the novel broad-spectrum filovirus inhibitors of the present invention. In a preferred embodiment, the mammal is a human.

Also disclosed are pharmaceutical compositions comprising a therapeutically effective amount of a novel filovirus inhibitor compound of the present invention, or a pharmaceutically acceptable salt thereof, and a pharmaceutically acceptable carrier. The pharmaceutical compositions are suitable for use in the disclosed methods for treating or preventing filovirus infections in a mammal. The pharmaceutical compositions may be formulated for both parenteral and/or nonparenteral administration to a subject or patient in need thereof.

More particularly, the invention is related to the identification of small molecule inhibitors for treating and/or preventing filovirus infections caused by Ebola virus, Sudan virus, Reston virus, Bundibugyo virus, Taï Forest virus, Marburg virus and Ravn virus. More particularly, the present invention is directed to the identification and characterization of small molecule filovirus inhibitors suitable for the treatment and/or prevention of an infection caused by Ebola virus.

In another embodiment, the small molecule inhibitors of the present invention may be administered to a subject in need thereof optionally in combination with one or more known antiviral agents.

In another embodiment, the small molecules of the present invention are formulated into a pharmaceutically-acceptable carrier and are applied/administered to a subject in need thereof by an injection, including, without limitation, intradermal, transdermal, intramuscular, intraperitoneal and intravenous. According to another embodiment of the invention, the administration is oral and the compound may be presented, for example, in the form of a tablet or encased in a gelatin capsule or a microcapsule, which simplifies oral application. The production of these forms of administration is within the general knowledge of a technical expert. Multiple routes of administration are envisioned for these drug-like molecules, and highly cost-effective production strategies can be easily achieved.

In a preferred embodiment, the filovirus inhibitors of the present invention will specifically target and inhibit the interaction of filovirus glycoprotein ($GP_{CL}$) with its host receptor, Niemann-Pick C1 (NPC1) protein, and thus block entry of the filovirus into a host cell and prevent infection.

In preferred embodiments, the filovirus inhibitor compounds of the present invention exhibit an inhibitory concentration of ≤10 µM against NPC1/$GP_{CL}$ binding and a cytotoxicity ($CC_{50}$) of ≥100 µM.

In one embodiment, a filovirus inhibitor compound of the present invention comprises a compound having the structural Formula I:

Formula I wherein:
X is hydrogen, C or N;
wherein, if X is other than hydrogen,
X and Y are connected by a double bond to form a 5-membered heteroaromatic ring; Y is C or N, with the proviso that at least one of X and Y is N, and X and Y may be independently unsubstituted or substituted with a hydrogen; A is C; the ring atoms U, V and Z are C or N atoms in one of the following configurations, taken in order UVZ: CCC, CCN, CNC, NCC, NCN, CNN, or NNN.

R1 is hydrogen, a straight-chain or branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl groups; or R1 is an aryl ring of 5-7 members wherein said aryl is optionally substituted with 1-5 substituents independently selected from alkyl, alkoxy, hydroxyl, carbonyl, carboxy, halogen, haloalkyl, nitro, haloalkoxy, alkylthio, sulfonyl, sulfinyl, alkoxyalkyl, alkoxycarbonyl, or aminocarbonyl groups; or R1 is a heteroaryl fused aryl ring system or heteroaryl bicyclic ring system of 9-11 members wherein said ring system is optionally substituted with 0-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups, with the proviso that if R1 is an aryl group, it must have at least one substituent;

R2 and R3 are independently selected from straight-chain or branched aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring, wherein the ring has 1-4 carbon substituents and 0-1 substituents on any present ring nitrogen, which are independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, substituted aryl, or substituted or unsubstituted heteroaryl rings, wherein substituted aryl or heteroaryl rings have 1-4 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein, if R1 is other than hydrogen, then R2 and R3 can independently be alkyl; cycloalkyl; heterocycloalkyl; aryl; heteroaryl; haloalkyl; nitro; halogen; alkoxy; alkylthio; haloalkoxy; sulfonyl; sulfinyl; carboxy; alkoxycarbonyl; or aminocarbonyl groups;

R4, R5 and R6 are independently selected from hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms, 0-1 oxygen atoms and bearing 0-3 substituents (in addition to the bond between W and the ring carbon in the formula) selected from alkyl, cycloalkyl, aryl, heteroaryl, haloalkyl, nitro, halogen, alkoxy, alkylthio, haloalkoxy, sulfonyl, or sulfinyl, optionally fused with one or more aromatic, heteroaromatic, cycloalkyl, or heterocycloalkyl rings, wherein said 0-3 substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and additionally W can be either a nitrogen or a saturated carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups, which optional substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl, which non-hydrogen substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; or, wherein, if X is hydrogen,
A is C or N; and where A is C, Y is hydrogen, hydroxyl, alkyl, alkoxy, haloalkyl, haloalkoxy, haloalkoxysulfonyl, halogen, nitro, cyano, or NRR', where R and R' are independently selected from hydrogen, alkyl, acetyl, sulfonyl, and alkylsulfonyl; the ring atoms U, V and Z are C or N atoms;

R1 is an aryl or heteroaryl ring of 5-7 members, or a fused aryl or heteroaryl bicyclic ring system of 9-11 members, which R1 aryl or heteroaryl ring or ring system is substituted with 0-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups, with the proviso that if R1 is an aryl group, it must have at least one substituent;

R2 and R3 are independently selected from branched aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring, wherein the ring has 1-4 carbon substituents and 0-1 substituents on any present ring nitrogen, which are independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, substituted aryl, or substituted or unsubstituted heteroaryl rings, wherein substituted aryl or heteroaryl rings have 1-4 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl;

R4, R5 and R6 are independently selected from hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a heterocyclic ring system containing 0-3 degrees of unsaturation and between 5-7 members and containing 1-2 nitrogen atoms, 0-1 oxygen atoms and bearing 0-3 substituents (in addition to the bond linking W and the ring carbon in the formula) including alkyl, cycloalkyl, heterocycloalkyl, aryl, heteroaryl, haloalkyl, acetyl, arylcarbonyl, heteroarylcarbonyl, aralkyl, alkoxyalkyl, nitro, halogen, alkoxy, alkylthio, haloalkoxy, sulfonyl, or sulfinyl, optionally fused with one or more aromatic, heteroaromatic, cycloalkyl, or heterocycloalkyl rings, wherein said 0-3 substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and additionally W can be either a nitrogen or a saturated carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups, which optional substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl, which non-hydrogen substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl, or a pharmaceutically acceptable salt thereof.

It will be understood by those skilled in the art that the recitation of possible substitutions/substituents or numbers of substitutions/substituents on the labeled/lettered elements shown for Formula I are in addition to the attachment point of that element to the structure illustrated in the formula. For example, possible substituents on element W are in addition to the bond attaching W to the aromatic ring illustrated in Formula I. It will also be understood by one skilled in the art that the recitation of the 0-3 substituents that may combine with R4 or R5 in Formula I to form a fused substituted or unsubstituted non-aromatic ring, are in addition to the attachment/fusion point with R4 or R5. Similarly, the 0-2 substituents included on the formed aromatic ring does not include the attachment point of the substituents to R4 or R5.

In particular embodiments, a filovirus inhibitor of the present invention will have the structure according to Formula II:

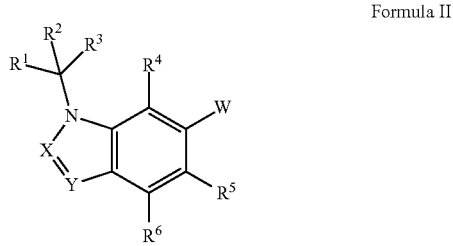

Formula II wherein:

X is C or N; Y is C or N; and at least one of X and Y is N;

R1 is hydrogen, a straight-chain or branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl groups; or R1 is an aryl or heteroaryl ring of 5-7 members, or a fused aryl or heteroaryl bicyclic ring system of 9-11 members, each ring substituted with 1-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups;

R2 and R3 can independently be branched-chain aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring bearing 1-4 carbon substituents and 0-1 nitrogen substituents which may be independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl, or heteroaryl rings; and wherein, if R1 is other than hydrogen, then R2 and R3 can independently be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5 and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms and bearing 0-3 substituents including alkyl, cycloalkyl, aryl, heteroaryl, haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; and additionally W can be either a nitrogen, a saturated carbon, or an olefinic carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl; or alternatively, W may be linked with R4 or R5 to produce fused cyclic structures;

or a pharmaceutically acceptable salt thereof.

It will be understood by those skilled in the art that the recitation of possible substitutions/substituents on the labeled/lettered elements shown for Formula II are in addition to the attachment point of that element to the structure illustrated in the formula.

In particular embodiments, a filovirus inhibitor compound of the present invention will have the structure of Formula III:

Formula III wherein:

X is C or N; Y is C or N; and at least one of X and Y is N;

Ar is

, where each R3 can independently be hydrogen, alkyl, haloalkyl, haloalkyl, nitro, halogen, alkoxy, alkylthio, haloalkoxy, sulfonyl, sulfinyl, carboxy, alkoxycarbonyl, or aminocarbonyl;

R1 is hydrogen, a straight-chain aliphatic group, a branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group;

R2 can independently be a branched chain aliphatic group, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl group, aryl, or heteroaryl; or R1 and R2 can be linked together to form a substituted aliphatic or heterocyclic ring bearing 1-4 substituents selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl or heteroaryl rings; and, additionally, if R1 is straight-chain aliphatic group, branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group, then R2 can be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5 and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms, 0-1 oxygen atoms, and bearing 0-3 substituents including alkyl, cycloalkyl, aryl, heteroaryl haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; and additionally, W can be either a nitrogen, a saturated carbon, or an olefinic carbon that is linked via a chain of 1-4 carbons to a basic nitrogen bearing independently hydrogen or aliphatic groups of less than nine carbon atoms that can be optionally substituted with haloalkyl, nitro, halogen, alkoxy, alkylthio, haloalkoxy, sulfonyl, sulfinyl, carboxy, alkoxycarbonyl, or aminocarbonyl groups; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl; or alternatively, W may be linked with R4 or R5 to produce fused cyclic structures; or W can be a nitrogen that is part of an aromatic heterocyclic ring system of between 5-7 members and containing 1-2 nitrogen atoms that may be unsubstituted or substituted and may optionally be fused with one or more aromatic, heteroaromatic, cycloalkyl, or heterocycloalkyl rings, and this group can also include connections through either R4 or R5 to produce fused bicyclic structures; or a pharmaceutically acceptable salt thereof.

It will be understood by those skilled in the art that the recitation of possible substitutions/substituents on the labeled/lettered elements shown for Formula III are in addition to the attachment point of that element to the structure illustrated in the formula.

In another embodiment, a filovirus inhibitor compound of the present invention will have the structure of Formula IV:

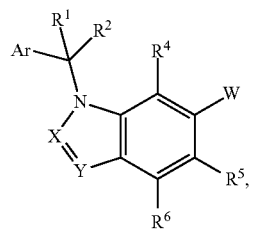

Formula IV wherein:

X can be carbon or nitrogen and Y can be a carbon or nitrogen, and at least one of X and Y is nitrogen, and wherein X and Y can be independently unsubstituted or substituted with a hydrogen, alkyl, halogen, hydroxy, carbonyl, thiol, amino, alkylamino, alkylthio, alkoxy, aryl, haloalkyl, nitro, halogen, alkoxy, alkylthio, haloalkoxy, sulfonyl, sulfinyl, carboxy, alkoxycarbonyl, or aminocarbonyl group;

Ar is

, where each R3 can independently be hydrogen, alkyl, haloalkyl, nitro, halogen, alkoxy, alkylthio, haloalkoxy, sulfonyl, sulfinyl, carboxy, alkoxycarbonyl, or an aminocarbonyl group;

R1 is a hydrogen, straight-chain aliphatic group, branched chain aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group;

R2 can independently be a branched chain aliphatic group, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl group, aryl, or heteroaryl; or R1 and R2 can be linked together to form a substituted aliphatic or heterocyclic ring bearing 1-4 substituents selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl or heteroaryl rings; and additionally, if R1 is a straight-chain aliphatic group, branched chain aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group, then R2 can be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5, and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups.

W can be a nitrogen that is part of an aromatic or non-aromatic heterocyclic ring system of between 5-7 members, containing 1-2 nitrogen atoms, 0-1 oxygen atoms, and bearing 0-3 substituents selected from alkyl, cycloalkyl, aryl, heteroaryl haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; or W can be a nitrogen that is linked via a chain of 1-4 carbon atoms to a basic nitrogen bearing independently hydrogen or aliphatic groups of less than nine carbon atoms that can be optionally substituted with haloalkyl, nitro, halogen, alkoxy, alkylthio, haloalkoxy, sulfonyl, sulfinyl, carboxy, alkoxycarbonyl, or aminocarbonyl groups; wherein the chain of carbon atoms is a saturated hydrocarbon chain or can be substituted with up to 4 non-hydrogen substituents selected from alkyl, fused cycloalkyl, aryl, fused aryl, haloalkyl, nitro, halogen, alkoxy, alkylthio, haloalkoxy, sulfonyl, sulfinyl, carboxy, alkoxycarbonyl, or aminocarbonyl, or this group can also include connections through either R4 or R5 to produce non-aromatic fused cyclic ring structures;

or a pharmaceutically acceptable salt thereof.

It will be understood by those skilled in the art that the recitation of possible substitutions/substituents on the labeled/lettered elements shown for Formula IV are in addition to the attachment point of that element to the structure illustrated in the formula.

In another embodiment, a filovirus inhibitor compound of the present invention will have the structure of Formula V:

Formula V wherein:

A is C or N; and where A is C, Y is hydrogen, hydroxyl, alkyl, alkoxy, haloalkyl, haloalkoxy, haloalkoxysulfonyl, halogen, nitro, cyano, or NRR', where R and R' are independently selected from hydrogen, alkyl, acetyl, sulfonyl, and alkylsulfonyl;

Ar is, independently, an aryl or heteroaryl ring of 5-7 members, or a fused aryl or heteroaryl bicyclic ring system of 9-11 members, each ring optionally substituted with 0-3 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups;

W is a ring nitrogen in a non-aromatic heterocyclic ring of from 5-7 members having 0-1 additional heteroatom selected from N or O or a fused non-aromatic bicyclic ring system of from 6 to 10 members having 0-1 additional heteroatom selected from N or O; where said heterocyclic ring or said bicyclic ring has 0-3 substituents independently selected from alkyl, cycloalkyl, heterocycloalkyl, aryl, heteroaryl, haloalkyl, acetyl, arylcarbonyl, heteroarylcarbonyl, aralkyl, alkoxyalkyl, nitro, halogen, alkoxy, alkylthio, haloalkoxy, sulfonyl, or sulfinyl, and where a cycloalkyl, heterocycloalkyl, aryl, or heteroaryl substituent may optionally be fused with one or more aromatic, heteroaromatic, cycloalkyl, or heterocycloalkyl rings; or W is NRR', where R is hydrogen or alkyl, and R' is alkyl, alkenyl, aminoalkyl, or aminoalkenyl, cycloalkyl, heterocycloalkyl, aryl, and heteroaryl, which R' group may optionally be further substituted with up to three substituents selected from alkyl, haloalkyl, nitro, halogen, alkoxy, alkylthio, haloalkoxy, sulfonyl, sulfinyl, carboxy, alkoxycarbonyl, or aminocarbonyl groups;

R1 and R2 are, independently, hydrogen, straight-chain or branched alkyl, cycloalkyl, haloalkyl, nitro, halogen, alkoxy, alkylthio, haloalkoxy, sulfonyl, sulfinyl, carboxy, alkoxycarbonyl, or aminocarbonyl groups; and wherein R2 can independently be Ar as defined above;

R4, R5, and R6 are independently selected from hydrogen, alkyl, haloalkyl, nitro, halogen, cyano, alkoxy, alkylthio, haloalkoxy, sulfonyl, sulfinyl, carboxy, alkoxycarbonyl, or aminocarbonyl groups;

or a pharmaceutically acceptable salt thereof.

It will be understood that the recitation of possible substitutions/substituents on the labeled/lettered elements shown for Formula V are in addition to the attachment point of that element to the structure illustrated in the formula.

In another embodiment, the present invention is directed to a composition for preventing or treating filovirus infection in a mammal, the composition comprising at least one compound according to Formulas I, II, III, IV, or V, formulated into a pharmaceutically acceptable carrier or excipient for parenteral and/or nonparenteral administration. In a preferred embodiment, the mammal is a human.

In yet another embodiment, the present invention is directed to a method for treating or preventing filovirus infections in a mammal by administration of a composition comprising a compound of Formula I, II, III, IV, or V. In a preferred embodiment of such method, the mammal is a human.

In yet another embodiment, the present invention is directed to a method for use in treating or preventing filovirus infections in a mammal by administration of a composition comprising a compound of Formula I, II, III, IV, or V. In a preferred embodiment of such method, the mammal is a human.

In another embodiment, the present invention is directed to the use of a composition comprising at least one compound according to Formulas I, II, III, IV, or V, in the manufacture of a medicament for treating or preventing filovirus infections in a mammal. In a preferred embodiment, the mammal is a human.

To identify inhibitors that prevent entry of the filovirus into host cells, a rVSV-EBOV-GP assay was developed as a model to mimic entry of the live filovirus into a host cell. The recombinant virus provides a means for safely replicating the viral entry mechanism and identifying inhibitors thereof, which inhibitors can then be tested against live viral infection under strict regulatory conditions that are not required for initial screenings with the recombinant viruses.

Definitions

A composition or method described herein as "comprising" (or "comprises") one or more named elements or steps is open-ended, meaning that the named elements or steps are essential, but other elements or steps may be added within the scope of the composition or method. To avoid prolixity, it is also understood that any composition or method described as "comprising" one or more named elements or steps also describes the corresponding, more limited, composition or method "consisting essentially of" (or "consists essentially of") the same named elements or steps, meaning that the composition or method includes the named essential elements and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other element or step. In any composition or method disclosed herein, known or disclosed equivalents of any named essential element or step may be substituted for that element or step, respectively.

As used herein, the term 'subject' can be a human, non-human primate, horse, pig, rabbit, dog, sheep, goat, cow, cat, guinea pig or rodent. A 'patient' or 'subject in need thereof' refers to a mammal afflicted with a disease or disorder. The term 'patient' includes human and veterinary subjects.

Terms such as 'parenteral', 'parenterally', and the like, refer to routes or modes of administration of a compound or composition to an individual other than along the alimentary canal. Examples of parenteral routes of administration include, without limitation, subcutaneous (s.c.), intravenous (i.v.), intramuscular (i.m.), intra-arterial (i.a.), intraperitoneal (i.p.), transdermal (absorption through the skin or dermal layers), nasal ('intranasal'; absorption across nasal mucosa), or pulmonary (e.g., inhalation for absorption across the lung tissue), vaginal, direct injections or infusions into body cavities or organs other than those of the alimentary canal, as well as by implantation of any of a variety of devices into the body (e.g., of a composition, depot, or device that permits active or passive release of a compound or composition into the body).

The terms 'non-parenteral', 'non-parenterally', 'enteral', 'enterally', 'oral', 'orally', and the like, refer to administration of a compound or composition to an individual by a route or mode along the alimentary canal. Examples of enteral routes of administration include, without limitation, oral, as in swallowing solid (e.g., tablet) or liquid (e.g., syrup) dosage forms, sublingual (absorption through the mucosal membranes lining the floor of the mouth, e.g., under the tongue), buccal (absorption through the mucosal membranes lining the cheeks), nasojejunal or gastrostomy tubes (delivery into the stomach), intraduodenal administration, as well as rectal administration (e.g., suppositories for release of a drug composition into and absorption by the lower intestinal tract of the alimentary canal).

In the present description, in a structural formula allowing for one or more substituent at a given position and listing suitable substituents, it will be understood that substituents may be "stacked" or combined to form compound substituents. For example, a listing of suitable substituents including alkyl and aryl substituents, aralkyl and alkaryl substituents are also contemplated.

The term 'hydrogen' is intended to mean a hydrogen radical.

The term 'halo' or 'halogen' means fluorine, chlorine, bromine, or iodine.

The term 'alkyl' as used herein is intended to mean a branched, straight-chain, or cyclic saturated hydrocarbon group of 1 to 24 carbon atoms, preferably 1-10 carbon atoms such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, and the like. The alkyl group can be cyclic or acyclic. The alkyl group can be branched or unbranched. The alkyl group can also be substituted or unsubstituted. For example, the "substituted alkyl" group denotes an alkyl group substituted with one or more groups including, but not limited to, alkyl, haloalkyl, nitro, halogen, alkoxy, alkylthio, haloalkoxy, sulfonyl, sulfinyl, carboxy, alkoxycarbonyl, or amido groups.

The term 'sulfonyl' is intended to mean a sulfur radical that is doubly bound to two oxygens (—SO$_2$—). A sulfonyl group may be linked via the sulfur atom with an amino, alkylamino, alkyl, cycloalkyl, aryl, heterocycloalkyl or heteroaryl moiety to produce a monovalent radical.

The term 'sulfinyl' is intended to mean a sulfur radical that is doubly bound to one oxygen (—S(O)—), and the sulfur atom may be substituted with an amino, alkylamino, alkyl, cycloalkyl, aryl, heterocycloalkyl or heteroaryl moiety to produce a monovalent radical.

The term 'hydroxyl' or 'hydroxy' is intended to mean the radical —OH.

The term 'alkoxy' is intended to mean the radical —OR, where R is an alkyl or cycloalkyl group.

The term 'haloalkyl' is intended to mean an alkyl moiety wherein one or more hydrogen atoms is replaced with the same or different halogen atoms, e.g., —CH$_2$Cl, —CF$_3$, —CH$_2$CF$_3$, —CH$_2$CCl$_3$, and the like.

The term 'haloalkoxy' is intended to mean an alkoxy radical wherein one or more hydrogen atoms are replaced with the same or different halogen atoms, e.g. —OCHF$_2$, —OCF$_3$, —OCH$_2$CF$_3$, —OCH$_2$CCl$_3$, and the like.

The term 'alkenyl' is intended to mean a straight-chain, branched, or cyclic hydrocarbon radical having from 2-8 carbon atoms and at least one double bond, e.g., ethenyl, 3-buten-1-yl, 3-hexen-1-yl, cyclopent-1-en-3-yl, and the like. The alkenyl group can be unsubstituted or substituted with one or more groups including, but not limited to, alkyl, haloalkyl, nitro, halogen, alkoxy, alkylthio, haloalkoxy, sulfonyl, sulfinyl, carboxy, alkoxycarbonyl, amido, cycloalkyl, alkenyl, cycloalkenyl, alkynyl, cycloalkynyl, aryl, heteroaryl, aldehyde, amino, carboxylic acid, ester, ether, hydroxy, ketone, or thiol.

The term 'alkynyl' is intended to mean a straight-chain or branched hydrocarbon radical having from 2-8 carbon atoms an at least one triple bond, e.g., ethynyl, 3-butyn-1-yl, 2-butyn-1-yl, 3-pentyn-1-yl, and the like. The alkynyl group can be unsubstituted or substituted with one or more groups including, but not limited to, alkyl, haloalkyl, nitro, halogen, alkoxy, alkylthio, haloalkoxy, sulfonyl, sulfinyl, carboxy, alkoxycarbonyl, amido, cycloalkyl, alkenyl, cycloalkenyl, alkynyl, cycloalkynyl, aryl, heteroaryl, aldehyde, amino, carboxylic acid, ester, ether, hydroxy, ketone, azide, nitro, or thiol, as described herein.

The term "carbon substituent" is intended to refer to substituent groups wherein the first atom of the substituent bound at the site of attachment is carbon, e.g., as in —CH$_3$ (methyl), —COOH (carboxyl), —C$_6$H$_5$(phenyl), —C≡N (cyano), etc., which may contrasted with "nitrogen substituents" such as —NH$_2$ (amino), —NO$_2$ (nitro), etc., wherein the first atom bound at the site of attachment is nitrogen.

The term 'cycloalkyl' is intended to mean a non-aromatic monovalent cyclic or polycyclic hydrocarbon radical having from 3-12 carbon atoms. 'Substituted cycloalkyl' groups, e.g., substituted cyclopentyl, cyclohexyl, decalinyl, may be substituted with one or more groups including, but not limited to, alkyl, haloalkyl, nitro, halogen, alkoxy, alkylthio, haloalkoxy, sulfonyl, sulfinyl, carboxy, alkoxycarbonyl, or amido cycloalkyl, alkoxy, amino, ether, hydroxy, or thiol as described herein.

The term 'heterocycloalkyl' is intended to mean a non-aromatic monovalent monocyclic or polycyclic radical having from 2-12 carbon atoms, and 1-5 heteroatoms selected from nitrogen (N), oxygen (O), or sulfur (S). 'Substituted heterocycloalkyl' groups, e.g., substituted pyrrolodinyl, tetrahydropyranyl, morpholinyl, piperazinyl, oxiranyl groups, and the like, may be substituted with one or more groups including, but not limited to, alkyl, haloalkyl, nitro, halogen, alkoxy, alkylthio, haloalkoxy, sulfonyl, sulfinyl, carboxy, alkoxycarbonyl, or amido, cycloalkyl, alkoxy, amino, ether, hydroxy, or thiol as described herein.

The term 'aryl' is intended to mean an aromatic, monovalent monocyclic or polycyclic radical comprising from 5 and 18 carbon ring members, e.g., phenyl, biphenyl, naphthyl, phenanthryl, and the like. A 'substituted aryl' group is an aryl group substituted with one or more groups including, but not limited to, alkyl, haloalkyl, nitro, halogen, alkoxy, alkylthio, haloalkoxy, sulfonyl, sulfinyl, carboxy, alkoxycarbonyl, or amido, cycloalkyl, alkoxy, alkenyl, cycloalkenyl, alkynyl, cycloalkynyl, aryl, heteroaryl, aldehyde, carboxylic acid, ester, ether, hydroxy, ketone, or thiol as described herein. In addition, the aryl group can be a single ring structure or comprise multiple ring structures that are either fused ring structures or attached via one or more bridging groups such as a carbon-carbon bond.

The term 'heteroaryl' is intended to mean an aromatic, monovalent monocyclic or polycyclic radical comprising from 3 and 18 carbon ring members and at least 1 heteroatom selected from nitrogen (N), oxygen (O), or sulfur (S), e.g., pyridyl, pyrazinyl, pyridizinyl, pyrimidinyl, furanyl, thienyl, triazolyl, quinolinyl, imidazolinyl, benzimidazolinyl, indolyl, and the like. 'Substituted heteroaryl' is a heteroaryl group substituted with one or more groups including, but not limited to, alkyl, haloalkyl, nitro, halogen, alkoxy, alkylthio, haloalkoxy, sulfonyl, sulfinyl, carboxy, alkoxycarbonyl, amido, cycloalkyl, amino, ether, hydroxy, or thiol as described herein. Heteroaryl groups can be monocyclic, or alternatively fused ring systems.

The term 'aryloxy' is intended to mean the radical —OAr where Ar is an aryl group.

The term 'heteroaryloxy' is intended to mean the radical —O(heteroAr) where heteroAr is a heteroaryl group.

The term 'acyl' is intended to mean a —C(O)R radical, where R is alkyl, alkenyl, alkynyl, cycloalkyl, aryl, heteroaryl, or heterocycloalkyl, e.g. acetyl, benzoyl, and the like.

The term 'alkoxycarbonyl' is intended to mean a RO—C(O)— radical where R is alkyl or cycloalkyl.

The term 'alkylcarbonyl' refers to a RC(O)— radical where R is alkyl or cycloalkyl.

The term 'aryloxycarbonyl' is intended to mean a RO—C(O)— radical where R is aryl; 'heteroaryloxycarbonyl' refers to a radical of the same structure RO—C(O)— where R is heteroaryl.

The term 'amino' is intended to mean the radical —NH$_2$.

The term 'alkylamino' is intended to mean the radical —NHR where R is an alkyl group, or —NRR', where R and R' are each independently, hydrogen or alkyl. Representative examples include, but are not limited to, methylamino, ethylamino, propylamino, isopropylamino, butylamino, isobutylamino, (sec-butyl)amino, (tert-butyl)amino, pentylamino, isopentylamino, (tert-pentyl)amino, hexylamino, dimethylamino, methylethylamino, diethylamino, methylpentylamino, and the like.

The term 'acylamino' is intended to mean the radical —NHC(O)R, where R is a monovalent organic radical such as, e.g., alkyl, alkenyl, alkynyl, cycloalkyl, aryl, heteroaryl, or heterocycloalkyl.

The term 'amido' in intended to mean the radical —C(O)NRR' where R and R' are, independently, hydrogen, or monovalent organic radicals, such as, e.g., alkyl, alkenyl, alkynyl, cycloalkyl, aryl, heteroaryl, or heterocycloalkyl.

The term 'basic nitrogen' as used herein is intended to mean a trisubstituted nitrogen atom either bound exclusively to hydrogen or carbon atoms in which the carbon atoms are each bound to a total of four distinct atoms, or nitrogen atoms contained within small rings of 3 or 4 total atoms in circumference.

The term 'alkylsulfonyl' is intended to mean the radical —SO$_2$R where R is a monovalent organic radical such as, e.g., alkyl, alkenyl, alkynyl, cycloalkyl, aryl, heteroaryl, or heterocycloalkyl.

The term 'sulfonylamino' is intended to mean the radical —NHSO$_2$R where R is a monovalent organic radical such as, e.g., alkyl, alkenyl, alkynyl, cycloalkyl, aryl, heteroaryl, or heterocycloalkyl.

The term 'aminosulfonyl' is intended to mean the radical —SO$_2$NRR' where R and R' are, independently, hydrogen, or a monovalent organic radical such as, e.g., alkyl, alkenyl, alkynyl, cycloalkyl, aryl, or heteroaryl, or heterocycloalkyl.

The term 'sulfhydryl' or 'mercapto' is intended to mean the radical —SH.

The term 'alkylthio' is intended to mean the radical —SR where R is an alkyl or cycloalkyl group.

The term 'arylthio' is intended to mean the radical —SAr where Ar is an aryl group.

BRIEF DESCRIPTION OF THE DRAWINGS

FIG. 5. Effects of PPZ analogs MBX 3574 and MBX 3587 on Vero cell infectivity of authentic EBOV, SUDV, and MARV.

DETAILED DESCRIPTION OF THE INVENTION

Figure 1:
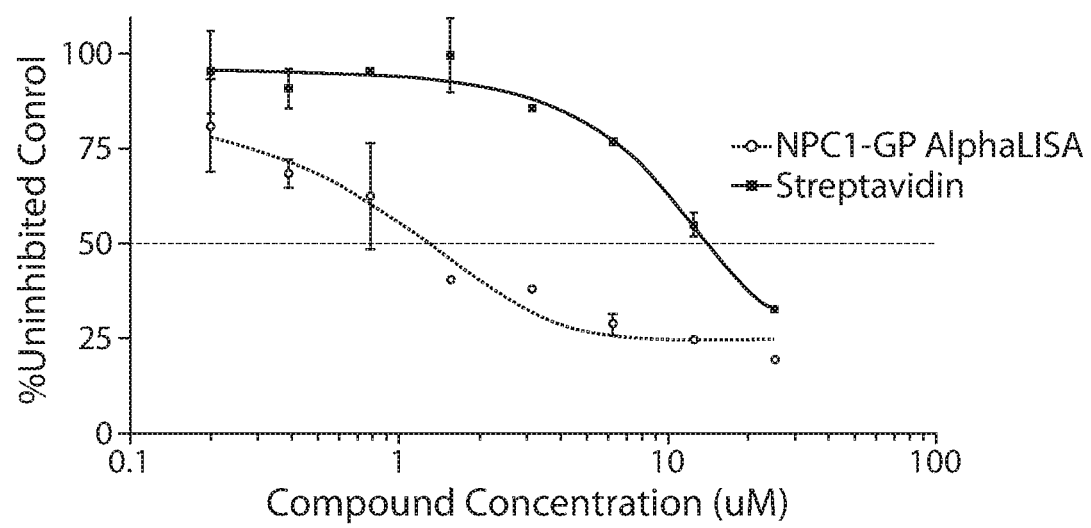
FIG. 1. PPZ analog MBX 3588 inhibits the AlphaLISA assay detecting the GP$_{CL}$-NPC1-C interaction much more potently than it inhibits the AlphaLISA detecting the interaction of biotin and streptavidin.

The endosomal cholesterol transport protein, Niemann-Pick C1 (NPC1) is a critical receptor for infection by all known filoviruses, and it is absolutely required for viral pathogenesis in human and non-human primate cells, and in mouse models of filovirus infection (Carette et al., Nature, 477: 340-343 (2011); Miller et al., EMBO J., 31: 1947-1960 (2012)). Our results demonstrate that a single luminal segment (domain C) in NPC1 mediates filovirus entry by binding specifically and directly to filovirus GP, which has been naturally proteolytically processed to GP$_{CL}$ (Miller et al., EMBO J., 31: 1947-1960 (2012)). Crystallographic studies have revealed that two loops of NPC1-C interact with a hydrophobic cavity in EBOV GP$_{CL}$(Cote et al., Nature, 477: 344-348 (2011)). Therefore, the GP$_{CL}$-NPC1 interaction represents a new and unique molecular target for developing broadly active anti-filovirus therapeutics.

It is an object of the present invention to develop new anti-filovirus therapeutics to target the binding interaction between NPC1 and GP$_L$. NPC1 is a lysosomnal membrane protein involved in lysosomal cholesterol transport and is essential for filovirus entry, infection, and in vivo pathogenesis. Multiple routes of administration are envisioned for these drug-like molecules, and highly cost-effective production strategies can be easily achieved.

We have identified a potent drug-like small molecule series that targets the filovirus glycoprotein (GP$_{CL}$) interaction with its endosomal receptor, NPC1, at sub-µM potency. This new chemical entity, a phenyl piperazine (PPZ) series, provides potent and broad protection against authentic filovirus infection in cell culture. Further, the compounds described herein are novel since no similar compounds have been described previously as inhibitors of filovirus infection.

This PPZ chemotype series is highly attractive for drug development. Without wishing to be limited to any particular mode of action, these novel inhibitors appear to act by specifically blocking or disrupting the crucial NPC1/GP$_{CL}$ interaction required for filovirus entry into a host cell. Members of the phenylpiperazine (PPZ) series were highly active against authentic EBOV, with IC$_{50}$ values ≤1 µM. Despite known minor differences between the EBOV and MARV GP structures, PPZ compounds also exhibit dose-dependent inhibition of authentic MARV infection with IC$_{50}$ values ≤5 µM. Therefore, unlike a previously described GP$_{CL}$-NPC1 inhibitor with a different core structure, i.e., compound 3.47 (Wang et al., *Cell*, 164: 258-268 (2016)), the PPZ chemotype provides broad-spectrum protection against authentic filovirus infection. Furthermore, members of the PPZ series are selective for filoviruses, exhibiting no significant activity against LASV (data not shown), consistent with their specificity for NPC1, which is dispensable for LASV entry. (Wang et al., *Cell*, 164: 258-268 (2016)).

Chemical optimization generated analogs with improved potency, metabolic stability, and optimal murine PK/PD properties, i.e., soluble to 100 mg/mL in isotonic saline, stable in serum, stable in the presence of liver microsomes (91% remaining after 1 h in the presence of NADPH), minimal inhibition of binding by a 30-member Eurofins/Panlabs receptor panel, murine elimination phase t$_{1/2}$>3 h, and a maximum tolerated dose of 100 mg/kg by intraperitoneal administration. An optimized PPZ analog demonstrated protection of mice from EBOV infection, providing in vivo proof of principle for this series.

Therefore, the present invention is related to the discovery of novel organic small molecule inhibitors against filovirus entry into host cells. The inhibitors described herein are suitable for use in a composition for the treatment and/or prevention of filovirus infections in a mammal. More particularly, the inhibitors described herein are suitable for the treatment and/or prevention of filovirus infections in humans.

In another embodiment, the novel small molecule inhibitors described herein are suitable for use in a method for treating or preventing filovirus infections in a mammal by administration of the inhibitors described herein to a patient or subject in need thereof. In a preferred embodiment, the filovirus inhibitors described herein are suitable for use in a method for treating or preventing filovirus infections in humans.

More particularly the invention described herein is related to the identification and characterization of small molecules (inhibitors) that treat or prevent filovirus infections, especially that treat or prevent infection by Ebola virus, Sudan virus, Reston virus, Bundibugyo virus, Taï Forest virus, Marburg virus, and/or Ravn virus in a subject or patient in need thereof.

In another embodiment, the inhibitor compounds of the present invention are suitable for use in a method for treating or preventing filovirus infections in a mammalian subject, and in particular preventing infection by Ebola virus, Sudan virus, Reston virus, Bundibugyo virus, Taï Forest virus, Marburg virus, and/or Ravn virus infection. In a preferred embodiment, the mammalian subject is a human and the filovirus inhibitor compound is administered to prevent Ebola virus infection.

Preferably, the filovirus inhibitors of the present invention will target, i.e., be specific for, the NPC-1/GP$_{CL}$ interaction that mediates filovirus entry into the host cell.

Additionally, the filovirus inhibitor compounds described herein can be administered as pharmaceutically acceptable salts. Such pharmaceutically acceptable salts include the gluconate, lactate, acetate, tartarate, citrate, phosphate, maleate, borate, nitrate, sulfate, and hydrochloride salts. The salts of the compounds described herein can be prepared, for example, by reacting the base compound with the desired acid in solution. After the reaction is complete, the salts are crystallized from solution by the addition of an appropriate amount of solvent in which the salt is insoluble. In some embodiments, the hydrochloride salt is made by passing hydrogen chloride gas into an ethanolic solution of the free base. Accordingly, in some embodiments, the pharmaceutically acceptable salt is a hydrochloride salt.

In another embodiment, the compounds are formulated into a pharmaceutically acceptable carrier or excipient for administration to a subject in need thereof. In another embodiment, the compounds may be formulated into a pharmaceutical formulation and further comprise an additional antiviral compound. In another embodiment, the pharmaceutical formulation may be formulated to be administered orally, parenterally, or topically.

Filovirus inhibitor compounds of the present invention comprise a compound having the structural Formula I:

Formula I wherein:
X is hydrogen, C or N;
wherein, if X is other than hydrogen,
X and Y are connected by a double bond to form a 5-membered heteroaromatic ring; Y is C or N, with the proviso that at least one of X and Y is N; A is C; the ring atoms U, V and Z are C or N atoms in one of the following configurations, taken in order UVZ: CCC, CCN, CNC, NCC, NCN, CNN, or NNN.
R1 is hydrogen, a straight-chain or branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl groups; or R1 is an aryl ring of 5-7 members wherein said aryl is optionally substituted with 1-5 substituents independently selected from alkyl, alkoxy, hydroxyl, carbonyl, carboxy, halogen, haloalkyl, nitro, haloalkoxy, alkylthio, sulfonyl, sulfinyl, alkoxyalkyl, alkoxycarbonyl, or aminocarbonyl groups; or R1 is a heteroaryl, fused aryl ring system or heteroaryl bicyclic ring system of 9-11 members wherein said ring system is optionally substituted with 0-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups, with the proviso that if R1 is an aryl group, it must have at least one substituent;

R2 and R3 are independently selected from straight-chain or branched aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring, wherein the ring has 1-4 carbon substituents and 0-1 substituents on any present ring nitrogen, which are independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, substituted aryl, or substituted or unsubstituted heteroaryl rings, wherein substituted aryl or heteroaryl rings have 1-4 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein, if R1 is other than hydrogen, then R2 and R3 can independently be alkyl; cycloalkyl; heterocycloalkyl; aryl; heteroaryl; haloalkyl; nitro; halogen; alkoxy; alkylthio; haloalkoxy; sulfonyl; sulfinyl; carboxy; alkoxycarbonyl; or aminocarbonyl groups;

R4, R5 and R6 are independently selected from hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms, 0-1 oxygen atoms and bearing 0-3 substituents (in addition to the bond between W and the ring carbon in the formula) selected from alkyl, cycloalkyl, aryl, heteroaryl, haloalkyl, nitro, halogen, alkoxy, alkylthio, haloalkoxy, sulfonyl, or sulfinyl, optionally fused with one or more aromatic, heteroaromatic, cycloalkyl, or heterocycloalkyl rings, wherein said 0-3 substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and additionally W can be either a nitrogen or a saturated carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups, which optional substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl, which non-hydrogen substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; or, wherein, if X is hydrogen, A is C or N; and where A is C, Y is hydrogen, hydroxyl, alkyl, alkoxy, haloalkyl, haloalkoxy, haloalkoxysulfonyl, halogen, nitro, cyano, or NRR', where R and R' are independently selected from hydrogen, alkyl, acetyl, sulfonyl, and alkylsulfonyl; the ring atoms U, V and Z are C or N atoms;

R1 is an aryl or heteroaryl ring of 5-7 members, or a fused aryl or heteroaryl bicyclic ring system of 9-11 members, which R1 aryl or heteroaryl ring or ring system is substituted with 0-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups, with the proviso that if R1 is an aryl group, it must have at least one substituent;

R2 and R3 are independently selected from branched aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring, wherein the ring has 1-4 carbon substituents and 0-1 substituents on any present ring nitrogen, which are independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, substituted aryl, or substituted or unsubstituted heteroaryl rings, wherein substituted aryl or heteroaryl rings have 1-4 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl;

R4, R5 and R6 are independently selected from hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a heterocyclic ring system containing 0-3 degrees of unsaturation and between 5-7 members and containing 1-2 nitrogen atoms, 0-1 oxygen atoms and bearing 0-3 substituents (in addition to the bond linking W and the ring carbon in the formula) including alkyl, cycloalkyl, heterocycloalkyl, aryl, heteroaryl, haloalkyl, acetyl, arylcarbonyl, heteroarylcarbonyl, aralkyl, alkoxyalkyl, nitro, halogen, alkoxy, alkylthio, haloalkoxy, sulfonyl, or sulfinyl, optionally fused with one or more aromatic, heteroaromatic, cycloalkyl, or heterocycloalkyl rings, wherein said 0-3 substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and additionally W can be either a nitrogen or a saturated carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups, which optional substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl, which non-hydrogen substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl, or a pharmaceutically acceptable salt thereof.

It will be understood that the recitation of possible substitutions/substituents or numbers of substitutions/substituents on the labeled/lettered elements shown for Formula I are in addition to the attachment point of that element to the structure illustrated in the formula.

It will also be understood by those skilled in the art that the recitation of the 0-3 substituents that may combine with R4 or R5 to form a fused substituted or unsubstituted non-aromatic ring, are in addition to the attachment/fusion point with R4 or R5. Similarly, the 0-2 substituents included on the formed aromatic ring does not include the attachment point of the substituents to R4 or R5.

In particular embodiments, a filovirus inhibitor of the present invention will have the structure according to Formula II:

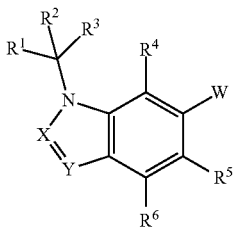

Formula II wherein:

X is C or N; Y is C or N; and at least one of X and Y is N;

R1 is hydrogen, a straight-chain or branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl groups; or R1 is an aryl or heteroaryl ring of 5-7 members, or a fused aryl or heteroaryl bicyclic ring system of 9-11 members, each ring substituted with 1-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups;

R2 and R3 can independently be branched-chain aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring bearing 1-4 carbon substituents and 0-1 nitrogen substituents which may be independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl, or heteroaryl rings; and wherein, if R1 is other than hydrogen, then R2 and R3 can independently be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5 and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms and bearing 0-3 substituents including alkyl, cycloalkyl, aryl, heteroaryl, haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; and additionally W can be either a nitrogen, a saturated carbon, or an olefinic carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl; or alternatively, W may be linked with R4 or R5 to produce fused cyclic structures;

or a pharmaceutically acceptable salt thereof.

It will be understood by those skilled in the art that the recitation of possible substitutions/substituents or numbers of substitutions/substituents on the labeled/lettered elements shown for Formula II are in addition to the attachment point of that element to the structure illustrated in the formula.

In particular embodiments, a filovirus inhibitor compound of the present invention will have the structure of Formula III:

Formula III wherein:

X is C or N; Y is C or N; and at least one of X and Y is N;

Ar is

, where each R3 can independently be hydrogen, alkyl, haloalkyl, haloalkyl, nitro, halogen, alkoxy, alkylthio, haloalkoxy, sulfonyl, sulfinyl, carboxy, alkoxycarbonyl, or aminocarbonyl;

R1 is hydrogen, a straight-chain aliphatic group, a branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group;

R2 can independently be a branched chain aliphatic group, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl group, aryl, or heteroaryl; or R1 and R2 can be linked together to form a substituted aliphatic or heterocyclic ring bearing 1-4 substituents selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl or heteroaryl rings; and, additionally, if R1 is straight-chain aliphatic group, branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group, then R2 can be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5 and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms, 0-1 oxygen atoms, and bearing 0-3 substituents including alkyl, cycloalkyl, aryl, heteroaryl haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; and additionally, W can be either a nitrogen, a saturated carbon, or an olefinic carbon that is linked via a chain of 1-4 carbons to a basic nitrogen bearing independently hydrogen or aliphatic groups of less than nine carbon atoms that can be optionally substituted with haloalkyl, nitro, halogen, alkoxy, alkylthio, haloalkoxy, sulfonyl, sulfinyl, carboxy, alkoxycarbonyl, or aminocarbonyl groups; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl; or alternatively, W may be linked with R4 or R5 to produce fused cyclic structures; or W can be a nitrogen that is part of an aromatic heterocyclic ring system of between 5-7 members and containing 1-2 nitrogen atoms that may be unsubstituted or substituted and may optionally be fused with one or more aromatic, heteroaromatic, cycloalkyl, or heterocycloalkyl rings, and this group can also include connections through either R4 or R5 to produce fused bicyclic structures; or a pharmaceutically acceptable salt thereof.

It will be understood that the recitation of possible substitutions/substituents or numbers of substitutions/substituents on the labeled/lettered elements shown for Formula III are in addition to the attachment point of that element to the structure illustrated in the formula.

In another embodiment, a filovirus inhibitor compound of the present invention will have the structure of Formula IV:

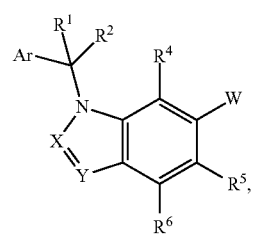

Formula IV wherein:

X can be carbon or nitrogen and Y can be a carbon or nitrogen, and at least one of X and Y is nitrogen, and wherein X and Y can be independently unsubstituted or substituted with a hydrogen, alkyl, halogen, hydroxy, carbonyl, thiol, amino, alkylamino, alkylthio, alkoxy, aryl, haloalkyl, nitro, halogen, alkoxy, alkylthio, haloalkoxy, sulfonyl, sulfinyl, carboxy, alkoxycarbonyl, or aminocarbonyl group;

Ar is where each R3 can independently be hydrogen, alkyl, haloalkyl, nitro, halogen, alkoxy, alkylthio, haloalkoxy, sulfonyl, sulfinyl, carboxy, alkoxycarbonyl, or an aminocarbonyl group;

R1 is a hydrogen, straight-chain aliphatic group, branched chain aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group;

R2 can independently be a branched chain aliphatic group, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl group, aryl, or heteroaryl; or R1 and R2 can be linked together to form a substituted aliphatic or heterocyclic ring bearing 1-4 substituents selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl or heteroaryl rings; and additionally, if R1 is a straight-chain aliphatic group, branched chain aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group, then R2 can be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5, and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups.

W can be a nitrogen that is part of an aromatic or non-aromatic heterocyclic ring system of between 5-7 members, containing 1-2 nitrogen atoms, 0-1 oxygen atoms, and bearing 0-3 substituents selected from alkyl, cycloalkyl, aryl, heteroaryl haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; or W can be a nitrogen that is linked via a chain of 1-4 carbon atoms to a basic nitrogen bearing independently hydrogen or aliphatic groups of less than nine carbon atoms that can be optionally substituted with haloalkyl, nitro, halogen, alkoxy, alkylthio, haloalkoxy, sulfonyl, sulfinyl, carboxy, alkoxycarbonyl, or aminocarbonyl groups; wherein the chain of carbon atoms is a saturated hydrocarbon chain or can be substituted with up to 4 non-hydrogen substituents selected from alkyl, fused cycloalkyl, aryl, fused aryl, haloalkyl, nitro, halogen, alkoxy, alkylthio, haloalkoxy, sulfonyl, sulfinyl, carboxy, alkoxycarbonyl, or aminocarbonyl, or this group can also include connections through either R4 or R5 to produce non-aromatic fused cyclic ring structures;

or a pharmaceutically acceptable salt thereof.

It will be understood by those skilled in the art that the recitation of possible substitutions/substituents or numbers of substitutions/substituents on the labeled/lettered elements shown for Formula IV are in addition to the attachment point of that element to the structure illustrated in the formula.

In another embodiment, the filovirus inhibitor compounds of the present invention will have the structure of Formula V:

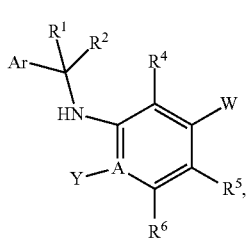

Formula V wherein:

A is C or N; and where A is C, Y is hydrogen, hydroxyl, alkyl, alkoxy, haloalkyl, haloalkoxy, haloalkoxysulfonyl, halogen, nitro, cyano, or NRR', where R and R' are independently selected from hydrogen, alkyl, acetyl, sulfonyl, and alkylsulfonyl;

Ar is, independently, an aryl or heteroaryl ring of 5-7 members, or a fused aryl or heteroaryl bicyclic ring system of 9-11 members, each ring optionally substituted with 0-3 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups;

W is a ring nitrogen in a non-aromatic heterocyclic ring of from 5-7 members having 0-1 additional heteroatom selected from N or O or a fused non-aromatic bicyclic ring system of from 6 to 10 members having 0-1 additional heteroatom selected from N or O; where said heterocyclic ring or said bicyclic ring has 0-3 substituents independently selected from alkyl, cycloalkyl, heterocycloalkyl, aryl, heteroaryl, haloalkyl, acetyl, arylcarbonyl, heteroarylcarbonyl, aralkyl, alkoxyalkyl, nitro, halogen, alkoxy, alkylthio, haloalkoxy, sulfonyl, or sulfinyl, and where a cycloalkyl, heterocycloalkyl, aryl, or heteroaryl substituent may optionally be fused with one or more aromatic, heteroaromatic, cycloalkyl, or heterocycloalkyl rings; or W is NRR', where R is hydrogen or alkyl, and R' is alkyl, alkenyl, aminoalkyl, or aminoalkenyl, cycloalkyl, heterocycloalkyl, aryl, and heteroaryl, which R' group may optionally be further substituted with up to three substituents selected from alkyl, haloalkyl, nitro, halogen, alkoxy, alkylthio, haloalkoxy, sulfonyl, sulfinyl, carboxy, alkoxycarbonyl, or aminocarbonyl groups;

R1 and R2 are, independently, hydrogen, straight-chain or branched alkyl, cycloalkyl, haloalkyl, nitro, halogen, alkoxy, alkylthio, haloalkoxy, sulfonyl, sulfinyl, carboxy, alkoxycarbonyl, or aminocarbonyl groups; and wherein R2 can independently be Ar as defined above;

R4, R5, and R6 are independently selected from hydrogen, alkyl, haloalkyl, nitro, halogen, cyano, alkoxy, alkylthio, haloalkoxy, sulfonyl, sulfinyl, carboxy, alkoxycarbonyl, or aminocarbonyl groups;

or a pharmaceutically acceptable salt thereof.

It will be understood by those skilled in the art that the recitation of possible substitutions/substituents or numbers of substitutions/substituents on the labeled/lettered elements shown for Formula V are in addition to the attachment point of that element to the structure illustrated in the formula.

In particular embodiments, the compounds of the present invention may be selected from:

1-benzhydryl-6-(4-benzylhomopiperazin-1-yl)-1H-benzo[d]imidazole;

1-benzhydryl-6-(4-benzylpiperazin-1-yl)-1H-benzo[d]imidazole;

1-benzhydryl-6-(4-but-2-enylpiperazin-1-yl)-1H-benzo[d]imidazole;

1-benzhydryl-6-(4-butylhomopiperazin-1-yl)-1H-benzo[d]imidazole;

1-benzhydryl-6-(4-butylpiperazin-1-yl)-1H-benzo[d]imidazole;

1-benzhydryl-6-(4-cyclobutylpiperazin-1-yl)-1H-benzo[d]imidazole;

1-benzhydryl-6-(4-cyclohexylpiperazin-1-yl)-1H-benzo[d]imidazole;

1-benzhydryl-6-(4-cyclopentylpiperazin-1-yl)-1H-benzo[d]imidazole;

1-benzhydryl-6-(4-cyclopropylmethylpiperazin-1-yl)-1H-benzo[d]imidazole;

1-benzhydryl-6-(4-decylpiperazin-1-yl)-1H-benzo[d]imidazole;

1-benzhydryl-6-(4-fluoroethylhomopiperazin-1-yl)-1H-benzo[d]imidazole;

1-benzhydryl-6-(4-fluoroethylpiperazin-1-yl)-1H-benzo[d]imidazole;

1-benzhydryl-6-(4-furan-2-ylmethylpiperazin-1-yl)-1H-benzo[d]imidazole;

1-benzhydryl-6-(4-furan-3-ylmethylpiperazin-1-yl)-1H-benzo[d]imidazole;

1-benzhydryl-6-(4-hexylpiperazin-1-yl)-1H-benzo[d]imidazole;

1-benzhydryl-6-(4-hydroxyethylhomopiperazin-1-yl)-1H-benzo[d]imidazole;

1-benzhydryl-6-(4-hydroxyethylpiperazin-1-yl)-1H-benzo[d]imidazole;

1-benzhydryl-6-(4-isopropylhomopiperazin-1-yl)-1H-benzo[d]imidazole;

1-benzhydryl-6-(4-isopropylpiperazin-1-yl)-1H-benzo[d]imidazole;

1-benzhydryl-6-(4-methoxyethylhomopiperazin-1-yl)-1H-benzo[d]imidazole;

1-benzhydryl-6-(4-methoxyethylpiperazin-1-yl)-1H-benzo[d]imidazole;

1-benzhydryl-6-(4-methylhomopiperazin-1-yl)-1H-benzo[d]imidazole;

1-benzhydryl-6-(4-methylpiperazin-1-yl)-1H-benzo[d]imidazole;

1-benzhydryl-6-(4-ethylpiperazin-1-yl)-1H-benzo[d]imidazole;
1-benzhydryl-6-(4-octylpiperazin-1-yl)-1H-benzo[d]imidazole;
1-benzhydryl-6-(4-pentyllpiperazin-1-yl)-1H-benzo[d]imidazole;
1-benzhydryl-6-(4-phenethylpiperazin-1-yl)-1H-benzo[d]imidazole;
1-benzhydryl-6-(4-propylpiperazin-1-yl)-1H-benzo[d]imidazole;
1-benzhydryl-6-(4-pyridine-2-ylmethylpiperazin-1-yl)-1H-benzo[d]imidazole;
1-benzhydryl-6-(4-pyridine-3-ylmethylpiperazin-1-yl)-1H-benzo[d]imidazole;
1-benzhydryl-6-(4-pyridine-4-ylmethylpiperazin-1-yl)-1H-benzo[d]imidazole;
1-benzhydryl-6-(4-t-butylhomopiperazin-1-yl)-1H-benzo[d]imidazole;
1-benzhydryl-6-(4-t-butylpiperazin-1-yl)-1H-benzo[d]imidazole;
1-benzhydryl-6-(4-trifluoromethylpiperazin-1-yl)-1H-benzo[d]imidazole;
1-benzhydryl-6-[4-(2,3-dihydro-1H-inden-2-yl)piperazin-1-yl]-1H-benzo[d]imidazole;
1-benzhydryl-6-[4-(2-cyanoethyl)piperazin-1-yl]-1H-benzo[d]imidazole;
1-benzhydryl-6-[4-(2-fluoroethyl)piperazin-1-yl]-1H-benzo[d]imidazole;
1-benzhydryl-6-[4-(2-methanesulfonylethyl)piperazin-1-yl]-1H-benzo[d]imidazole;
1-benzhydryl-6-[4-(2-methoxyethyl)piperazin-1-yl]-1H-benzo[d]imidazole;
1-benzhydryl-6-[4-(3-hydroxypropyl)piperazin-1-yl]-1H-benzo[d]imidazole;
1-benzhydryl-6-[4-(3-methanesulfonylaminopropyl)piperazin-1-yl]-1H-benzo[d]imidazole;
1-benzhydryl-6-[4-(3-methoxypropyl)piperazin-1-yl]-1H-benzo[d]imidazole;
1-benzhydryl-6-[4-(3-morpholinocarbonylpropyl)piperazin-1-yl]-1H-benzo[d]imidazole;
1-benzhydryl-6-[4-(dimethylaminocarbonylmethyl)piperazin-1-yl]-1H-benzo[d]imidazole;
1-benzhydryl-6-[4-(ethoxycarbonylmethyl)piperazin-1-yl]-1H-benzo[d]imidazole;
1-benzhydryl-6-[4-(pyrrolodinocarbonylmethyl)piperazin-1-yl]-1H-benzo[d]imidazole;
1-benzhydryl-6-{4-[2-(2-oxoimidazolidin-1-yl)ethyl]piperazin-1-yl}-1H-benzo[d]imidazole;
1-(benzhydrylamino)-5-(piperazin-1-yl)-2-cyanobenzene;
1-(benzhydrylamino)-5-(piperazin-1-yl)-2-fluorobenzene;
1-(benzhydrylamino)-5-(piperazin-1-yl)-2-methanesulfonylbenzene;
1-(benzhydrylamino)-5-(piperazin-1-yl)-2-nitrobenzene;
1-(benzhydrylamino)-5-(piperazin-1-yl)-2-trifluoromethoxybenzene;
1-(benzhydrylamino)-5-(piperazin-1-yl)-2-trifluoromethylbenzene;
1-(benzhydrylamino)-5-(piperazin-1-yl)benzene;
1-benzhydryl-6-(piperazin-1-yl)-1H-benzo[d]imidazole;
1-(benzhydrylamino)-5-(homopiperazin-1-yl)-2-cyanobenzene;
1-(benzhydrylamino)-5-(homopiperazin-1-yl)-2-fluorobenzene;
1-(benzhydrylamino)-5-(homopiperazin-1-yl)-2-methanesulfonylbenzene;
1-(benzhydrylamino)-5-(homopiperazin-1-yl)-2-nitrobenzene;
1-(benzhydrylamino)-5-(homopiperazin-1-yl)-2-trifluoromethoxybenzene;
1-(benzhydrylamino)-5-(homopiperazin-1-yl)-2-trifluoromethylbenzene;
1-(benzhydrylamino)-5-(homopiperazin-1-yl)benzene;
1-benzhydryl-6-(homopiperazin-1-yl)-1H-benzo[d]imidazole;
1-benzhydryl-6-(hexahydropyrrolo[1,2-a]pyrazin-2(1H)-yl)-1H-benzo[d]imidazole;
2-(1-benzhydryl-1H-benzo[d]imidazol-6-yl)octahydro-1H-pyrido[1,2-a]pyrazine;
1-benzhydryl-6-(3,4-dimethylpiperazin-1-yl)-1H-benzo[d]imidazole;
3-benzhydryl-5-(piperazin-1-yl)-3H-imidazo[4,5-c]pyridine;
6-(4-methylpiperazin-1-yl)-1-(2-phenylpropan-2-yl)-1H-benzo[d]imidazole;
1-(cyclohexyl(phenyl)methyl)-6-(4-methylpiperazin-1-yl)-1H-benzo[d]imidazole;
1-(2,2-dimethyl-1-phenylpropyl)-6-(4-methylpiperazin-1-yl)-1H-benzo[d]imidazole;
1-(2-cyclopropyl-1-phenethyl)-6-(4-methylpiperazin-1-yl)-1H-benzo[d]imidazole;
1-benzhydryl-5-methyl-6-(4-methylpiperazin-1-yl)-1H-benzo[d]imidazole;
3-((2-nitro-5-(piperazin-1-yl)phenyl)amino)-3-phenylpropanoic acid;
3-((2-nitro-5-(4-methylpiperazin-1-yl)phenyl)amino)-3-phenylpropanoic acid;
ethyl 2-((5-(4-methylpiperazin-1-yl)-2-nitrophenyl)amino)-2-phenylacetate;
ethyl 2-((5-(piperazin-1-yl)-2-nitrophenyl)amino)-2-phenylacetate;
1-benzhydryl-6-[4-(thiophen-2-ylmethyl)piperazin-1-yl]-1H-benzo[d]imidazole;
1-(1-benzhydryl-1H-benzo[d]imidazol-6-yl)-N,N-dimethylpiperidin-4-amine;
1-benzhydryl-7-fluoro-6-[4-methylpiperazin-1-yl]-1H-benzo[d]imidazole;
6-([1,4'-bipiperidin]-1'-yl)-1-benzhydryl-1H-benzo[d]imidazole;
1-(benzhydrylamino)-5-(4-methylpiperazin-1-yl)benzene;
1-(benzhydrylamino)-5-(4-trifluoromethylpiperazin-1-yl)benzene;
1-(benzhydrylamino)-5-(4-isopropylpiperazin-1-yl)benzene;
1-(benzhydrylamino)-5-(4-t-butylpiperazin-1-yl)benzene;
1-(benzhydrylamino)-5-(4-hydroxyethylpiperazin-1-yl)benzene;
1-(benzhydrylamino)-5-(4-methoxyethylpiperazin-1-yl)benzene;
1-(benzhydrylamino)-5-(4-fluoroethylpiperazin-1-yl)benzene;
1-(benzhydrylamino)-5-(4-furan-2-ylmethylpiperazin-1-yl)benzene;
1-(benzhydrylamino)-5-(4-furan-3-ylmethylpiperazin-1-yl)benzene;
1-(benzhydrylamino)-5-(4-t-butylhomopiperazin-1-yl)benzene;
1-(benzhydrylamino)-5-(4-trifluoromethylpiperazin-1-yl)-2-nitrobenzene;
1-(benzhydrylamino)-5-(4-propylpiperazin-1-yl)-2-nitrobenzene;
1-(benzhydrylamino)-5-(4-isopropylpiperazin-1-yl)-2-nitrobenzene;
1-(benzhydrylamino)-5-(4-butylpiperazin-1-yl)-2-nitrobenzene;

1-(benzhydrylamino)-5-(4-but-2-enylpiperazin-1-yl)-2-nitrobenzene;
1-(benzhydrylamino)-5-(4-cyclopropylmethylpiperazin-1-yl)-2-nitrobenzene;
1-(benzhydrylamino)-5-(4-t-butylpiperazin-1-yl)-2-nitrobenzene;
1-(benzhydrylamino)-5-(4-methylpiperazin-1-yl)-3-cyano-2-nitrobenzene;
1-(benzhydrylamino)-5-(4-cyclobutylpiperazin-1-yl)-2-nitrobenzene;
1-(benzhydrylamino)-5-(4-pentyllpiperazin-1-yl)-2-nitrobenzene;
1-(benzhydrylamino)-5-(4-cyclopentylpiperazin-1-yl)-2-nitrobenzene;
1-(benzhydrylamino)-5-(4-hexylpiperazin-1-yl)-2-nitrobenzene;
1-(benzhydrylamino)-5-(4-cyclohexylpiperazin-1-yl)-2-nitrobenzene;
1-(benzhydrylamino)-5-(4-octylpiperazin-1-yl)-2-nitrobenzene;
1-(benzhydrylamino)-5-(4-decylpiperazin-1-yl)-2-nitrobenzene;
1-(benzhydrylamino)-5-(4-benzylpiperazin-1-yl)-2-nitrobenzene;
1-(benzhydrylamino)-5-(4-phenethylpiperazin-1-yl)-2-nitrobenzene;
1-(benzhydrylamino)-5-(4-pyridine-2-ylmethylpiperazin-1-yl)-2-nitrobenzene;
1-(benzhydrylamino)-5-(4-pyridine-3-ylmethylpiperazin-1-yl)-2-nitrobenzene;
1-(benzhydrylamino)-5-(4-pyridine-4-ylmethylpiperazin-1-yl)-2-nitrobenzene;
1-(benzhydrylamino)-5-(4-furan-2-ylmethylpiperazin-1-yl)-2-nitrobenzene;
1-(benzhydrylamino)-5-(4-furan-3-ylmethylpiperazin-1-yl)-2-nitrobenzene;
1-(benzhydrylamino)-5-[4-(2,3-dihydro-1H-inden-2-yl)piperazin-1-yl]-2-nitrobenzene;
1-(benzhydrylamino)-5-[4-(ethoxycarbonylmethyl)piperazin-1-yl]-2-nitrobenzene;
1-(benzhydrylamino)-5-[4-(dimethylaminocarbonylmethyl)piperazin-1-yl]-2-nitrobenzene;
1-(benzhydrylamino)-5-[4-(pyrrolodinocarbonylmethyl)piperazin-1-yl]-2-nitrobenzene;
1-(benzhydrylamino)-5-[4-(2-methyoxyethyl)piperazin-1-yl]-2-nitrobenzene;
1-(benzhydrylamino)-5-[4-(2-cyanoethyl)piperazin-1-yl]-2-nitrobenzene;
1-(benzhydrylamino)-5-[4-(2-fluoroethyl)piperazin-1-yl]-2-nitrobenzene;
1-(benzhydrylamino)-5-[4-(2-methanesulfonylethyl)piperazin-1-yl]-2-nitrobenzene;
1-(benzhydrylamino)-5-{-4-[2-(2-oxoimidazolidin-1-yl)ethyl]piperazin-1-yl}-2-nitrobenzene;
1-(benzhydrylamino)-5-[4-(3-hydroxypropyl)piperazin-1-yl]-2-nitrobenzene;
1-(benzhydrylamino)-5-[4-(3-methoxypropyl)piperazin-1-yl]-2-nitrobenzene;
1-(benzhydrylamino)-5-[4-(3-morpholinocarbonylpropyl)piperazin-1-yl]-2-nitrobenzene;
1-(benzhydrylamino)-5-[4-(3-methanesulfonylaminopropyl)piperazin-1-yl]-2-nitrobenzene;
1-(benzhydrylamino)-5-(4-methylhomopiperazin-1-yl)-2-nitrobenzene;
1-(benzhydrylamino)-5-(4-isopropylhomopiperazin-1-yl)-2-nitrobenzene;
1-(benzhydrylamino)-5-(4-butylhomopiperazin-1-yl)-2-nitrobenzene;
1-(benzhydrylamino)-5-(4-t-butylhomopiperazin-1-yl)-2-nitrobenzene;
1-(benzhydrylamino)-5-(4-benzylhomopiperazin-1-yl)-2-nitrobenzene;
1-(benzhydrylamino)-5-(4-hydroxyethylhomopiperazin-1-yl)-2-nitrobenzene;
1-(benzhydrylamino)-5-(4-methoxyethylhomopiperazin-1-yl)-2-nitrobenzene;
1-(benzhydrylamino)-5-(4-fluoroethylhomopiperazin-1-yl)-2-nitrobenzene;
1-(benzhydrylamino)-5-(4-methylpiperazin-1-yl)-2-trifluoromethylbenzene;
1-(benzhydrylamino)-5-(4-trifluoromethylpiperazin-1-yl)-2-trifluoromethylbenzene;
1-(benzhydrylamino)-5-(4-isopropylpiperazin-1-yl)-2-trifluoromethylbenzene;
1-(benzhydrylamino)-5-(4-t-butylpiperazin-1-yl)-2-trifluoromethylbenzene;
1-(benzhydrylamino)-5-(4-hydroxyethylpiperazin-1-yl)-2-trifluoromethylbenzene;
1-(benzhydrylamino)-5-(4-methoxyethylpiperazin-1-yl)-2-trifluoromethylbenzene;
1-(benzhydrylamino)-5-(4-fluoroethylpiperazin-1-yl)-2-trifluoromethylbenzene;
1-(benzhydrylamino)-5-(4-furan-2-ylmethylpiperazin-1-yl)-2-trifluoromethylbenzene;
1-(benzhydrylamino)-5-(4-furan-3-ylmethylpiperazin-1-yl)-2-trifluoromethylbenzene;
1-(benzhydrylamino)-5-(4-t-butylhomopiperazin-1-yl)-2-trifluoromethylbenzene;
1-(benzhydrylamino)-5-(4-methylpiperazin-1-yl)-2-fluorobenzene;
1-(benzhydrylamino)-5-(4-trifluoromethylpiperazin-1-yl)-2-fluorobenzene;
1-(benzhydrylamino)-5-(4-isopropylpiperazin-1-yl)-2-fluorobenzene;
1-(benzhydrylamino)-5-(4-t-butylpiperazin-1-yl)-2-fluorobenzene;
1-(benzhydrylamino)-5-(4-hydroxyethylpiperazin-1-yl)-2-fluorobenzene;
1-(benzhydrylamino)-5-(4-methoxyethylpiperazin-1-yl)-2-fluorobenzene;
1-(benzhydrylamino)-5-(4-fluoroethylpiperazin-1-yl)-2-fluorobenzene;
1-(benzhydrylamino)-5-(4-furan-2-ylmethylpiperazin-1-yl)-2-fluorobenzene;
1-(benzhydrylamino)-5-(4-furan-3-ylmethylpiperazin-1-yl)-2-fluorobenzene;
1-(benzhydrylamino)-5-(4-t-butylhomopiperazin-1-yl)-2-fluorobenzene;
1-(benzhydrylamino)-5-(4-methylpiperazin-1-yl)-2-cyanobenzene;
1-(benzhydrylamino)-5-(4-trifluoromethylpiperazin-1-yl)-2-cyanobenzene;
1-(benzhydrylamino)-5-(4-isopropylpiperazin-1-yl)-2-cyanobenzene;
1-(benzhydrylamino)-5-(4-t-butylpiperazin-1-yl)-2-cyanobenzene;
1-(benzhydrylamino)-5-(4-hydroxyethylpiperazin-1-yl)-2-cyanobenzene;
1-(benzhydrylamino)-5-(4-methoxyethylpiperazin-1-yl)-2-cyanobenzene;
1-(benzhydrylamino)-5-(4-fluoroethylpiperazin-1-yl)-2-cyanobenzene;

1-(benzhydrylamino)-5-(4-furan-2-ylmethylpiperazin-1-yl)-2-cyanobenzene;
1-(benzhydrylamino)-5-(4-furan-3-ylmethylpiperazin-1-yl)-2-cyanobenzene;
1-(benzhydrylamino)-5-(4-t-butylhomopiperazin-1-yl)-2-cyanobenzene;
1-(benzhydrylamino)-5-(4-methylpiperazin-1-yl)-2-trifluoromethoxybenzene;
1-(benzhydrylamino)-5-(4-trifluoromethylpiperazin-1-yl)-2-trifluoromethoxybenzene;
1-(benzhydrylamino)-5-(4-isopropylpiperazin-1-yl)-2-trifluoromethoxybenzene;
1-(benzhydrylamino)-5-(4-t-butylpiperazin-1-yl)-2-trifluoromethoxybenzene;
1-(benzhydrylamino)-5-(4-hydroxyethylpiperazin-1-yl)-2-trifluoromethoxybenzene;
1-(benzhydrylamino)-5-(4-methoxyethylpiperazin-1-yl)-2-trifluoromethoxybenzene;
1-(benzhydrylamino)-5-(4-trifluoromethylethylpiperazin-1-yl)-2-trifluoromethoxybenzene;
1-(benzhydrylamino)-5-(4-furan-2-ylmethylpiperazin-1-yl)-2-trifluoromethoxybenzene;
1-(benzhydrylamino)-5-(4-furan-3-ylmethylpiperazin-1-yl)-2-trifluoromethoxybenzene;
1-(benzhydrylamino)-5-(4-t-butylhomopiperazin-1-yl)-2-trifluoromethoxybenzene;
1-(benzhydrylamino)-5-(4-methylpiperazin-1-yl)-2-methanesulfonylbenzene;
1-(benzhydrylamino)-5-(4-trifluoromethylpiperazin-1-yl)-2-methanesulfonylbenzene;
1-(benzhydrylamino)-5-(4-isopropylpiperazin-1-yl)-2-methanesulfonylbenzene;
1-(benzhydrylamino)-5-(4-t-butylpiperazin-1-yl)-2-methanesulfonylbenzene;
1-(benzhydrylamino)-5-(4-hydroxyethylpiperazin-1-yl)-2-methanesulfonylbenzene;
1-(benzhydrylamino)-5-(4-methoxyethylpiperazin-1-yl)-2-methanesulfonylbenzene;
1-(benzhydrylamino)-5-(4-trifluoromethylethylpiperazin-1-yl)-2-methanesulfonylbenzene;
1-(benzhydrylamino)-5-(4-furan-2-ylmethylpiperazin-1-yl)-2-methanesulfonylbenzene;
1-(benzhydrylamino)-5-(4-furan-3-ylmethylpiperazin-1-yl)-2-methanesulfonylbenzene;
1-(benzhydrylamino)-5-(4-t-butylhomopiperazin-1-yl)-2-methanesulfonylbenzene;
1-(benzhydrylamino)-5-(4-methylpiperazin-1-yl)-2-aminosulfonylbenzene;
1-(benzhydrylamino)-5-(4-trifluoromethylpiperazin-1-yl)-2-aminosulfonylbenzene;
1-(benzhydrylamino)-5-(4-isopropylpiperazin-1-yl)-2-aminosulfonylbenzene;
1-(benzhydrylamino)-5-(4-t-butylpiperazin-1-yl)-2-aminosulfonylbenzene;
1-(benzhydrylamino)-5-(4-hydroxyethylpiperazin-1-yl)-2-aminosulfonylbenzene;
1-(benzhydrylamino)-5-(4-methoxyethylpiperazin-1-yl)-2-aminosulfonylbenzene;
1-(benzhydrylamino)-5-(4-trifluoromethylethylpiperazin-1-yl)-2-aminosulfonylbenzene;
1-(benzhydrylamino)-5-(4-furan-2-ylmethylpiperazin-1-yl)-2-aminosulfonylbenzene;
1-(benzhydrylamino)-5-(4-furan-3-ylmethylpiperazin-1-yl)-2-aminosulfonylbenzene; and
1-(benzhydrylamino)-5-(4-t-butylhomopiperazin-1-yl)-2-aminosulfonylbenzene.

It is preferable to develop an orally active therapeutic, since that is the most convenient and rapid method to administer a drug to a large exposed population in case of pandemic. However, it is also expected that the filovirus inhibitors described herein will be suitable for intravenous (i.v.) administration, because it is envisioned that in case of a natural outbreak the infected patients may require i.v. administration. Therefore, the inhibitors described herein will provide an effective, safe, and easy therapeutic option for any newly emerged pandemic strain(s).

To identify inhibitors that prevent entry of the filovirus into host cells, a rVSV-EBOV-GP high throughput screen (HTS) assay was developed as a model to mimic entry of the live filovirus into a host cell. The recombinant virus provides a means for safely replicating the viral entry mechanism and identifying inhibitors thereof, which inhibitors can then be tested against live viral infection under strict regulatory conditions that are not required for initial screenings with the recombinant viruses.

Therefore, in another aspect, the present invention describes the development of a high throughput screen (HTS) assay for rapidly screening large libraries containing potential small molecule inhibitors of filovirus entry into host cells. The assay described herein is designed to measure the virus entry using the recombinant viruses described herein to screen for inhibitors of the NPC1/GP$_{CL}$ binding interaction. As described herein, the assay was optimized for rapid screening of a large (>200,000) library of structurally diverse small molecules to identify potent inhibitors (IC$_{50}$<10 μM) of filovirus entry and having a minimal mammalian cytotoxicity (CC$_{50}$) of preferably ≥100 μM.

Compositions and Methods

Unless otherwise indicated, it is understood that description of the use of a filovirus inhibitor compound in a composition or method also encompasses the embodiment wherein one or a combination of two or more filovirus inhibitor compounds are employed as the source of filovirus inhibitory activity in a composition or method of the invention.

Pharmaceutical compositions according to the invention comprise a filovirus inhibitor compound as described herein, or a pharmaceutically acceptable salt thereof, as the 'active ingredient' and a pharmaceutically acceptable carrier (or 'vehicle'), which may be a liquid, solid, or semi-solid compound.

In some embodiments, the presently disclosed subject matter is related to a method of treating or preventing a filovirus infection in a subject in need of treatment thereof wherein the method comprises administering to the subject an effective amount of a composition comprising a compound of one of Formulas I, II, III, IV, or V. The compounds may be administered alone or optionally in combination with one or more additional antiviral agents.

The compositions and methods of the presently disclosed invention are useful for treating and/or preventing filovirus infections in that they inhibit the onset, growth, or spread of the condition, cause regression of the condition, cure the condition, or otherwise improve the general well-being of a mammalian subject, preferably a human, afflicted with, or at risk of, contracting the condition. Thus, in accordance with the presently disclosed subject matter, the terms 'treat', 'treating', and grammatical variations thereof, as well as the phrase 'method of treating' or 'use for treating', are meant to encompass any desired therapeutic intervention, including but not limited to a method for treating an existing filovirus infection in a subject, and a method for the prophylaxis (i.e., prevention) of filovirus infection, such as in a subject that has been exposed to a virus as disclosed herein or that has an expectation of being exposed to the virus as disclosed herein.

In another aspect, the invention relates to pharmaceutical compositions comprising one or more compounds according to Formulas I, II, III, IV, or V herein, or a pharmaceutically acceptable salt, solvate, hydrate, or polymorph thereof, and a pharmaceutically acceptable carrier. That is, a pharmaceutical composition can be provided comprising at least one disclosed compound of the present invention, at least one product of a disclosed method, or a pharmaceutically acceptable salt, solvate, hydrate, or polymorph thereof, and a pharmaceutically acceptable carrier. In one aspect, the invention relates to pharmaceutical compositions comprising a pharmaceutically acceptable carrier and at least one compound according to Formulas I, II, III, IV, or V herein, or a pharmaceutically acceptable salt, hydrate, solvate, or polymorph thereof.

In one aspect of the invention, a pharmaceutical composition will comprise an effective amount of at least one compound according to Formulas I, II, III, IV, or V, herein or a pharmaceutically acceptable salt, solvate, hydrate, or polymorph thereof, and a pharmaceutically acceptable carrier. In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition is used to treat a mammal. In a yet further aspect, the mammal is a human. In a further aspect, the mammal has been diagnosed with a filoviral infection. In a still further aspect, the mammal has been diagnosed with a need for treatment of a filoviral infection. In an even further aspect, the mammal is a human.

In a further aspect, the pharmaceutical composition is a solid dosage form selected from a capsule, a tablet, a pill, a powder, a granule, an effervescing granule, a gel, a paste, a troche, and a pastille. In a still further aspect, the pharmaceutical composition is a liquid dosage form selected from an emulsion, a solution, a suspension, a syrup, and an elixir.

In various aspects, the pharmaceutical composition of the present invention comprises a pharmaceutically acceptable carrier; an effective amount of at least one disclosed compound of the present invention; or a pharmaceutically acceptable salt, solvate, or polymorph thereof; and further comprises a second active agent. In a further aspect, the second active agent is an antiviral agent.

In certain aspects, the disclosed pharmaceutical compositions comprise the disclosed compounds according to Formulas I, II, III, IV, or V herein, (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc, and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets, or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents, and the like can be used to form oral liquid preparations such as suspensions, elixirs, and solutions; while carriers such as starches, sugars, microcrystalline cellulose, diluents, granulating agents, lubricants, binders, disintegrating agents, and the like can be used to form oral solid preparations such as powders, capsules, and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active, or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol, and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouthwashes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants), and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The present invention is further directed to a method for the manufacture of a medicament for filovirus infection in mammals (e.g., humans) comprising combining one or more disclosed compounds of the present invention, products, or compositions with a pharmaceutically acceptable carrier or diluent. Thus, in one aspect, the invention relates to a method for manufacturing a medicament comprising combining at least one disclosed compound according to the present invention or at least one disclosed product with a pharmaceutically acceptable carrier or diluent.

The disclosed pharmaceutical compositions can further comprise other active compounds, which are usually applied in the treatment of the above mentioned conditions. In another embodiment, the disclosed pharmaceutical compositions can further comprise other therapeutically active compounds, which are usually applied in the treatment of the above mentioned conditions.

It is understood that the disclosed compositions can be prepared from the disclosed compounds of the present invention. It is also understood that the disclosed compositions can be employed in the disclosed methods of using.

Also provided is a method of use of a disclosed compound, composition, or medicament, comprising at least one of Formulas I, II, III, IV, or V herein. In a further aspect, the disclosed compounds of the present invention can be used as single agents or in combination with one or more other drugs in the treatment, prevention, control, amelioration, or reduction of risk of the aforementioned diseases, disorders, and conditions for which the compound or the other drugs have utility, where the combination of drugs together are safer or more effective than either drug alone. The other drug(s) can be administered by a route and in an amount commonly used therefore, contemporaneously or sequentially with a disclosed compound of the present invention. When a disclosed compound of the present invention is used contemporaneously with one or more other drugs, a pharmaceutical composition in unit dosage form containing such drugs and the disclosed compound of the present invention is preferred. However, the combination therapy can also be administered on overlapping schedules. It is also envisioned that the combination of one or more active ingredients and a disclosed compound of the present invention can be more efficacious than either as a single agent.

In one aspect, the invention relates to a kit comprising at least one compound according to Formulas I, II, III, IV, or V herein, or a pharmaceutically acceptable salt, solvate, or polymorph thereof; and one or more of:
a) at least one agent known to inhibit the interaction of filovirus glycoprotein ($GP_{CL}$) with its host receptor, Niemann-Pick C1 (NPC1) protein;
b) optionally at least one additional agent known to have antiviral activity;
c) instructions for treating a filovirus related disease;
d) instructions for administering the compound in connection with treating a filovirus infection; or
e) instructions for administering the compound with at least one agent known to treat a filovirus related disease.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound of the present invention and/or product and another component for delivery to a patient.

In a further aspect, the kit further comprises a plurality of dosage forms, the plurality comprising one or more doses; wherein each dose comprises an amount of the compound and the agent known to have antiviral activity. In another aspect, the kit further comprises a plurality of dosage forms, the plurality comprising one or more doses; wherein each dose comprises an effective amount of the compound and the agent known to have antiviral activity.

In a further aspect, an effective amount is a therapeutically effective amount. In a still further aspect, an effective amount is a prophylactically effective amount.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1. An AlphaLISA Assay to Measure Inhibition of the $EBOV\text{-}GP_{CL}$/NPC1-C Interaction The AlphaLISA platform (Perkin-Elmer) was adapted to measure inhibition of the interaction between cleaved Ebola virus glycoprotein ($EBOV\text{-}GP_{CL}$) and human NPC1 domain C in a 384-well plate format. Protein G-tagged AlphaLISA acceptor beads (PerkinElmer Cat. No. AL102R), anti-EBOV-GP monoclonal antibody KZ52 (Miller et al., *EMBO J.*, 31: 1947-1960 (2012); Maruyama et al., *J. Virol.*, 73: 6024-6030 (1999)), and FLAG®-tagged NPC1-C loop fragment (also known as NPC1 domain 2) (Miller et al., *EMBO J.*, 31: 1947-1960 (2012); Deffieu M S and Pfeffer S R., *Proc. Natl. Acad. Sci. USA*, 108: 18932-18936 (2011)) were mixed together in buffer consisting of phosphate buffered saline and 0.1% bovine serum albumin and then added to wells of 384-well microplates (PerkinElmer OptiPlate-384 white opaque 384-well microplates; Vendor, Cat. No. 6007299) containing potential inhibitory compounds at a range of concentrations (final DMSO concentration ≤2%). Plates were incubated for 1 hr at room temperature. Then, anti-FLAG® Alpha donor beads (PerkinElmer Cat. No. AS 103R) and thermolysin cleaved EBOV-GP ($EBOV\text{-}GP_{CL}$) were added to each well to bring the volume to 25 µL. After another 1 hr incubation at room temperature, fluorescence was measured using an Alpha-compatible plate reader (Envision Multilabel Reader with Alpha HTS option, PerkinElmer). The $EBOV\text{-}GP_{CL}$ interaction with NPC1 brings the acceptor and donor beads into close proximity, allowing energy transfer from donor to acceptor bead, and inducing light emission at 615 nm. Addition of an inhibitor of the $EBOV\text{-}GP_{CL}$ interaction with NPC1-C reduces the fluorescence in proportion to the concentration and potency of the inhibitor. EBOV-GP was produced as the full length glycoprotein minus the transmembrane domain and cytoplasmic tail which was replaced with a $HIS_6$ tag, which was used to purify the protein. Cleaved EBOV GP ($EBOV\text{-}GP_{CL}$) was generated in vitro using the bacterial protease thermolysin (250 µg/ml) (Sigma-Aldrich, St. Louis, Mo.) for 1 h at 37° C. as described previously (Schornberg et al., *J. Virol.*, 80: 4174-4178 (2006); Wong et al., J. Virol., 84: 163-175 (2010)), and the reaction was stopped by adding the metalloprotease inhibitor phosphoramidon (1 mM) (Sigma-Aldrich); thermolysin cleavage removes the $HIS_6$ tag. The concentration of each assay component was determined by assay optimization and is as follows: KZ52 antibody (0.2 ng/µL), $EBOV\text{-}GP_{CL}$ (1.4 ng/µL), NPC1-C loop fragment (0.8 ng/µL) and donor and acceptor beads (6.6 ng/µL each). Inhibitors that exhibited >80% inhibition of the $EBOV\text{-}GP_{CL}$/NPC1 AlphaLISA assay were tested for specificity by ensuring that they exhibited <20% inhibition of a biotin-streptavidin Alpha counter-screen (PerkinElmer AlphaScreen TruHits kit, Cat. No. 6760627D). The dose-response curves for PPZ analog MBX 3588 in the $EBOV\text{-}GP_{CL}$/NPC1 and the biotin-streptavidin AlphaLISA assays are shown in FIG. 1. The selectivity of this analog for inhibition of the $EBOV\text{-}GP_{CL}$/NPC1-C interaction vs. the biotin-streptavidin interaction is acceptable and is about 10-fold.

Example 2. Inhibition of Infectivity of Recombinant VSVs Expressing Glycoproteins from Zaire Ebolavirus, Sudan Ebolavirus, Bundybugyo Ebolavirus, and Lassa Arenavirus Recombinant vesicular stomatitis viruses (VSVs) (serotype Indiana) expressing eGFP and EBOV, SUDV, or BDBV GP in place of VSV G, as well as those expressing RFP and LASV GP in place of VSV G (rVSV-EBOV/SUDV/BUDV/LASV GP) were produced, recovered, and amplified as described previously (Miller et al., *EMBO J.*, 31: 1947-1960 (2012); Wong et al., J. Virol., 84: 163-175 (2010); Ng et al., *Virology*, 468-470: 637-646 (2014); Geisbert et al., *PLoS Med.*, 2:e183 (2005)). The EBOV, SUDV, BDBV and LASV GP genes encoded by these viruses were derived from the following isolates: Genbank accession numbers NP_066246, YP_138523, YP_003815435, and ADY11070, respectively.

Figure 2:
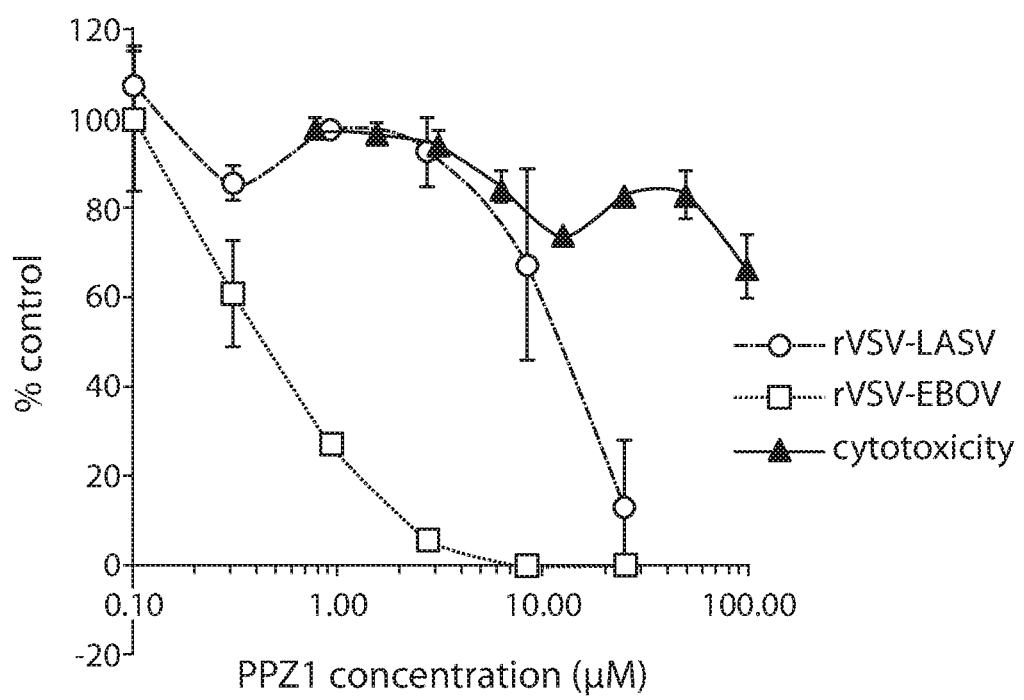
FIG. 2. Evaluation of PPZ 2 for effects on Vero cell infectivity of rVSV-EBOV GP, rVSV-LASV GP, and for cytotoxicity (nuclei count).

The infectivity of the rVSVs expressing different viral glycoproteins in place of VSV G and the effect of added inhibitor were measured as follows. Vero or U2OS cells were seeded at 300,000 cells/ml in 50 µl in 96-well black plates with clear bottoms. After 24 hrs, cells were treated with compounds in 3-fold serial dilution series starting at 200 µM, followed by infection 1 hr later with appropriate rVSVs (e.g., rVSV-EBOV GP, rVSV-SUDV GP, rVSV-BDBV GP, or rVSV-LASV GP). The MOI (~0.1 infectious units/cell) was chosen to keep the infection percentage between 40 and 60%. Cells were fixed with 4% formaldehyde at 12-14 hr post infection for 30 min prior to staining with Hoechst 33342 for 15 min at room temperature. Nuclei, and individual eGFP or RFP-positive cells were counted using a Cytation 3 automated fluorescence microscopy cell imager equipped with GFP, DAPI, and Texas Red filter cubes (BioTek Instruments, Inc., Winooski, Vt.). An example with PPZ2 (Chembridge #6179974) is shown in FIG. 2. The analog exhibits a high degree of selectivity for inhibition of infection by rVSV-EBOV GP (squares) as compared to rVSV-LASV GP (circles), and the nuclei count (triangles) remains nearly constant, reflecting low cytotoxicity of the compound.

Figure 3:
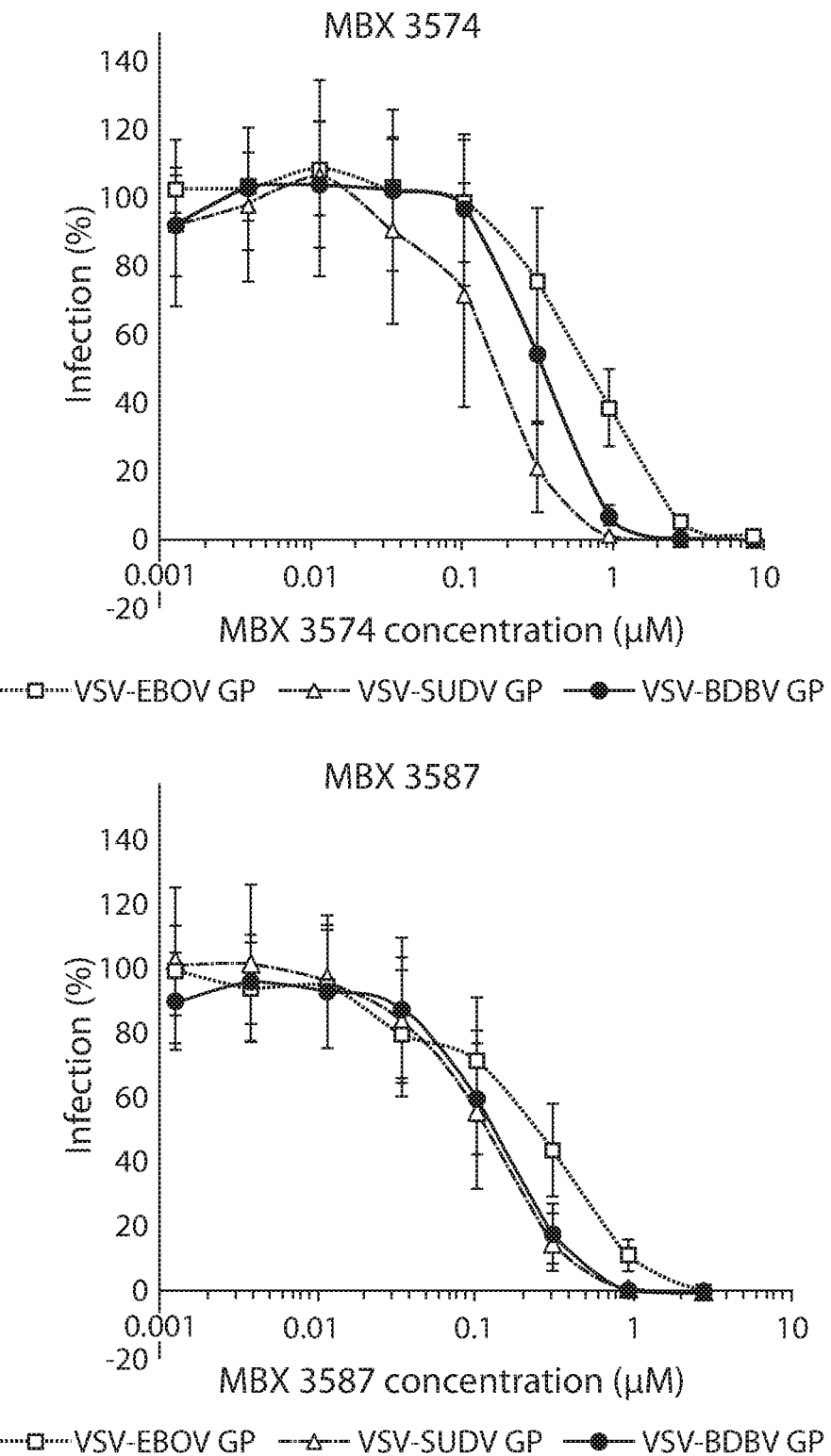
FIG. 3. Evaluation of the effect of MBX 3574 and MBX 3587 on Vero cell infectivity of rVSV-EBOV GP, rVSV-SUDV GP, and rVSV-BDBV GP.

The rVSV assay was also used to compare the potency of MBX 3574 and MBX 3587 vs. rVSV-EBOV GP (squares), rVSV-SUDV GP (triangles), and rVSV-BDBV GP (circles) in FIG. 3. MBX 3574 and MBX 3587 are potent inhibitors of infection of Vero cells by rVSV carrying each of the three GP proteins, demonstrating a broad spectrum of anti-filoviral activity.

Example 3. Cytotoxicity Measurements of PPZ Analogs

Figure 4:
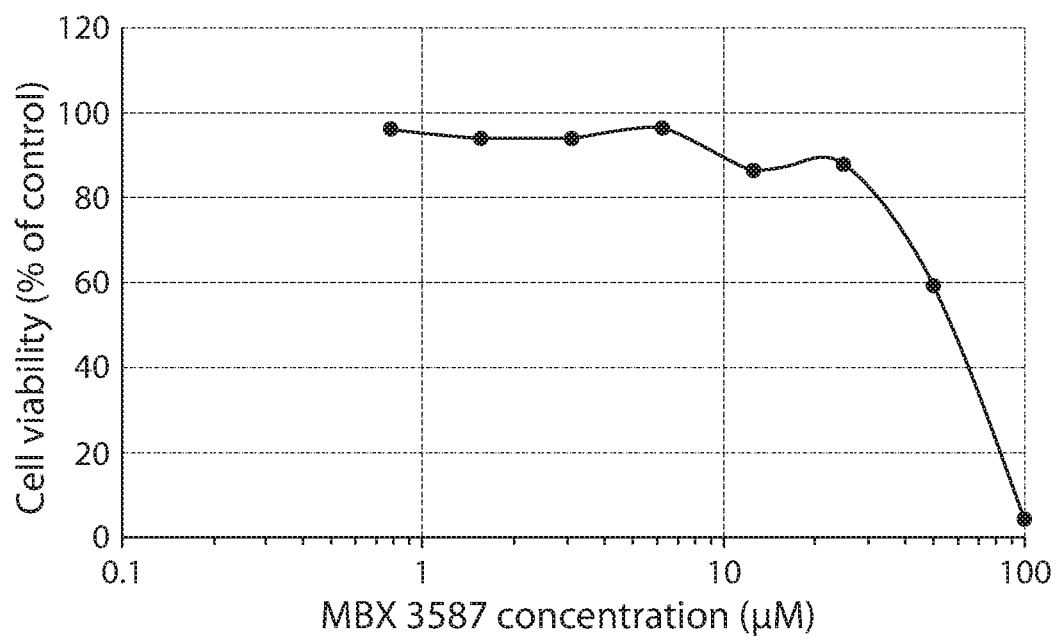
FIG. 4. Cytotoxicity measurements of PPZ analog MBX 3587.

The $CC_{50}$ of inhibitors for cultured mammalian cells (Vero or HeLa cells; American Type Culture Collection, Manassas, Va.) was determined as the concentration of compound that inhibits 50% of the conversion of MTS to formazan (Marshall et al., *Growth Regul.*, 5:69-84 (1995)). Briefly, 96-well plates were seeded with Vero or HeLa cells at a density of $4 \times 10^3$ per well in appropriate media such as Eagle's Minimum Essential Medium (ATCC Catalog No. 30-2003) with 10% fetal bovine serum (FBS) for HeLa or 2% FBS with 1% nonessential amino acids and 1% sodium pyruvate for Vero cells in the presence or absence of serial dilutions of an inhibitor compound dissolved in DMSO. Following incubation for 3 days at 37° C., cell viability was measured with the vital tetrazolium salt stain 3-(4,5-dimethylthiazol-2-yl)-2,5 diphenyltetrazolium bromide according to the manufacturer's instructions (CellTiter 96® AQueous One Solution Cell Proliferation Assay, Promega, Madison, Wis.). Values were determined in duplicate using dilutions of inhibitory compound from 100 to 0.2 µM and reading absorbancy at 490 nm ($A_{490}$) using a Wallac Victor 1420 Multilabel plate reader. Evaluation of MBX 3587 for cytotoxicity is shown in FIG. 4. Other PPZ analogs were analyzed in the same manner to determine $CC_{50}$ values (the concentration of compound that causes cytotoxicity of 50% of the cells). High values of $CC_{50}$ are favorable and indicate that PPZ analogs exhibit limited cytotoxicity.

Example 4. Inhibition of Authentic Filovirus Infections in Cell Culture Assays

Figure 5:
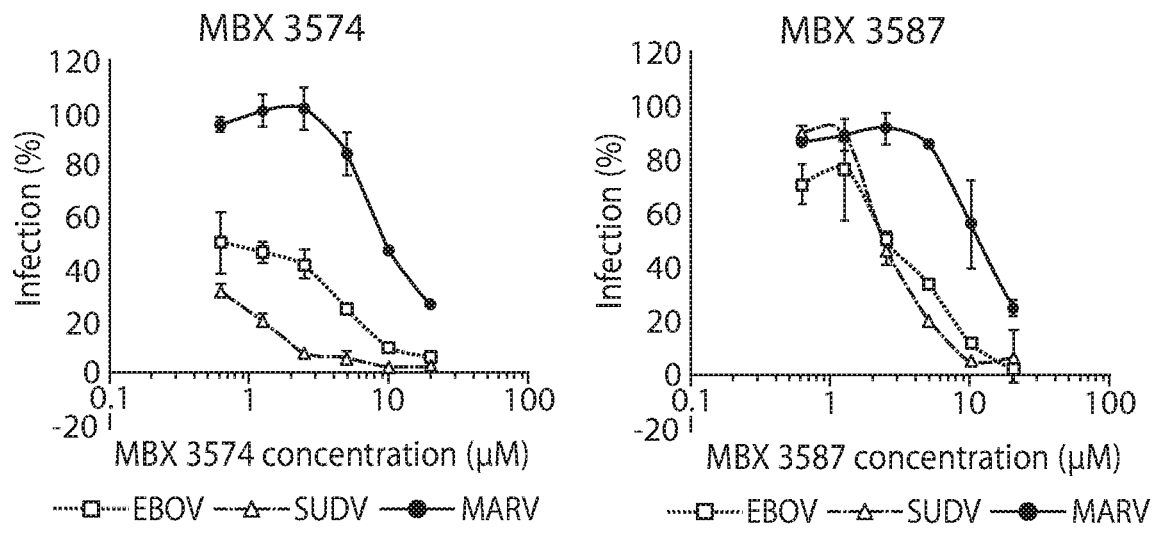

The authentic filoviruses Ebola virus/*H. sapiens*-tc/COD/1995/Kikwit-9510621 (EBOV/Kik-9510621; 'EBOV-Zaire 1995') (Jahrling et al., *J. Infect. Dis.*, 179 Suppl 1:S224-234 (1999)), Sudan virus/*H. sapiens*-gp-tc/SDN/1976/Boniface-USAMRIID 111808 (SUDV/Bon-USAMRIID 111808; 'SUDV-Boniface 1976') (Anonymous, Ebola haemorrhagic fever in Sudan, 1976. Report of a WHO/International Study Team. *Bull World Health Organ.*, 56(2): 247-270 (1978)), and Marburg virus/*H. sapiens*-tc/DEU/1967/Hesse-Ci67 (MARV/Ci67) (Towner et al., *PLoS Pathog.*, 4(11): e1000212 (2008)) were used in these studies under BSL-4 containment and procedures. Vero cells were pre-treated with the inhibitor compound added to each well (or in replicate wells) in a dilution series (typically two-fold diluted, beginning with 25 or 50 µM as the highest concentration) for 1 hour prior to addition of EBOV, SUDV or MARV at a multiplicity of infection (MOI) of 1 diluted in culture media. After a 1 hr incubation with virus, in the presence of inhibitor compound, virus inoculum was removed and replaced with fresh culture media containing compounds in a dilution series (typically two-fold diluted, beginning with 25 or 50 µM as the highest concentration). At 48 h post-infection, cells were fixed with formalin, and blocked with 1% bovine serum albumin. EBOV-, SUDV- or MARV-infected cells and uninfected controls were incubated with EBOV GP-specific mAb KZ52 (Lee et al., *Nature*, 454:177-182 (2008)), SUDV GP-specific Ab 3C10 (Herbert et al., *M Bio*, 6: e00565-15 (2015)), or MARV GP-specific mAb 9G4 (Swenson et al., *FEMS Immunol. Med. Microbiol.*, 40: 27-31 (2004)). Cells were washed with PBS prior to incubation with either goat anti-mouse IgG or goat anti-human IgG conjugated to Alexa 488. Cells were counterstained with Hoechst 33342 stain (Invitrogen), washed with PBS and stored at 4° C. Infected cells were quantitated by fluorescence microscopy and automated image analysis. Images were acquired at 20 fields/well with a 20× objective lens on an Operetta high content device (Perkin Elmer, Waltham, Mass.). Operetta images were analyzed with a customized algorithm built from image analysis functions available in Harmony software. Evaluation of the effects of MBX 3574 and MBX 3587 on the infectivity of authentic EBOV, SUDV, and MARV is shown in FIG. 5. Other analogs were analyzed in the same manner to confirm efficacy against infectious filoviruses.

Example 5. Selectivity Vs. Mammalian Receptors, Murine Dose Tolerance and Pharmacokinetics The following studies were undertaken to assess the selectivity and toxicity of test compounds and to determine the maximum tolerated dose (MTD) in BALB/c mice. The MTD is the upper limit of the dose range evaluated for efficacy. Two PPZ analogs, MBX 3587 and MBX 3673 were evaluated at 10 µM for inhibition of over 30 mammalian receptors and enzymes at Eurofins Pharma Discovery Services (Eurofins Panlabs Inc., Redmond, Wash. USA)(Table). Results revealed that neither analog displayed significant (e.g., >50%) inhibition of many mammalian receptors, indicating favorable selectivity. (See, Table 7.)

For safety reasons, in the BSL-4 facility, murine infectious EBOV studies were done by intraperitoneal (IP) dosing of compounds; therefore, two IP formulations were developed. Both formulations take advantage of the protonatable amine, which appears to be important for potency. Compounds as the free base were dissolved at concentrations up to 20 mg/mL in 0.05% acetic acid and 36% w/v (2 hydroxypropyl)-β-cyclodextrin. Alternatively, compounds were prepared as the HCl salt and were readily dissolved at concentrations up to 100 mg/mL in isotonic saline. Groups of 6 mice (female, BALB/c, 20-25 g each; 5 animals per dose plus vehicle controls) were treated with increasing dose levels of test compounds in a suitable vehicle by i.p. administration once for single dose studies, or once or twice a day for multiple dose studies. Three to five dose levels of test compound were given (e.g., 10, 20, 40, 70, and 100 mg/kg or 10, 35, and 50 mg/kg). Dose levels that caused more than temporary discomfort were considered the minimal toxic dose, and the next lower dose was designated the MTD. Potentially useful inhibitors will exhibit an MTD of at least two-fold higher than the half-maximal effective dose ($ED_{50}$) and preferably 5-10-fold higher than the $ED_{50}$ in order to facilitate attaining a high therapeutic index (MTD/$ED_{50}$).

Pharmacokinetic (PK) experiments were done to determine the plasma concentrations and stability of efficacious inhibitor compounds in order to develop optimal dosing regimens for i.p. efficacy studies in the mouse infection models. The following experiments were performed. (i) Analytical methods. Methods for accurate, quantitative determination of compound levels in plasma were developed and validated using HPLC detection, or LC-MS as known in the art (Aitken et al., *J. Antimicrob. Chemother.*, 71: 727-730 (2016)). (ii) i.p. formulations. Standard approaches were used to evaluate solvent vehicles (Sweetana S. and Akers M J., *PDA J. Pharm. Sci. Technol.*, 50: 330-342 (1996)) and carriers such as the cyclodextrins (Rajewski R A and Stella V J., *J. Pharm. Sci.*, 85: 1142-1169 (1996)). Various aqueous pH, organic co-solvents and emulsifiers were tested. Addition of cyclodextrins and formation of salts were evaluated (Matsubara et al., *J. Pharm. Sci.*, 84: 1295-1300 (1995); Leonard et al., *J. Pharm. Sci.*, 94: 1736-1746 (2005)). Suitable formulations for most PPZ analogs include freebase forms of PPZ analogs formulated at 10 mg/ml in acetate/cyclodextrin or HCl salt forms of PPZ analogs formulated in isotonic saline at 50 mg/ml. (iii) PK experiments. Compounds were administered by the i.p. route. Blood samples were obtained at 6 time intervals (0, 0.25, 1, 2, 4, 8, 12 h). An appropriate dose of each agent (the MTD) was injected in a suitable formulation via i.p. to a series of 18 mice, and at a series of times following injection, 3 mice were anesthetized with halothane, and blood was collected via cardiac puncture (for plasma level determinations). Animals were then humanely euthanized by cervical dislocation. Three plasma levels for each time point were averaged, and the data graphed and analyzed by non-compartmental methods using the PK program WinNonlin™ (Pharsight Corp.). Results were used to estimate the rate and extent of uptake, the peak plasma concentration ($C_{max}$) and time to onset, the effective plasma half-life $t_{1/2}$, the "area under the curve" (AUC), and volume of distribution (Vd) by established methods (Gibaldi M. and Perrier D., *Drugs and the Pharmaceutical Sciences, Pharmacokinetics*, vol 15, Marcel Dekker, Inc., N.Y (1975)). If plasma or lung levels of drug were not sustained above the desired concentration (5-10× $IC_{50}$) for a period expected to demonstrate in vivo efficacy, the PK software package was employed to design a dosing regimen that allows for the maintenance of acceptable plasma levels.

Figure 6:
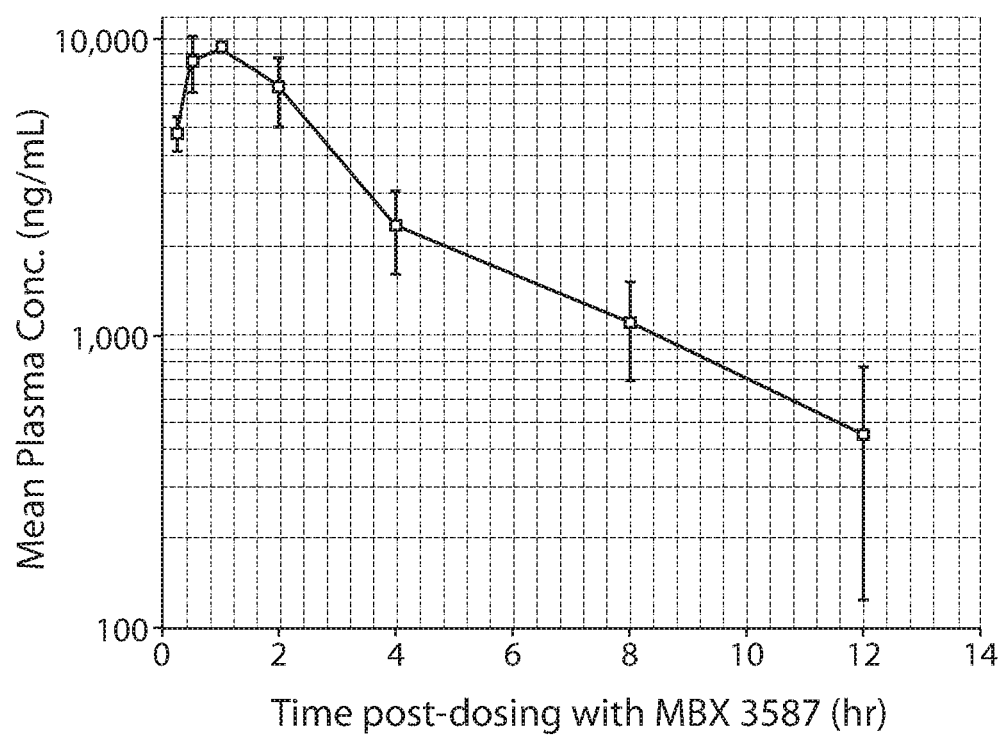
FIG. 6. Pharmacokinetic analysis of MBX 3587 in mice.

Evaluation of seven analogs in murine PK studies using this method revealed that the benzimidazole compound MBX 3587 displayed the most prolonged plasma 3-elimination phase $t_{1/2}$-3.2 h (FIG. 6). Dose range studies indicated that single doses of up to 100 mg/Kg were well-tolerated, and up to 20 mg/Kg was tolerated in 2 doses per day for 10 days. (FIG. 6.)

Figure 7A:
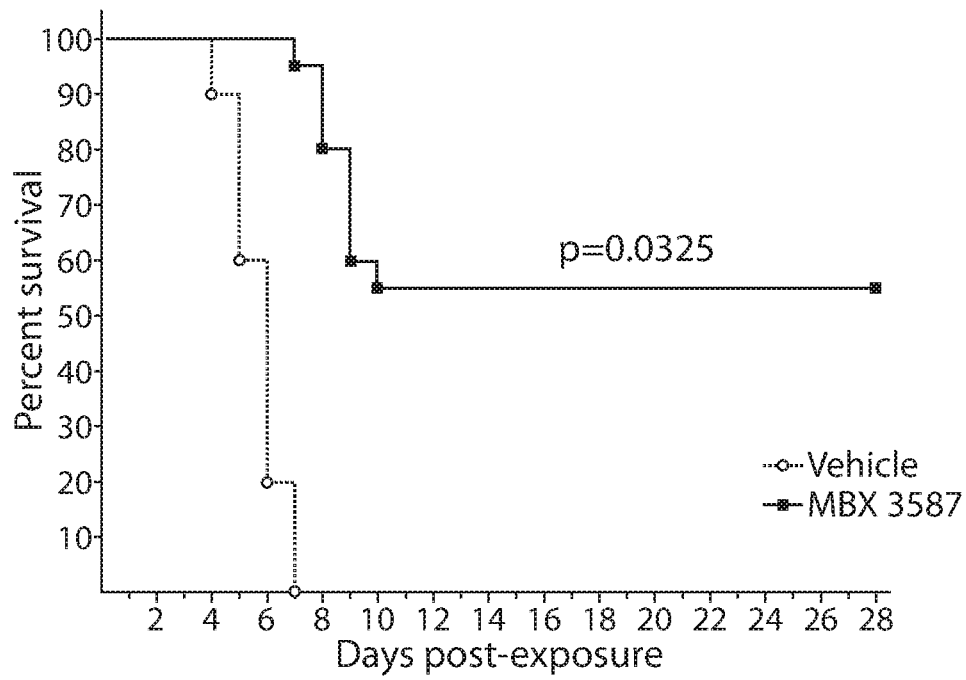
FIG. 7. Evaluation of PPZ analog MBX 3587 in a murine EBOV infection model.
Figure 7B:
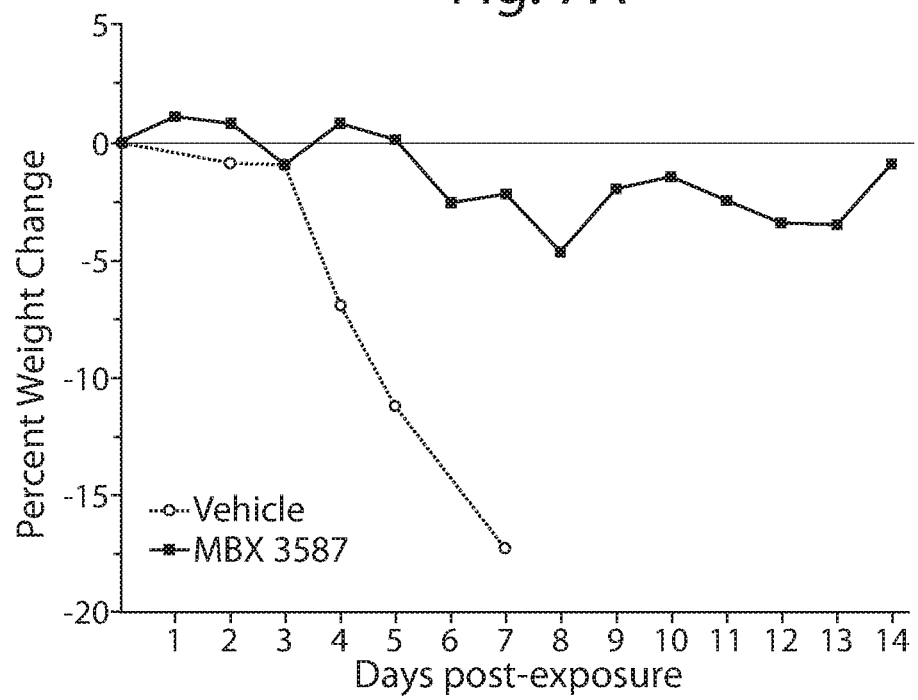

Example 6. Inhibition of Authentic Ebola Virus Infections in a Murine Lethal Infection Study The efficacy of PPZ analogs for rescuing mice from lethal filovirus infections was determined as follows. Female BALB/c mice (Jackson Labs, Bar Harbor, Me.) (n=10 for infected, vehicle group; n=20 for infected, MBX 3587 group) were challenged via the i.p. route with 100 PFU (~3,000 $LD_{50}$) of mouse-adapted EBOV (EBOV-MA; derived from Mayinga variant) (Bray et al., *J. Infect. Dis.*, 178: 651-661 (1998)). Mice were dosed twice daily (12 hours apart) i.p., starting 1 day prior to challenge through day 10 post-challenge, with MBX 3587 (50 mg/kg) or an equal volume (0.1 ml) of vehicle alone. Mice were observed daily for clinical signs of disease and lethality. Daily observations were increased to a minimum of twice daily while mice were exhibiting signs of disease. Moribund mice were humanely euthanized on the basis of IACUC-approved criteria. Results revealed statistically significant protection of 50% of the mice from the lethal effects of EBOV challenge by MBX 3587 (FIG. 7A). Monitoring animal weight revealed the expected weight loss in untreated infected animals and showed that MBX 3587 prevented weight loss in surviving infected animals treated with MBX 3587 (FIG. 7B). Taken together, these data indicate that MBX 3587 provided protection from EBOV infection, but that the 50 mg/Kg dosing level exhibited some toxic effects when administered twice daily for 10 days. Lower doses are expected to be efficacious without toxicity, and other analogs that appear to be even more selective (e.g., MBX 3673, SAR Table) are expected to rescue mice effectively.

Animal Welfare Statement.

Murine challenge studies were conducted under IACUC-approved protocols in compliance with the Animal Welfare Act, PHS Policy, and other applicable federal statutes and regulations relating to animals and experiments involving animals. The facilities where this research was conducted (Albert Einstein College of Medicine and USAMRIID) are accredited by the Association for Assessment and Accreditation of Laboratory Animal Care, International (AAALAC) and adhere to principles stated in the Guide for the Care and Use of Laboratory Animals, National Research Council, 2011.

Example 7. Synthesis of Exemplary Filovirus Inhibitor Compounds

Specific compounds were prepared following the syntheses scheme of General Method A and General Method B:

General Method A: Preparation of Aryl F Starting Material

To a round bottom flask of 2,4-difluoronitrobenzene (0.07 mL, 0.620 mmol, 1 eq) was added acetonitrile (10 mL, 0.062M). Benzhydrylamine (0.11 mL, 0.620 mmol, 1 eq) was then added, followed by diisopropylethylamine (0.11 mL, 0.620 mmol, 1 eq). The reaction was heated to 70° C. for 24 h. The reaction was then cooled to r.t., concentrated, and purified on a 40 g silica column, eluting with 0-10% EtOAc:hexanes to yield a sticky yellow solid (0.049 g, 0.152 mmol, 25%).

Rf: 0.63 (10% EtOAc:hexanes)

$^1$H NMR (DMSO): 8.70 (d, 1H), 8.23 (q, 1H), 7.47-7.37 (m, 8H), 7.33-7.28 (m, 2H), 6.69-6.57 (m, 2H), 6.12 (d, 1H).

Analogues containing substituents on the central aryl ring, as well as analogues containing variations on either aryl ring of the benzhydryl moiety or with an alternative substitution on the N of the benzhydrylamine, were obtained in the same manner.

General Method B: Preparation of MBX 3556/PPZ-1

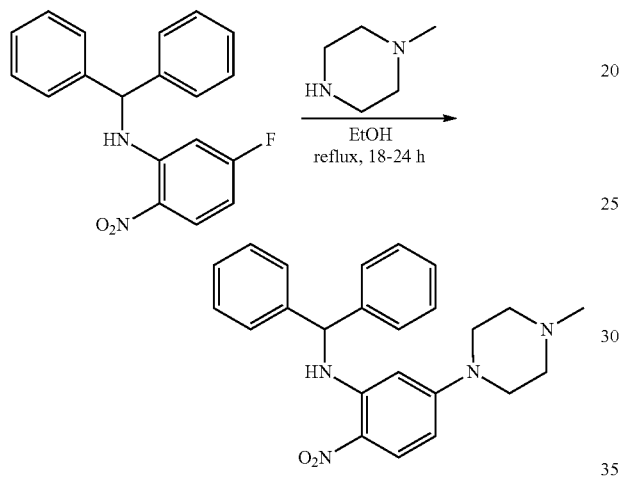

N-benzhydryl-5-fluoro-2-nitroaniline (0.043 g, 0.133 mmol, 1 eq), N-methylpiperazine (0.067 g, 0.667 mmol, 5 eq), and 20 mL ethanol were heated to reflux for 24 h. The reaction was then cooled, filtered, and concentrated. The concentrate was purified on a 4 g silica column, eluting with 0-10% MeOH:DCM to yield PPZ1 as a yellow powder (0.041 mg, 0.106 mmol, 79%).

Rf: 0.13 (5% MeOH:DCM)

LC/MS: 389.3 (M+1)

$^1$H NMR (CDCl3): 8.99 (d, 1H), 8.08 (d, 1H), 7.40-7.26 (m, 10H), 6.20 (dd, 1H), 5.75 (d, 1H), 5.65 (d, 1H), 3.13 (t, 4H), 2.84 (t, 4H).

Analogues containing substituents on the central aryl ring, as well as analogues containing variations on either aryl ring of the benzhydryl moiety or with an alternative substitution on the N of the benzhydrylamine, were obtained in the same manner.

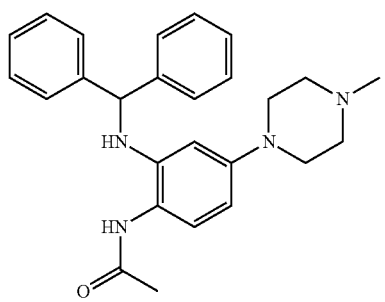 [SMILES: CC(=O)Nc1ccc(N2CCN(C)CC2)cc1NC(c1ccccc1)c1ccccc1]

MBX 3525: 2-(benzhydrylamino)-4-(4-methylpiperazin-1-yl)-1-acetamidobenzene

Procedure: A mixture of PPZ1 (0.3 g) and Pd/C (10% Pd, 0.05 g) in EtOAc (100 mL) was placed in a thick wall glass vessel connected to a Parr shaker apparatus. The vessel was purged with hydrogen 3 times, sealed under hydrogen (42 psi), and shaken for 4 h. Hydrogen was released. The reaction mixture was treated with acetic anhydride (100 uL) and kept under nitrogen. After 16 h, celite (10 g) was added, solvent was evaporated. The material adsorbed on celite was purified by silica gel column chromatography (40 g of SiO2, DCM to 10% MeOH in DCM) to provide 359-119 (103 mg). Pale yellow solid, mp 66-70° C. R$_f$: 0.66 (86:13:1 CHCl3:MeOH:NH3). $^1$H NMR (DMSO, 300 MHz, ppm) 9.30 (s, 1H), 7.58-7.43 (m, 4H), 7.34-7.29 (m, 4H), 7.23-7.18 (m, 2H), 6.90 (d, 1H), 6.15 (dd, 1H), 6.05 (d, 1H), 5.68 (d, 1H), 5.46 (d, 1H), 2.85 (m, 4H), 2.32 (m, 4H), 2.16 (s, 3H), 2.02 (s, 3H). m/z 415.2 (M+1)

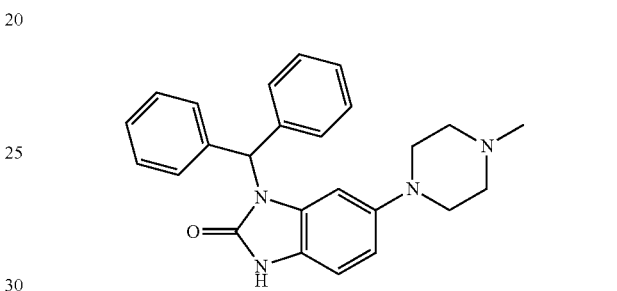

MBX 3526: 1-benzhydryl-6-(4-methylpiperazin-1-yl)-1H-benzo[d]imidazol-2(3H)-one

Prepared in the same manner as MBX 3525, treating with CDI instead of acetic anhydride. Grey solid, mp 250-255° C. (decomp.). R$_f$: 0.44 (86:13:1 CHCl3:MeOH:NH3). $^1$H NMR (CDCl$_3$, 300 MHz, ppm) 10.38 (br s, 1H), 7.32-7.25 (m, 10H), 7.02 (s, 1H), 6.91 (d, 1H), 6.59 (dd, 1H), 6.09 (d, 1H), 2.82 (m, 4H), 2.47 (m, 4H), 2.30 (s, 3H). m/z 399.2 (M+1)

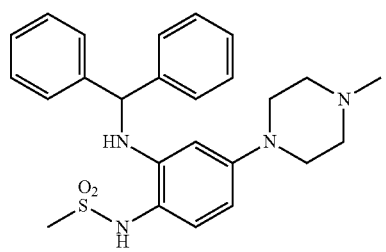

MBX 3536A: 2-(benzhydrylamino)-4-(4-methylpiperazin-1-yl)-1-(methylsulfonamido)benzene (TFA Salt)

Prepared in the same manner as MBX 3525, treating with MeSO$_2$Cl and TEA instead of acetic anhydride. Pale purple solid, mp 227-229° C. (decomp). R$_f$: 0.61 (86:13:1 CHCl3:MeOH:NH3). $^1$H NMR (MeOD, 300 MHz, ppm) 7.41 (m, 4H), 7.31 (t, 4H), 7.23 (m, 2H), 7.06 (d, 1H), 6.28 (dd, 1H), 6.05 (d, 1H), 5.60 (s, 1H), 3.25 (br m, 8H), 2.97 (s, 3H), 2.87 (s, 3H). m/z 451.1 (M+1)

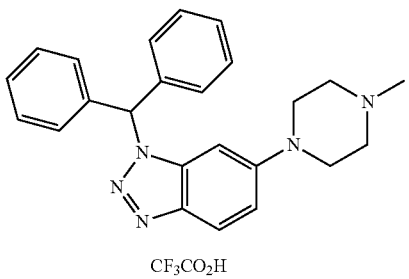 [SMILES: CN1CCN(c2ccc3nnn(C(c4ccccc4)c4ccccc4)c3c2)CC1 ; "CF3CO2H"]

CF₃CO₂H

MBX 3537A: 1-benzhydryl-6-(4-methylpiperazin-1-yl)-benzo[d][1,2,3]triazole (TFA Salt)

Prepared in the same manner as MBX 3525, treating with isopentyl nitrite instead of acetic anhydride, adding a second equivalent and heating to 50° C. after 16 h. Brown viscous oil, $R_f$: 0.65 (86:13:1 CHCl3:MeOH:NH3). $^1$H NMR (DMSO, 300 MHz, ppm) 9.89 (br s, 1H), 7.92 (d, 1H), 7.43-7.23 (m, 12H), 3.92 (br m, 2H), 3.58 (br m, 2H), 3.17 (br m, 2H), 3.04 (br m, 2H), 2.87 (s, 3H). m/z 384.2 (M+1)

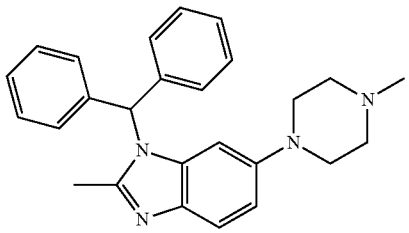 [SMILES: Cc1nc2ccc(N3CCN(C)CC3)cc2n1C(c1ccccc1)c1ccccc1]

MBX 3539: 1-benzhydryl-2-methyl-6-(4-methylpiperazin-1-yl)benzo[d]imidazole

Procedure: A solution of N-benzhydryl-5-(4-methylpiperazin-1-yl)-2-nitroaniline (0.138 g, 0.343 mmol, 1.0 eq) and acetaldehyde (0.019 mL, 0.343 mmol, 1.0 eq) in 4 mL DMSO:EtOH (1:1) was prepared. Then Na₂S₂O₄ (1 M aqueous) was added and the solution was stirred at 80° C. for 2 days. The reaction was then cooled to r.t. and quenched with aq. NH₄OH. Upon diluting the reaction mixture with 75 mL H2O, a yellow precipitate formed and was collected via filtration. The crude product was purified on a 4 g silica column, eluting with 0-8% MeOH:CH2Cl2 over 15 min, to yield the product (0.034 g, 0.086 mmol, 25%). Yellow powder, $R_f$: 0.45 (86:13:1 CHCl3:MeOH:NH3). $^1$H NMR (DMSO, 300 MHz, ppm) 7.54 (d, 1H), 7.35-7.31 (m, 6H), 7.16-7.12 (m, 4H), 6.88-6.82 (m, 2H), 5.99 (d, 1H), 2.87 (t, 4H), 2.50-2.47 (m, 7H), 2.30 (s, 3H). m/z: 397.1 (M+1)

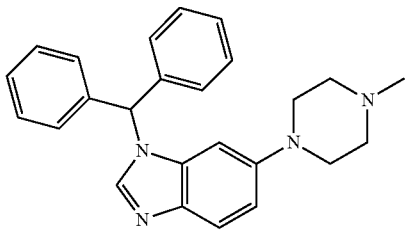 [SMILES: CN1CCN(c2ccc3ncn(C(c4ccccc4)c4ccccc4)c3c2)CC1]

MBX 3540: 1-benzhydryl-6-(4-methylpiperazin-1-yl)benzo[d]imidazole

Prepared in the same manner as MBX 3539, treating with paraformaldehyde instead of acetaldehyde. Beige crystalline solid, $R_f$: 0.41 (10% MeOH:DCM). $^1$H NMR (DMSO, 300 MHz, ppm) 7.68 (d, 1H), 7.50 (s, 1H), 7.37-7.35 (m, 6H), 7.17-7.14 (m, 4H), 6.98 (dd, 1H), 6.68 (s, 1H), 6.55 (d, 1H), 3.12-3.09 (t, 4H), 2.62-2.51 (m, 4H), 2.37 (s, 3H). m/z: 383.0 (M+1)

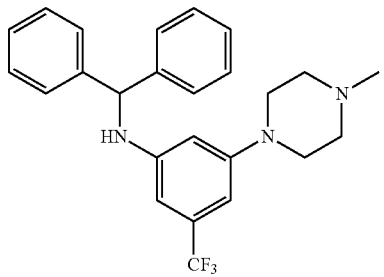 [SMILES: CN1CCN(c2cc(NC(c3ccccc3)c3ccccc3)cc(C(F)(F)F)c2)CC1]

MBX 3555: 1-(benzhydrylamino)-3-(4-methylpiperazin-1-yl)-5-(trifluoromethyl)benzene Step 1:

A solution of benzophenone (0.1 g) and TiCl4 (66 uL) in DCM (4 mL) was kept at 0° C. After 15 minutes 3-bromo-5-(trifluoromethyl)aniline (0.24 g) was added, the reaction mixture became a thick, yellow suspension. After 2.5 h, a turbid solution of NaBH3CN in MeOH (5 mL) was added slowly. The mixture was allowed to warm up to rt. After 16 h, NaHCO3 saturated solution (5 mL) was added. Product was extracted with DCM (5 mL×2), dried over MgSO4 and concentrated. The residue was purified by column chromatography (8 g of silica gel, eluent: hexanes to 60% EtOAc in hexanes, 12 min) to provide N-benzhydryl-3-bromo-5-(trifluoromethyl)aniline (155 mg) as a colorless oil. NMR analysis showed that it contained trace of diphenylmethanol (ca. 10%). Rf 0.77 (25% EtOAc in hexanes). $^1$H NMR (CDCl3): 7.37-7.25 (m, 10H), 7.07 (s, 1H), 6.79 (s, 1H), 6.69 (s, 1H), 5.50 (d, 1H), 4.51 (br d, 1H).

Step 2:

To a solution of N-benzhydryl-3-bromo-5-(trifluoromethyl)aniline (82 mg), Pd2(dba)3 (21 mg), in toluene (5 mL) was added t-Bu3P (12 uL); the solution changed color from purple to brown. After 10 minutes, N-methylpiperazine (30 uL) and t-BuONa (30 mg) were added. The solution was stirred and heated at 70 C for 5 h then cooled to rt. The mixture was loaded on a silica gel column (30 g), eluted with hexanes (50 mL) then CHCl₃ to (CHCl₃:MeOH:NH₃, 86:13:1), 20 min) to provide slightly impure product. This material was purified by preparative TLC on silica gel (CHCl₃:MeOH:NH₃, 186:13:1) to provide MBX3555 (32 mg, 37%). Pale yellow grease, $R_f$: 0.66 (86:13:1 CHCl₃:MeOH:NH₃). $^1$H NMR (CDCl₃, 300 MHz, ppm) 7.34 (m, 10H), 6.48 (s, 1H), 6.29 (s, 1H), 6.15 (s, 1H), 5.50 (d, 1H), 4.37 (d, 1H), 3.07 (m, 4H), 2.48 (m, 4H), 2.31 (s, 3H). m/z: 426.2 (M+1)

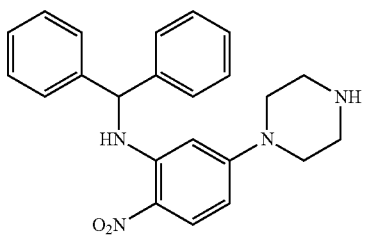 [SMILES: O=[N+]([O-])c1ccc(N2CCNCC2)cc1NC(c1ccccc1)c1ccccc1]

MBX 3556: 1-(benzhydrylamino)-5-(piperazin-1-yl)-2-nitrobenzene

Prepared following General Method A and B, substituting piperazine for N-methylpiperazine. Yellow powder, $R_f$: 0.19 (5% MeOH:DCM). $^1$H NMR (CDCl$_3$, 300 MHz, ppm) 8.99 (d, 1H), 8.08 (d, 1H), 7.39-7.26 (m, 10H), 6.20 (dd, 1H), 5.75 (d, 1H), 5.65 (d, 1H), 3.12 (t, 4H), 2.84 (t, 4H). m/z: 389.1 (M+1)

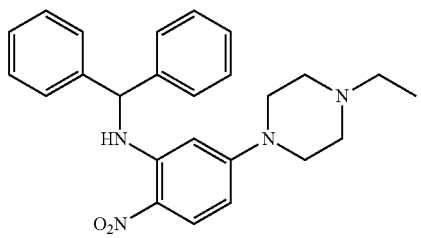 [SMILES: CCN1CCN(c2ccc([N+](=O)[O-])c(NC(c3ccccc3)c3ccccc3)c2)CC1]

MBX 3557: 1-(benzhydrylamino)-5-(4-ethylpiperazin-1-yl)-2-nitrobenzene

Procedure: Benzhydryl-2-nitro-5-(piperazin-1-yl)aniline (0.100 g, 0.257 mmol, 1.0 eq) and acetaldehyde (0.014 mL, 0.257 mmol, 1.0 eq) were mixed in dichloromethane (3 mL) and treated with sodium triacetoxyborohydride (0.076 g, 0.360 mmol, 1.4 eq). The reaction was stirred at r.t. under an argon atmosphere for 3 h. The reaction was then quenched with 5 M aq. NaOH (3 mL) and extracted twice with dichloromethane. The combined organic fractions were washed with brine, dried (Na1SO4), filtered, and concentrated. The crude product was purified on a 4 g silica column, 0-4% MeOH:DCM to yield MBX 3557 (0.046 g, 0.110 mmol, 43%). Yellow powder, $R_f$: 0.19 (5% MeOH:DCM). $^1$H NMR (CDCl$_3$, 300 MHz, ppm) 9.00 (s, 1H), 8.08 (d, 1H), 7.37-7.26 (m, 10H), 6.21 (d, 1H), 5.76 (s, 1H), 5.65 (d, 1H), 3.18 (t, 4H), 2.43-2.40 (m, 6H), 1.08 (t, 3H). m/z: 417.2 (M+1)

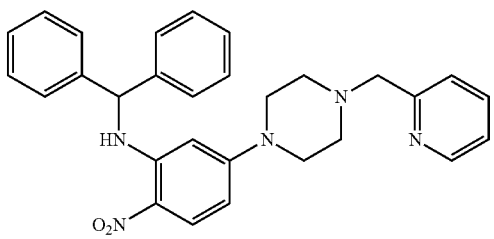 [SMILES: O=[N+]([O-])c1ccc(N2CCN(Cc3ccccn3)CC2)cc1NC(c1ccccc1)c1ccccc1]

MBX 3558: 1-(benzhydrylamino)-5-[4-(pyridin-2-ylmethyl)piperazin-1-yl]-2-nitrobenzene Prepared in the same manner as MBX 3557, treating with 2-pyridinecarboxaldehyde instead of 2-pyridinecarboxaldehyde. Orange crystalline solid, mp 183-185° C. $R_f$: 0.62 (10% MeOH:DCM). $^1$H NMR (CDCl$_3$, 300 MHz, ppm) 9.00 (d, 1H), 8.58 (d, 1H), 8.07 (d, 1H), 7.68-7.64 (m, 1H), 7.39-7.27 (m, 11H), 7.22-7.17 (m, 1H), 6.20 (dd, 1H), 5.75 (d, 1H), 5.64 (d, 1H), 3.65 (s, 2H), 3.19 (t, 4H), 2.50 (t, 4H). m/z: 480.0 (M+1)

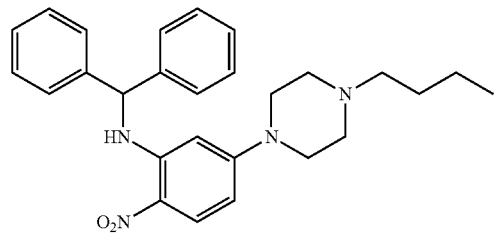 [SMILES: CCCCN1CCN(c2ccc([N+](=O)[O-])c(NC(c3ccccc3)c3ccccc3)c2)CC1]

MBX 3559: 1-(benzhydrylamino)-5-(4-butylpiperazin-1-yl)-2-nitrobenzene

Procedure: To a solution of benzhydryl-2-nitro-5-(piperazin-1-yl)aniline (0.075 g, 0.193 mmol, 1.0 eq) in 3 mL acetone was added K$_2$CO$_3$ (0.077 g, 0.560 mmol, 2.9 eq) and KI (0.008 g, 0.048 mmol, 0.25 eq). Iodobutane (0.02 mL, 0.193 mmol, 1.0 eq) was then added dropwise. The mixture was stirred at r.t. for 2 h and then at reflux overnight. The reaction was then cooled, filtered, and concentrated. The crude product was purified on a 4 g silica column, eluting with 0-10% MeOH:CH$_2$Cl$_2$ over 15 min to yield MBX 3559 (0.036 g, 0.081 mmol, 42%). Yellow powder, mp 142-143° C. $R_f$: 0.70 (10% MeOH:DCM). $^1$H NMR (CDCl$_3$, 300 MHz, ppm) 8.99 (d, 1H), 8.07 (d, 1H), 7.39-7.26 (m, 10H), 6.20 (dd, 1H), 5.75 (d, 1H), 5.65 (d, 1H), 3.16 (t, 4H), 2.40 (t, 4H), 2.31 (t, 2H), 1.49-1.25 (m, 4H), 0.92 (t, 3H). m/z: 445.3 (M+1)

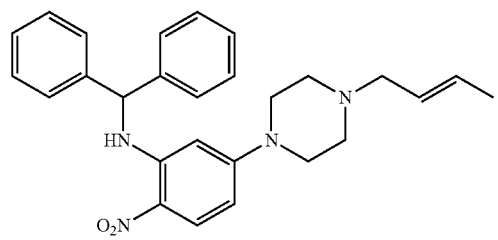 [SMILES: C/C=C/CN1CCN(c2ccc([N+](=O)[O-])c(NC(c3ccccc3)c3ccccc3)c2)CC1]

MBX 3560: 1-(benzhydrylamino)-5-[4-(but-2-enyl)piperazin-1-yl]-2-nitrobenzene

Prepared in the same manner as MBX 3557, treating with crotonaldehyde instead of acetaldehyde. Orange powder, mp 145-147° C. $R_f$: 0.70 (10% MeOH:DCM.). $^1$H NMR (CDCl$_3$, 300 MHz, ppm) 8.99 (s, 1H), 8.07 (d, 1H), 7.36-7.26 (m, 10H), 6.20 (d, 1H), 5.75 (s, 1H), 5.65-5.58 (m, 2H), 5.49-5.44 (m, 1H), 3.17 (br s, 4H), 2.90 (d, 2H), 2.40 (br s, 4H), 1.72-1.63 (m, 3H). m/z: 443.3 (M+1)

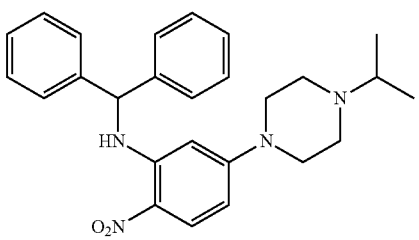 [SMILES: CC(C)N1CCN(c2ccc([N+](=O)[O-])c(NC(c3ccccc3)c3ccccc3)c2)CC1]

MBX 3561: 1-(benzhydrylamino)-5-(4-isopropylpiperazin-1-yl)-2-nitrobenzene

Prepared in the same manner as MBX 3559, treating with 2-iodopropane instead of iodobutane. Yellow powder, mp 120-121° C. $R_f$: 0.27 (5% MeOH:DCM).). $^1$H NMR (CDCl$_3$, 300 MHz, ppm) 8.99 (d, 1H), 8.07 (d, 1H), 7.39-7.26 (m, 10H), 6.20 (dd, 1H), 5.75 (d, 1H), 5.65 (d, 1H), 3.17 (t, 4H), 2.70-2.62 (m, 1H), 2.48 (t, 4H), 1.02 (d, 6H). m/z: 431.4 (M+1)

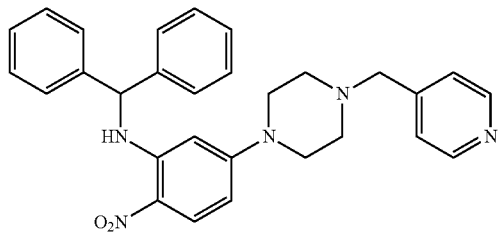 [SMILES: O=[N+]([O-])c1ccc(N2CCN(Cc3ccncc3)CC2)cc1NC(c1ccccc1)c1ccccc1]

MBX 3562: 1-(benzhydrylamino)-5-[4-(pyridin-4-ylmethyl)piperazin-1-yl]-2-nitrobenzene Prepared in the same manner as MBX 3557, treating with 4-pyridinecarboxaldehyde instead of acetaldehyde. Yellow powder, mp 159-160° C. $R_f$: 0.54 (10% MeOH:DCM).). $^1$H NMR (CDCl$_3$, 300 MHz, ppm) 8.98 (d, 1H), 8.56 (d, 2H), 8.08 (d, 1H), 7.34-7.26 (m, 12H), 6.21 (dd, 1H), 5.76 (s, 1H), 5.64 (d, 1H), 3.49 (s, 2H), 3.18 (t, 4H), 2.43 (t, 4H). m/z: 480.0 (M+1)

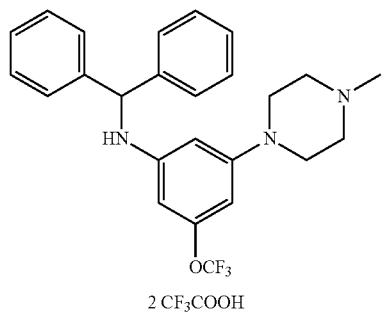 [SMILES: CN1CCN(c2cc(NC(c3ccccc3)c3ccccc3)cc(OC(F)(F)F)c2)CC1]

2 CF$_3$COOH

MBX3564A: 1-(benzhydrylamino)-5-(4-methylpiperazin-1-yl)-3-(trifloromethoxy)benzene (di-TFA Salt)

Step 1:

A solution of 3-bromo-5-(trifluoromethoxy)aniline (0.3 g) and benzhydrylbromide (0.3 g) and DIPEA (0.3 mL) in THF (5 mL) was heated at 55 C in a sealed tube for 20 h. After cooling to rt, the reaction mixture was concentrated. The residue was purified by column chromatography (40 g of silica gel, eluent: hexanes to 30% EtOAc in hexanes, 25 min) to provide 359-167 (0.43 g) as a yellow grease. NMR analysis showed that it contained ca 15% of benzhydrylbromide. This material was used for the next step.

$R_f$ 0.80 (25% EtOAc in hexanes)

Step 2:

Prepared in the same manner as Step 2 of MBX 3555 (225 mg, TFA salt, 34%). Brown sticky solid. $R_f$: 0.63 (86:13:1 CHCl$_3$:MeOH:NH$_3$). $^1$H NMR (CDCl$_3$, 300 MHz, ppm) 12.15 (br s, 1H), 8.05 (br s, 2H), 7.36-7.21 (m, 10H), 6.07 (s, 2H), 5.96 (s, 1H), 5.44 (s, 1H), 3.58 (d, 2H), 3.47 (d, 2H), 3.19 (t 2H), 2.87 (t, 2H), 2.83 (s, 3H). m/z: 442.3 (M+1)

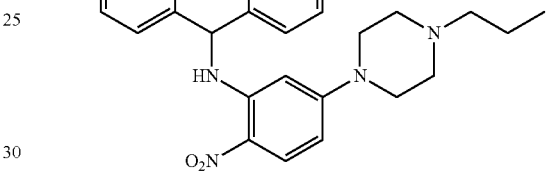

MBX 3566: 1-(benzhydrylamino)-5-(4-propylpiperazin-1-yl)-2-nitrobenzene

Prepared in the same manner as MBX 3559, treating with iodopropane instead of iodobutane. Yellow powder, mp 156-158° C. $R_f$: 0.43 (5% MeOH:DCM).). $^1$H NMR (CDCl$_3$, 300 MHz, ppm) 8.97 (d, 1H), 8.08 (d, 1H), 7.39-7.26 (m, 10H), 6.20 (dd, 1H), 5.76 (d, 1H), 5.65 (d, 1H), 3.24-3.20 (m, 4H), 2.46-2.34 (m, 6H), 1.55-1.52 (m, 2H), 0.92 (t, 3H). m/z: 431.4 (M+1)

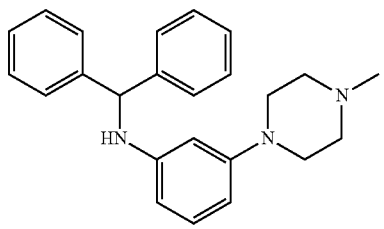 [SMILES: CN1CCN(c2cccc(NC(c3ccccc3)c3ccccc3)c2)CC1]

MBX 3567: 1-(benzhydrylamino)-3-(4-methylpiperazin-1-yl)benzene

Step 1:

To a solution of 3-bromoaniline (0.32 mL, 2.91 mmol, 1.0 eq) in 25 mL acetone was added K$_2$CO$_3$ (1.17 g, 8.44 mmol, 2.9 eq) and KI (0.121 g, 0.728 mmol, 0.25 eq). Benzhydrylbromide (0.647 g, 2.62 mmol, 0.9 eq) was then added and the reaction was heated under reflux for 24 h. The reaction was then cooled, filtered, concentrated, and purified on a 40 g silica column, eluting with 0-10% EtOAc:hexanes over 25 min, to yield a reddish-brown viscous oil (0.440 g, 1.30 mmol, 50%).

R$_f$: 0.49 (10% EtOAc:hexanes)
LC/MS: 338.3, 340.3
$^1$H NMR (DMSO): 7.40-7.20 (m, 10H), 6.95 (t, 1H), 6.83-6.82 (m, 1H), 6.75 (d, 1H), 6.63 (d, 2H), 5.65 (d, 1H).
Step 2:
Prepared in the same manner as Step 2 of MBX 3555 (64 mg, 34%). Off-white solid, mp 96-98° C. R$_f$: 0.44 (10% MeOH:DCM).). $^1$H NMR (CDCl3, 300 MHz, ppm) 7.37-7.21 (m, 10H), 6.99 (t, 1H), 6.30 (d, 1H), 6.11-6.06 (m, 2H), 5.49 (s, 1H), 4.20 (s, 1H), 3.10 (t, 4H), 2.54 (t, 4H), 2.34 (s, 3H). m/z: 358.3 (M+1)

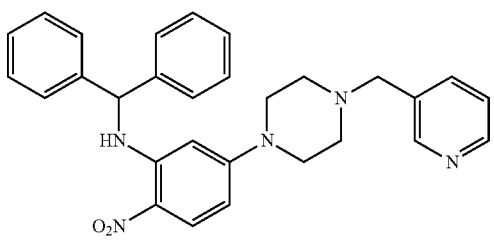

MBX 3568: 1-(benzhydrylamino)-5-[4-(pyridin-3-ylmethyl) piperazin-1-yl]-2-nitrobenzene Prepared in the same manner as MBX 3557, treating with 3-pyridinecarboxaldehyde instead of acetaldehyde. Yellow powder, mp 151-153° C. R$_f$: 0.29 (5% MeOH:DCM). $^1$H NMR (CDCl3, 300 MHz, ppm) 8.97 (d, 1H), 8.54 (s, 2H), 8.08 (d, 1H), 7.65 (d, 1H), 7.36-7.26 (m, 11H), 6.19 (dd, 1H), 5.75 (d, 1H), 5.63 (d, 1H), 3.50 (s, 2H), 3.16 (t, 4H), 2.42 (t, 4H). m/z: 480.1 (M+1)

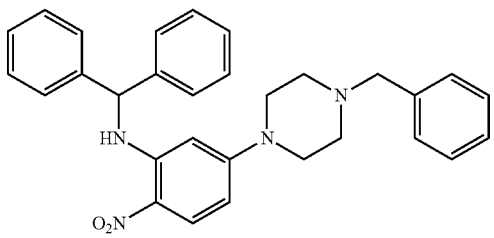

MBX 3569: 1-(benzhydrylamino)-5-(4-benzylpiperazin-1-yl)-2-nitrobenzene

Prepared in the same manner as MBX 3559, treating with benzyl bromide instead of iodobutane. Yellow crystals, mp 179-180° C. R$_f$: 0.55 (2% MeOH:DCM). $^1$H NMR (CDCl3, 300 MHz, ppm) 8.99 (dd, 1H), 8.07 (d, 1H), 7.37-7.26 (m, 15H), 6.19 (dd, 1H), 5.74 (s, 1H), 5.63 (d, 1H), 3.48 (s, 2H), 3.16 (t, 4H), 2.42 (t, 4H). m/z: 479.3 (M+1)

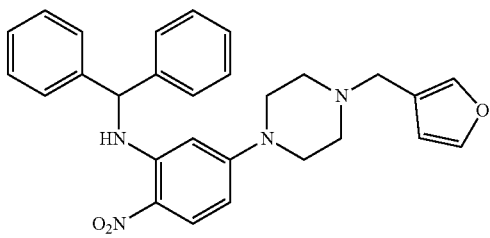 [SMILES: O=[N+]([O-])c1ccc(N2CCN(Cc3ccoc3)CC2)cc1NC(c1ccccc1)c1ccccc1]

MBX 3574: 1-(benzhydrylamino)-5-[4-(furan-3-ylmethyl)piperazin-1-yl]-2-nitrobenzene Prepared in the same manner as MBX 3557, treating with furan-3-carbaldehyde instead of acetaldehyde. Yellow needle crystals, mp 148-150° C. R$_f$: 0.51 (5% MeOH: DCM). $^1$H NMR (CDCl3, 300 MHz, ppm) 8.98 (d, 1H), 8.08 (d, 1H), 7.40-7.26 (m, 12H), 6.37 (s, 1H), 6.19 (d, 1H), 5.75 (s, 1H), 5.63 (d, 1H), 3.36 (s, 2H), 3.16 (t, 4H), 2.41 (t, 4H). m/z: 469.3 (M+1)

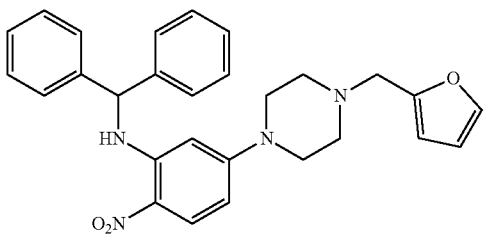 [SMILES: O=[N+]([O-])c1ccc(N2CCN(Cc3ccco3)CC2)cc1NC(c1ccccc1)c1ccccc1]

MBX 3575: 1-(benzhydrylamino)-5-[4-(furan-2-ylmethyl)piperazin-1-yl]-2-nitrobenzene Prepared in the same manner as MBX 3557, treating with furan-2-carbaldehyde instead of acetaldehyde. Crystalline yellow solid, mp 162-164° C. R$_f$: 0.31 (5% MeOH:DCM). $^1$H NMR (CDCl3, 300 MHz, ppm) 8.98 (d, 1H), 8.07 (d, 1H), 7.40-7.26 (m, 11H), 6.33 (t, 1H), 6.22-6.17 (m, 2H), 5.74 (d, 1H), 5.63 (d, 1H), 3.53 (s, 2H), 3.18 (t, 4H), 2.45 (t, 4H). m/z: 469.2 (M+1)

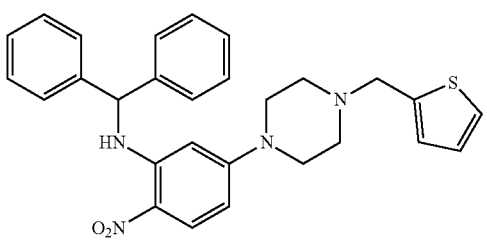

MBX 3576: 1-(benzhydrylamino)-5-[4-(thiophen-2-ylmethyl)piperazin-1-yl]-2-nitrobenzene Prepared in the same manner as MBX 3557, treating with thiophene-2-carbaldehyde instead of acetaldehyde. Yellow needle crystals, mp 170-171° C. R$_f$: 0.66 (5% MeOH: DCM). $^1$H NMR (CDCl3, 300 MHz, ppm) 8.98 (d, 1H), 8.07 (d, 1H), 7.38-7.24 (m, 11H), 6.97-6.90 (m, 2H), 6.19 (dd, 1H), 5.74 (d, 1H), 5.63 (d, 1H), 3.70 (s, 2H), 3.17 (t, 4H), 2.46 (t, 4H). m/z: 485.2 (M+1)

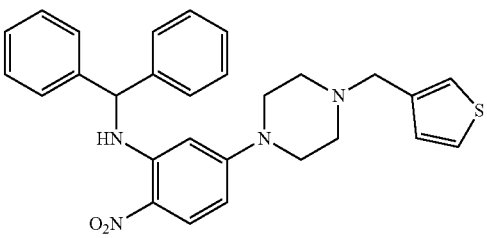 [SMILES: O=[N+]([O-])c1ccc(N2CCN(Cc3ccsc3)CC2)cc1NC(c1ccccc1)c1ccccc1]

MBX 3577: 1-(benzhydrylamino)-5-[4-(thiophen-3-ylmethyl)piperazin-1-yl]-2-nitrobenzene Prepared in the same manner as MBX 3557, treating with thiophene-3-carbaldehyde instead of acetaldehyde. Flaky yellow crystals, mp 174-176° C. Rf: 0.59 (5% MeOH:DCM). $^1$H NMR (CDCl3, 300 MHz, ppm) 8.98 (d, 1H), 8.07 (d, 1H), 7.36-7.26 (m, 11H), 7.11 (s, 1H), 7.04 (d, 1H), 6.19 (dd, 1H), 5.74 (d, 1H), 5.63 (d, 1H), 3.51 (s, 2H), 3.16 (t, 4H), 2.41 (t, 4H). m/z: 485.3 (M+1)

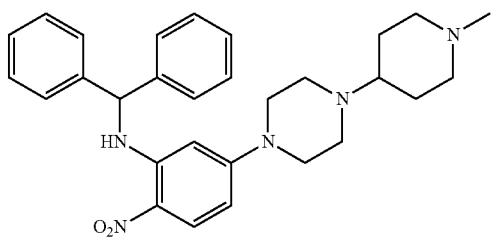 [SMILES: CN1CCC(N2CCN(c3ccc([N+](=O)[O-])c(NC(c4ccccc4)c4ccccc4)c3)CC2)CC1]

MBX 3578: 1-(benzhydrylamino)-5-[4-(1-methylpiperidin-4-yl)piperazin-1-yl]-2-nitrobenzene Prepared in the same manner as MBX 3557, treating with 1-methylpiperidin-4-one instead of acetaldehyde. Yellow powder, mp 193-194° C. Rf: 0.14 (10% MeOH:DCM). $^1$H NMR (CDCl3, 300 MHz, ppm) 8.99 (d, 1H), 8.07 (d, 1H), 7.39-7.25 (m, 10H), 6.20 (dd, 1H), 5.75 (d, 1H), 5.65 (d, 1H), 3.16 (t, 4H), 2.93 (d, 2H), 2.51 (t, 4H), 2.29-2.20 (m, 4H), 1.97 (t, 2H), 1.76 (d, 2H), 1.58 (q, 2H). m/z: 486.2 (M+1)

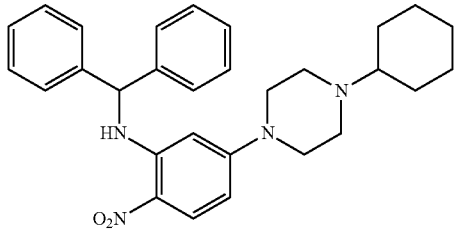

MBX 3579: 1-(benzhydrylamino)-5-(4-cyclohexylpiperazin-1-yl)-2-nitrobenzene

Prepared in the same manner as MBX 3557, treating with cyclohexanone instead of acetaldehyde. Yellow crystals, mp 171-172° C. Rf: 0.47 (5% MeOH:DCM). $^1$H NMR (CDCl3, 300 MHz, ppm) 8.99 (d, 1H), 8.07 (d, 1H), 7.40-7.25 (m, 10H), 6.20 (dd, 1H), 5.75 (d, 1H), 5.65 (d, 1H), 2.54 (br s, 4H), 2.27 (br s, 4H), 1.82 (t, 4H), 1.64 (d, 2H), 1.25-1.07 (m, 6H). m/z: 471.5 (M+1)

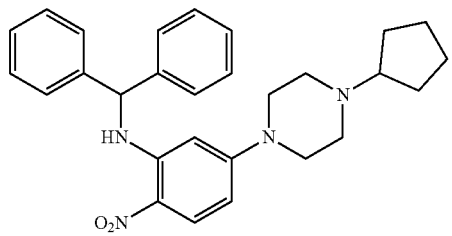 [SMILES: O=[N+]([O-])c1ccc(N2CCN(C3CCCC3)CC2)cc1NC(c1ccccc1)c1ccccc1]

MBX 3580: 1-(benzhydrylamino)-5-(4-cyclopentylpiperazin-1-yl)-2-nitrobenzene Prepared in the same manner as MBX 3557, treating with cyclopentanone instead of acetaldehyde. Yellow powder, mp 186-187° C. Rf: 0.64 (5% MeOH:DCM). $^1$H NMR (CDCl3, 300 MHz, ppm) 8.99 (d, 1H), 8.07 (d, 1H), 7.36-7.27 (m, 10H), 6.20 (dd, 1H), 5.75 (s, 1H), 5.65 (d, 1H), 3.17 (t, 4H), 2.48-2.46 (m, 5H), 1.85-1.83 (m, 2H), 1.72-1.54 (m, 4H), 1.41-1.38 (m, 2H). m/z: 457.4 (M+1)

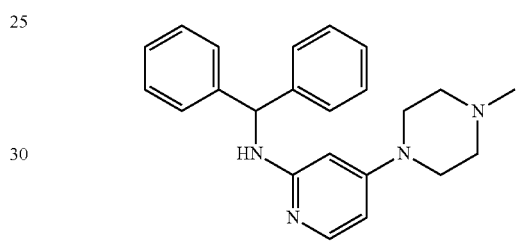

MBX 3586: 2-(benzhydrylamino)-4-(4-methylpiperazin-1-yl)pyridine

Step 1:
To a solution of benzophenone (0.71 g) in DCM (20 mL) at 0 C was added TiCl$_4$. After stirring for 10 min, compound 4-bromopyridin-2-amine (1.0 g) was added. After 2.5 h, a turbid solution of NaBH$_3$CN in MeOH (5 mL) was added slowly. The mixture was allowed to warm up to rt. After 16 h, NaHCO$_3$ saturated solution (11 mL) was added. Product was extracted with ether (50 mL×2), dried over MgSO4 and concentrated. The residue was purified by column chromatography (40 g of silica gel, eluent: hexanes to 60% EtOAc in hexanes, 25 min) to provide 0.68 g of a white solid. NMR analysis showed that it was a mixture of N-benzhydryl-4-bromopyridin-2-amine and diphenylmethanol (ca. 2:1). This material was used for the next step. $^1$H NMR (CDCl$_3$): 7.90 (d, 1H), 7.39-7.23 (m, 10H), 6.57 (dd, 1H), 6.28 (d, 1H), 5.83 (d, 1H), 5.32 (br d, 1H).
m/z=295.1 (M+1)

Step 2:
A mixture of N-benzhydryl-4-bromopyridin-2-amine from Step 1 (120 mg), N-methylpiperazine (0.56 mL), DIPEA (0.27 mL) and n-BuOH was heated at 145° C. in a sealed tube. After 4 days, the mixture was cooled to rt and concentrated in a rotary evaporator. The residue was purified by column chromatography (24 g of silica gel, eluent: DCM to (CHCl$_3$:MeOH:NH$_3$, 86:13:1), 20 min) to provide 103 mg of MBX3586. White solid, mp 135-136° C. Rf: 0.62 (86:13:1 CHCl$_3$:MeOH:NH$_3$). $^1$H NMR (CDCl3, 300 MHz, ppm) 7.77 (d, 1H), 7.38-7.20 (m, 10H), 6.13 (dd, 1H), 5.75

(d, 1H), 5.59 (d, 1H), 5.40 (br s, 1H), 3.16 (t, 4H), 2.42 (t, 4H), 2.29 (s, 3H). m/z: 359.2 (M+1)

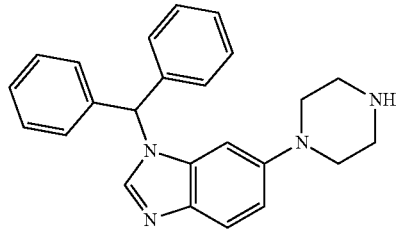 [SMILES: c1ccc(C(c2ccccc2)n2cnc3ccc(N4CCNCC4)cc32)cc1]

MBX 3587: 1-benzhydryl-6-(piperazin-1-yl)benzo[d]imidazole

Step 1:
To a 10 mL rbf of MBX 3556 (0.605 g, 1.56 mmol, 1 eq) in DCM (6 mL) was added Boc20 (0.340 g, 1.56 mmol, 1 eq). The reaction was cooled to 0° C., and TEA (0.22 mL, 1 eq) was added dropwise. The reaction was allowed to warm to room temperature. After three hours, the reaction was poured over H$_2$O (20 mL), extracted with DCM (3×10 mL), the combined organic layers were dried (Na$_2$SO$_4$), filtered and concentrated to yield Boc-protected intermediate (0.719 g, 1.47 mmol, 94%). The intermediate was used without further purification.

Step 2:
To a 100 mL rbf of Boc-protected MBX 3556 (2.97 g, 6.08 mmol, 1 eq) was added Pd/C (5%, 1.30 g, 10 mol %) and HCO$_2$Na (12.43 g, 182 mmol, 30 eq). CH(OEt)$_3$ (75 mL) and HCO$_2$H (7.5 mL) were added, and the reaction was stirred at 110° C. for two days. The reaction was cooled and filtered over a bed of Celite washing with DCM, and the filtrate was concentrated. The concentrate was slowly added to a stirring solution of aq. Na$_2$CO$_3$ (5% w/v), and the resulting precipitate was collected to yield tert-butyl 4-(1-benzhydryl-1H-benzo[d]imidazol-6-yl)piperazine-1-carboxylate (2.17 g, 4.62 mmol, 76%).

Step 3:
To a 50 mL rbf of tert-butyl 4-(1-benzhydryl-1H-benzo[d]imidazol-6-yl)piperazine-1-carboxylate (2.26 g, 4.81 mmol, 1 eq) in DCM (20 mL) was added dropwise TFA (7.5 mL, 19 eq). The reaction was stirred at r.t. for 18 hours, then washed with aq. NaOH (1N, 30 mL), brine (30 mL) and H$_2$O (30 mL). The organic layer was dried (Na$_2$SO$_4$), filtered and concentrated to yield 0.88 g (50%). LC/MS of the aqueous layer revealed about half product remained in aqueous layer. Beige powder, mp 179-181° C. Rf: 0.45 (86:13:1 CHCl$_3$:MeOH:NH$_3$). $^1$H NMR (DMSO, 300 MHz, ppm) 7.77 (s, 1H), 7.50-7.38 (m, 8H), 7.22 (d, 4H), 7.13 (s, 1H), 6.91 (d, 1H), 6.80 (s, 1H), 2.91 (br s, 4H), 2.80 (br s, 4H). m/z: 369.1 (M+1)

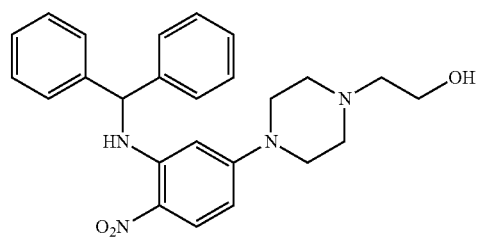 [SMILES: O=[N+]([O-])c1ccc(N2CCN(CCO)CC2)cc1NC(c1ccccc1)c1ccccc1]

MBX 3588: 1-(benzhydrylamino)-5-[4-(2-hydroxyethyl)piperazin-1-yl]-2-nitrobenzene Prepared in the same manner as MBX 3559, treating with 2-bromoethanol instead of iodobutane. Yellow solid, mp 121-123° C. Rf: 0.18 (5% MeOH:DCM). $^1$H NMR (CDCl$_3$, 300 MHz, ppm) 8.98 (d, 1H), 8.09 (d, 1H), 7.39-7.26 (m, 10H), 6.21 (dd, 1H), 5.76 (s, 1H), 5.65 (d, 1H), 3.63 (t, 2H), 3.17 (t, 4H), 2.56-2.48 (m, 6H). m/z: 433.2 (M+1)

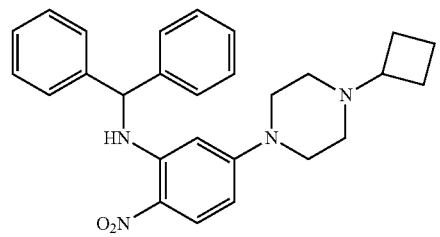 [SMILES: O=[N+]([O-])c1ccc(N2CCN(C3CCC3)CC2)cc1NC(c1ccccc1)c1ccccc1]

MBX 3589: 1-(benzhydrylamino)-5-[4-(cyclobutyl)piperazin-1-yl]-2-nitrobenzene

Prepared in the same manner as MBX 3557, treating with cyclobutanone instead of acetaldehyde. Yellow powder, mp 142-144° C. Rf: 0.38 (5% MeOH:DCM). $^1$H NMR (CDCl$_3$, 300 MHz, ppm) 8.98 (d, 1H), 8.08 (d, 1H), 7.39-7.26 (m, 10H), 6.20 (dd, 1H), 5.75 (d, 1H), 5.65 (d, 1H), 3.16 (t, 4H), 2.69 (t, 1H), 2.29 (t, 4H), 2.04-1.99 (m, 2H), 1.89-1.80 (m, 2H), 1.75-1.66 (m, 2H). m/z: 443.4 (M+1)

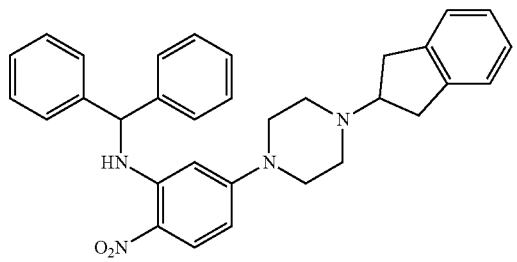 [SMILES: O=[N+]([O-])c1ccc(N2CCN(C3Cc4ccccc4C3)CC2)cc1NC(c1ccccc1)c1ccccc1]

MBX 3590: 1-(benzhydrylamino)-5-[4-(2,3-dihydro-1H-inden-2-yl)piperazin-1-yl]-2-nitrobenzene Prepared in the same manner as MBX 3557, treating with 2-indanone instead of acetaldehyde. Yellow crystalline solid, mp 226-227° C. Rf: 0.54 (5% MeOH:DCM). $^1$H NMR (CDCl$_3$, 300 MHz, ppm) 8.99 (d, 1H), 8.09 (d, 1H), 7.39-7.26 (m, 10H), 7.19-7.16 (m, 4H), 6.21 (dd, 1H), 5.77 (s, 1H), 5.65 (d, 1H), 3.22-3.03 (m, 7H), 2.91-2.84 (m, 2H), 2.53 (t, 4H). m/z: 505.4 (M+1)

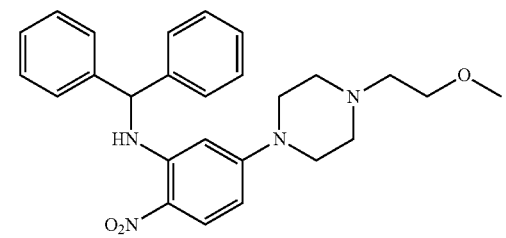

MBX 3591: 1-(benzhydrylamino)-5-[4-(2-methoxyethyl)piperazin-1-yl]-2-nitrobenzene Prepared in the same manner as MBX 3559, treating with 2-bromoethyl methyl ether instead of iodobutane. Yellow powder, mp 143-145° C. Rf: 0.64 (5% MeOH:DCM). ¹H NMR (CDCl₃, 300 MHz, ppm) 8.98 (d, 1H), 8.08 (d, 1H), 7.39-7.26 (m, 10H), 6.20 (dd, 1H), 5.75 (d, 1H), 5.64 (d, 1H), 3.50 (t, 2H), 3.36 (s, 3H), 3.18 (t, 4H), 2.56 (t, 2H), 2.47 (t, 4H). m/z: 477.4 (M+1)

MBX 3592: 1-(benzhydrylamino)-5-[4-(1,2,3,4-tetrahydronaphthalen-2-yl)piperazin-1-yl]-2-nitrobenzene Prepared in the same manner as MBX 3557, treating with 2-tetralone instead of acetaldehyde. Orange-brown powder, mp 197-198° C. Rf: 0.82 (5% MeOH:DCM). ¹H NMR (CDCl₃, 300 MHz, ppm) 8.99 (d, 1H), 8.09 (d, 1H), 7.39-7.26 (m, 10H), 7.13-7.09 (m, 4H), 6.22 (dd, 1H), 5.77 (d, 1H), 5.66 (d, 1H), 3.21 (t, 4H), 2.92-2.73 (m, 5H), 2.63-2.61 (m, 4H), 2.07 (br d, 1H), 1.69-1.57 (m, 1H). m/z: 519.4 (M+1)

MBX 3594: 2-benzhydrylamino-4-(2,6-dimethylmorpholino)pyridine

Prepared in the same manner as MBX 3586, treating with 2,6-dimethylmorpholine in Step 2 instead of N-methylpiperazine. Beige solid, mp 184-185° C. Rf: 0.65 (86:13:1 CHCl₃:MeOH:NH₃). ¹H NMR (CDCl₃, 300 MHz, ppm) 7.78 (d, 1H), 7.38-7.20 (m, 10H), 6.12 (dd, 1H), 5.76 (d, 1H), 5.57 (d, 1H), 5.23 (br s, 1H), 3.61 (m, 2H), 3.33 (dd, 2H), 2.37 (t, 2H), 1.18 (d, 6H). m/z: 374.3 (M+1)

MBX 3595: 2-benzhydrylamino-4-[4-(2-methoxyethyl)piperazin-1-yl]pyridine

Prepared in the same manner as MBX 3586, treating with 2-methoxyethyl-N-piperazine in Step 2 instead of N-methylpiperazine. Brown solid, mp 93-95° C. Rf: 0.62 (86:13:1 CHCl₃:MeOH:NH₃). ¹H NMR (CDCl₃, 300 MHz, ppm) 7.75 (d, 1H), 7.38-7.20 (m, 10H), 6.12 (dd, 1H), 5.74 (d, 1H), 5.58 (d, 1H), 5.50 (br s, 1H), 3.51 (t, 2H), 3.35 (s, 3H), 3.18 (t, 4H), 2.58 (t, 2H), 2.51 (t, 4H). m/z: 403.4 (M+1)

MBX 3597: 1-[1-(4-fluorophenyl)-2-(2-oxopyrrolidin-1-yl)ethylamino]-5-(2,6-dimethylmorpholino)-2-nitrobenzene Step 1:

Intermediate prepared in the same manner as General Method A, treating with 1-(2-amino-2-(4-fluorophenyl)ethyl)pyrrolidin-2-one instead of benzhydrylamine.

Step 2:

A mixture of intermediate from Step 1 (0.228 g), 2,6-dimethylmorpholine (0.15 mL), EtOH (5 mL) was heated to 75° C. for 40 hours. The mixture was cooled to rt, the solid was collected by filtration, rinsed with EtOH and dried in vaccum to provide MBX 3597 (178 mg). Yellow solid, mp 230-231° C. Rf: 0.30 (186:13:1 CHCl₃:MeOH:NH₃). ¹H NMR (CDCl₃, 300 MHz, ppm) 8.85 (d, 1H), 8.06 (d, 1H), 7.42-7.38 (m, 2H), 7.11-7.06 (m, 2H), 6.20 (dd, 1H), 5.86 (d, 1H), 4.86 (q, 1H), 3.79 (dd, 1H), 3.68-3.37 (m, 6H), 3.08 (dd, 1H), 2.49 (m, 2H), 2.37 (t, 2H), 1.95 (quint, 2H), 1.23 (d, 3H), 1.20 (d, 3H). m/z: 457.0 (M+1)

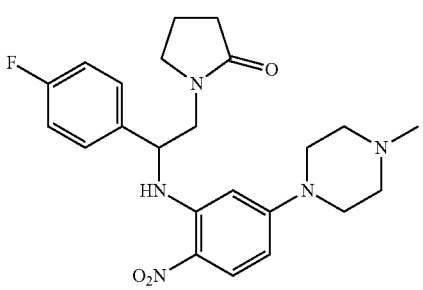 [SMILES: CN1CCN(c2ccc([N+](=O)[O-])c(NC(CN3CCCC3=O)c3ccc(F)cc3)c2)CC1]

MBX 3598: 1-[1-(4-fluorophenyl)-2-(2-oxopyrrolidin-1-yl)ethylamino]-5-(4-methylpiperazin-1-yl)-2-nitrobenzene Prepared in the same manner as MBX 3597, treating with N-methylpiperazine in Step 2 instead of 2,6-dimethylmorpholine. Yellow solid, mp 155-156° C. Rf: 0.37 (186:13:1 CHCl$_3$:MeOH:NH$_3$). $^1$H NMR (CDCl$_3$, 300 MHz, ppm) 8.88 (d, 1H), 8.06 (d, 1H), 7.41 (d, 1H), 7.38 (d, 1H), 7.07 (t, 2H), 6.21 (dd, 1H), 5.86 (d, 1H), 4.87 (dd, 1H), 3.76 (dd, 1H), 3.53-3.12 (m, 6H), 3.08 (dd, 1H), 2.43 (t, 4H), 2.34 (t, 2H), 2.30 (s, 3H), 1.95 (sep, 2H). m/z: 442.1 (M+1)

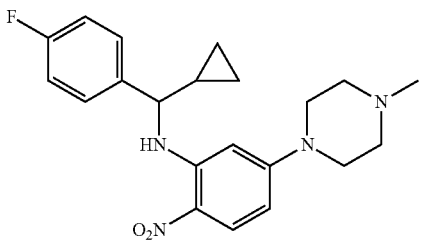 [SMILES: CN1CCN(c2ccc([N+](=O)[O-])c(NC(c3ccc(F)cc3)C3CC3)c2)CC1]

MBX 3599: 1-[cyclopropyl(4-fluorophenyl)methylamino]-5-(4-methylpiperazin-1-yl)-2-nitrobenzene Prepared in the same manner as MBX 3598, treating with cyclopropyl(4-fluorophenyl)methanamine in Step 1 instead of 1-(2-amino-2-(4-fluorophenyl)ethyl)pyrrolidin-2-one. Yellow solid, mp 141-142° C. Rf: 0.38 (186:13:1 CHCl$_3$:MeOH:NH$_3$). $^1$H NMR (CDCl$_3$, 300 MHz, ppm) 8.95 (d, 1H), 8.05 (d, 1H), 7.31 (dd, 2H), 7.03 (t, 2H), 6.16 (dd, 1H), 5.51 (d, 1H), 3.84 (dd, 1H), 3.19 (m, 2H), 3.08 (m, 2H), 2.36 (m, 4H), 2.28 (s, 3H), 1.29 (m, 1H), 0.72 (m, 1H), 0.62 (m, 1H), 0.41 (m, 2H). m/z: 385.3 (M+1)

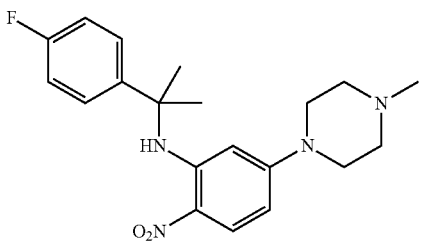 [SMILES: CN1CCN(c2ccc([N+](=O)[O-])c(NC(C)(C)c3ccc(F)cc3)c2)CC1]

MBX 3600: 1-[2-(4-fluorophenyl)propan-2-ylamino]-5-(4-methylpiperazin-1-yl)-2-nitrobenzene Prepared in the same manner as MBX 3598, treating with 2-(4-fluorophenyl)propan-2-amine in Step 1 instead of 1-(2-amino-2-(4-fluorophenyl)ethyl)pyrrolidin-2-one. Yellow solid, mp 179-180° C. Rf: 0.38 (186:13:1 CHCl$_3$:MeOH:NH$_3$). $^1$H NMR (CDCl$_3$, 300 MHz, ppm) 8.97 (br s, 1H), 8.05 (d, 1H), 7.72 (dd, 2H), 7.03 (t, 2H), 6.13 (dd, 1H), 5.34 (d, 1H), 2.99 (t, 4H), 2.30 (t, 4H), 2.26 (s, 3H), 1.76 (s, 6H). m/z: 373.2 (M+1)

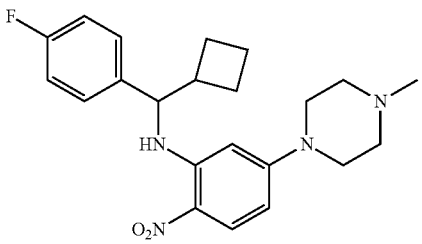 [SMILES: CN1CCN(c2ccc([N+](=O)[O-])c(NC(c3ccc(F)cc3)C3CCC3)c2)CC1]

MBX 3601: 1-[cyclobutyl(4-fluorophenyl)methylamino]-5-(4-methylpiperazin-1-yl)-2-nitrobenzene Prepared in the same manner as MBX 3598, treating with cyclobutyl(4-fluorophenyl)methanamine in Step 1 instead of 1-(2-amino-2-(4-fluorophenyl)ethyl)pyrrolidin-2-one. Yellow solid, mp 161-162° C. Rf: 0.38 (186:13:1 CHCl$_3$:MeOH:NH$_3$). $^1$H NMR (CDCl$_3$, 300 MHz, ppm) 8.76 (d, 1H), 8.05 (d, 1H), 7.26 (t, 2H), 7.01 (t, 2H), 6.17 (dd, 1H), 5.59 (d, 1H), 4.28 (dd, 1H), 3.22 (m, 2H), 3.11 (m, 2H), 2.67 (m, 1H), 2.39 (m, 4H), 2.29 (s, 3H), 2.21 (m, 1H), 1.87 (m, 5H). m/z: 399.4 (M+1)

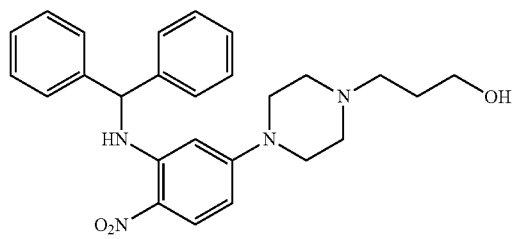 [SMILES: O=[N+]([O-])c1ccc(N2CCN(CCCO)CC2)cc1NC(c1ccccc1)c1ccccc1]

MBX 3610: 2-(benzhydrylamino)-4-[4-(3-hydroxypropyl)piperazin-1-yl]nitrobenzene

Prepared in the same manner as MBX 3559, treating with 3-iodopropan-1-ol instead of iodobutane. Yellow solid, mp 143-145° C. Rf: 0.31 (5% MeOH:DCM). $^1$H NMR (CDCl$_3$, 300 MHz, ppm) 8.96 (d, 1H), 8.08 (d, 1H), 7.37-7.26 (m, 10H), 6.20 (dd, 1H), 5.75 (d, 1H), 5.64 (d, 1H), 4.68 (br s, 1H), 3.80 (t, 2H), 3.16 (t, 4H), 2.60 (t, 2H), 2.50 (t, 4H), 1.77-1.70 (m, 2H). m/z: 447.1 (M+1)

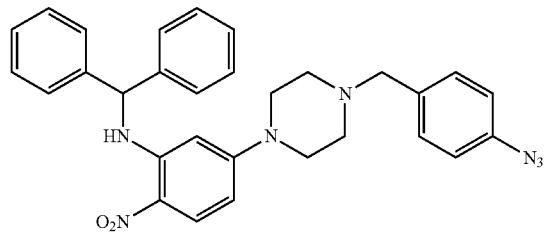 [SMILES: [N-]=[N+]=Nc1ccc(CN2CCN(c3ccc([N+](=O)[O-])c(NC(c4ccccc4)c4ccccc4)c3)CC2)cc1]

MBX 3611: 2-(benzhydrylamino)-4-[4-(4-azidobenzyl)piperazin-1-yl]nitrobenzene Prepared in the same manner as MBX 3557, treating with 4-azidobenzaldehyde instead of acetaldehyde. Yellow crystalline solid, mp>65° C. (decomp.). Rf: 0.79 (10% MeOH:DCM). $^{1}$H NMR (CDCl$_3$, 300 MHz, ppm) 8.98 (d, 1H), 8.07 (d, 1H), 7.37-7.26 (m, 12H), 6.99 (d, 2H), 6.19 (dd, 1H), 5.74 (s, 1H), 5.63 (d, 1H), 3.45 (s, 2H), 3.16 (t, 4H), 2.40 (t, 4H). m/z: 520.2 (M+1)

MBX 3623: 2-benzhydrylamino-4-(4-phenethylpiperazin-1-yl)nitrobenzene

Prepared in the same manner as MBX 3559, treating with (2-bromoethyl)benzene instead of iodobutane. Yellow powder, mp 126-128° C. Rf: 0.72 (5% MeOH:DCM). $^{1}$H NMR (CDCl$_3$, 300 MHz, ppm) 8.99 (d, 1H), 8.08 (d, 1H), 7.39-7.18 (m, 15H), 6.21 (dd, 1H), 5.77 (s, 1H), 5.65 (d, 1H), 3.19 (t, 4H), 2.79 (m, 2H), 2.59 (m, 2H), 2.49 (t, 4H). m/z: 493.4 (M+1)

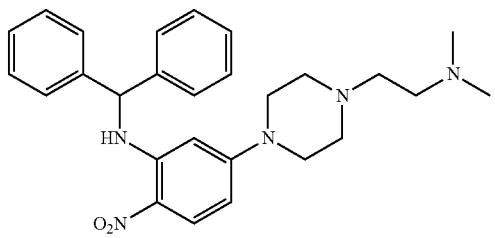 [SMILES: CN(C)CCN1CCN(c2ccc([N+](=O)[O-])c(NC(c3ccccc3)c3ccccc3)c2)CC1]

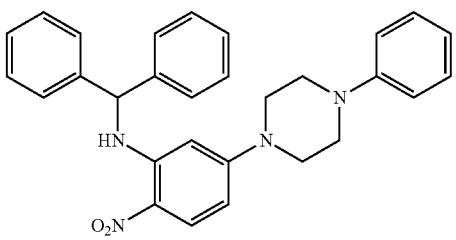

MBX 3612: 2-(benzhydrylamino)-5-{4-[2-(dimethylamino)ethyl]piperazin-1-yl}nitrobenzene Prepared in the same manner as MBX 3559, treating with 2-bromo-N,N-dimethylethylamine hydrobromide instead of iodobutane. Yellow powder, mp 184-186° C. Rf: 0.34 (86:13:1 CHCl$_3$:MeOH:NH$_3$). $^{1}$H NMR (CDCl$_3$, 300 MHz, ppm) 8.98 (d, 1H), 8.08 (d, 1H), 7.39-7.26 (m, 10H), 6.19 (dd, 1H), 5.75 (d, 1H), 5.64 (d, 1H), 3.18 (t, 4H), 2.68-2.47 (m, 14H). m/z: 460.1 (M+1)

MBX 3624: 2-benzhydrylamino-4-(4-phenylpiperazin-1-yl)nitrobenzene

Prepared in the same manner as General Method B, treating with 1-phenylpiperazine instead of N-methylpiperazine. Orange crystalline solid, mp 157-159° C. Rf: 0.68 (50% EtOAc:hexanes). $^{1}$H NMR (CDCl$_3$, 300 MHz, ppm) 8.99 (d, 1H), 8.11 (d, 1H), 7.40-7.26 (m, 12H), 6.92-6.87 (m, 3H), 6.24 (dd, 1H), 5.80 (s, 1H), 5.67 (d, 1H), 3.33 (t, 4H), 3.18 (t, 4H). m/z: 465.3 (M+1)

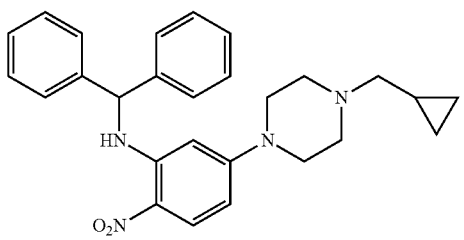 [SMILES: O=[N+]([O-])c1ccc(N2CCN(CC3CC3)CC2)cc1NC(c1ccccc1)c1ccccc1]

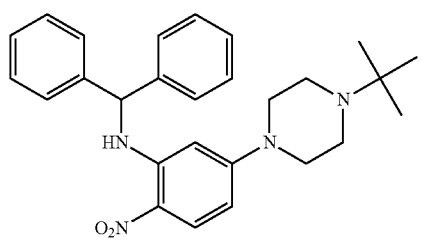

MBX 3613: 2-(benzhydrylamino)-5-[4-(cyclopropylmethyl)piperazin-1-yl]nitrobenzene Prepared in the same manner as MBX 3559, treating with (bromomethyl)cyclopropane instead of iodobutane. Yellow crystalline solid, mp 67-69° C. Rf: 0.65 (5% MeOH:DCM). $^{1}$H NMR (CDCl$_3$, 300 MHz, ppm) 8.99 (d, 1H), 8.08 (d, 1H), 7.39-7.26 (m, 10H), 6.21 (dd, 1H), 5.76 (d, 1H), 5.65 (d, 1H), 3.20 (t, 4H), 2.49 (t, 4H), 2.24 (d, 2H), 0.87-0.82 (m, 1H), 0.53 (q, 2H), 0.08 (q, 2H). m/z: 443.4 (M+1)

MBX 3625: 2-benzhydrylamino-4-(4-tert-butylpiperazin-1-yl)nitrobenzene

Prepared in the same manner as General Method B, treating with 1-tert-butylpiperazine instead of N-methylpiperazine. Yellow powder, mp 161-163° C. Rf: 0.32 (5% MeOH:DCM). $^{1}$H NMR (CDCl$_3$, 300 MHz, ppm) 9.00 (d, 1H), 8.07 (d, 1H), 7.40-7.26 (m, 10H), 6.20 (dd, 1H), 5.74 (s, 1H), 5.65 (d, 1H), 3.16 (t, 4H), 2.54 (t, 4H), 1.05 (s, 9H). m/z: 445.3 (M+1)

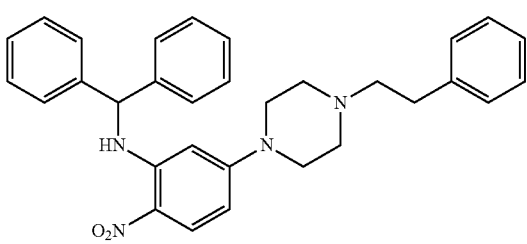 [SMILES: O=[N+]([O-])c1ccc(N2CCN(CCc3ccccc3)CC2)cc1NC(c1ccccc1)c1ccccc1]

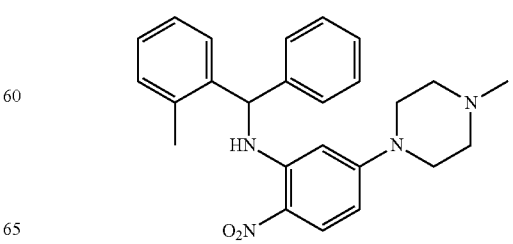

MBX 3633: 2-[phenyl(o-tolyl)methylamino]-4-(4-methylpiperazin-1-yl)nitrobenzene Prepared in the same manner as PPZ1, treating with 1-(2-methylphenyl)-1-phenylmethanamine instead of benzhydrylamine. Yellow powder, mp 139-141° C. Rf: 0.46 (5% MeOH:DCM). $^1$H NMR (CDCl3, 300 MHz, ppm) 8.80 (d, 1H), 8.08 (d, 1H), 7.35-7.26 (m, 6H), 7.20-7.17 (m, 3H), 6.20 (dd, 1H), 5.80 (d, 1H), 5.67 (d, 1H), 3.16 (t, 4H), 2.39-2.35 (m, 7H), 2.28 (s, 3H). m/z: 417.3 (M+1)

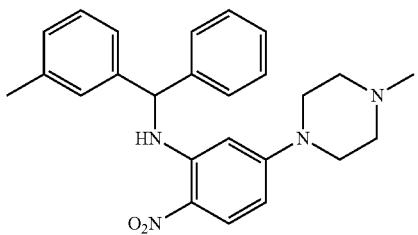

MBX 3634: 2-[phenyl(m-tolyl)methylamino]-4-(4-methylpiperazin-1-yl)nitrobenzene Prepared in the same manner as PPZ1, treating with 1-(3-methylphenyl)-1-phenylmethanamine instead of benzhydrylamine. Yellow solid, mp>148° C. (decomp.). Rf: 0.61 (10% MeOH:DCM). $^1$H NMR (CDCl3, 300 MHz, ppm) 8.97 (d, 1H), 8.08 (d, 1H), 7.40-7.15 (m, 8H), 7.08 (d, 1H), 6.20 (dd, 1H), 5.77 (d, 1H), 5.60 (d, 1H), 3.18 (t, 4H), 2.38 (t, 4H), 2.32 (s, 3H), 2.82 (s, 3H). m/z: 417.3 (M+1)

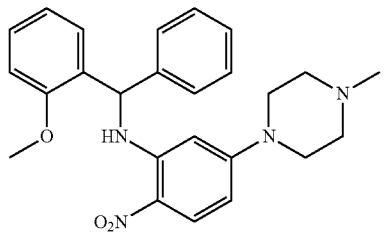 [SMILES: COc1ccccc1C(Nc1cc(N2CCN(C)CC2)ccc1[N+](=O)[O-])c1ccccc1]

MBX 3635: 2-[phenyl(2-methoxyphenyl)methylamino]-4-(4-methylpiperazin-1-yl)nitrobenzene Prepared in the same manner as PPZ1, treating with 1-(2-methoxyphenyl)-1-phenylmethanamine instead of benzhydrylamine. Yellow powder, mp 179-180° C. Rf: 0.61 (10% MeOH:DCM). $^1$H NMR (CDCl3, 300 MHz, ppm) 9.11 (d, 1H), 8.07 (d, 1H), 7.41-7.23 (m, 7H), 6.97-6.89 (m, 2H), 6.19 (dd, 1H), 6.10 (d, 1H), 5.83 (s, 1H), 3.86 (s, 3H), 3.21 (t, 4H), 2.40 (t, 4H), 2.29 (s, 3H). m/z: 433.3 (M+1)

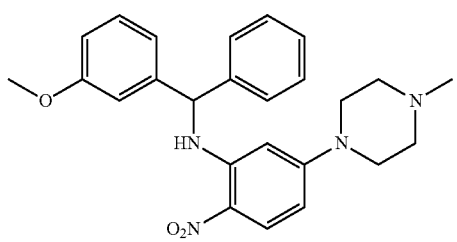

MBX 3641: 2-[(3-methoxyphenyl)(phenyl)methylamino]-4-(4-methylpiperazin-1-yl)nitrobenzene Prepared in the same manner as PPZ1, treating with 1-(3-methoxyphenyl)-1-phenylmethanamine instead of benzhydrylamine. Brittle yellow solid, mp>60° C. (decomp.). Rf: 0.47 (10% MeOH:DCM). $^1$H NMR (CDCl3, 300 MHz, ppm) 8.99 (d, 1H), 8.07 (d, 1H), 7.40-7.24 (m, 6H), 6.97 (d, 1H), 6.92 (t, 1H), 6.81 (dd, 1H), 6.21 (dd, 1H), 5.77 (d, 1H), 5.61 (d, 1H), 3.77 (s, 3H), 3.18 (t, 4H), 2.38 (t, 4H), 2.28 (s, 3H). m/z: 433.3 (M+1)

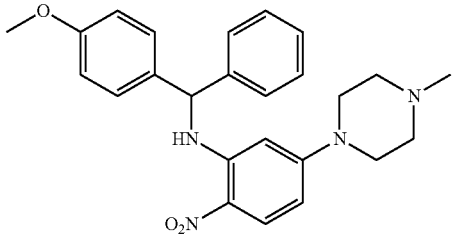

MBX 3642: 2-[(4-methoxyphenyl)(phenyl)methylamino]-4-(4-methylpiperazin-1-yl)nitrobenzene Prepared in the same manner as PPZ1, treating with 1-(4-methoxyphenyl)-1-phenylmethanamine instead of benzhydrylamine. Brittle yellow solid, mp>65° C. (decomp.). Rf: 0.66 (10% MeOH:DCM). $^1$H NMR (CDCl3, 300 MHz, ppm) 8.92 (d, 1H), 8.07 (d, 1H), 7.36-7.25 (m, 7H), 6.89-6.86 (m, 2H), 6.20 (dd, 1H), 5.77 (d, 1H), 5.61 (d, 1H), 3.79 (s, 3H), 3.18 (t, 4H), 2.38 (t, 4H), 2.28 (s, 3H). m/z: 433.2 (M+1)

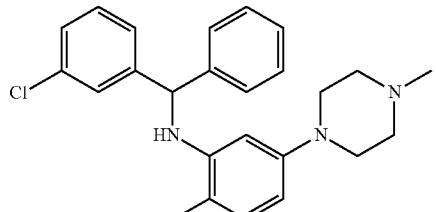

MBX 3643: 2-[(3-chlorophenyl)(phenyl)methylamino]-4-(4-methylpiperazin-1-yl)nitrobenzene Prepared in the same manner as PPZ1, treating with 1-(3-chlorophenyl)-1-phenylmethanamine instead of benzhydrylamine. Yellow powder, mp 157-158° C. Rf: 0.69 (10% MeOH:DCM). $^1$H NMR (CDCl3, 300 MHz, ppm) 8.95 (d, 1H), 8.09 (d, 1H), 7.37-7.26 (m, 9H), 6.23 (dd, 1H), 5.72 (s, 1H), 5.61 (d, 1H), 3.19 (t, 4H), 2.39 (t, 4H), 2.29 (s, 3H). m/z: 437.4 (M+1)

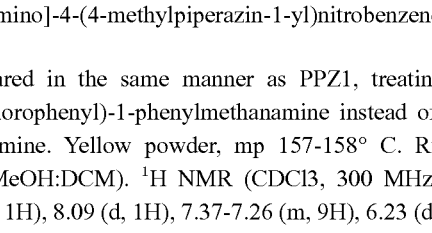

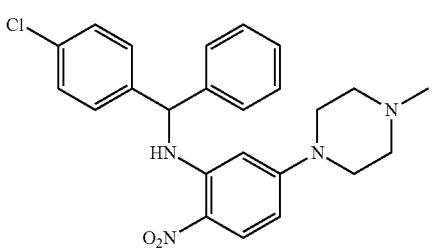 [SMILES: CN1CCN(c2ccc([N+](=O)[O-])c(NC(c3ccccc3)c3ccc(Cl)cc3)c2)CC1]

MBX 3644: 2-[(4-chlorophenyl)(phenyl)methyl-amino]-4-(4-methylpiperazin-1-yl)nitrobenzene Prepared in the same manner as PPZ1, treating with 1-(4-chlorophenyl)-1-phenylmethanamine instead of benzhydrylamine. Yellow powder, mp 179-181° C. Rf: 0.68 (10% MeOH:DCM). $^1$H NMR (CDCl3, 300 MHz, ppm) 8.94 (d, 1H), 8.09 (d, 1H), 7.34-7.26 (m, 9H), 6.22 (dd, 1H), 5.71 (s, 1H), 5.63 (d, 1H), 3.18 (t, 4H), 2.39 (t, 4H), 2.29 (s, 3H). m/z: 437.3 (M+1)

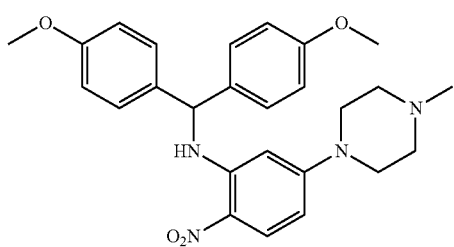

MBX 3645: 2-[bis(4-methoxyphenyl)methylamino]-4-(4-methylpiperazin-1-yl)nitrobenzene Prepared in the same manner as PPZ1, treating with 1-(bis(4-methoxyphenyl))-1-phenylmethanamine hydrochloride instead of benzhydrylamine. Brittle yellow solid, mp>60° C. (decomp.). Rf: 0.64 (10% MeOH:DCM). $^1$H NMR (CDCl3, 300 MHz, ppm) 8.88 (d, 1H), 8.07 (d, 1H), 7.25 (d, 4H), 6.87 (d, 4H), 6.20 (dd, 1H), 5.78 (s, 1H), 5.57 (d, 1H), 3.79 (s, 6H), 3.19 (t, 4H), 2.39 (t, 4H), 2.29 (s, 3H). m/z: 463.1 (M+1)

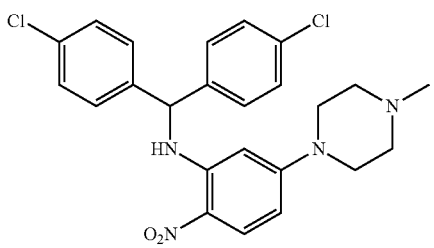 [SMILES: CN1CCN(c2ccc([N+](=O)[O-])c(NC(c3ccc(Cl)cc3)c3ccc(Cl)cc3)c2)CC1]

MBX 3646: 2-[bis(4-chlorophenyl)methylamino]-4-(4-methylpiperazin-1-yl)nitrobenzene Prepared in the same manner as PPZ1, treating with 1-(bis(4-chlorophenyl))-1-phenylmethanamine hydrochloride instead of benzhydrylamine. Yellow solid, mp 208-210° C. Rf: 0.64 (10% MeOH:DCM). $^1$H NMR (CDCl3, 300 MHz, ppm) 8.89 (d, 1H), 8.09 (d, 1H), 7.35-7.26 (m, 8H), 6.24 (dd, 1H), 5.67 (d, 1H), 5.61 (d, 1H), 3.20 (t, 4H), 2.39 (t, 4H), 2.29 (s, 3H). m/z: 471.3 (M+1)

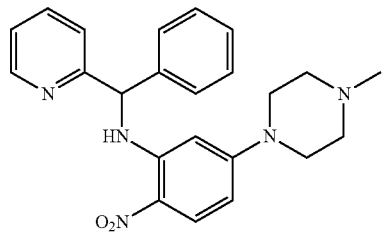 [SMILES: CN1CCN(c2ccc([N+](=O)[O-])c(NC(c3ccccc3)c3ccccn3)c2)CC1]

MBX 3647: 2-[(pyridin-2-yl)(phenyl)methylamino]-4-(4-methylpiperazin-1-yl)nitrobenzene Prepared in the same manner as PPZ1, treating with phenyl(pyridine-2-yl)methanamine instead of benzhydrylamine. Yellow powder, mp 188-190° C. Rf: 0.53 (10% MeOH:DCM). $^1$H NMR (CDCl3, 300 MHz, ppm) 9.77 (d, 1H), 8.65-8.62 (m, 1H), 8.09 (d, 1H), 7.64 (t, 1H), 7.48 (d, 2H), 7.35 (t, 3H), 7.29-7.24 (m, 1H), 7.21-7.17 (m, 1H), 6.19 (dd, 1H), 5.83 (d, 1H), 5.75 (d, 1H), 3.21 (t, 4H), 2.40 (t, 4H), 2.29 (s, 3H). m/z: 404.0 (M+1)

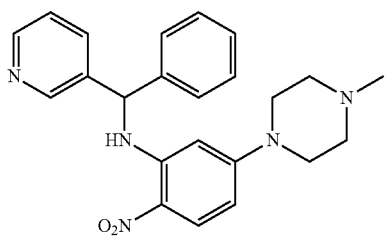 [SMILES: CN1CCN(c2ccc([N+](=O)[O-])c(NC(c3ccccc3)c3cccnc3)c2)CC1]

MBX 3648: 2-[(pyridin-3-yl)(phenyl)methylamino]-4-(4-methylpiperazin-1-yl)nitrobenzene Prepared in the same manner as PPZ1, treating with phenyl(pyridine-3-yl)methanamine instead of benzhydrylamine. Yellow powder, mp 138-139° C. Rf: 0.37 (10% MeOH:DCM). $^1$H NMR (CDCl3, 300 MHz, ppm) 8.96 (d, 1H), 8.65 (s, 1H), 8.56-8.54 (m, 1H), 8.09 (d, 1H), 7.71-7.68 (m, 1H), 7.38-7.26 (m, 6H), 6.23 (dd, 1H), 5.73-5.70 (m, 2H), 3.19 (t, 4H), 2.39 (t, 4H), 2.29 (s, 3H). m/z: 404.2 (M+1)

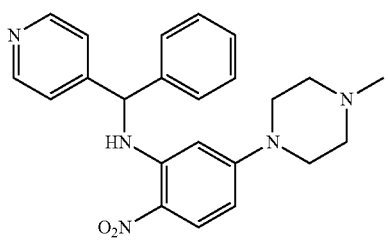 [SMILES: CN1CCN(c2ccc([N+](=O)[O-])c(NC(c3ccccc3)c3ccncc3)c2)CC1]

MBX 3670: 2-[(pyridin-4-yl)(phenyl)methylamino]-4-(4-methylpiperazin-1-yl)nitrobenzene Prepared in the same manner as PPZ1, treating with phenyl(pyridine-4-yl)methanamine instead of benzhydrylamine. Orange crystalline solid, mp 167-169° C. Rf: 0.34 (10% MeOH:DCM). ¹H NMR (CDCl3, 300 MHz, ppm) 8.99 (d, 1H), 8.60 (dd, 2H), 8.10 (d, 1H), 7.41-7.31 (m, 7H), 6.24 (dd, 1H), 5.67 (d, 1H), 5.62 (d, 1H), 3.28-3.12 (m, 4H), 2.39 (t, 4H), 2.29 (s, 3H). m/z: 404.0 (M+1)

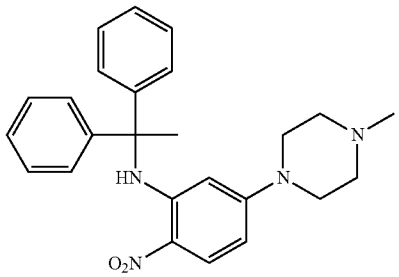 [SMILES: CN1CCN(c2ccc([N+](=O)[O-])c(NC(C)(c3ccccc3)c3ccccc3)c2)CC1]

MBX 3671: 2-(1,1-diphenylethylamino)-4-(4-methylpiperazin-1-yl)nitrobenzene

Prepared in the same manner as PPZ1, treating with 1,1,diphenylethanamine instead of benzhydrylamine and heating for three days. Yellow solid, mp 159-161° C. Rf: 0.63 (10% MeOH:DCM). ¹H NMR (CDCl3, 300 MHz, ppm) 9.62 (s, 1H), 8.07 (d, 1H), 7.46-7.24 (m, 10H), 6.13 (dd, 1H), 5.49 (d, 1H), 2.95 (t, 4H), 2.30-2.25 (m, 7H), 2.15 (s, 3H). m/z: 417.2 (M+1)

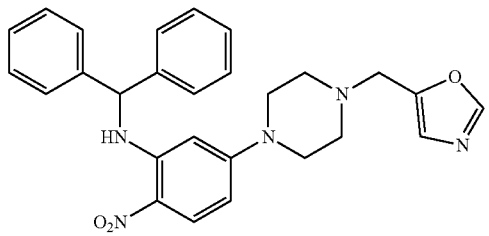 [SMILES: O=[N+]([O-])c1ccc(N2CCN(Cc3cnco3)CC2)cc1NC(c1ccccc1)c1ccccc1]

MBX 3672: 2-benzhydrylamino-4-[4-(oxazol-5-ylmethyl)piperazin-1-yl]nitrobenzene

Prepared in the same manner as MBX 3557, treating with 5-oxazolecarboxaldehyde instead of acetaldehyde. Brown glassy solid, mp>65° C. (decomp.). Rf: 0.55 (10% MeOH:DCM). ¹H NMR (CDCl3, 300 MHz, ppm) 8.97 (d, 1H), 8.08 (d, 1H), 7.86 (s, 1H), 7.36-7.26 (m, 10H), 6.98 (s, 1H), 6.19 (dd, 1H), 5.75 (s, 1H), 5.63 (d, 1H), 3.60 (s, 2H), 3.18 (t, 4H), 2.46 (t, 4H). m/z: 470.3 (M+1)

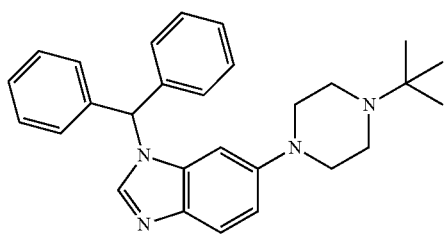 [SMILES: CC(C)(C)N1CCN(c2ccc3ncn(C(c4ccccc4)c4ccccc4)c3c2)CC1]

MBX 3673: 1-benzhydryl-6-(4-tert-butylpiperazin-1-yl)benzimidazole

Prepared in the same manner as MBX 3540, cyclizing from MBX 3625 instead of PPZ1. Light yellow solid, mp 171-172° C. Rf: 0.39 (10% MeOH:DCM). ¹H NMR (CDCl3, 300 MHz, ppm) 7.68 (d, 1H), 7.49 (s, 1H), 7.37-7.35 (m, 6H), 7.15 (dd, 4H), 6.98 (dd, 1H), 6.68 (s, 1H), 6.55 (d, 1H), 3.17 (br s, 4H), 2.82 (br s, 4H), 1.18 (s, 9H). m/z: 425.2 (M+1)

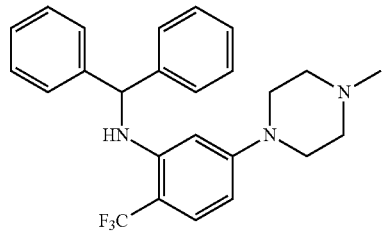 [SMILES: CN1CCN(c2ccc(C(F)(F)F)c(NC(c3ccccc3)c3ccccc3)c2)CC1]

MBX 3684: 1-benzhydrylamino-5-(4-methylpiperazin-1-yl)-2-(trifluoromethyl)benzene Step 1:
Prepared in the same manner as step 1 of MBX 3586, treating with 5-bromo-2-(trifluoromethyl)aniline instead of 4-bromopyridin-2-amine.

Step 2:
The intermediate from step 1 (208 mg) was mixed with $K_3PO_4$ (217 mg), DMPAO (99 mg) and CuI (49 mg) in DMSO (2 mL) at 50° C. for 5 min under Ar. N-methyl piperazine (0.1 mL) was added. The mixture was heated at 90 C for 24 h. Water was added. The product was extracted with EtOAc and purified by column chromatography (SiO2, hexanes to EtOAc then 7.5% MeOH in EtOAc) to provide MBX 3684 (62 mg, 28%) Yellow wax. Rf: 0.20 (10:1 EtOAc:MeOH). ¹H NMR (CDCl3, 300 MHz, ppm) 7.37-7.22 (m, 11H), 6.22 (dd, 1H), 5.97 (d, 1H), 5.56 (d, 1H), 4.91 (s, 1H), 3.01 (t, 4H), 2.41 (t, 4H), 2.28 (s, 3H). m/z: 426.2 (M+1)

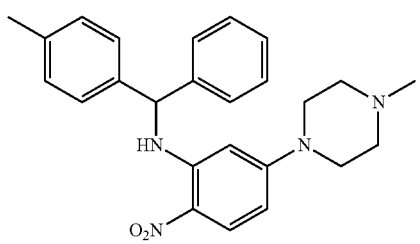

MBX 3687: 2-[(phenyl)(p-tolyl)methylamino]-4-(4-methylpiperazin-1-yl)nitrobenzene Prepared in the same manner as PPZ1, treating with 1-(4-methylphenyl)-1-phenylmethanamine instead of benzhydrylamine and N-methylpiperazine instead of piperazine. Yellow powder, mp 157-159° C. Rf: 0.55 (10% MeOH:DCM). ¹H NMR (CDCl3, 300 MHz, ppm) 8.96 (d, 1H), 8.07 (d, 1H), 7.38-7.24 (m, 7H), 7.14 (d, 2H), 6.20 (dd, 1H), 5.77 (d, 1H), 5.61 (d, 1H), 3.18 (t, 4H), 2.38 (t, 4H), 2.32 (s, 3H), 2.28 (s, 3H). m/z: 417.2 (M+1)

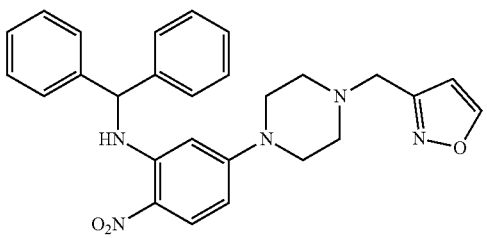 [SMILES: O=[N+]([O-])c1ccc(N2CCN(Cc3ccon3)CC2)cc1NC(c1ccccc1)c1ccccc1]

MBX 3688: 2-benzhydrylamino-5-[4-(isoxazol-3-ylmethyl)piperazin-1-yl]nitrobenzene Prepared in the same manner as MBX 3557, treating with isoxazole-3-carbaldehyde instead of acetaldehyde. Yellow powder, mp 195-196° C. Rf: 0.62 (5% MeOH:DCM). $^1$H NMR (CDCl3, 300 MHz, ppm) 8.97 (d, 1H), 8.38 (s, 1H), 8.08 (d, 1H), 7.38-7.26 (m, 10H), 6.36 (s, 1H), 6.19 (dd, 1H), 5.75 (d, 1H), 5.63 (d, 1H), 3.63 (s, 2H), 3.16 (t, 4H), 2.48 (t, 4H). m/z: 470.1 (M+1)

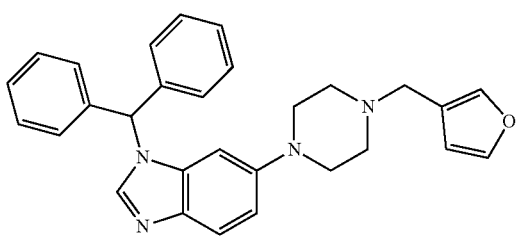 [SMILES: c1ccc(C(c2ccccc2)n2cnc3ccc(N4CCN(Cc5ccoc5)CC4)cc32)cc1]

MBX 3689: 1-benzhydryl-6-[4-(furan-3-ylmethyl)piperazin-1-yl]benzo[d]imidazole

Prepared in the same manner as MBX 3540, cyclizing from MBX 3574 instead of PPZ1. Pale brown powder, mp 144-146° C. Rf: 0.66 (10% MeOH:DCM). $^1$H NMR (CDCl3, 300 MHz, ppm) 7.67 (d, 1H), 7.48 (s, 1H), 7.39-7.34 (m, 8H), 7.14 (dd, 4H), 6.98 (dd, 1H), 6.67 (s, 1H), 6.53 (d, 1H), 6.40 (s, 1H), 3.42 (s, 2H), 3.07 (t, 4H), 2.58 (t, 4H). m/z: 449.1 (M+1)

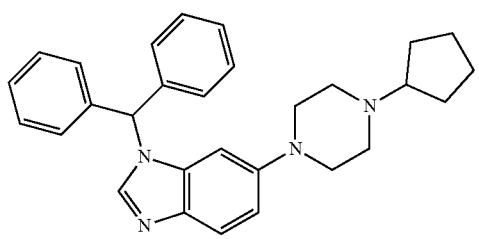 [SMILES: c1ccc(C(c2ccccc2)n2cnc3ccc(N4CCN(C5CCCC5)CC4)cc32)cc1]

MBX 3690: 1-benzhydryl-6-(4-cyclopentylpiperazin-1-yl)benzo[d]imidazole

Prepared in the same manner as MBX 3540, cyclizing from MBX 3580 instead of PPZ1. Pale brown powder, mp 178-180° C. Rf: 0.54 (10% MeOH:DCM). $^1$H NMR (CDCl3, 300 MHz, ppm) 7.67 (d, 1H), 7.49 (s, 1H), 7.37-7.34 (m, 6H), 7.15 (dd, 4H), 6.99 (dd, 1H), 6.67 (s, 1H), 6.54 (d, 1H), 3.08 (t, 4H), 2.65 (t, 4H), 2.56-2.50 (m, 1H), 1.90-1.85 (m, 2H), 1.71-1.68 (m, 2H), 1.62-1.53 (m, 2H), 1.49-1.43 (m, 2H). m/z: 437.1 (M+1)

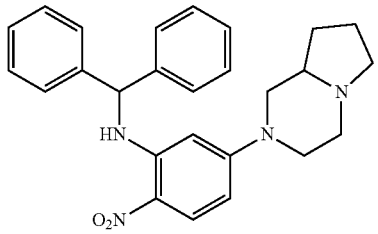 [SMILES: O=[N+]([O-])c1ccc(N2CCN3CCCC3C2)cc1NC(c1ccccc1)c1ccccc1]

MBX 3691: 2-benzhydrylamino-4-[hexahydropyrrolo[1,2-a]pyrazin-2(1H)-yl]nitrobenzene Prepared in same manner as PPZ1, treating with octahydropyrrolo[1,2-a]pyrazine instead of N-methylpiperazine. Yellow powder, mp 168-169° C. Rf: 0.58 (10% MeOH:DCM). $^1$H NMR (CDCl$_3$, 300 MHz, ppm) 8.98 (d, 1H), 8.08 (d, 1H), 7.40-7.26 (m, 10H), 6.22 (dd, 1H), 5.76 (d, 1H), 5.65 (d, 1H), 3.57 (dd, 2H), 3.09-2.86 (m, 3H), 2.53 (t, 1H), 2.18-2.07 (m, 2H), 1.90-1.75 (m, 4H), 1.45-1.39 (m, 1H). m/z: 429.4 (M+1)

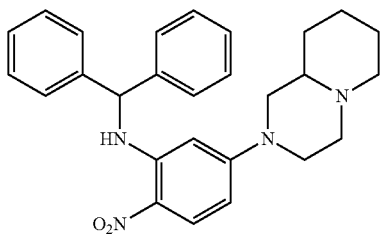 [SMILES: O=[N+]([O-])c1ccc(N2CCN3CCCCC3C2)cc1NC(c1ccccc1)c1ccccc1]

MBX 3692: 2-benzhydrylamino-4-[dihydro-1H-pyrido[1,2-a]pyrazin-2(6H,7H,8H,9H,9aH)-yl]nitrobenzene Prepared in same manner as PPZ1, treating with octahydro-1H-pyrido[1,2-a]pyrazine instead of N-methylpiperazine. Yellow powder, mp 138-139° C. Rf: 0.65 (10% MeOH:DCM). $^1$H NMR (CDCl$_3$, 300 MHz, ppm) 8.97 (d, 1H), 8.07 (d, 1H), 7.40-7.26 (m, 10), 6.19 (dd, 1H), 5.72 (d, 1H), 5.64 (d, 1H), 3.50 (d, 1H), 3.29 (d, 1H), 2.95 (td, 1H), 2.81 (d, 1H), 2.70 (d, 1H), 2.50 (dd, 1H), 2.12 (td, 1H), 1.97 (td, 1H), 1.81-1.75 (m, 2H), 1.64-1.56 (m, 3H), 1.46-1.43 (m, 1H), 1.34-1.22 (m, 1H). m/z: 443.4 (M+1)

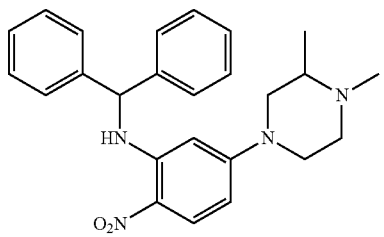 [SMILES: CC1CN(c2ccc([N+](=O)[O-])c(NC(c3ccccc3)c3ccccc3)c2)CCN1C]

MBX 3693: 2-benzhydrylamino-4-(3,4-dimethylpiperazin-1-yl)nitrobenzene

Prepared in same manner as PPZ1, treating with 1,2-dimethylpiperazine instead of N-methylpiperazine. Yellow crystalline solid, mp 205-206° C. Rf: 0.61 (10% MeOH:DCM). $^1$H NMR (CDCl$_3$, 300 MHz, ppm) 8.96 (d, 1H), 8.07 (d, 1H), 7.40-7.26 (m, 10H), 6.19 (dd, 1H), 5.73 (s, 1H), 5.64 (d, 1H), 3.46 (d, 1H), 3.28 (d, 1H), 2.94 (t, 1H), 2.73 (d, 1H), 2.52 (t, 1H), 2.26 (s, 3H), 2.15 (t, 1H), 2.01-1.97 (m, 1H), 1.01 (d, 3H). m/z: 417.3 (M+1)

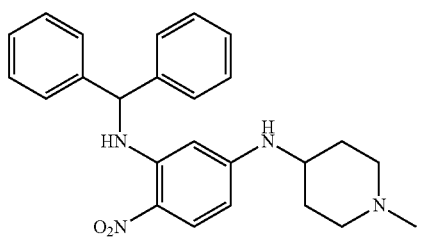

MBX 3694: 2-benzhydrylamino-4-(1-methylpiperidin-4-ylamino)nitrobenzene

Prepared in same manner as PPZ1, treating with 1-methylpiperidin-4-amine instead of N-methylpiperazine. Yellow flakey solid, mp>130° C. (decomp.). Rf: 0.30 (10% MeOH:DCM). 1H NMR (CDCl$_3$, 300 MHz, ppm) 9.07 (d, 1H), 8.02 (d, 1H), 7.37-7.26 (m, 10H), 5.85 (dd, 1H), 5.63 (d, 1H), 5.48 (s, 1H), 4.19 (d, 1H), 2.98-2.93 (m, 1H), 2.69 (d, 2H), 2.27 (s, 3H), 1.92 (t, 2H), 1.63 (d, 2H), 1.38-1.30 (m, 2H). m/z: 417.3 (M+1)

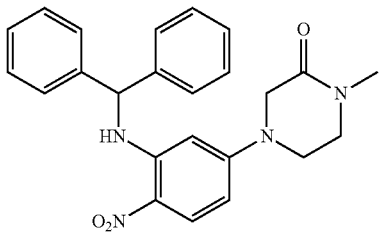 [SMILES: CN1CCN(c2ccc([N+](=O)[O-])c(NC(c3ccccc3)c3ccccc3)c2)CC1=O]

MBX 3695: 2-benzhydrylamino-4-(4-methyl-3-oxopiperazin-1-yl)nitrobenzene

Prepared in same manner as PPZ1, treating with 1-methylpiperazin-2-one instead of N-methylpiperazine. Yellow flakey solid, mp 233-235° C. Rf: 0.61 (10% MeOH:DCM). $^1$H NMR (CDCl$_3$, 300 MHz, ppm) 8.99 (d, 1H), 8.12 (d, 1H), 7.38-7.26 (m, 10H), 6.13 (dd, 1H), 5.71 (s, 1H), 5.66 (d, 1H), 3.78 (s, 2H), 3.39 (dd, 4H), 3.00 (s, 3H). m/z: 417.0 (M+1)

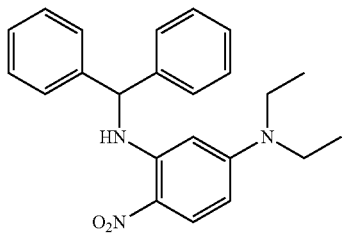 [SMILES: CCN(CC)c1ccc([N+](=O)[O-])c(NC(c2ccccc2)c2ccccc2)c1]

MBX 3696: 2-benzhydrylamino-4-(diethylamino)nitrobenzene

Prepared in same manner as PPZ1, treating with diethylamine instead of N-methylpiperazine. Fluffy yellow solid, mp 159-160° C. Rf: 0.68 (50% EtOAc:hexanes). $^1$H NMR (CDCl$_3$, 300 MHz, ppm) 9.02 (d, 1H), 8.07 (d, 1H), 7.40-7.24 (m, 10H), 6.03 (dd, 1H), 5.61 (d, 1H), 5.51 (s, 1H), 3.20 (q, 4H), 0.94 (t, 6H). m/z: 376.3 (M+1)

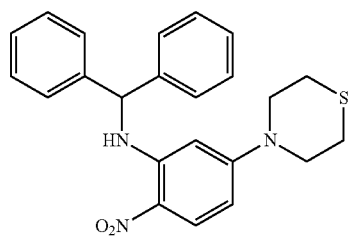 [SMILES: O=[N+]([O-])c1ccc(N2CCSCC2)cc1NC(c1ccccc1)c1ccccc1]

MBX 3699: 2-benzhydrylamino-4-thiomorpholino-1-nitrobenzene

Prepared in same manner as PPZ1, treating with thiomorpholine instead of N-methylpiperazine. Yellow powder, mp 157-158° C. Rf: 0.32 (20% EtOAc:hexanes). $^1$H NMR (CDCl$_3$, 300 MHz, ppm) 8.96 (s, 1H), 8.08 (d, 1H), 7.37-7.26 (m, 10H), 6.13 (d, 1H), 5.69 (s, 1H), 5.62 (d, 1H), 3.60 (br s, 4H), 2.39 (br s, 4H). m/z: 406.2 (M+1)

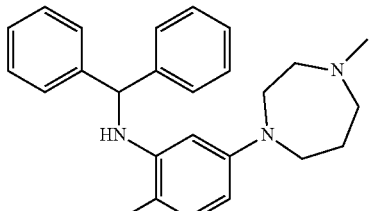

MBX 3700: 2-benzhydrylamino-4-(4-methyl-1,4-diazepan-1-yl)-1-nitrobenzene

Prepared in same manner as PPZ1, treating with N-methylhomopiperazine instead of N-methylpiperazine. Yellow solid, mp 126-127° C. Rf: 0.59 (10% MeOH:DCM). $^1$H NMR (CDCl$_3$, 300 MHz, ppm) 9.00 (d, 1H), 8.07 (d, 1H), 7.40-7.24 (m, 10H), 6.07 (dd, 1H), 5.62 (d, 1H), 5.54 (d, 1H), 3.41-3.32 (m, 4H), 2.38 (q, 4H), 2.28 (s, 3H), 1.78-1.70 (m, 2H). m/z: 417.3 (M+1)

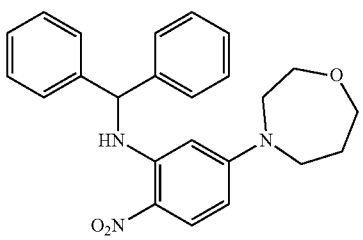 [SMILES: O=[N+]([O-])c1ccc(N2CCCOCC2)cc1NC(c1ccccc1)c1ccccc1]

MBX 3701: 2-benzhydrylamino-4-(1,4-oxazepan-4-yl)-1-nitrobenzene

Procedure: A solution of N-benzhydryl-5-fluoro-2-nitroaniline (0.160 g, 0.496 mmol, 2 eq) and 1,4-oxazepane hydrochloride (0.034 g, 0.248 mmol, 1 eq), and triethylamine (0.10 mL, 0.744 mmol, 3 eq) in 5 mL acetonitrile was heated to reflux overnight. The reaction was then concentrated, adsorbed onto Celite, and purified on a 40 g silica column, eluting with 0-50% EtOAx:Hex. Fractions were combined and concentrated to yield MBX 3701 (0.035 g, 0.087 mmol, 35%). Yellow fluffy solid, mp 166-167° C. Rf: 0.37 (50% EtOAc:hexanes). $^1$H NMR (CDCl$_3$, 300 MHz, ppm) 8.97 (d, 1H), 8.09 (d, 1H), 7.39-7.26 (m, 10H), 6.08 (dd, 1H), 5.61 (d, 1H), 5.57 (d, 1H), 3.50-3.44 (m, 8H), 1.71-1.63 (m, 2H). m/z: 404.0 (M+1)

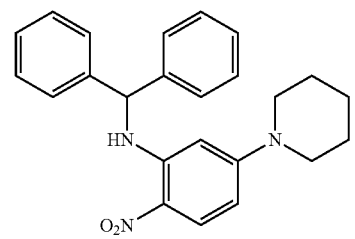 [SMILES: O=[N+]([O-])c1ccc(N2CCCCC2)cc1NC(c1ccccc1)c1ccccc1]

MBX 3702: 2-benzhydrylamino-4-(piperidin-1-yl)-1-nitrobenzene

Prepared in same manner as PPZ1, treating with piperidine instead of N-methylpiperazine. Yellow powder, mp 180-181° C. Rf: 0.35 (10% EtOAc:hexanes). $^1$H NMR (CDCl$_3$, 300 MHz, ppm) 9.02 (d, 1H), 8.06 (d, 1H), 7.40-7.24 (m, 10H), 6.19 (dd, 1H), 5.72 (d, 1H), 5.64 (d, 1H), 3.19 (t, 4H), 1.59-1.55 (m, 2H), 1.48-1.46 (m, 4H). m/z: 488.3 (M+1)

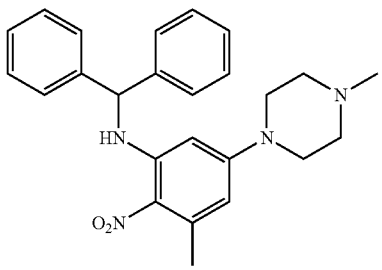 [SMILES: Cc1cc(N2CCN(C)CC2)cc(NC(c2ccccc2)c2ccccc2)c1[N+](=O)[O-]]

MBX 3728: 2-(benzhydrylamino)-6-methyl-4-(4-methylpiperazin-1-yl)-1-nitrobenzene Prepared in same manner as PPZ1, starting with 3,5-difluoro-2-nitrotoluene instead of 2,4-difluoronitrobenzene. Bright orange powder, mp 170-171° C. Rf: 0.30 (5% MeOH:DCM). $^1$H NMR (CDCl$_3$, 300 MHz, ppm) 8.57 (d, 1H), 7.38-7.23 (m, 10H), 6.06 (d, 1H), 5.72 (d, 1H), 5.59 (d, 1H), 3.13 (t, 4H), 2.54 (s, 3H), 2.36 (t, 4H), 2.27 (s, 3H). m/z: 417.3 (M+1)

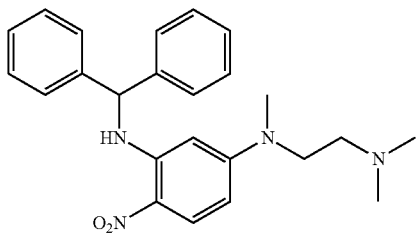 [SMILES: CN(C)CCN(C)c1ccc([N+](=O)[O-])c(NC(c2ccccc2)c2ccccc2)c1]

MBX 3729: 2-(benzhydrylamino)-4-{[2-(dimethylamino)ethyl](methyl)amino}-1-nitrobenzene Prepared in same manner as PPZ1, treating with N$^1$,N$^1$,N$^2$-trimethylethane-1,2-diamine instead of N-methylpiperazine. Bright yellow solid, mp 116-117° C. Rf: 0.19 (5% MeOH:DCM). $^1$H NMR (CDCl$_3$, 300 MHz, ppm) 9.04 (d, 1H), 8.08 (d, 1H) 7.39-7.24 (m, 10H), 6.06 (dd, 1H), 5.66 (d, 1H), 5.54 (d, 1H), 3.32 (t, 2H), 2.85 (s, 3H), 2.27-2.18 (m, 8H). m/z: 405.1 (M+1)

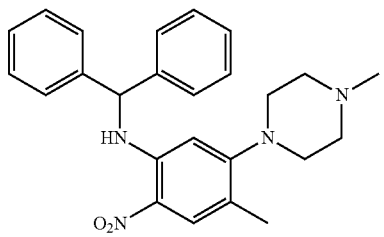

MBX 3730: 2-(benzhydrylamino)-5-methyl-4-(4-methylpiperazin-1-yl)-1-nitrobenzene Prepared in same manner as PPZ1, starting with 2,4-difluoro-5-nitrotoluene instead of 2,4-difluoronitrobenzene. Yellow powder, mp 176-177° C. Rf: 0.53 (10% MeOH:DCM). $^1$H NMR (CDCl$_3$, 300 MHz, ppm) 8.73 (d, 1H), 7.97 (s, 1H), 7.38-7.26 (m, 10H), 6.05 (s, 1H), 5.66 (d, 1H), 2.79 (t, 4H), 2.45 (br s, 4H), 2.31 (s, 3H), 2.15 (s, 3H). m/z: 417.3 (M+1)

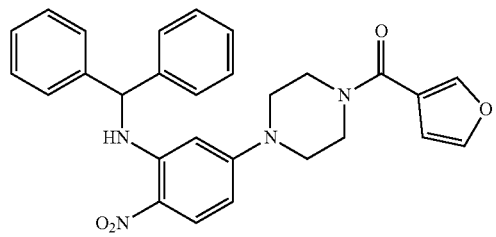 [SMILES: O=C(c1ccoc1)N1CCN(c2ccc([N+](=O)[O-])c(NC(c3ccccc3)c3ccccc3)c2)CC1]

MBX 3731: 2-(benzhydrylamino)-4-[4-(furan-3-carbonyl)piperazin-1-yl]-1-nitrobenzene Procedure: To a solution of 3-furoic acid (0.035 g, 0.311 mmol, 1 eq) in 10 mL tetrahydrofuran was added HATU (0.177 g, 0.466 mmol, 1.5 eq) and DIPEA (0.14 mL, 0.777 mmol, 2.5 eq) at 0° C. The mixture was stirred at 0° C. for 30 min, then N-(diphenylmethyl)-2-nitro-5-(piperazin-1-yl) aniline (0.181 g, 0.466 mmol, 1.5 eq) was added. The reaction was allowed to warm to r.t. and then stirred at r.t. for 1.5 hr. The reaction was then poured into ice water and washed with ethyl acetate (3×30 mL). The combined organic fractions were washed with brine and dried ($Na_2SO_4$), filtered, and concentrated. The concentrate was adsorbed onto Celite and purified on a 16 g silica column, eluting with 0-75% EtOAc:hexanes. Fractions were combined and concentrated to yield MBX 3731 (0.091 g, 0.189 mmol, 61%). Yellow solid, mp 197-198° C. Rf: 0.85 (10% MeOH:DCM). $^1$H NMR ($CDCl_3$, 300 MHz, ppm) 8.96 (d, 1H), 8.11 (d, 1H), 7.72 (s, 1H), 7.45 (t, 1H), 7.37-7.26 (m, 10H), 6.55 (d, 1H), 6.18 (dd, 1H), 5.76 (d, 1H), 5.64 (d, 1H), 3.70 (t, 4H), 3.23 (t, 4H). m/z: 483.0 (M+1)

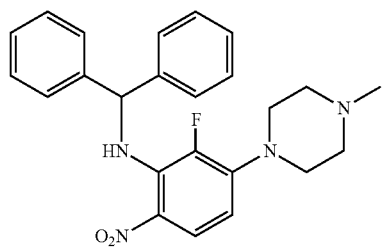 [SMILES: CN1CCN(c2ccc([N+](=O)[O-])c(NC(c3ccccc3)c3ccccc3)c2F)CC1]

MBX 3732: 2-(benzhydrylamino)-3-fluoro-4-(4-methylpiperazin-1-yl)-1-nitrobenzene Prepared in same manner as PPZ1, starting with 2,3,4-trifluoronitrobenzene instead of 2,4-difluoronitrobenzene. Yellow powder, mp 144-145° C. Rf: 0.37 (5% MeOH:DCM). $^1$H NMR (DMSO, 300 MHz, ppm) 8.47 (d, 1H), 7.87 (d, 1H), 7.37-7.25 (m, 10H), 6.49 (t, 1H), 6.22 (d, 1H), 3.11 (br s, 4H), 2.34 (br s, 4H), 2.17 (s, 3H). m/z: 421.3 (M+1)

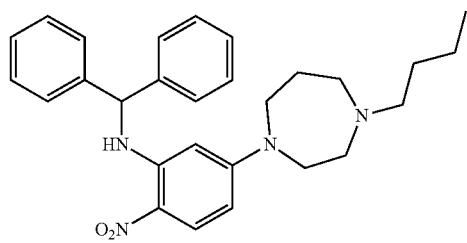 [SMILES: CCCCN1CCCN(c2ccc([N+](=O)[O-])c(NC(c3ccccc3)c3ccccc3)c2)CC1]

MBX 3735: 2-(benzhydrylamino)-4-(4-butyl-1,4-diazepan-1-yl)-1-nitrobenzene

Prepared in same manner as PPZ1, treating with N-butyl-homopiperazine instead of N-methylpiperazine. Yellow powder, mp 95-96° C. Rf: 0.26 (5% MeOH:DCM). $^1$H NMR (DMSO, 300 MHz, ppm) 8.99 (d, 1H), 7.90 (d, 1H), 7.46 (d, 4H), 7.38 (t, 4H), 7.30-7.25 (m, 2H), 6.27 (dd, 1H), 5.97 (d, 1H), 5.64 (d, 1H), 3.40-3.36 (m, 4H), 2.37-2.25 (m, 6H), 1.55 (s, 2H), 1.29-1.19 (m, 4H), 0.84 (t, 3H). m/z: 459.4 (M+1)

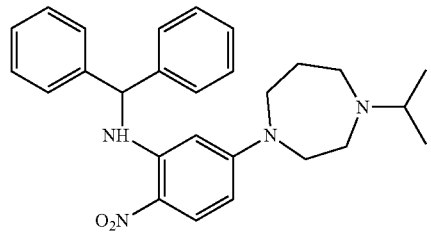 [SMILES: CC(C)N1CCCN(c2ccc([N+](=O)[O-])c(NC(c3ccccc3)c3ccccc3)c2)CC1]

MBX 3736: 2-(benzhydrylamino)-4-(4-isopropyl-1,4-diazepan-1-yl)-1-nitrobenzene Prepared in same manner as PPZ1, treating with N-isopropyl-homopiperazine instead of N-methylpiperazine. Light orange powder, mp 75-77° C. Rf: 0.23 (5% MeOH:DCM). $^1$H NMR (DMSO, 300 MHz, ppm) 8.99 (d, 1H), 7.90 (d, 1H), 7.47 (d, 4H), 7.38 (t, 4H), 7.30-7.25 (m, 2H), 6.27 (dd, 1H), 5.97 (d, 1H), 5.64 (d, 1H), 3.40 (d, 4H), 2.73-2.72 (m, 1H), 2.37 (bs, 2H), 2.24 (bs, 2H), 1.48 (bs, 2H), 0.84 (d, 6H). m/z: 445.4 (M+1)

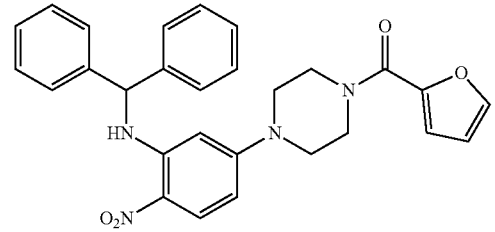 [SMILES: O=C(c1ccco1)N1CCN(c2ccc([N+](=O)[O-])c(NC(c3ccccc3)c3ccccc3)c2)CC1]

MBX 3737: 2-(benzhydrylamino)-4-[4-(furan-2-carbonyl)piperazin-1-yl]-1-nitrobenzene Prepared in same manner as PPZ1, treating with 1-(2-furoyl)-piperazine instead of N-methylpiperazine. Bright yellow powder, mp 184-185° C. Rf: 0.86 (5% MeOH:DCM). $^1$H NMR (DMSO, 300 MHz, ppm) 9.03 (d, 1H), 7.96 (d, 1H), 7.87 (s, 1H), 7.48-7.29 (m, 10H), 7.03 (d, 1H), 6.65 (s, 1H), 6.40 (d, 1H), 6.09 (d, 1H), 5.93 (s, 1H), 3.71 (bs, 4H), 3.42 (bs, 4H). m/z: 482.9 (M+1)

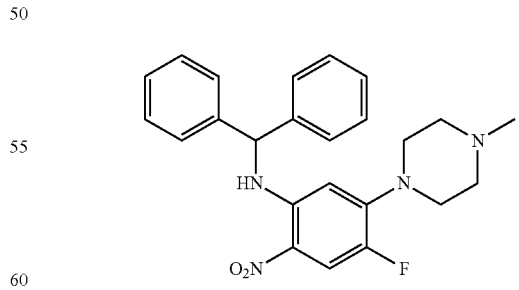

MBX 3740: 2-benzhydrylamino-4-(4-methylpiperazin-1-yl)-5-fluoro-1-nitrobenzene Prepared in same manner as PPZ1, starting with 1,3,4-trifluoro-5-nitrobenzene instead of 2,4-difluoronitrobenzene. Yellow-orange powder, mp 141-142° C. Rf: 0.25 (5% MeOH:DCM). ¹H NMR (CDCl₃, 300 MHz, ppm) 8.82 (d, 1H), 7.84 (d, 1H), 7.37-7.26 (m, 10H), 5.88 (d, 1H), 5.63 (d, 1H), 3.06 (t, 4H), 2.43 (d, 4H), 2.29 (s, 3H). m/z: 421.3 (M+1)

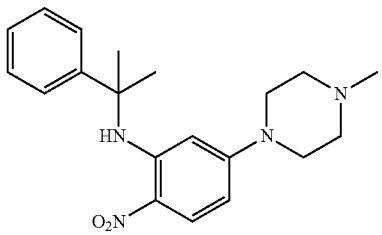 [SMILES: CN1CCN(c2ccc([N+](=O)[O-])c(NC(C)(C)c3ccccc3)c2)CC1]

MBX 3741: 2-(2-phenylpropan-2-ylamino)-4-(4-methylpiperazin-1-yl)-1-nitrobenzene Prepared in same manner as PPZ1, treating with 2-phenylpropan-2-amine instead of benzhydrylamine. Yellow powder, mp 143-144° C. Rf: 0.30 (5% MeOH:DCM). ¹H NMR (CDCl₃, 300 MHz, ppm) 8.98 (s, 1H), 8.04 (d, 1H), 7.45 (d, 2H), 7.34 (t, 2H), 7.26-7.20 (m, 1H), 6.11 (dd, 1H), 5.36 (d, 1H), 2.94 (t, 4H), 2.29-2.24 (m, 7H), 1.77 (s, 6H). m/z: 355.2 (M+1)

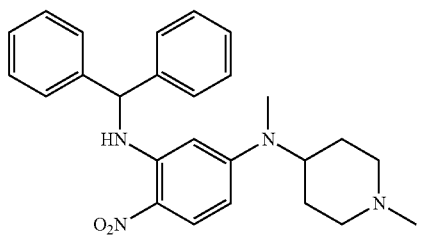 [SMILES: CN1CCC(N(C)c2ccc([N+](=O)[O-])c(NC(c3ccccc3)c3ccccc3)c2)CC1]

MBX 3742: 2-(benzhydrylamino)-4-[methyl(1-methylpiperidin-4-yl)amino]-1-nitrobenzene Prepared in same manner as PPZ1, treating with N,1-dimethylpiperidin-4-amine instead of N-methylpiperazine. Bright yellow powder, mp 155-157° C. Rf: 0.18 (5% MeOH:DCM). ¹H NMR (CDCl₃, 300 MHz, ppm) 8.98 (s, 1H), 8.07 (d, 1H), 7.37-7.26 (m, 10H), 6.10 (d, 1H), 5.64-5.58 (m, 2H), 3.45-3.43 (m, 1H), 3.06 (d, 2H), 2.70 (s, 3H), 2.43 (s, 3H), 2.15-2.12 (m, 2H), 1.97-1.94 (m, 2H), 1.51 (d, 2H). m/z: 431.1 (M+1)

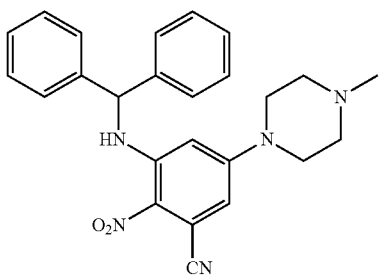 [SMILES: CN1CCN(c2cc(C#N)c([N+](=O)[O-])c(NC(c3ccccc3)c3ccccc3)c2)CC1]

MBX 3743: 2-(benzhydrylamino)-4-(4-methylpiperazin-1-yl)-6-cyano-1-nitrobenzene

Prepared in same manner as PPZ1, starting with 3,5-difluoro-2-nitrobenzonitrile instead of 2,4-difluoronitrobenzene. Light green powder, mp 223-225° C. Rf: 0.23 (5% MeOH:DCM). ¹H NMR (CDCl₃, 300 MHz, ppm) 9.05 (d, 1H), 7.39-7.26 (m, 10H), 6.65 (d, 1H), 5.91 (d, 1H), 5.62 (d, 1H), 3.15 (t, 4H), 2.37 (t, 4H), 2.28 (s, 3H). m/z: 428.3 (M+1)

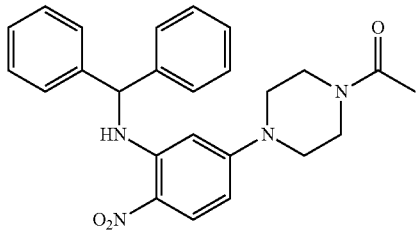 [SMILES: CC(=O)N1CCN(c2ccc([N+](=O)[O-])c(NC(c3ccccc3)c3ccccc3)c2)CC1]

MBX 3744: 2-(benzhydrylamino)-4-(4-acetylpiperazin-1-yl)-1-nitrobenzene

Prepared in the same manner as MBX 3731, treating with acetic acid instead of 3-furoic acid. Yellow solid, mp 209-210° C. Rf: 0.64 (10% MeOH:DCM). ¹H NMR (DMSO, 300 MHz, ppm) 9.02 (d, 1H), 7.94 (d, 1H), 7.49-7.27 (m, 10H), 6.42 (d, 1H), 6.08 (d, 1H), 5.75 (s, 1H), 3.45 (br s, 4H), 3.29-3.28 (m, 4H), 1.91 (s, 3H). m/z: 430.6 (M+1)

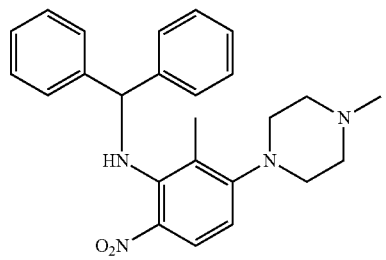 [SMILES: Cc1c(N2CCN(C)CC2)ccc([N+](=O)[O-])c1NC(c1ccccc1)c1ccccc1]

MBX 3745: 2-(benzhydrylamino)-4-(4-acetylpiperazin-1-yl)-3-methyl-1-nitrobenzene Prepared in same manner as PPZ1, starting with 1,3-difluoro-2-methyl-4-nitrobenzene instead of 2,4-difluoronitrobenzene. Brittle orange solid, mp>50° C. (decomp.). Rf: 0.44 (10% MeOH:DCM). ¹H NMR (CDCl₃, 300 MHz, ppm) 8.01 (d, 1H), 7.90 (d, 1H), 7.28-7.22 (m, 10H), 6.48 (d, 1H), 5.67 (d, 1H), 3.02 (t, 4H), 2.56 (br s, 4H), 2.36 (s, 3H), 2.32 (s, 3H). m/z: 417.2 (M+1)

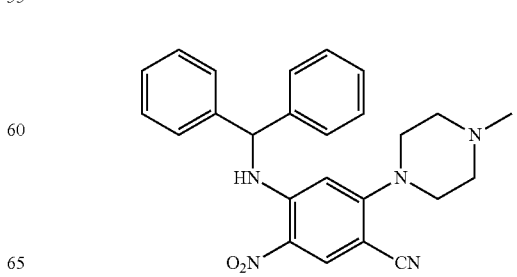

MBX 3746: 2-(benzhydrylamino)-4-(4-methypiperazin-1-yl)-5-cyano-1-nitrobenzene Prepared in same manner as PPZ1, starting with 2,4-difluoro-5-nitrobenzonitrile instead of 2,4-difluoronitrobenzene. Bright yellow powder, mp 93-95° C. Rf: 0.24 (5% MeOH:DCM). ¹H NMR (CDCl₃, 300 MHz, ppm) 8.98 (d, 1H), 8.46 (s, 1H), 7.40-7.26 (m, 10H), 5.91 (s, 1H), 5.66 (d, 1H), 3.17-3.13 (m, 4H), 2.47 (t, 4H), 2.31 (s, 3H). m/z: 428.4 (M+1)

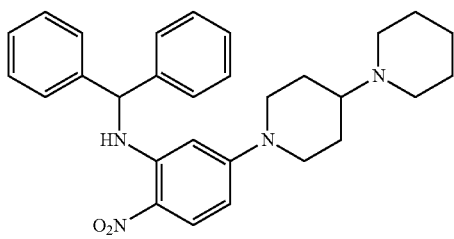 [SMILES: O=[N+]([O-])c1ccc(N2CCC(N3CCCCC3)CC2)cc1NC(c1ccccc1)c1ccccc1]

MBX 3747: 2-(benzhydrylamino)-4-[(1,4'-bipiperidin)-1'-yl]-1-nitrobenzene

Prepared in same manner as PPZ1, treating with 1,4'-bipiperidine instead of N-methylpiperazine. Yellow solid, mp 108-110° C. Rf: 0.15 (5% MeOH:DCM). ¹H NMR (CDCl₃, 300 MHz, ppm) 8.98 (d, 1H), 8.07 (d, 1H), 7.40-7.26 (m, 10H), 6.19 (dd, 1H), 5.74 (d, 1H), 5.64 (d, 1H), 3.69 (d, 2H), 2.77 (t, 2H), 2.51 (s, 4H), 1.78 (d, 3H), 1.65 (s, 4H), 1.46-1.38 (m, 2H), 1.35-1.25 (m, 2H). m/z: 471.4 (M+1)

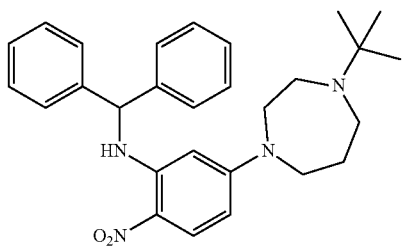 [SMILES: CC(C)(C)N1CCCN(c2ccc([N+](=O)[O-])c(NC(c3ccccc3)c3ccccc3)c2)CC1]

MBX 3748: 2-(benzhydrylamino)-4-[4-(tert-butyl)-1,4-diazepan-1-yl]-1-nitrobenzene Prepared in same manner as PPZ1, treating with N-tert-butyl-homopiperazine instead of N-methylpiperazine. Bright yellow powder, mp 99-101° C. Rf: 0.13 (5% MeOH:DCM). ¹H NMR (CDCl₃, 300 MHz, ppm) 9.01 (d, 1H), 8.06 (d, 1H), 7.40-7.24 (m, 10H), 6.07 (dd, 1H), 5.61 (d, 1H), 5.53 (d, 1H), 3.42 (t, 2H), 3.33 (s, 2H), 2.45 (s, 2H), 2.35 (s, 2H), 1.51 (s, 2H), 0.99 (s, 9H). m/z: 459.3 (M+1)

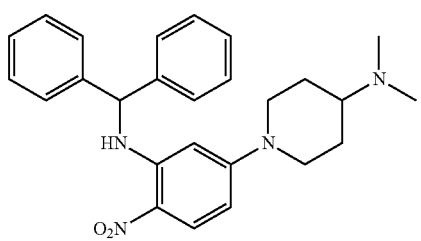 [SMILES: CN(C)C1CCN(c2ccc([N+](=O)[O-])c(NC(c3ccccc3)c3ccccc3)c2)CC1]

MBX 3749: 2-(benzhydrylamino)-4-[4-(dimethylamino)piperidin-1-yl]-1-nitrobenzene Prepared in same manner as PPZ1, treating with N,N-dimethylpiperidin-4-amine instead of N-methylpiperazine. Bright yellow powder, mp 148-150° C. Rf: 0.22 (5% MeOH:DCM). ¹H NMR (CDCl₃, 300 MHz, ppm) 8.98 (d, 1H), 8.07 (d, 1H), 7.40-7.26 (m, 10H), 6.19 (dd, 1H), 5.75 (d, 1H), 5.54 (d, 1H), 3.68 (d, 2H), 2.78 (t, 2H), 2.45 (d, 1H), 2.31 (s, 6H), 1.79 (d, 2H), 1.40-1.25 (m, 2H). m/z: 431.3 (M+1)

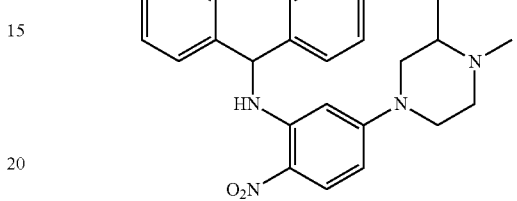

MBX 3939: 2-(benzhydrylamino)-4-[4-methyl-3-(hydroxymethyl)piprazin-1-yl]-1-nitrobenzene Preparation: To a 10 mL rbf of N-benzhydryl-5-fluoro-2-nitroaniline (0.108 g, 0.335 mmol, 1 eq) in DMF (5 mL) was added (1-methylpiperazin-2-yl)methanol (0.050 g, 0.354 mmol, 1.15 eq). The reaction was stirred at 80° C. for two days, at which point the reaction mixture was cooled, partitioned between brine and EtOAc, and the aqueous layer was extracted with EtOAc (3×15 mL). The combined organic layers were washed with brine, dried (Na₂SO₄), filtered, and concentrated. The concentrate was adsorbed onto silica and purified on a 16 g silica column, eluting with 0-7% MeOH:DCM. Fractions were combined and concentrated to yield MBX 3939 (0.059 g, 0.136 mmol, 41%). Dark yellow solid, mp 190-193° C. (decomp.). Rf: 0.24 (5% MeOH:DCM). ¹H NMR (CDCl₃, 300 MHz, ppm) 8.96 (m, 1H), 8.10 (d, 1H), 7.37-7.29 (m, 10H), 6.21-6.17 (m, 1H), 5.74 (m, 1H), 5.64 (d, 1H), 3.80-3.75 (m, 1H), 3.49-3.46 (d, 1H), 3.40-3.71 (d, 1H), 3.03-2.96 (m, 2H), 2.81-2.77 (m, 1H), 2.31 (s, 3H), 2.28-2.24 (m, 1H), 2.04 (m, 1H), 1.88-1.78 (bs, 1H). m/z: 433.3 (M+1)

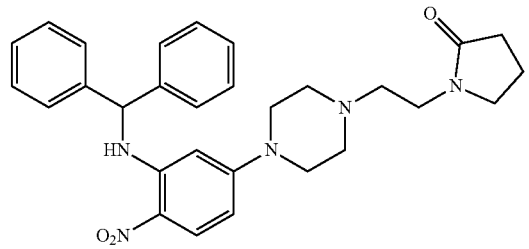 [SMILES: O=C1CCCN1CCN1CCN(c2ccc([N+](=O)[O-])c(NC(c3ccccc3)c3ccccc3)c2)CC1]

MBX 3940: 2-(benzhydrylamino)-4-{4-[2-(2-oxopyrrolidin-1-yl)ethyl]piperazin-1-yl}-1-nitrobenzene Prepared in the same manner as MBX 3559, treating with 2-chloro-1-(pyrrolidin-1-yl)ethanone instead of iodobutane. Yellow solid, mp 93-97° C. (decomp.). Rf: 0.37 (5% MeOH:DCM). ¹H NMR (CDCl₃, 300 MHz, ppm) 8.88 (m, 1H), 8.13 (d, 1H), 7.38-7.26 (m, 10H), 6.16 (m, 1H), 5.79 (m, 1H), 5.65 (m, 1H), 3.63 (m, 2H), 3.49-3.41 (m, 7H), 3.19-3.14 (m, 2H), 3.12-3.10 (m, 3H), 2.44-2.39 (m, 2H), 2.07-2.02 (m, 2H). m/z: 500.1 (M+1)

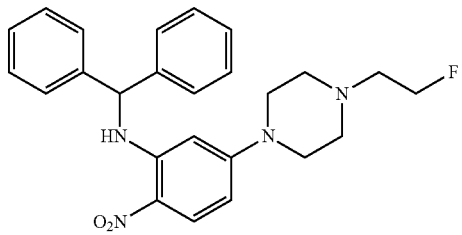 [SMILES: O=[N+]([O-])c1ccc(N2CCN(CCF)CC2)cc1NC(c1ccccc1)c1ccccc1]

MBX 3941: 2-(benzhydrylamino)-4-[4-(2-fluoro-ethyl)piprazin-1-yl]-1-nitrobenzene Prepared in the same manner as MBX 3559, treating with 1-fluoro-2-iodoethane instead of iodobutane. Yellow solid, mp 119-121° C. Rf: 0.63 (5% MeOH:DCM). $^1$H NMR (CDCl$_3$, 300 MHz, ppm) 8.97 (m, 1H), 8.1-8.07 (d, 1H), 7.37-7.28 (m, 10H), 6.29 (m, 1H), 5.76 (s, 1H), 5.64 (m, 1H), 4.64 (m, 1H), 4.48 (m, 1H), 3.17 (m, 4H), 2.73 (m, 1H), 2.63 (m, 1H), 2.51 (m, 4H). m/z: 435.2 (M+1)

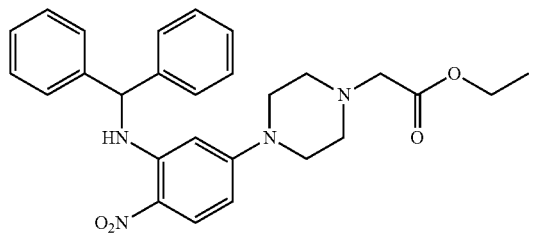 [SMILES: CCOC(=O)CN1CCN(c2ccc([N+](=O)[O-])c(NC(c3ccccc3)c3ccccc3)c2)CC1]

MBX 3947: 2-(benzhydrylamino)-4-[4-(2-ethoxy-2-oxoethyl)piperazin-1-yl]-1-nitrobenzene Prepared in the same manner as MBX 3559, treating with ethyl 2-chloroacetate instead of iodobutane. Yellow solid, mp 145-150° C. Rf: 0.61 (5% MeOH:DCM). $^1$H NMR (CDCl$_3$, 300 MHz, ppm) 8.88 (m, 1H), 8.14-8.10 (d, 1H), 7.37-7.26 (m, 10H), 6.19-6.16 (m, 1H), 5.80 (m, 1H), 5.64 (m, 1H), 4.29-4.22 (q, 2H), 3.71 (s, 2H), 3.44 (m, 4H), 3.18 (m, 4H), 1.30 (t, 3H). m/z: 475.2 (M+1)

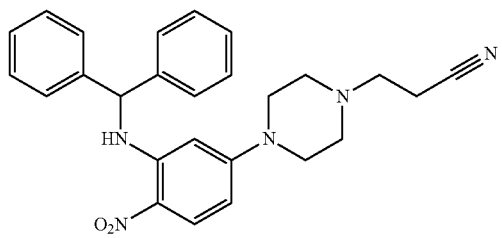 [SMILES: N#CCCN1CCN(c2ccc([N+](=O)[O-])c(NC(c3ccccc3)c3ccccc3)c2)CC1]

MBX 3948: 2-(benzhydrylamino)-4-[4-(2-cyanoeth-1-yl)piperazin-1-yl]-1-nitrobenzene Procedure: To a 10 mL rbf of N-benzhydryl-5-fluoro-2-nitroaniline (0.0445 g, 0.115 mmol, 1 eq) in EtOH (5 mL) was added acrylonitrile (0.019 g, 0.361 mmol, 3.15 eq). The reaction was stirred at reflux for five days, at which point the reaction mixture was cooled, concentrated, and purified with HPLC (10-90% MeCN:H$_2$O with 0.1% TFA) to yield MBX 3948 (0.0384 g, 0.136 mmol, 76%). Yellow solid, mp 95-100° C. (decomp.). Rf: 0.66 (5% MeOH:DCM). $^1$H NMR (CDCl$_3$, 300 MHz, ppm) 8.88 (m, 1H), 8.15 (m, 1H), 7.37-7.26 (m, 10H), 6.19 (m, 1H), 5.80 (m, 1H), 5.65 (m, 1H), 3.40-3.38 (m, 4H), 3.13-3.09 (m, 2H), 2.98-2.96 (m, 4H), 2.88-2.84 (m, 2H). m/z: 442.2 (M+1)

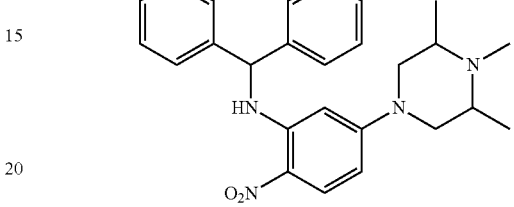

MBX 3959: 2-benzhydrylamino-4-(3,4,5-trimethylpiperazin-1-yl)-1-nitrobenzene

Prepared in the same manner as PPZ1, treating with 1,2,6-trimethylpiperazine instead of N-methylpiperazine. Yellow solid, mp 175-178° C. (decomp.). Rf: 0.28 (5% MeOH:DCM). $^1$H NMR (CDCl$_3$, 300 MHz, ppm) 8.86 (m, 1H), 8.02 (m, 1H), 7.34-7.17 (m, 10H), 6.12-6.08 (m, 1H), 5.64 (s, 1H), 5.56 (m, 1H), 3.27-3.23 (d, 2H), 2.54-2.51 (m, 2H), 2.16 (s, 3H), 2.03 (m, 2H), 0.99-0.98 (m, 6H). m/z: 431.3 (M+1)

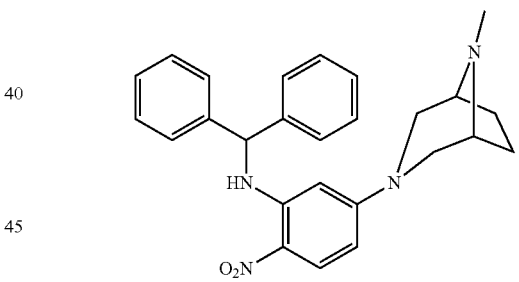

MBX 3961: 2-(benzhydrylamino)-4-(8-methyl-3,8-diazabicyclo[3.2.1]octan-3-yl)-1-nitrobenzene Procedure: To a 10 mL rbf of N-benzhydryl-5-fluoro-2-nitroaniline (0.050 g, 0.16 mmol, 1 eq) in pyridine (3 mL) was added (1R,5S)-8-methyl-3,8-diazabicyclo[3.2.1]octane hydrochloride (0.047 g, 0.29 mmol, 1.8 eq), followed by DBU (0.01 mL, 0.4 eq). The reaction was stirred at 80° C. for four hours, at which point another 0.4 eq DBU was added, and the reaction was heated to reflux overnight. The next day, the reaction was cooled, quenched with H$_2$O (15 mL), extracted with EtOAc (3×15 mL), dried (Na$_2$SO$_4$), filtered and concentrated. The crude product was purified with HPLC (15-95% MeCN:H$_2$O with 0.1% TFA) to yield MBX 3961 (0.0065 g, 0.015 mmol, 10%). Yellow solid, mp 110-112° C. (decomp.). Rf: 0.25 (5% MeOH:DCM). $^1$H NMR (CDCl$_3$, 300 MHz, ppm) 8.16-8.80 (m, 1H), 8.04-8.01 (m, 1H), 7.29-7.18 (m, 10H), 6.07-6.03 (m, 1H), 5.66-5.64

(m, 1H), 5.56-5.55 (m, 1H), 3.78 (m, 2H), 3.42-3.18 (m, 4H), 2.70 (s, 3H), 2.12-2.08 (m, 2H), 1.93-1.83 (m, 2H). m/z: 429.3 (M+1)

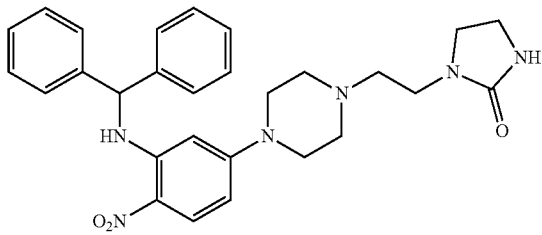 [SMILES: O=C1NCCN1CCN1CCN(c2ccc([N+](=O)[O-])c(NC(c3ccccc3)c3ccccc3)c2)CC1]

MBX 3966: 2-(benzhydrylamino)-4-{4-[2-(2-oxo-imidazolidin-1-yl)ethyl]piperazin-1-yl}-1-nitrobenzene Prepared in the same manner as MBX 3559, treating with 1-(2-chloroethyl)imidazolidin-2-one instead of iodobutane. Yellow solid, mp 96-99° C. Rf: 0.27 (5% MeOH:DCM). $^1$H NMR (CDCl$_3$, 300 MHz, ppm) 8.98 (m, 1H), 8.09-8.06 (m, 1H), 7.37-7.26 (m, 10H), 6.21-6.17 (m, 1H), 5.76-5.75 (m, 1H), 5.65-5.64 (m, 1H), 4.27 (s, 1H), 3.49-3.31 (m, 6H), 3.17-3.14 (m, 4H), 2.51-2.45 (m, 6H). m/z: 501.0 (M+1)

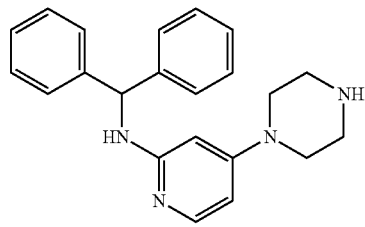 [SMILES: c1ccc(C(Nc2cc(N3CCNCC3)ccn2)c2ccccc2)cc1]

MBX 4022: 2-(benzhydrylamino)-4-(piperazin-2-yl)pyridine

Prepared in the same manner as MBX 3586, treating with piperazine instead of N-methylpiperazine. Light yellow solid, mp 135-139° C. Rf: 0.46 (86:13:1 CHCl$_3$:MeOH:NH$_3$). $^1$H NMR (CDCl$_3$, 300 MHz, ppm) 7.80 (m, 1H), 7.37-7.23 (m, 10H), 6.14-6.11 (m, 1H), 5.77-5.75 (m, 1H), 5.60-5.59 (m, 1H), 5.15 (m, 1H), 3.11-3.07 (m, 4H), 2.90-2.87 (m, 4H), 2.01 (br s, 1H). m/z: 345.2 (M+1)

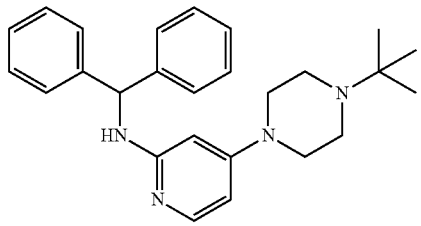 [SMILES: CC(C)(C)N1CCN(c2ccnc(NC(c3ccccc3)c3ccccc3)c2)CC1]

MBX 4023: 2-(benzhydrylamino)-4-[4-(tert-butyl)piperazin-2-yl]pyridine

Prepared in the same manner as MBX 3586, treating with N-tert-butyl-piperazine instead of N-methylpiperazine. Light pink solid, mp 67-70° C. Rf: 0.70 (86:13:1 CHCl$_3$:MeOH:NH$_3$). $^1$H NMR (CDCl$_3$, 300 MHz, ppm) 8.91-8.89 (m, 1H), 7.59-7.28 (m, 10H), 6.20-6.16 (m, 1H), 5.57 (m, 2H), 3.69 (m, 6H), 2.74-2.67 (m, 2H), 1.42 (s, 9H). m/z: 401.1 (M+1)

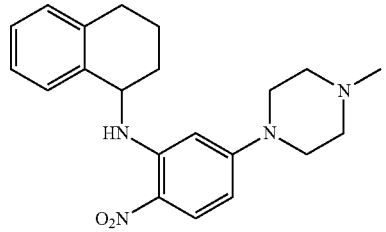 [SMILES: CN1CCN(c2ccc([N+](=O)[O-])c(NC3CCCc4ccccc43)c2)CC1]

MBX 4048: 2-[(1,2,3,4-tetrahydronaphthalen-1-yl)amino]-4-(4-methylpiperazin-1-yl)-1-nitrobenzene Step 1:
To a rbf of 2-bromo-4-fluoro-1-nitrobenzene (2.49 g, 11.36 mmol, 1 eq) in EtOH (30 mL) was added N-methylpiperazine (5.96 g, 56.82 mmol, 5 eq). The reaction was heated to reflux for 24 hours, after which the crude mixture was cooled, concentrated, adsorbed onto silica and purified on 40 g silica column (0-3% MeOH:DCM with 1% NH$_3$) to yield 1-(3-bromo-4-nitrophenyl)-4-methylpiperazine (2.95 g, 9.83 mmol, 87%).

$^1$H (CDCl$_3$): 8.03-7.99 (d, 1H), 7.08-7.07 (m, 1H), 6.79-6.75 (dd, 1H), 3.42-3.39 (m, 4H), 2.56-2.52 (m, 4H), 2.35 (s, 3H)

Step 2:
To a rbf of 1-(3-bromo-4-nitrophenyl)-4-methylpiperazine (0.045 g, 0.150 mmol, 1 eq), Pd$_2$(dba)$_3$-CHCl$_3$ (1 mol %), rac-BINAP (2 mol %), and NaOtBu (0.017 g, 0.180 mmol, 1.2 eq) was added anhydrous toluene (2.5 mL) and 1,2,3,4-tetrahydronaphthalen-1-amine (0.045 g, 0.150 mmol, 1 eq). The reaction was stirred under N$_2$ at 100° C. for 24 hours, after which the reaction was cooled, taken up in EtOAc, washed with water, dried (Na$_2$SO$_4$), and concentrated. The crude product was purified on HPLC (5-95% MeCN:H$_2$O with 0.1% TFA) to yield MBX 4048 (21 mg, 0.057 mmol, 38%). Yellow solid, mp 212-215° C. Rf: 0.75 (86:13:1 CHCl$_3$:MeOH:NH$_3$). $^1$H NMR (CDCl$_3$, 300 MHz, ppm) 8.67-8.65 (m, 1H), 8.15-8.12 (m, 1H), 7.26-7.17 (m, 4H), 6.21-6.18 (m, 1H), 6.12-6.11 (m, 1H), 4.79-4.77 (m, 1H), 3.74-3.58 (m, 6H), 2.85 (m, 6H), 2.07-1.96 (m, 5H). m/z: 367.2 (M+1)

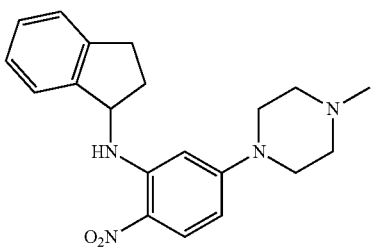 [SMILES: CN1CCN(c2ccc([N+](=O)[O-])c(NC3CCc4ccccc43)c2)CC1]

MBX 4049: 2-[(2,3-dihydro-1H-inden-1-yl)amino]-4-(4-methylpiperazin-1-yl)-1-nitrobenzene Prepared in the same manner as MBX 4048, treating with BrettPhos precatalyst instead of Pd$_2$(dba)$_3$-CHCl$_3$ and rac- BINAP. Yellow film, mp N/A. Rf: 0.25 (5% MeOH:DCM). $^1$H NMR (CDCl$_3$, 300 MHz, ppm) 8.64 (m, 1H), 8.16-8.13 (m, 1H), 7.32-7.26 (m, 4H), 6.25-6.17 (m, 2H), 5.14-5.09 (m, 1H), 3.61-3.49 (m, 6H), 3.12-2.90 (m, 4H), 2.86 (s, 3H), 2.68-2.62 (m, 1H), 2.09-2.02 (m, 1H). m/z: 353.1 (M+1)

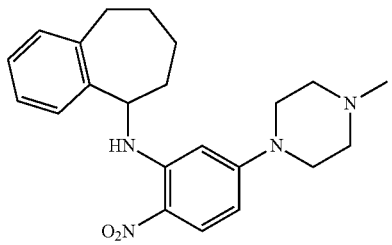 [SMILES: CN1CCN(c2ccc([N+](=O)[O-])c(NC3CCCCc4ccccc43)c2)CC1]

MBX 4050: 2-[(6,7,8,9-tetrahydro-5H-benzo[7]annulen-5-yl)amino]-4-(4-methylpiperazin-1-yl)-1-nitrobenzene Prepared in the same manner as MBX 4048, treating with BrettPhos precatalyst instead of Pd$_2$(dba)$_3$.CHCl$_3$ and rac-BINAP. Yellow film, mp N/A. Rf: 0.25 (5% MeOH:DCM). $^1$H NMR (CDCl$_3$, 300 MHz, ppm) 8.83-8.81 (m, 1H), 8.14-8.11 (d, 1H), 7.17-7.14 (m, 4H), 6.16-6.12 (m, 1H), 5.66-5.65 (s, 1H), 4.71-4.66 (m, 1H), 3.71-3.40 (m, 6H), 2.97-2.92 (m, 2H), 2.75 (s, 3H), 2.17-1.96 (m, 8H). m/z: 381.2 (M+1)

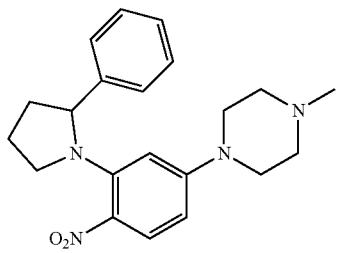 [SMILES: CN1CCN(c2ccc([N+](=O)[O-])c(N3CCCC3c3ccccc3)c2)CC1]

MBX 4051: 2-(2-phenylpyrrolidin-1-yl)-4-(4-methylpiperazin-1-yl)-1-nitrobenzene

Prepared in the same manner as MBX 4048, treating with BrettPhos precatalyst instead of Pd$_2$(dba)$_3$.CHCl$_3$ and rac-BINAP. Red/yellow oil, mp N/A. Rf: 0.28 (5% MeOH:DCM). $^1$H NMR (CDCl$_3$, 300 MHz, ppm) 7.77-7.74 (d, 1H), 7.34-7.21 (m, 5H), 6.18-6.15 (m, 1H), 5.97-5.96 (m, 1H), 4.80-4.75 (m, 1H), 3.95-3.88 (m, 1H), 3.70-3.42 (m, 3H), 3.28-3.27 (m, 3H), 2.90-2.84 (m, 2H), 2.77 (m, 3H), 2.53-2.50 (m, 2H), 2.12-2.10 (m, 1H), 1.91-1.90 (m, 2H). m/z: 367.1 (M+1)

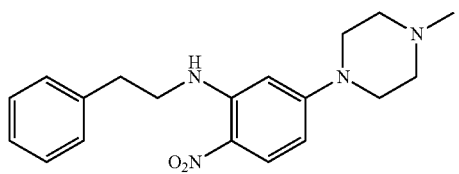 [SMILES: CN1CCN(c2ccc([N+](=O)[O-])c(NCCc3ccccc3)c2)CC1]

MBX 4052: 2-(phenethylamino)-4-(4-methylpiperazin-1-yl)-1-nitrobenzene

Prepared in the same manner as MBX 4048, treating with BrettPhos precatalyst instead of Pd$_2$(dba)$_3$.CHCl$_3$ and rac-BINAP. Red oil, mp N/A. Rf: 0.29 (5% MeOH:DCM). $^1$H NMR (CDCl$_3$, 300 MHz, ppm) 8.66-8.65 (m, 1H), 8.10-8.07 (m, 1H), 7.35-7.27 (m, 5H), 6.14-6.10 (m, 1H), 5.69 (m, 1H), 4.60-4.56 (m, 1H), 3.68-3.39 (m, 6H), 2.73 (s, 3H), 2.63 (s, 1H), 1.67-1.63 (m, 4H). m/z: 341.2 (M+1)

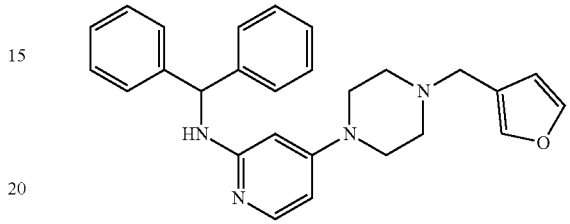

MBX 4053: 2-benzhydrylamino-4-[4-(furan-3-ylmethyl)piperazin-1-yl]pyridine

Procedure: To a vial of MBX 4022 (0.028 g, 0.0813 mmol, 1 eq), NaBH(OAc)$_3$ (0.047 g, 0.222 mmol, 2.7 eq) in THF (1 mL) was added AcOH (0.014 mL, 0.244 mmol, 3 eq) and furan-3-carbaldehyde (0.014 mL, 0.163 mmol, 2 eq). The reaction was stirred at r.t. for an hour, at which point the crude mixture was poured over sat. NaHCO$_3$ (10 mL), extracted with EtOAc (3×10 mL), dried (Na$_2$SO$_4$), filtered and concentrated. The crude product was purified with HPLC (5-95% MeCN:H$_2$O with 0.1% TFA) to yield MBX 4053 (8.1 mg, 0.019 mmol, 23%). Beige oil, mp N/A. Rf: 0.30 (5% MeOH:DCM). $^1$H NMR (CDCl$_3$, 300 MHz, ppm) 8.28 (m, 1H), 7.53-7.25 (m, 11H), 6.36 (s, 1H), 6.15-6.12 (m, 1H), 5.57-5.55 (d, 1H), 5.51-5.50 (m, 1H), 3.39 (s, 2H), 3.27-3.24 (m, 4H), 2.48-2.44 (m, 4H), 2.00 (s, 1H). m/z: 425.3 (M+1)

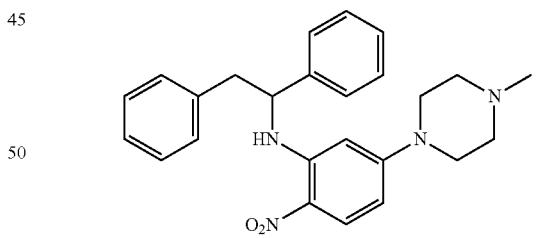

MBX 4090: 2-(1,2-diphenylethylamino)-4-(4-methylpiperazin-1-yl)-1-nitrobenzene

Prepared in the same manner as PPZ1, treating with 1,2-diphenylethanamine instead of benzhydrylamine. Yellow solid, mp 172-174° C. Rf: 0.66 (5:94:1 MeOH:DCM:NH$_3$). $^1$H NMR (CDCl$_3$, 300 MHz, ppm) 8.96-8.95 (m, 1H), 8.01-7.97 (d, 1H), 7.31-7.16 (m, 10H), 6.13-6.10 (m, 1H), 5.60 (m, 1H), 4.69-4.63 (m, 1H), 3.21-3.15 (m, 4H), 3.09-3.03 (m, 2H), 2.36-2.26 (m, 4H), 1.86 (s, 3H). m/z: 417.4 (M+1)

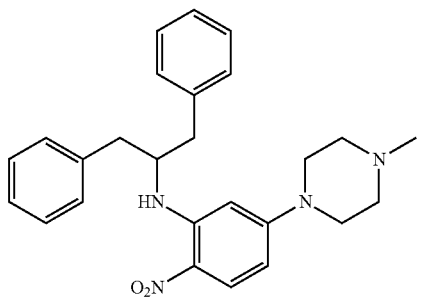 [SMILES: CN1CCN(c2ccc([N+](=O)[O-])c(NC(Cc3ccccc3)Cc3ccccc3)c2)CC1]

MBX 4091: 2-(1,3-diphenylpropan-2-ylamino)-4-(4-methylpiperazin-1-yl)-1-nitrobenzene Prepared in the same manner as PPZ1, treating with 1,3-diphenylpropan-2-amine instead of benzhydrylamine. Yellow solid, mp 164-166° C. Rf: 0.66 (5:94:1 MeOH:DCM:NH$_3$). $^1$H NMR (CDCl$_3$, 300 MHz, ppm) 8.65-8.62 (d, 1H), 8.02-7.98 (d, 1H), 7.30-7.19 (m, 10H), 6.15-6.11 (m, 1H), 5.68 (m, 1H), 4.01-3.95 (m, 1H), 3.27-3.26 (m, 4H), 3.02-2.85 (m, 4H), 2.49-2.46 (m, 4H), 2.34 (s, 3H). m/z: 431.5 (M+1)

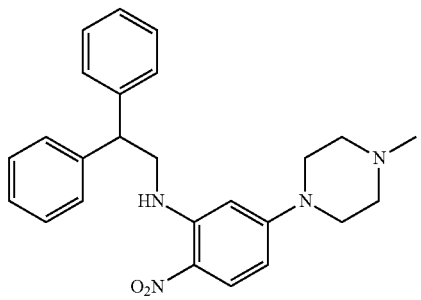 [SMILES: CN1CCN(c2ccc([N+](=O)[O-])c(NCC(c3ccccc3)c3ccccc3)c2)CC1]

MBX 4092: 2-(2,2-diphenylethylamino)-4-(4-methylpiperazin-1-yl)-1-nitrobenzene

Prepared in the same manner as PPZ1, treating with 2,2-diphenylethanamine instead of benzhydrylamine. Yellow solid, mp 146-147° C. Rf: 0.66 (5:94:1 MeOH:DCM:NH$_3$). $^1$H NMR (CDCl$_3$, 300 MHz, ppm) 8.39 (m, 1H), 8.03-8.00 (d, 1H), 7.34-7.22 (m, 10H), 6.22-6.18 (m, 1H), 5.90-5.89 (m, 1H), 4.40-4.35 (t, 1H), 3.87-3.83 (m, 2H), 3.40-3.37 (m, 4H), 2.53-2.50 (m, 4H), 2.34 (s, 3H). m/z: 417.1 (M+1)

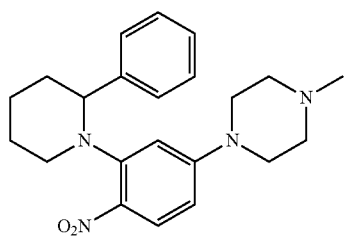 [SMILES: CN1CCN(c2ccc([N+](=O)[O-])c(N3CCCCC3c3ccccc3)c2)CC1]

MBX 4145: 4-(4-methylpiperazin-1-yl)-2-(2-phenylpiperidin-1-yl)-1-nitrobenzene

Prepared in the same manner as PPZ1, treating with 2-phenylpiperidine instead of benzhydrylamine. Red oil, mp N/A. Rf: 0.61 (10:89:1 MeOH:DCM:NH$_3$). $^1$H NMR (CDCl$_3$+1H-TFA, 300 MHz, ppm) 7.96-7.92 (d, 1H), 7.64 (s, 1H), 7.29-7.14 (m, 5H), 6.76-6.72 (m, 1H), 5.11-5.07 (m, 1H), 4.29-4.11 (m, 3H), 3.84-3.75 (m, 3H), 3.63-3.55 (t, 2H), 3.37-3.25 (m, 2H), 3.00 (s, 3H), 2.48-1.95 (m, 6H). m/z: 381.2 (M+1)

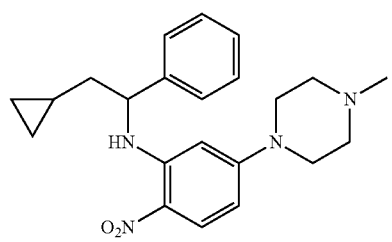 [SMILES: CN1CCN(c2ccc([N+](=O)[O-])c(NC(CC3CC3)c3ccccc3)c2)CC1]

MBX 4146: 2-[(2-cyclopropyl-1-phenylethyl)amino]-4-(4-methylpiperazin-1-yl)-1-nitrobenzene Prepared in the same manner as PPZ1, treating with 2-cyclopropyl-1-phenylethanamine instead of benzhydrylamine. Yellow solid, mp 137-139° C. Rf: 0.65 (10:89:1 MeOH:DCM:NH$_3$). $^1$H NMR (CDCl$_3$, 300 MHz, ppm) 9.01 (m, 1H), 8.07-8.03 (d, 1H), 7.34-7.23 (m, 5H), 6.18-6.13 (m, 1H), 5.67-5.66 (m, 1H), 4.54-4.52 (q, 1H), 3.24-3.07 (m, 4H), 3.07-2.37 (m, 4H), 2.27 (s, 3H), 1.86-1.80 (m, 2H), 0.56-0.51 (m, 3H), 0.20-0.15 (m, 2H). m/z: 381.2 (M+1)

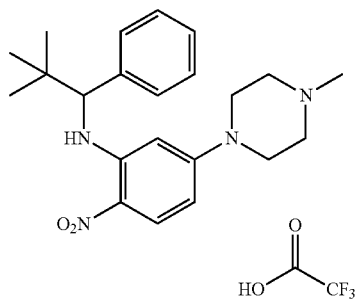 [SMILES: CN1CCN(c2ccc([N+](=O)[O-])c(NC(c3ccccc3)C(C)(C)C)c2)CC1 ; O=C(O)C(F)(F)F]

MBX 4147A: 2-[(2,2-dimethyl-1-phenylpropyl)amino]-4-(4-methylpiperazin-1-yl)-1-nitrobenzene
(1 TFA Salt)

Prepared in the same manner as PPZ1, treating with 2,2-dimethyl-1-phenylpropan-1-amine instead of benzhydrylamine. Yellow solid, mp 90-93° C. Rf: 0.67 (10:89:1 MeOH:DCM:NH$_3$). $^1$H NMR (CDCl$_3$, 300 MHz, ppm) 9.17-9.16 (m, 1H), 8.09-8.06 (m, 1H), 7.35-7.25 (m, 5H), 6.10-6.06 (m, 1H), 5.63-5.62 (m, 1H), 4.17-4.15 (m, 1H), 3.77-3.36 (m, 6H), 2.73 (s, 3H), 2.42-2.40 (m, 1H), 1.82-1.75 (m, 2H), 1.08 (s, 9H). m/z: 383.5 (M+1)

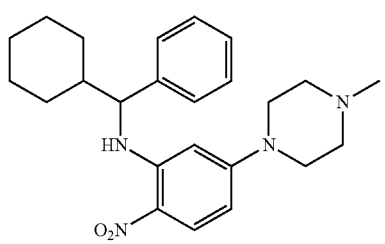 [SMILES: CN1CCN(c2ccc([N+](=O)[O-])c(NC(c3ccccc3)C3CCCCC3)c2)CC1]

MBX 4148: 2-{[cyclohexyl(phenyl)methyl]amino}-4-(4-methylpiperazin-1-yl)-1-nitrobenzene Prepared in the same manner as PPZ1, treating with cyclohexyl(phenyl)methanamine instead of benzhydrylamine. Yellow-red oil, mp N/A. Rf: 0.75 (10:89:1 MeOH:DCM:NH$_3$). $^1$H NMR (CDCl$_3$, 300 MHz, ppm) 8.97-8.95 (m, 1H), 8.08-8.04 (d, 1H), 7.35-7.22 (m, 5H), 6.11-6.07 (m, 1H), 5.68-5.67 (m, 1H), 4.24-4.20 (t, 1H), 3.49-3.40 (m, 6H), 2.74 (s, 3H), 1.98-1.94 (m, 1H), 1.80-1.57 (m, 6H), 1.25-1.11 m, 6H). m/z: 383.5 (M+1)

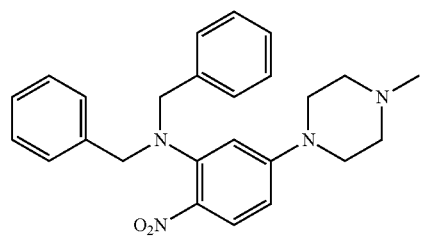 [SMILES: CN1CCN(c2ccc([N+](=O)[O-])c(N(Cc3ccccc3)Cc3ccccc3)c2)CC1]

MBX 4149: 2-(dibenzylamino)-4-(4-methylpiperazin-1-yl)-1-nitrobenzene

Prepared in the same manner as PPZ1, treating with dibenzylamine instead of benzhydrylamine. Red oil, mp N/A. Rf: 0.72 (10:89:1 MeOH:DCM:NH$_3$). $^1$H NMR (CDCl$_3$, 300 MHz, ppm) 7.94-7.91 (d, 1H), 7.32-7.21 (m, 10H), 6.40-6.36 (m, 1H), 6.20-6.19 (m, 1H), 4.25 (s, 4H), 3.57-3.41 (m, 6H), 2.80 (s, 3H), 1.25 (m, 2H). m/z: 417.2 (M+1)

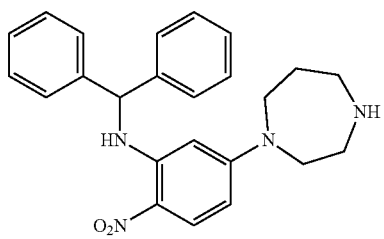 [SMILES: O=[N+]([O-])c1ccc(N2CCCNCC2)cc1NC(c1ccccc1)c1ccccc1]

MBX 4150: 2-(benzhydrylamino)-4-(1,4-diazepan-1-yl)-1-nitrobenzene

Prepared in the same manner as PPZ1, treating with homopiperazine instead of N-methylpiperazine. Yellow solid, mp 144-146° C. Rf: 0.56 (10:89:1 MeOH:DCM:NH$_3$). $^1$H NMR (CDCl$_3$, 300 MHz, ppm) 9.01-8.99 (m, 1H), 8.09-8.06 (d, 1H), 7.40-7.26 (m, 10H), 6.10-6.06 (m, 1H), 5.63-5.61 (m, 1H), 5.56-5.55 (m, 1H), 4.16-4.08 (m, 4H), 3.45-3.36 (m, 4H), 1.59-1.55 (m, 2H). m/z: 403.4 (M+1)

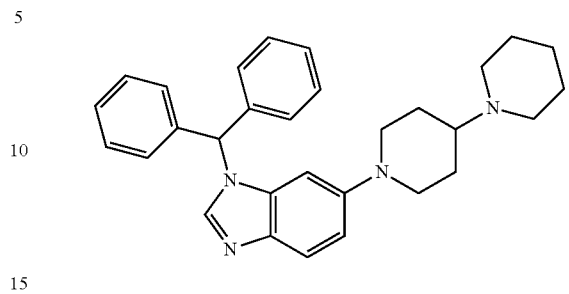

MBX 4151: 6-[(1,4'-bipiperidin)-1'-yl]-1-benzhydryl-1H-benzo[d]imidazole

Procedure: In a 10 mL of reaction tube, MBX 3747 (15 mg, 0.032 mmol, 1.0 equiv), 88% formic acid (0.4 mL, 0.08 M), HCO$_2$Na (7 mg, 0.10 mmol, 30 equiv) and Pd/C (5%, 14 mg, 20 mol %) were mixed at room temperature. The tube was sealed and heated for 2 h at 90° C. After the reaction was done, the reaction mixture was filtered through a pad of celite and washed with formic acid. The filtrate was concentrated and purified by HPLC (MeCN:H$_2$O with 0.1% TFA) to provide MBX 4151 (2.5 mg, 17%). Sticky yellow solid, mp N/A. Rf: 0 (EtOAc). $^1$H NMR (MeOD, 300 MHz, ppm) 9.05 (s, 1H), 7.67 (s, 1H), 7.35-7.23 (m, 8H), 7.14-7.11 (m, 4H), 6.24 (s, 1H), 3.60-3.50 (m, 2H), 3.40-3.30 (m, 1H), 3.10-2.90 (m, 4H), 2.90-2.80 (m, 2H), 2.10-1.50 (m, 10H). m/z: 451.3 (M+1)

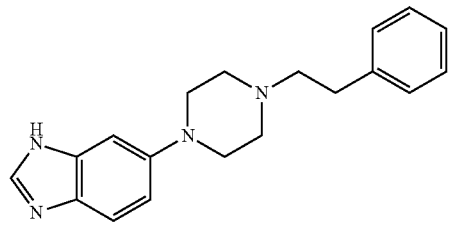 [SMILES: c1ccc(CCN2CCN(c3ccc4nc[nH]c4c3)CC2)cc1]

MBX 4152: 6-(4-phenethylpiperazin-1-yl)-1H-benzo[d]imidazole

Prepared in the same manner as MBX 4164, produced as a side product. Sticky brown solid, mp N/A. Rf: 0 (EtOAc). $^1$H NMR (MeOD, 300 MHz, ppm) 9.22 (s, 1H), 7.78 (d, 1H), 7.47-7.30 (m, 7H), 4.00-3.40 (m, 10H), 3.20-3.10 (t, 2H). m/z: 307.3 (M+1)

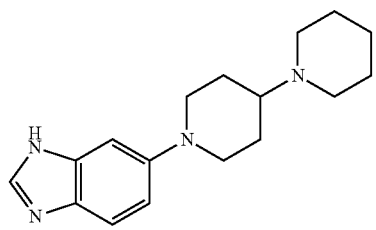 [SMILES: c1nc2ccc(N3CCC(N4CCCCC4)CC3)cc2[nH]1]

MBX 4153: 6-[(1,4'-bipiperidin)-1'-yl]-1H-benzo[d]imidazole

Prepared in the same manner as MBX 4151, produced as a side product. Pink oil, mp N/A. Rf: 0 (EtOAc). $^1$H NMR (MeOD, 300 MHz, ppm) 9.19 (s, 1H), 7.72 (d, 1H), 7.43 (dd, 1H), 7.28 (d, 1H), 4.00-3.96 (m, 2H), 3.61-3.52 (m, 2H), 3.48-3.36 (m, 1H), 3.15-3.02 (m, 2H), 2.97-2.89 (m, 2H), 2.28-2.20 (m, 2H), 2.04-1.76 (m, 7H), 1.61-1.53 (m, 1H). m/z: 285.2 (M+1)

MBX 4158: 1-benzhydryl-7-fluoro-6-(4-methylpiperazin-1-yl)-1H-benzo[d]imidazole

Prepared in the same manner as MBX 4165, cyclizing MBX 3732 instead of MBX 3558. Brown solid, mp 123-128° C. Rf: 0 (EtOAc). $^1$H NMR (MeOD, 300 MHz, ppm) 7.60-7.10 (m, 14H), 3.60-3.40 (m, 4H), 3.40-3.10 (m, 4H), 2.91 (s, 3H). m/z: 401.5 (M+1)

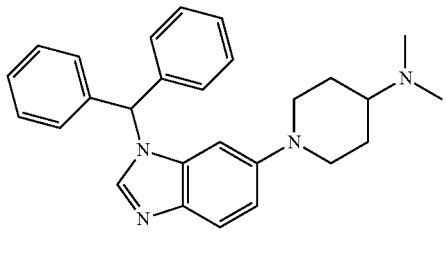

MBX 4159: 1-benzhydryl-6-[4-(dimethylamino)piperidin-1-yl]-1H-benzo[d]imidazole

Prepared in the same manner as MBX 4165, cyclizing MBX 3749 instead of MBX 3558. Brown solid, mp 110-115° C. Rf: 0 (EtOAc). $^1$H NMR (MeOD, 300 MHz, ppm) 8.71 (s, 1H), 7.70 (d, 1H), 7.52-7.20 (m, 12H), 6.87 (s, 1H), 3.80 (b, 2H), 2.90-2.67 (m, 9H), 2.12 (m, 2H), 1.77-1.60 (m, 2H). m/z: 411.2 (M+1)

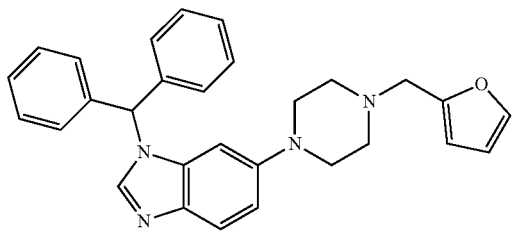 [SMILES: c1ccc(C(c2ccccc2)n2cnc3ccc(N4CCN(Cc5ccco5)CC4)cc32)cc1]

MBX 4154: 1-benzhydryl-6-[4-(furan-2-ylmethyl)piperazin-1-yl]-1H-benzo[d]imidazole Prepared in the same manner as MBX 4165, cyclizing MBX 3574 instead of MBX 3558. Brown solid, mp 50-60° C. Rf: 0 (EtOAc). $^1$H NMR (MeOD, 300 MHz, ppm) 8.70 (s, 1H), 7.77 (d, 1H), 7.71-7.70 (m, 1H), 7.50-7.39 (m, 7H), 7.32-7.25 (m, 5H), 7.01 (d, 1H), 6.77 (d, 1H), 6.58-6.56 (m, 1H), 4.50 (s, 2H), 3.43-3.38 (m, 8H). m/z: 449.3 (M+1)

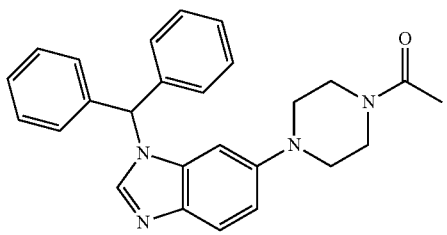

MBX 4160: 1-benzhydryl-6-(4-acetylpiperazin-1-yl)-1H-benzo[d]imidazole

Prepared in the same manner as MBX 4165, cyclizing MBX 3544 instead of MBX 3558. Brown solid, mp 99-106° C. Rf: 0 (EtOAc). $^1$H NMR (MeOD, 300 MHz, ppm) 8.73 (s, 1H), 7.70 (d, 1H), 7.50-7.20 (m, 12H), 6.87 (s, 1H), 3.70-3.60 (m, 4H), 3.20-3.00 (m, 4H), 2.10 (s, 3H). m/z: 411.3 (M+1)

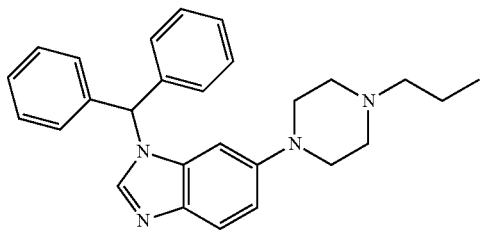 [SMILES: CCCN1CCN(c2ccc3ncn(C(c4ccccc4)c4ccccc4)c3c2)CC1]

MBX 4155: 1-benzhydryl-6-(4-propylpiperazin-1-yl)-1H-benzo[d]imidazole

Prepared in the same manner as MBX 4165, cyclizing MBX 3566 instead of MBX 3558. Brown solid, mp 86-90° C. Rf: 0 (EtOAc). $^1$H NMR (MeOD, 300 MHz, ppm) 8.58 (s, 1H), 7.67 (d, 1H), 7.38-7.29 (m, 7H), 7.22-7.15 (m, 5H), 6.90 (s, 1H), 3.80-3.30 (m, 4H), 3.20-2.80 (m, 6H), 1.76-1.64 (m, 2H), 0.96 (t, 3H). m/z: 411.2 (M+1)

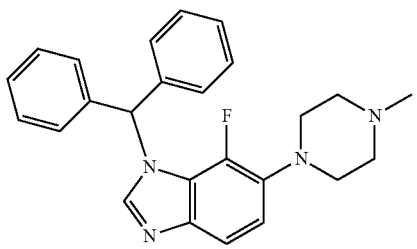 [SMILES: CN1CCN(c2ccc3ncn(C(c4ccccc4)c4ccccc4)c3c2F)CC1]

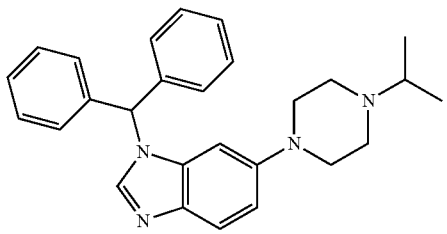 [SMILES: CC(C)N1CCN(c2ccc3ncn(C(c4ccccc4)c4ccccc4)c3c2)CC1]

MBX 4161: 1-benzhydryl-6-(4-isopropylpiperazin-1-yl)-1H-benzo[d]imidazole

Prepared in the same manner as MBX 4165, cyclizing MBX 3561 instead of MBX 3558. Brown solid, mp N/A. Rf: 0 (EtOAc). $^1$H NMR (MeOD, 300 MHz, ppm) 8.54 (s, 1H), 7.74 (d, 1H), 7.52-7.20 (m, 12H), 6.96 (s, 1H), 3.85-3.75 (m, 1H), 3.65-3.50 (m, 4H), 3.40-3.30 (m, 2H), 3.10-2.90 (m, 2H), 1.41 (s, 3H), 1.38 (s, 3H). m/z: 411.2 (M+1)

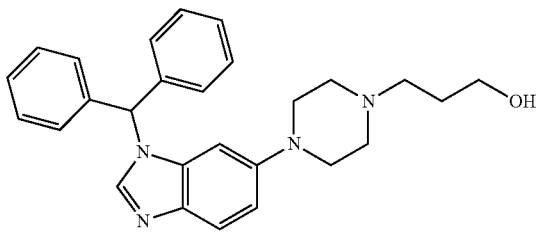 [SMILES: OCCCN1CCN(c2ccc3ncn(C(c4ccccc4)c4ccccc4)c3c2)CC1]

MBX 4162: 1-benzhydryl-6-[4-(3-hydroxypropyl)piperazin-1-yl]-1H-benzoldimidazole Prepared in the same manner as MBX 4165, cyclizing MBX 3610 instead of MBX 3558. Brown solid, mp 98-109° C. Rf: 0 (EtOAc). $^1$H NMR (MeOD, 300 MHz, ppm) 8.30 (s, 1H), 7.37 (d, 1H), 7.18-6.80 (m, 12H), 6.60 (s, 1H), 3.00-2.80 (m, 12H), 1.70-1.50 (m, 2H). m/z: 427.3 (M+1)

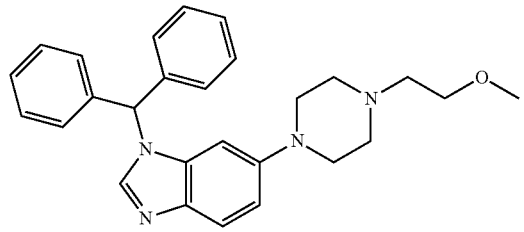 [SMILES: COCCN1CCN(c2ccc3ncn(C(c4ccccc4)c4ccccc4)c3c2)CC1]

MBX 4163: 1-benzhydryl-6-[4-(2-methoxyethyl)piperazin-1-yl]-1H-benzo[d]imidazole Prepared in the same manner as MBX 4165, cyclizing MBX 3591 instead of MBX 3558. Brown solid, mp N/A. Rf: 0 (EtOAc). $^1$H NMR (MeOD, 300 MHz, ppm) 8.56 (s, 1H), 7.74 (d, 1H), 7.50-7.20 (m, 12H), 6.87 (s, 1H), 3.80-3.70 (m, 2H), 3.70-3.30 (m, 13H). m/z: 427.2 (M+1)

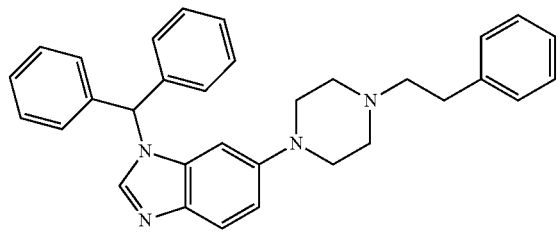 [SMILES: c1ccc(CCN2CCN(c3ccc4ncn(C(c5ccccc5)c5ccccc5)c4c3)CC2)cc1]

MBX 4164: 1-benzhydryl-6-(4-phenethylpiperazin-1-yl)-1H-benzo[d]imidazole

Procedure: In a 10 mL of reaction tube, MBX 3623 (10 mg, 0.02 mmol, 1.0 equiv), 88% formic acid (0.04 mL, 0.5 M) and HCl (5 N, 0.008 mL, 0.04 mmol, 2.0 equiv) were mixed at room temperature and iron powder (7 mg, 0.12 mmol, 6.0 equiv) was added. The tube was sealed and heated for 2 h at 90° C. The reaction mixture was filtered through a syringe filter and concentrated. The residue was purified by HPLC (MeCN:H$_2$O with 0.1% TFA) to provide MBX 4164 (1.2 mg, 13%). Brown solid, mp 75-82° C. Rf: 0 (EtOAc). $^1$H NMR (MeOD, 300 MHz, ppm) 8.78 (s, 1H), 7.79 (d, 1H), 7.50-7.20 (m, 17H), 7.02 (s, 1H), 4.00-3.50 (m, 4H), 3.50-3.40 (m, 2H), 3.40-3.20 (m, 4H), 3.20-3.00 (m, 2H). m/z: 473.3 (M+1)

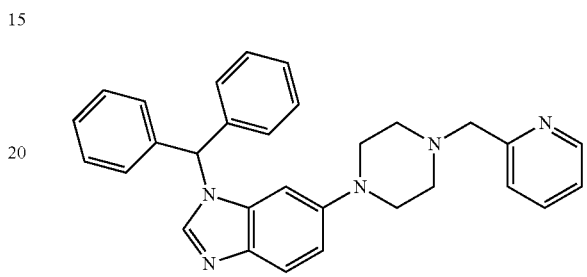

MBX 4165: 1-benzhydryl-6-[4-(pyridin-2-ylmethyl)piperazin-1-yl]-1H-benzo[d]imidazole Procedure: In a 10 mL of reaction tube, MBX 3558 (30 mg, 0.06 mmol, 1.0 equiv), 88% formic acid (0.12 mL, 50 equiv), NH$_4$Cl (34 mg, 0.63 mmol, 10 equiv) and iron powder (35 mg, 0.63 mmol, 10 equiv) were mixed in iPrOH (0.3 mL) at room temperature. The tube was sealed and heated for 18 h at 80° C. The reaction mixture was cooled, filtered through a syringe filter and concentrated. The residue was purified by HPLC (MeCN:H$_2$O with 0.1% TFA) to provide MBX 4165 (23 mg, 94%). Brown solid, mp 75-81° C. Rf: 0 (EtOAc). $^1$H NMR (MeOD, 300 MHz, ppm) 8.80 (s, 1H), 8.70 (d, 1H), 7.96 (t, 1H), 7.79 (d, 1H), 7.56 (d, 1H), 7.50-7.40 (m, 8H), 7.40-7.20 (m, 5H), 7.02 (s, 1H), 4.55 (s, 2H), 3.60-3.40 (m, 8H). m/z: 460.4 (M+1)

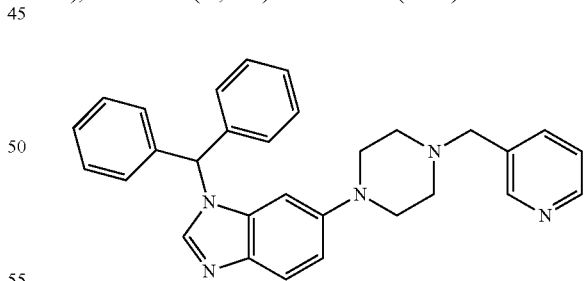

MBX 4166: 1-benzhydryl-6-[4-(pyridin-3-ylmethyl)piperazin-1-yl]-1H-benzo[d]imidazole Prepared in the same manner as MBX 4165, cyclizing MBX 3568 instead of MBX 3558. Brown solid, mp 60-64° C. Rf: 0 (EtOAc). $^1$H NMR (MeOD, 300 MHz, ppm) 8.84-8.69 (m, 3H), 8.28 (d, 1H), 7.77-7.70 (m, 2H), 7.50-7.40 (m, 7H), 7.35-7.25 (m, 5H), 6.98 (s, 1H), 4.51 (s, 2H), 3.50-3.35 (m, 8H). m/z: 460.2 (M+1)

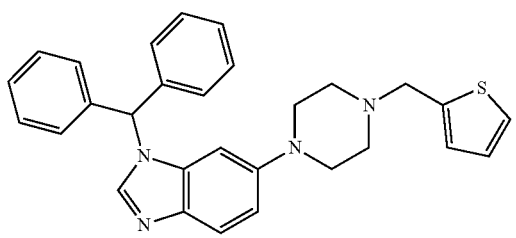 [SMILES: c1ccc(C(c2ccccc2)n2cnc3ccc(N4CCN(Cc5cccs5)CC4)cc32)cc1]

MBX 4167: 1-benzhydryl-6-[4-(thiophen-2-ylmethyl)piperazin-1-yl]-1H-benzo[d]imidazole Prepared in the same manner as MBX 4165, cyclizing MBX 3576 instead of MBX 3558. Brown solid, mp 100-104° C. Rf: 0 (EtOAc). ¹H NMR (MeOD, 300 MHz, ppm) 8.77 (s, 1H), 7.77 (d, 1H), 7.66 (d, 1H), 7.50-7.25 (m, 13H), 7.18-7.15 (m, 1H), 7.00 (s, 1H), 4.66 (s, 2H), 3.50-3.35 (m, 8H). m/z: 465.3 (M+1)

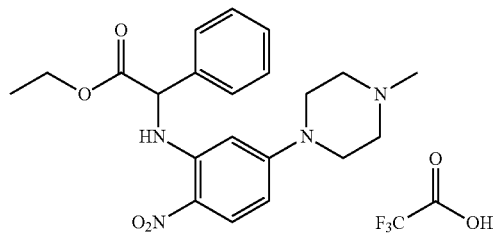

MBX 4172A: 2-[(2-ethoxy-2-oxo-1-phenylethyl)amino]-4-(4-methylpiperazin-1-yl)-1-nitrobenzene (TFA Salt)

Prepared in the same manner as PPZ1, treating with ethyl 2-amino-2-phenylacetate hydrochloride instead of benzhydrylamine. Yellow oil, mp N/A. Rf: 0.55 (10:89:1 MeOH:DCM:NH₃). ¹H NMR (CDCl₃, 300 MHz, ppm) 9.38-9.36 (m, 1H), 8.10-8.07 (d, 1H), 7.49-7.46 (m, 2H), 7.41-7.34 (m, 3H), 6.16-6.15 (m, 1H), 5.63-5.62 (m, 1H), 5.13-5.12 (m, 1H), 4.31-4.16 (m, 2H), 3.78-3.43 (m, 8H), 2.67 (s, 3H), 1.26-1.21 (t, 3H). m/z: 399.3 (M+1)

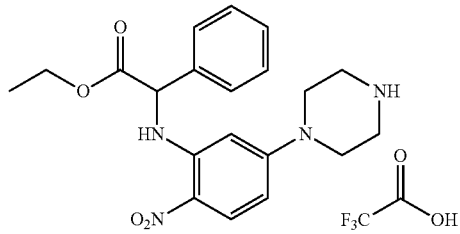

MBX 4173A: 2-[(2-ethoxy-2-oxo-1-phenylethyl)amino]-4-(piperazin-1-yl)-1-nitrobenzene (TFA Salt)

Prepared in the same manner as PPZ1, treating with ethyl 2-amino-2-phenylacetate hydrochloride instead of benzhydrylamine and piperazine instead of N-methyl piperazine. Yellow solid, mp N/A. Rf: 0.36 (10:89:1 MeOH:DCM:NH₃). ¹H NMR (CDCl₃, 300 MHz, ppm) 9.80 (bs, 1H), 9.64-9.58 (m, 1H), 8.14-8.11 (d, 1H), 7.50-7.47 (m, 2H), 7.41-7.36 (m, 3H), 6.20-6.16 (m, 1H), 5.68 (m, 1H), 5.15 (m, 1H), 4.30-4.16 (m, 2H), 3.78-3.35 (m, 4H), 3.23-3.18 (m, 4H), 1.23 (t, 3H). m/z: 385.4 (M+1)

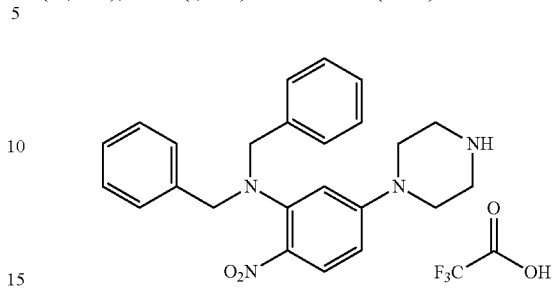

MBX 4174A: 2-(dibenzylamino)-4-(piperazin-1-yl)-1-nitrobenzene (TFA Salt)

Step 1:
To a vial of 2,4-difluoronitrobenzene (0.03 g, 0.188 mmol, 1 eq) in TEA (0.1 mL, 3.8M) was added dibenzylamine (0.041 g, 0.207 mmol, 1.1 eq). The reaction was stirred at 120° C. for six hours, at which point an additional 0.4 mL TEA was added. After 45 minutes, the reaction was cooled, taken up in EtOAc (5 mL), washed with sat. aq. NH₄Cl (2×10 mL), H₂O (10 mL), and aq. NaHCO₃ (10 mL). The organic layer was dried (Na₂SO₄), filtered and concentrated. The crude product was purified with HPLC (MeCN:H₂O with 0.1% TFA) to yield N,N-dibenzyl-5-fluoro-2-nitroaniline (0.0327 g, 55%).

Step 2:
MBX 4147A prepared in the same manner as PPZ1 (General Method B), starting with N,N-dibenzyl-5-fluoro-2-nitroaniline and treating with piperazine instead of N-methylpiperazine. Yellow oil, mp N/A. Rf: 0.65 (10:89:1 MeOH:DCM:NH₃). ¹H NMR (DMSO, 300 MHz, ppm) 8.67-8.66 (m, 1H), 7.87-7.84 (d, 1H), 7.34-7.23 (m, 10H), 6.61-6.57 (d, 1H), 6.54 (s, 1H), 4.27 (s, 4H), 3.45-3.44 (m, 4H), 3.14-3.12 (m, 4H). m/z: 403.1 (M+1)

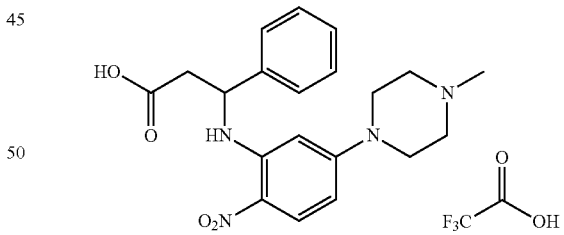

MBX 4175A: 2-[(2-carboxy-1-phenylethyl)amino]-4-(4-methylpiperazin-1-yl)-1-nitrobenzene (TFA Salt)

Step 1:
To a vial of 2,4-difluoronitrobenzene (0.028 g, 0.174 mmol, 1 eq) in DCM (1 mL) was added ethyl 3-amino-3-phenylpropanoate hydrochloride (0.040 g, 0.174 mmol, 1 eq) and TEA (0.05 mL, 2 eq). The reaction was stirred at r.t. for 18 h, then heated to 60° C. for 48 h. The reaction was cooled, concentrated and used for the next step without further purification.

Step 2:

The crude product was taken up in THF and H₂O (1:1, 2 mL) and LiOH (0.037 g, 5 eq) was added. The reaction was stirred at r.t. for 18 h, quenched with HCl (1N, 10 mL), extracted with EtOAc (3×10 mL), dried (Na₂SO₄), filtered and concentrated. The crude product was purified with HPLC (MeCN:H₂O with 0.1% TFA) to yield 3-((5-fluoro-2-nitrophenyl)amino)-3-phenylpropanoic acid (24 mg, 45%).

Step 3:

Prepared in the same manner as PPZ1, starting with the intermediate from Step 2. Yellow solid, mp 205-206° C. Rf: 0.10 (10:89:1 MeOH:DCM:NH₃). ¹H NMR (MeOD, 300 MHz, ppm) 8.05-8.02 (d, 1H), 7.45-7.42 (m, 2H), 7.38-7.33 (m, 2H), 7.29-7.26 (m, 1H), 6.38-6.34 (m, 1H), 5.96-5.95 (m, 1H), 5.12-5.07 (m, 1H), 3.53-3.36 (m, 4H), 3.14-3.12 (m, 4H), 2.91-2.89 (m, 2H), 2.79 (s, 3H). m/z: 385.0 (M+1)

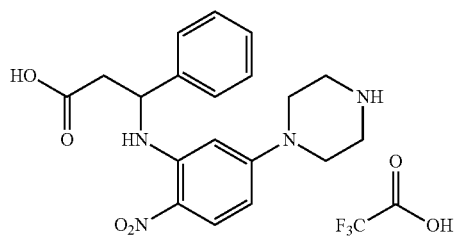

MBX 4176A: 2-[(2-carboxy-1-phenylethyl)amino]-4-(piperazin-1-yl)-1-nitrobenzene (TFA Salt)

Prepared in the same manner as MBX 4175A, treating with piperazine instead of N-methylpiperazine. Yellow solid, mp 207-208° C. Rf: 0.04 (10:89:1 MeOH:DCM:NH₃). ¹H NMR (MeOD, 300 MHz, ppm) 8.06-8.03 (d, 1H), 7.45-7.42 (m, 2H), 7.38-7.33 (m, 2H), 7.29-7.26 (m, 1H), 6.38-6.34 (m, 1H), 5.98-5.97 (m, 1H), 5.12-5.08 (t, 1H), 3.54-3.39 (m, 4H), 3.24-3.18 (m, 4H), 2.92-2.90 (m, 2H). m/z: 371.0 (M+1)

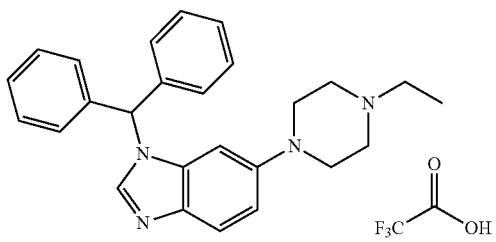 [SMILES: CCN1CCN(c2ccc3ncn(C(c4ccccc4)c4ccccc4)c3c2)CC1 ; O=C(O)C(F)(F)F]

MBX 4177A: 1-benzhydryl-6-(4-ethylpiperazin-1-yl)-1H-benzo[d]imidazole (TFA Salt)

Prepared in the same manner as MBX 3587, cyclizing MBX 3557 instead of Boc-protected MBX 3556. Clear oil, mp N/A. Rf: 0.33 (10:89:1 MeOH:DCM:NH₃). ¹H NMR (CDCl₃, 300 MHz, ppm) 8.05 (s, 1H), 7.93-7.90 (d, 1H), 7.44-7.43 (m, 6H), 7.18-7.10 (m, 5H), 6.79 (s, 1H), 6.58 (s, 1H), 3.69-3.66 (m, 2H), 3.49-3.29 (m, 4H), 3.17-3.10 (q, 2H), 2.96-2.90 (m, 2H), 1.42-1.37 (t, 3H). m/z: 397.2 (M+1)

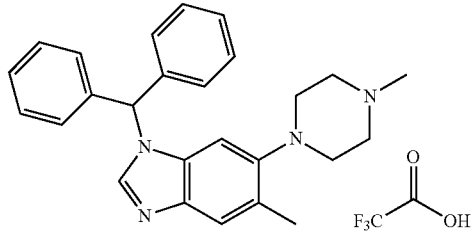

MBX 4178A: 1-benzhydryl-5-methyl-6-(4-methylpiperazin-1-yl)-1H-benzo[d]imidazole (TFA Salt)

Prepared in the same manner as MBX 3587, cyclizing MBX 3730 instead of Boc-protected MBX 3556. Clear oil, mp N/A. Rf: 0.31 (10:89:1 MeOH:DCM:NH₃). ¹H NMR (CDCl₃, 300 MHz, ppm) 8.05 (s, 1H), 7.86 (s, 1H), 7.44-7.42 (m, 6H), 7.18-7.15 (m, 4H), 6.82-6.81 (d, 2H), 3.62-3.59 (d, 2H), 3.16-3.11 (m, 2H), 3.02-3.00 (m, 4H), 2.87 (s, 3H), 2.40 (s, 3H). m/z: 397.1 (M+1)

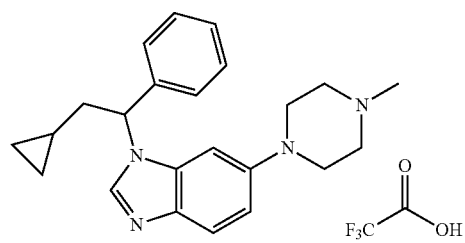

MBX 4179A: 1-(2-cyclopropyl-1-phenylethyl)-6-(4-methylpiperazin-1-yl)-1H-benzo[d]imidazole (TFA Salt)

Prepared in the same manner as MBX 3587, cyclizing MBX 4146 instead of Boc-protected MBX 3556. Clear oil, mp N/A. Rf: 0.31 (10:89:1 MeOH:DCM:NH₃). ¹H NMR (CDCl₃, 300 MHz, ppm) 8.91 (s, 1H), 7.85-7.82 (d, 1H), 7.43-7.27 (m, 6H), 7.1307.10 (m, 1H), 6.74-6.73 (m, 1H), 5.60-5.55 (t, 1H), 3.49-3.30 (m, 5H), 2.88 (s, 3H), 2.323-2.27 (t, 2H), 0.61-0.56 (m, 1H), 0.54-0.50 (m, 2H), 0.17-0.13 (m, 2H). m/z: 361.3 (M+1)

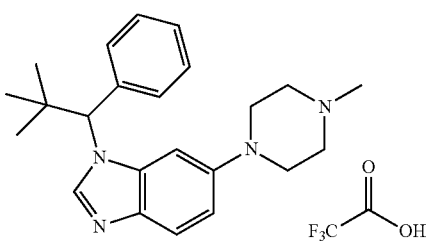

MBX 4180A: 1-(2,2-dimethyl-1-phenylpropyl)-6-(4-methylpiperazin-1-yl)-1H-benzo[d]imidazole (TFA Salt)

Prepared in the same manner as MBX 3587, cyclizing MBX 4147A instead of Boc-protected MBX 3556. Off-white solid, mp N/A. Rf: 0.20 (10:89:1 MeOH:DCM:NH$_3$). $^1$H NMR (CDCl$_3$, 300 MHz, ppm) 9.21 (s, 1H), 7.86-7.83 (d, 1H), 7.39-7.36 (m, 5H), 7.14-7.13 (m, 1H), 7.11-7.10 (d, 1H), 6.91 (m, 1H), 5.27 (s, 1H), 3.89-3.30 (m, 6H), 3.29-3.05 (m, 2H), 2.62 (s, 3H), 1.18 (s, 9H). m/z: 363.3 (M+1)

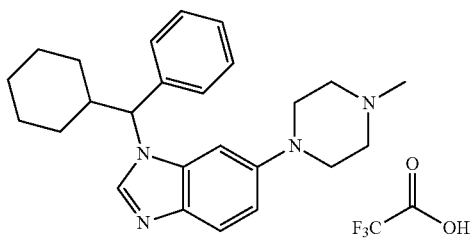

MBX 4181A: 1-[cyclohexyl(phenyl)methyl]-6-(4-methylpiperazin-1-yl)-1H-benzo[d]imidazole (TFA Salt)

Prepared in the same manner as MBX 3587, cyclizing MBX 4148 instead of Boc-protected MBX 3556. Yellow oil, mp N/A. Rf: 0.20 (10:89:1 MeOH:DCM:NH$_3$). $^1$H NMR (MeOD, 300 MHz, ppm) 9.59 (s, 1H), 7.71-7.68 (d, 1H), 7.58-7.55 (m, 2H), 7.47-7.36 (m, 5H), 5.56-5.52 (d, 1H), 4.10-3.31 (m, 8H), 3.00 (s, 3H), 2.69-2.57 (m, 1H), 1.78-1.74 (m, 3H), 1.56-1.51 (m, 2H), 1.41-1.10 (m, 5H). m/z: 389.4 (M+1)

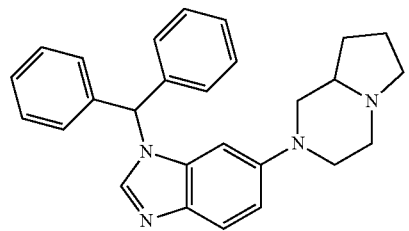 [SMILES: c1ccc(C(c2ccccc2)n2cnc3ccc(N4CCN5CCCC5C4)cc32)cc1]

MBX 4210: 1-benzhydryl-6-(hexahydropyrrolo[1,2-a]pyrazin-2(1H)-yl)-1H-benzo[d]imidazole Prepared in the same manner as MBX 3587, cyclizing MBX 3691 instead of Boc-protected MBX 3556. Yellow oil, mp N/A. Rf: 0.62 (10:89:1 MeOH:DCM:NH$_3$). $^1$H NMR (CDCl$_3$, 300 MHz, ppm) 8.36 (s, 1H), 7.88-7.85 (d, 1H), 7.47-7.30 (m, 6H), 7.22-7.19 (m, 5H), 6.93-6.88 (m, 1H), 6.76-6.62 (m, 1H), 4.11-3.44 (m, 4H), 3.40-3.25 (m, 4H), 3.04-2.82 (m, 1H), 2.28-2.18 (m, 4H). m/z: 409.1 (M+1)

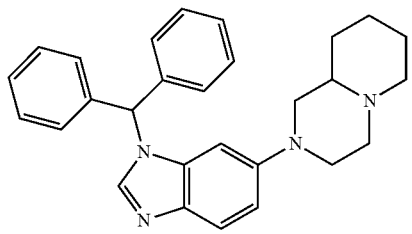 [SMILES: c1ccc(C(c2ccccc2)n2cnc3ccc(N4CCN5CCCCC5C4)cc32)cc1]

MBX 4211: 2-(1-benzhydryl-1H-benzo[d]imidazol-6-yl)octahydro-1H-pyrido[1,2-a]pyrazine Prepared in the same manner as MBX 3587, cyclizing MBX 3692 instead of Boc-protected MBX 3556. Yellow oil, mp N/A. Rf: 0.62 (10:89:1 MeOH:DCM:NH$_3$). $^1$H NMR (CDCl$_3$, 300 MHz, ppm) 8.02 (s, 1H), 7.88-7.85 (d, 1H), 7.44-7.41 (m, 6H), 7.18-7.07 (m, 5H), 6.80 (s, 1H), 6.56 (m, 1H), 3.66-3.38 (m, 4H), 3.33-2.75 (m, 4H), 2.66-2.58 (m, 1H), 2.04-1.83 (m, 5H), 1.54-1.50 (m, 1H). m/z: 423.0 (M+1)

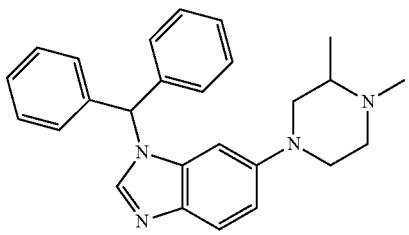 [SMILES: CC1CN(c2ccc3ncn(C(c4ccccc4)c4ccccc4)c3c2)CCN1C]

MBX 4212: 1-benzhydryl-6-(3,4-dimethylpiperazin-1-yl)-1H-benzo[d]imidazole

Prepared in the same manner as MBX 3587, cyclizing MBX 3693 instead of Boc-protected MBX 3556. Colorless oil, mp N/A. Rf: 0.63 (10:89:1 MeOH:DCM:NH$_3$). $^1$H NMR (CDCl$_3$, 300 MHz, ppm) 8.02 (s, 1H), 7.86 (d, 1H), 7.44-7.40 (m, 6H), 7.19-7.15 (m, 4H), 7.10-7.09 (d, 1H), 6.79 (s, 1H), 6.57 (m, 1H), 3.72-3.68 (m, 1H), 3.48-3.21 (m, 3H), 3.16-3.13 (m, 2H), 3.00-2.94 (m, 1H), 2.85-2.62 (s, 3H), 1.52-1.47 (m, 3H). m/z: 396.9 (M+1)

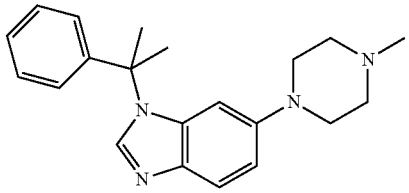 [SMILES: CN1CCN(c2ccc3ncn(C(C)(C)c4ccccc4)c3c2)CC1]

MBX 4213: 6-(4-methylpiperazin-1-yl)-1-(2-phenylpropan-2-yl)-1H-benzo[d]imidazole Prepared in the same manner as MBX 3587, cyclizing MBX 3741 instead of Boc-protected MBX 3556. Colorless oil, mp N/A. Rf: 0.60 (10:89:1 MeOH:DCM:NH$_3$). $^1$H NMR (CDCl$_3$, 300 MHz, ppm) 9.18 (s, 1H), 7.85-7.82 (d, 1H), 7.85-7.82 (m, 3H), 7.24-7.09 (m, 2H), 7.09-7.06 (m, 1H), 6.07 (m, 1H), 3.57-2.85 (m, 8H), 2.83 (s, 3H), 2.13 (s, 6H). m/z: 335.0 (M+1)

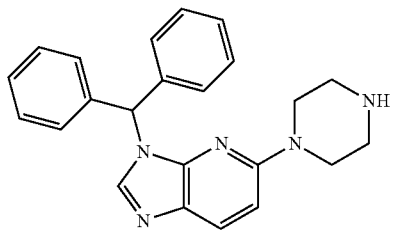 [SMILES: c1ccc(C(c2ccccc2)n2cnc3ccc(N4CCNCC4)nc32)cc1]

MBX 4214: 3-benzhydryl-5-(piperazin-1-yl)-3H-imidazo[4,5-b]pyridine

Step 1:

To a vial of 2,6-dibromo-3-nitropyridine (0.05 g, 1 eq.) in ethanol (1.5 mL) was added benzhydryl amine (0.033 g, 1 eq.) and triethylamine (0.05 mL, 2 eq.). The reaction was heated to 60° C. for 24 h. Reaction cooled, concentrated, and crude material purified with HPLC (5-95% MeCN:H$_2$O with 0.1% TFA) to yield N-benzhydryl-6-bromo-3-nitropyridin-2-amine (0.043 g, 0.112 mmol, 63%).

Step 2:

N-benzhydryl-6-bromo-3-nitropyridin-2-amine (0.022 g, 1 eq.), 1-Boc piperazine (0.010 g, 1 eq.), potassium carbonate (0.016 g, 2 eq.) in acetonitrile (1 mL) heated to 70° C. overnight. Reaction cooled to room temperature and concentrated. Crude material partitioned between water and ethyl acetate and the organic layer was separated. The aqueous layer was extracted twice with ethyl acetate, and the combined organic was dried with sodium sulfate anhydrous, filtered and concentrated to yield tert-butyl 4-(6-(benzhydrylamino)-5-nitropyridin-2-yl)piperazine-1-carboxylate (0.028 g, 0.057 mmol, 100%). Crude material used without further purification.

Step 3:

Prepared in the same manner as MBX 3587, cyclizing and deprotecting tert-butyl 4-(6-(benzhydrylamino)-5-nitropyridin-2-yl)piperazine-1-carboxylate (0.020 g) instead of Boc-protected MBX 3556. Colorless oil, mp N/A. Rf: 0.37 (10:89:1 MeOH:DCM:NH$_3$). $^1$H NMR (MeOD, 300 MHz, ppm) 8.45 (s, 1H), 8.02-7.99 (d, 1H), 7.44-7.38 (m, 6H), 7.30-7.24 (m, 5H), 7.12-7.09 (d, 1H), 3.84-3.30 (m, 4H), 3.25-3.21 (m, 4H). m/z: 369.9 (M+1)

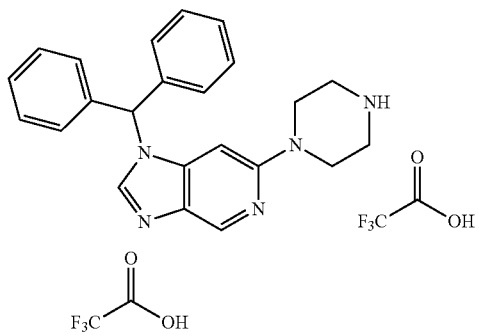

MBX 4215A: 1-benzhydryl-6-(piperazin-1-yl)-1H-imidazo[4,5-c]pyridine bis(2,2,2-trifluoroacetate)

Prepared in the same manner as MBX 4214, starting with 2,4-dibromo-5-nitropyridine instead of 2,6-dibromo-3-nitropyridine. Colorless oil, mp N/A. Rf: 0.27 (10:89:1 MeOH:DCM:NH$_3$). $^1$H NMR (CDCl$_3$, 300 MHz, ppm) 13.01-12.71 (bs, 1H), 9.78 (bs, 1H), 8.74 (s, 1H), 7.90 (s, 1H), 7.42-7.39 (m, 6H), 7.17-7.14 (m, 4H), 6.84 (s, 1H), 6.55 (m, 1H), 3.69 (m, 4H), 3.33 (m, 4H), 2.68 (s, 1H). m/z: 370.1 (M+1)

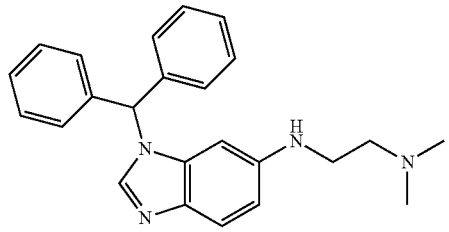 [SMILES: CN(C)CCNc1ccc2ncn(C(c3ccccc3)c3ccccc3)c2c1]

MBX 4251: N$^1$-(1-benzhydryl-1H-benzo[d]imidazol-6-yl)-N$^2$,N$^2$-dimethylethane-1,2-diamine Step 1:

Prepared in the same manner as MBX 3587, cyclizing MBX 4334 instead of Boc-protected MBX 3556, to yield N-(1-benzhydryl-1H-benzo[d]imidazol-6-yl)-N-(2-(dimethylamino)ethyl)formamide.

Step 2:

N-(1-benzhydryl-1H-benzo[d]imidazol-6-yl)-N-(2-(dimethylamino)ethyl)formamide (0.0075 g, 1 eq.) was dissolved in methanol (0.5 mL) and 2M HCl in diethyl ether (0.15 mL) and stirred at room temperature for four hours. Crude reaction concentrated and purified with HPLC (5-95% MeCN:H$_2$O with 0.1% TFA) to provide MBX 4251 (4.6 mg, 0.012 mmol, 65%). Purple oil, mp N/A. Rf: 0.62 (10:89:1 MeOH:DCM:NH$_3$). $^1$H NMR (CDCl$_3$, 300 MHz, ppm) 7.62-7.59 (d, 1H), 7.39-7.35 (m, 7H), 7.17-7.13 (m, 4H), 6.68-6.64 (m, 2H), 6.27-6.26 (m, 2H), 3.05-3.01 (t, 2H), 2.52-2.48 (t, 2H), 2.22 (s, 6H). m/z: 371.2 (M+1)

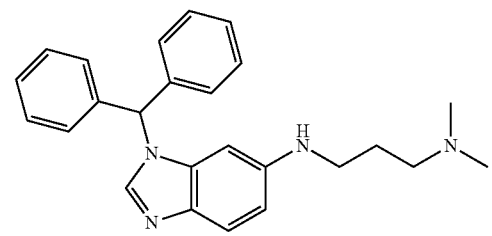 [SMILES: CN(C)CCCNc1ccc2ncn(C(c3ccccc3)c3ccccc3)c2c1]

MBX 4252: N$^1$-(1-benzhydryl-1H-benzo[d]imidazol-6-yl)-N$^3$,N$^3$-dimethylpropane-1,3-diamine Prepared in the same manner as MBX 4251, starting from MBX 4335 instead of 4334. Purple oil, mp N/A. Rf: 0.41 (10:89:1 MeOH:DCM:NH$_3$). $^1$H NMR (CDCl$_3$, 300 MHz, ppm) 7.60-7.57 (d, 1H), 7.37-7.34 (m, 7H), 7.16-7.13 (m, 4H), 6.65 (s, 1H), 6.63-6.59 (m, 1H), 6.23 (m, 1H), 3.08-3.03 (t, 2H), 2.37-2.33 (t, 2H), 2.21 (s, 6H), 1.74-1.69 (q, 2H). m/z: 385.1 (M+1)

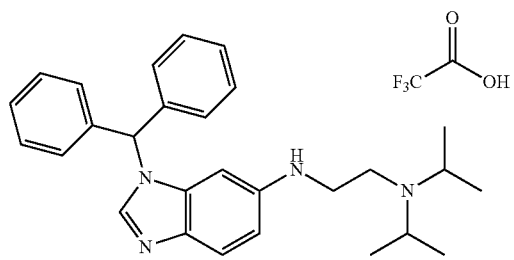

MBX 4253: N1-(1-benzhydryl-1H-benzo[d]imidazol-6-yl)-N2,N2-diisopropylethane-1,2-diamine 2,2,2-trifluoroacetate Prepared in the same manner as MBX 4251, starting from MBX 4336 instead of 4334. Purple oil, mp N/A. Rf: 0.75 (10:89:1 MeOH:DCM:NH$_3$). $^1$H NMR (CDCl$_3$, 300 MHz, ppm) 10.53 (bs, 1H), 8.02 (s, 1H), 7.69-7.66 (d, 1H), 7.42-7.40 (m, 6H), 7.19-7.15 (m, 4H), 6.88 (s, 1H), 6.81-6.77 (dd, 1H), 6.38-6.37 (m, 1H), 3.60-3.54 (m, 4H), 2.92 (m, 2H), 2.65 (s, 1H), 1.25-1.21 (m, 12H). m/z: 427.1 (M+1)

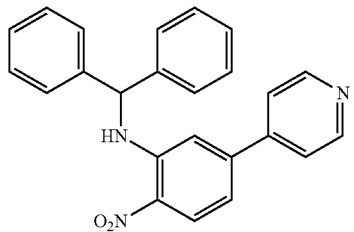

MBX 4277: N-benzhydryl-2-nitro-5-(pyridin-4-yl)aniline

Step 1:
Intermediate prepared according to general method A, starting with 4-bromo-2-fluoro-1-nitrobenzene to yield N-benzhydryl-5-bromo-2-nitroaniline.
Step 2:
N-benzhydryl-5-bromo-2-nitroaniline (0.050 g, 1 eq.), 4-(4,4,5,5-tetramethyl-1,3,2-dioxaborolan-2-yl)pyridine (0.030 g, 1.1 eq.), Pd(dppf)Cl$_2$. DCM (0.011 g, 0.1 eq.) cesium carbonate (0.128 g, 3 eq.) in dioxane (0.7 mL) and water (0.3 mL) were sealed in a microwave vial under nitrogen and heated to 130° C. in a microwave reactor for 20 minutes. After cooling to room temperature, the crude reaction mixture was partitioned between water and ethyl acetate. The organic layer was removed and the aqueous layer was extracted twice more with ethyl acetate. The combined organic layers were washed with brine, dried with sodium sulfate anhydrous, filtered and concentrated. The crude material was purified with HPLC (5-95% MeCN:H$_2$O with 0.1% TFA) to yield MBX 4277 (0.047 mg, 0.123 mmol, 94%). Orange solid, mp 155-158° C. Rf: 0.80 (10:89:1 MeOH:DCM:NH$_3$). $^1$H NMR (CDCl$_3$, 300 MHz, ppm) 8.82-8.80 (d, 2H), 8.70-8.68 (d, 1H), 8.39-8.37 (d, 1H), 7.57-7.54 (m, 2H), 7.54-7.33 (m, 10H), 6.95-6.91 (m, 2H), 5.79-5.77 (d, 1H). m/z: 382.3 (M+1)

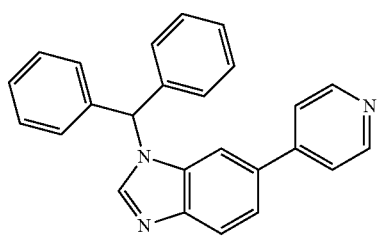 [SMILES: c1ccc(C(c2ccccc2)n2cnc3ccc(-c4ccncc4)cc32)cc1]

MBX 4278: 1-benzhydryl-6-(pyridin-4-yl)-1H-benzo[d]imidazole

Prepared in the same manner as MBX 3587, cyclizing MBX 4277 instead of Boc-protected MBX 3556. White solid, mp 140-145° C. Rf: 0.70 (10:89:1 MeOH:DCM:NH$_3$). $^1$H NMR (CDCl$_3$, 300 MHz, ppm) 8.85-8.83 (d, 2H), 8.20-8.17 (m, 2H), 7.86-7.84 (d, 2H), 7.78-7.75 (d, 1H), 7.50-7.45 (m, 7H), 7.23-7.21 (m, 4H), 6.95 (s, 1H). m/z: 362.3 (M+1)

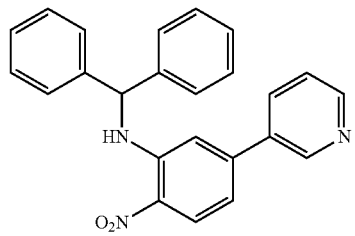 [SMILES: O=[N+]([O-])c1ccc(-c2cccnc2)cc1NC(c1ccccc1)c1ccccc1]

MBX 4279: N-benzhydryl-2-nitro-5-(pyridin-3-yl)aniline

Prepared in the same manner as MBX 4277, treating with 3-(4,4,5,5-tetramethyl-1,3,2-dioxaborolan-2-yl)pyridine instead of 4-(4,4,5,5-tetramethyl-1,3,2-dioxaborolan-2-yl)pyridine. Orange solid, mp 80-84° C. Rf: 0.84 (10:89:1 MeOH:DCM:NH$_3$). $^1$H NMR (CDCl$_3$, 300 MHz, ppm) 8.73-8.68 (m, 3H), 8.34-8.33 (d, 1H), 7.98-7.95 (m, 1H), 7.70-7.66 (m, 1H), 7.40-7.32 (m, 10H), 6.90-6.85 (m, 2H), 5.82-5.80 (d, 1H). m/z: 382.3 (M+1)

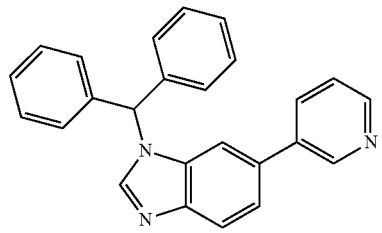 [SMILES: c1ccc(C(c2ccccc2)n2cnc3ccc(-c4cccnc4)cc32)cc1]

MBX 4294: 1-benzhydryl-6-(pyridin-3-yl)-1H-benzo[d]imidazole

Prepared in the same manner as MBX 3587, cyclizing MBX 4279 instead of Boc-protected MBX 3556. Colorless oil, mp N/A. Rf: 0.81 (10:89:1 MeOH:DCM:NH$_3$). $^1$H NMR (CDCl$_3$, 300 MHz, ppm) 8.99 (s, 1H), 8.77-8.76 (d, 1H), 8.32-8.30 (m, 2H), 8.24-8.21 (d, 1H), 7.87-7.84 (m, 1H), 7.73-7.70 (m, 1H), 7.49-7.45 (m, 7H), 7.22-7.21 (m, 4H), 7.00 (s, 1H). m/z: 362.1 (M+1)

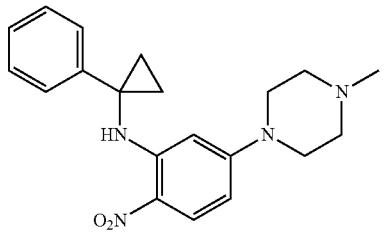 [SMILES: CN1CCN(c2ccc([N+](=O)[O-])c(NC3(c4ccccc4)CC3)c2)CC1]

MBX 4295: 5-(4-methylpiperazin-1-yl)-2-nitro-N-(1-phenylcyclopropyl)aniline

Prepared in the same manner as PPZ1, treating with 1-phenylcyclopropanamine instead of benzhydrylamine. Yellow solid, mp 170-175° C. Rf: 0.79 (10:89:1 MeOH:DCM:NH$_3$). $^1$H NMR (CDCl$_3$, 300 MHz, ppm) 8.83 (s, 1H), 8.13-8.10 (d, 1H), 7.32-7.15 (m, 5H), 6.21-6.17 (m, 1H), 6.13-6.12 (m, 1H), 3.88-3.38 (m, 8H), 2.79 (s, 3H), 1.49-1.34 (m, 4H). m/z: 353.3 (M+1)

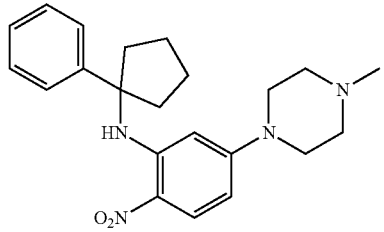 [SMILES: CN1CCN(c2ccc([N+](=O)[O-])c(NC3(c4ccccc4)CCCC3)c2)CC1]

MBX 4296: 5-(4-methylpiperazin-1-yl)-2-nitro-N-(1-phenylcyclopentyl)aniline

Prepared in the same manner as PPZ1, treating with 1-phenylcyclopentanamine instead of benzhydrylamine. Yellow solid, mp 195-200° C. Rf: 0.80 (10:89:1 MeOH:DCM:NH$_3$). $^1$H NMR (CDCl$_3$, 300 MHz, ppm) 8.96 (s, 1H), 8.10-8.17 (d, 1H), 7.46-7.21 (m, 5H), 6.10-6.06 (m, 1H), 5.55 (m, 1H), 3.39 (m, 6H), 2.72 (s, 3H), 2.48 (m, 2H), 2.23-2.21 (m, 4H), 1.94-1.92 (m, 4H). m/z: 381.5 (M+1)

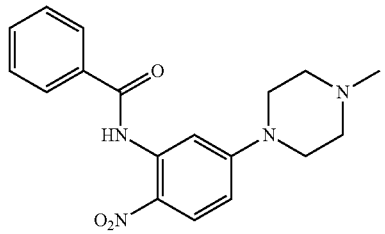 [SMILES: CN1CCN(c2ccc([N+](=O)[O-])c(NC(=O)c3ccccc3)c2)CC1]

MBX 4328: N-[5-(4-methylpiperazin-1-yl)-2-nitrophenyl]benzamide

Step 1:
To a stirring vial of 5-(4-methylpiperazin-1-yl)-2-nitroaniline (0.050 g, 1 eq.), pyridine (0.5 mL, 2 eq.) in DCM (1.2 mL) was added benzoyl chloride (0.07 mL, 2 eq.) dropwise. Reaction stirred for three hours, then concentrated. Crude reaction mixture partitioned between DCM and water, organic layer removed, and aqueous layer extracted twice with DCM. Combined organic layer washed with brine, dried with sodium sulfate anhydrous, filtered and concentrated. Crude material purified with column chromatography (0-100% DCM:hex) to yield N-(5-fluoro-2-nitrophenyl)benzamide. Resulting intermediate impure; continued without further purification.

Step 2:
Prepared according to general method B, starting with N-(5-fluoro-2-nitrophenyl)benzamide instead of N-benzhydryl-5-fluoro-2-nitroaniline to yield MBX 4328. Yellow solid, mp 174-176° C. Rf: 0.75 (10:89:1 MeOH:DCM:NH$_3$). $^1$H NMR (CDCl$_3$, 300 MHz, ppm) 8.59 (s, 1H), 8.22-8.19 (d, 1H), 8.03-8.00 (m, 2H), 7.60-7.51 (m, 3H), 6.59-6.55 (m, 1H), 3.58-3.55 (m, 4H), 2.58-2.55 (m, 4H), 2.37 (s, 3H). m/z: 341.2 (M+1)

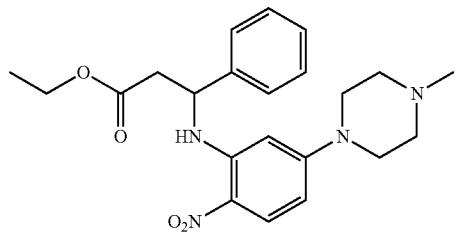 [SMILES: CCOC(=O)CC(Nc1cc(N2CCN(C)CC2)ccc1[N+](=O)[O-])c1ccccc1]

MBX 4329: ethyl 3-((5-(4-methylpiperazin-1-yl)-2-nitrophenyl)amino)-3-phenylpropanoate Prepared in the same manner as PPZ1, treating with ethyl 3-amino-3-phenylpropanoate instead of benzhydrylamine. Yellow solid, mp 144-147° C. Rf: 0.77 (10:89:1 MeOH:DCM:NH$_3$). $^1$H NMR (CDCl$_3$, 300 MHz, ppm) 9.00 (m, 1H), 8.06-8.03 (d, 1H), 7.39-7.29 (m, 5H), 6.20-6.16 (dd, 1H), 5.74 (m, 1H), 5.01-4.94 (q, 1H), 4.18-4.11 (q, 2H), 3.29-3.11 (m, 4H), 2.95-2.82 (m, 2H), 2.42-2.28 (m, 4H), 2.38 (s, 3H), 1.25-1.20 (t, 3H). m/z: 413.3 (M+1)

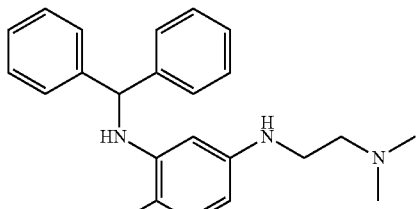

MBX 4334: N$^3$-benzhydryl-N$^1$-(2-(dimethylamino)ethyl)-4-nitrobenzene-1,3-diamine Prepared in the same manner as PPZ1, treating with N$^1$,N$^1$-dimethylethane-1,2-diamine instead of piperazine. Dark yellow solid, mp 110-115° C. Rf: 0.55 (10% MeOH:DCM). $^1$H NMR (CDCl$_3$, 300 MHz, ppm) 9.05-9.03 (m, 1H), 8.03-8.00 (d, 1H), 7.37-7.27 (m, 10H), 5.97-5.93 (m, 1H), 5.68-5.67 (d, 1H), 5.46-5.45 (m, 1H), 3.40-3.36 (t, 2H), 2.75-2.71 (t, 2H), 2.67 (s, 6H). m/z: 391.2 (M+1)

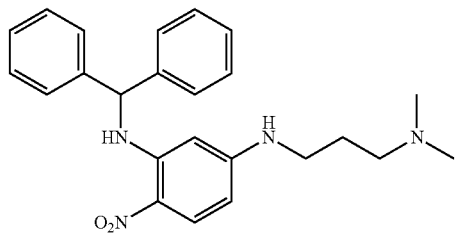 [SMILES: CN(C)CCCNc1ccc([N+](=O)[O-])c(NC(c2ccccc2)c2ccccc2)c1]

MBX 4335: $N^3$-benzhydryl-$N^1$-(2-(dimethylamino)propyl)-4-nitrobenzene-1,3-diamine Prepared in the same manner as PPZ1, treating with $N^1,N^1$-dimethylpropane-1,3-diamine instead of piperazine.

Yellow solid, mp 212-215° C. Rf: 0.54 (10% MeOH:DCM). $^1$H NMR (CDCl$_3$+MeOD, 300 MHz, ppm) 8.05-8.02 (d, 1H), 7.37-7.27 (m, 10H), 5.99-5.95 (dd, 1H), 5.67 (s, 1H), 5.50-5.49 (m, 1H), 3.12-3.08 (t, 2H), 2.96-2.91 (t, 2H), 2.73 (s, 6H), 1.73-1.69 (m, 2H). m/z: 405.1 (M+1)

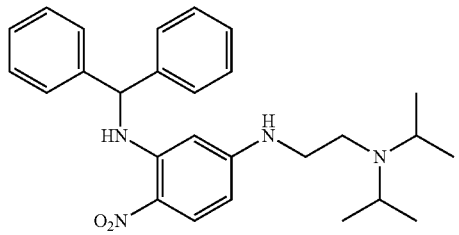 [SMILES: CC(C)N(CCNc1ccc([N+](=O)[O-])c(NC(c2ccccc2)c2ccccc2)c1)C(C)C]

MBX 4336: $N^3$-benzhydryl-$N^1$-(2-(diisopropylamino)ethyl)-4-nitrobenzene-1,3-diamine Prepared in the same manner as PPZ1, treating with $N^1,N^1$-diisopropylethane-1,2-diamine instead of piperazine. Yellow solid, mp 123-125° C. Rf: 0.86 (10% MeOH:DCM). $^1$H NMR (CDCl$_3$, 300 MHz, ppm) 9.09-9.07 (m, 1H), 8.05-8.02 (d, 1H), 7.41-7.27 (m, 10H), 6.04-6.00 (m, 1H), 5.69-5.67 (m, 1H), 5.37 (m, 1H), 3.48-3.46 (m, 2H), 3.40-3.38 (m, 2H), 2.37 (m, 2H), 1.23-1.21 (d, 6H), 1.12-1.09 (d, 6H). m/z: 447.4 (M+1)

Exemplary compounds were tested according to the assays set forth above in Examples 2-6, and the results are set forth in Tables 1-10 below:

TABLE 1

Activity and cytotoxicity of NPC-1 inhibitors with varying alkylpiperidine substituents.

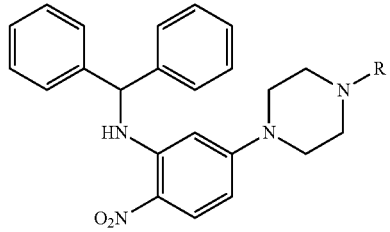

| Compound # | R | rVSV-EBOV IC$_{50}$ (µM) | infectious EBOV-Z IC$_{50}$ (µm) | Vero CC$_{50}$ (µM) |
|---|---|---|---|---|
| PPZ-1 | —Me | 1.2 | 2.3 | 61 |
|

TABLE 3

Activity and cytotoxicity of NPC-1 inhibitors with piperazine surrogates.

| Compound # | R | rVSV-EBOV IC$_{50}$ (μM) | infectious EBOV-Z IC$_{50}$ (μM) | Vero CC$_{50}$ (μM) |
|---|---|---|---|---|
| PPZ-1 | N-methylpiperazine | 1.2 | 2.3 | 61 |
| PPZ-10 | morpholine | 5.5 | | >100 |
| 3699 | thiomorpholine | >25 | | >100 |
| 3702 | piperidine | >25 | | >100 |
| 3695 | 4-methyl-2-oxopiperazine | 16 | | >100 |
| 3700 | N-methylazepane | <0.1 | | 7.6 |
| 3748 | N-tert-butylazepane | 0.25 | 0.7 | 23 |
| 3747 | 4-piperidinopiperidine | 0.58 | | 7.5 |

TABLE 3-continued

Activity and cytotoxicity of NPC-1 inhibitors with piperazine surrogates.

| Compound # | R | rVSV-EBOV IC$_{50}$ (μ

TABLE 3-continued

Activity and cytotoxicity of NPC-1 inhibitors with piperazine surrogates.

| Compound # | R | rVSV-EBOV IC$_{50}$ (μM) | infectious EBOV-Z IC$_{50}$ (μM) | Vero CC$_{50}$ (μM) |
|---|---|---|---|---|
| 4279 | 3-pyridyl | 12.39 | | 49 |

TABLE 4

Activity and cytotoxicity of NPC-1 inhibitors with nitro group replacements.

| Compound # | X—R | rVSV-EBOV IC$_{50}$ (μM) | infectious EBOV-Z IC$_{50}$ (μm) | Vero CC$_{50}$ (μM) |
|---|---|---|---|---|
| PPZ-1 | C—NO$_2$ | 1.2 | 2.3 | 61 |
| 3567 | C—H | 2.5 | 4.1 | 19 |
| 3586 | N | 7.0 | 2.6 | 70 |
| 3525 | C—NHAc | 4.0 | >20 | 100 |
| 3536 | C—NHSO$_2$Me | 2.9 | 3.1 | 26 |
| 3743 | C—NO$_2$, with 3-cyano | 2.0 | 2.0 | >100 |

TABLE 5

Activity and cytotoxicity of NPC-1 inhibitors with cyclized cores.

| Compound # | X—R, Y | rVSV-EBOV IC$_{50}$ (μM) | infectious EBOV-Z IC$_{50}$ (μM) | Vero CC$_{50}$ (μM) |
|---|---|---|---|---|
| PPZ-1 | [nitrophenyl] | 1.2 | 2.3 | 61 |
| 3540 | C—H, Me | 0.8 | 0.9 | 58 |
| 3539 | C—Me, Me | 14 | >20 | 77 |
| 3526 | C—OH, Me | 2.9 | | 26 |
| 3537 | N, Me | 2.3 | 2.3 | 41 |
| 3587 | C—H, H | 1.8 | 2.2 | 37 |
| 3673 | C—H, tert-butyl | 1.7 | 2.5 | 77 |

TABLE 6

Activity and cytotoxicity of NPC-1 inhibitors with substituted benzhydryl functionalities.

| Compound # | R, R' | rVSV-EBOV IC$_{50}$ (μM) | infectious EBOV-Z IC$_{50}$ (μM) | Vero CC$_{50}$ (μM) |
|---|---|---|---|---|
| PPZ-1 | Ph | 1.2 | 2.3 | 61 |
| 3514 | H, H | 9.5 | 15 | 26 |
| 3633 | 2-MePh | 1.5 | 1.3 | 15 |
| 3634 | 3-MePh | 3.4 | 3.0 | >100 |
| 3687 | 4-MePh | 2.2 | | 16 |
| 3643 | 3-ClPh | 0.85 | >20 | 21 |
| 3644 | 4-ClPh | 1.4 | | 18 |
| 3635 | 2-OMePh | 2.5 | | 14 |
| 3641 | 3-OMePh | >25 | | 26 |
| 3642 | 4-OMePh | >25 | | 33 |
| 3647 | 2-pyridyl | >25 | | >100 |
| 3648 | 3-pyridyl | >25 | | 17 |
| 3670 | 4-pyridyl | 4.5 | | 45 |
| 3741 | Me, Me | 3.1 | 10.3 | 85 |
| 4295 | Cyclopropyl | 16.23 | | 58 |
| 4296 | Cyclopentanyl | 5.89 | | >200 |
| 4328 | Carbonyl | 11.46 | | 60 |

TABLE 6-continued

Activity and cytotoxicity of NPC-1 inhibitors with substituted benzhydryl functionalities.

| Compound # | R, R' | rVSV-EBOV IC$_{50}$ (μM) | infectious EBOV-Z IC$_{50}$ (μM) | Vero CC$_{50}$ (μM) |
|---|---|---|---|---|
| 4329 | (CH$_2$C(O)OCH$_2$CH$_3$) | 10.39 | | 45 |

TABLE 7

Activity and cytotoxicity of NPC-1 inhibitors with cyclized cores and piperazine surrogates.

| Compound # | R | rVSV-EBOV IC$_{50}$ (μM) | infectious EBOV-Z IC$_{50}$ (μM) | Vero CC$_{50}$ (μM) |
|---|---|---|---|---|
| PPZ-1 | 4-methylpiperazin-1-yl | 1.2 | 2.3 | 61 |
| 4210 | octahydropyrrolo[1,2-a]pyrazin-2-yl | 1.6 | 1.8 | >200 |
| 4211 | octahydro-2H-pyrido[1,2-a]pyrazin-2-yl | 2.0 | | 195 |

TABLE 7-continued

Activity and cytotoxicity of NPC-1 inhibitors with cyclized cores and piperazine surrogates.

| Compound # | R | rVSV-EBOV IC$_{50}$ (μM) | infectious EBOV-Z IC$_{50}$ (μM) | Vero CC$_{50}$ (μM) |
|---|---|---|---|---|
| 4212 | (2-methyl-4-methylpiperazinyl) | 1.60 | 0.53 | 170 |
| 4251 | -NH-CH$_2$CH$_2$-N(Me)$_2$ | 2.01 | 2.66 | 105 |
| 4252 | -NH-CH$_2$CH$_2$CH$_2$-N(Me)$_2$ | 3.93 | 8.62 | 50 |
| 4253A | -NH-CH$_2$CH$_2$-N(iPr)$_2$ | 1.30 | 1.85 | 95 |
| 4278 | 4-pyridyl | 8.98 | | 4.2 |
| 4294 | 3-pyridyl | 15.63 | | 59 |

TABLE 8

Activity and cytotoxicity of NPC-1 inhibitors with cyclized cores and substituted benzhydryl functionalities.

| Compound # | R, R' | rVSV-EBOV IC$_{50}$ (μM) | infectious EBOV-Z IC$_{50}$ (μM) | Vero CC$_{50}$ (μM) |
|---|---|---|---|---|
| PPZ-1 | Ph [nitrophenyl] | 1.2 | 2.3 | 61 |
| 4213 | Me, Me | 200 | | >200 |
| 4511 | -CH$_2$-C(O)-O-Et | 225 | | >200 |

TABLE 9
Activity and cytotoxicity of NPC-1 inhibitors with cyclized cores and phenyl group replacements.
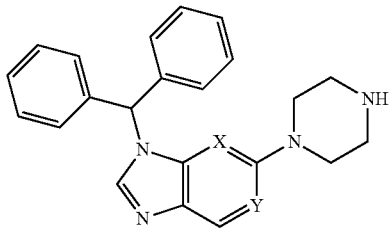
| Compound # | X, Y | rVSV-EBOV IC$_{50}$ (µM) | infectious EBOV-Z IC$_{50}$ (µM) | Vero CC$_{50}$ (µM) |
|---|---|---|---|---

R4, R5 and R6 are independently selected from hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms, 0-1 oxygen atoms and bearing 0-3 substituents (in addition to the bond between W and the ring carbon in the formula) selected from alkyl, cycloalkyl, aryl, heteroaryl, haloalkyl, nitro, halogen, alkoxy, alkylthio, haloalkoxy, sulfonyl, or sulfinyl, optionally fused with one or more aromatic, heteroaromatic, cycloalkyl, or heterocycloalkyl rings, wherein said 0-3 substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and additionally W can be either a nitrogen or a saturated carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups, which optional substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl, which non-hydrogen substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; or, wherein, if X is hydrogen, A is C or N; and where A is C, Y is hydrogen, hydroxyl, alkyl, alkoxy, haloalkyl, haloalkoxy, haloalkoxysulfonyl, halogen, nitro, cyano, or NRR', where R and R' are independently selected from hydrogen, alkyl, acetyl, sulfonyl, and alkylsulfonyl; the ring atoms U, V and Z are C or N atoms;

R1 is an aryl or heteroaryl ring of 5-7 members, or a fused aryl or heteroaryl bicyclic ring system of 9-11 members, which R1 aryl or heteroaryl ring or ring system is substituted with 0-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups, with the proviso that if R1 is an aryl group, it must have at least one substituent;

R2 and R3 are independently selected from branched aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring, wherein the ring has 1-4 carbon substituents and 0-1 substituents on any present ring nitrogen, which are independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, substituted aryl, or substituted or unsubstituted heteroaryl rings, wherein substituted aryl or heteroaryl rings have 1-4 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl;

R4, R5 and R6 are independently selected from hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a heterocyclic ring system containing 0-3 degrees of unsaturation and between 5-7 members and containing 1-2 nitrogen atoms, 0-1 oxygen atoms and bearing 0-3 substituents (in addition to the bond linking W and the ring carbon in the formula) including alkyl, cycloalkyl, heterocycloalkyl, aryl, heteroaryl, haloalkyl, acetyl, arylcarbonyl, heteroarylcarbonyl, aralkyl, alkoxyalkyl, nitro, halogen, alkoxy, alkylthio, haloalkoxy, sulfonyl, or sulfinyl, optionally fused with one or more aromatic, heteroaromatic, cycloalkyl, or heterocycloalkyl rings, wherein said 0-3 substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and additionally W can be either a nitrogen or a saturated carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups, which optional substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl, which non-hydrogen substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl;

or a pharmaceutically acceptable salt thereof.

2. The compound according to claim 1 further comprising a pharmaceutically acceptable carrier or excipient.

3. The compound according to claim 2, wherein said pharmaceutically acceptable carrier or excipient further comprises an additional antiviral compound.

4. The compound according to claim 1 formulated for oral, parenteral, or topical administration.

5. A composition comprising a compound of Formula II:

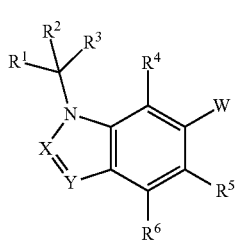

Formula II wherein:
X is C or N; Y is C or N; and at least one of X and Y is N;
R1 is hydrogen, a straight-chain or branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl groups; or R1 is an aryl or heteroaryl ring of 5-7 members, or a fused aryl or heteroaryl bicyclic ring system of 9-11 members, each ring substituted with 1-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups;
R2 and R3 can independently be branched-chain aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring bearing 1-4 carbon substituents and 0-1 nitrogen substituents which may be independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl, or heteroaryl rings; and wherein, if R1 is other than hydrogen, then R2 and R3 can independently be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;
R4, R5 and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups; and
W can be either a nitrogen or a carbon that is part of a non-aromatic heterocyclic ring system of between 5-7 members and containing 1-2 nitrogen atoms and bearing 0-3 substituents including alkyl, cycloalkyl, aryl, heteroaryl, haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; and additionally W can be either a nitrogen, a saturated carbon, or an olefinic carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl; or alternatively, W may be linked with R4 or R5 to produce fused cyclic structures;
or a pharmaceutically acceptable salt thereof.

6. The compound according to claim 5 further comprising a pharmaceutically acceptable carrier or excipient.

7. The compound according to claim 6, wherein said pharmaceutically acceptable carrier or excipient further comprises an additional antiviral compound.

8. The compound according to claim 5 formulated for oral, parenteral, or topical administration.

9. A compound of Formula III:

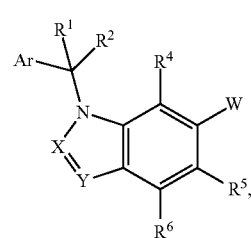

Formula III wherein:
X is C or N; Y is C or N; and at least one of X and Y is N;
Ar is

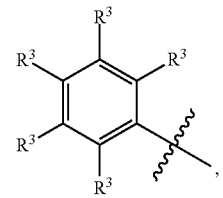

where each R3 can independently be hydrogen, alkyl, haloalkyl, haloalkyl, nitro, halogen, alkoxy, alkylthio, haloalkoxy, sulfonyl, sulfinyl, carboxy, alkoxycarbonyl, or aminocarbonyl;
R1 is hydrogen, a straight-chain aliphatic group, a branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group;
R2 can independently be a branched chain aliphatic group, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl group, aryl, or heteroaryl; or R1 and R2 can be linked together to form a substituted aliphatic or heterocyclic ring bearing 1-4 substituents selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl or heteroaryl rings; and, additionally, if R1 is straight-chain aliphatic group, branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group, then R2 can be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5 and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms, 0-1 oxygen atoms, and bearing 0-3 substituents including alkyl, cycloalkyl, aryl, heteroaryl haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; and additionally, W can be either a nitrogen, a saturated carbon, or an olefinic carbon that is linked via a chain of 1-4 carbons to a basic nitrogen bearing independently hydrogen or aliphatic groups of less than nine carbon atoms that can be optionally substituted with haloalkyl, nitro, halogen, alkoxy, alkylthio, haloalkoxy, sulfonyl, sulfinyl, carboxy, alkoxycarbonyl, or aminocarbonyl groups; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl; or alternatively, W may be linked with R4 or R5 to produce fused cyclic structures; or W can be a nitrogen that is part of an aromatic heterocyclic ring system of between 5-7 members and containing 1-2 nitrogen atoms that may be unsubstituted or substituted and may optionally be fused with one or more aromatic, heteroaromatic, cycloalkyl, or heterocycloalkyl rings, and this group can also include connections through either R4 or R5 to produce fused bicyclic structures;

or a pharmaceutically acceptable salt thereof.

10. The compound according to claim 9 further comprising a pharmaceutically acceptable carrier or excipient.

11. The compound according to claim 10, wherein said pharmaceutically acceptable carrier or excipient further comprises an additional antiviral compound.

12. The compound according to claim 9 formulated for oral, parenteral, or topical administration.

13. A compound of Formula IV:

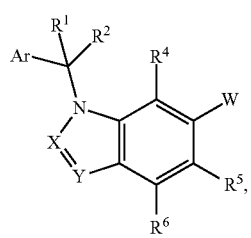

Formula IV wherein:

X can be carbon or nitrogen and Y can be a carbon or nitrogen, and at least one of X and Y is nitrogen, and wherein X and Y can be independently unsubstituted or substituted with a hydrogen, alkyl, halogen, hydroxy, carbonyl, thiol, amino, alkylamino, alkylthio, alkoxy, aryl, haloalkyl, nitro, halogen, alkoxy, alkylthio, haloalkoxy, sulfonyl, sulfinyl, carboxy, alkoxycarbonyl, or aminocarbonyl group;

Ar is

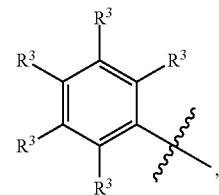

where each R3 can independently be hydrogen, alkyl, haloalkyl, nitro, halogen, alkoxy, alkylthio, haloalkoxy, sulfonyl, sulfinyl, carboxy, alkoxycarbonyl, or an aminocarbonyl group;

R1 is a hydrogen, straight-chain aliphatic group, branched chain aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group;

R2 can independently be a branched chain aliphatic group, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl group, aryl, or heteroaryl; or R1 and R2 can be linked together to form a substituted aliphatic or heterocyclic ring bearing 1-4 substituents selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl or heteroaryl rings; and additionally, if R1 is a straight-chain aliphatic group, branched chain aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group, then R2 can be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5, and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups, W can be a nitrogen that is part of an aromatic or non-aromatic heterocyclic ring system of between 5-7 members, containing 1-2 nitrogen atoms, 0-1 oxygen atoms, and bearing 0-3 substituents selected from alkyl, cycloalkyl, aryl, heteroaryl haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; or W can be a nitrogen that is linked via a chain of 1-4 carbon atoms to a basic nitrogen bearing independently hydrogen or aliphatic groups of less than nine carbon atoms that can be optionally substituted with haloalkyl, nitro, halogen, alkoxy, alkylthio, haloalkoxy, sulfonyl, sulfinyl, carboxy, alkoxycarbonyl, or aminocarbonyl groups; wherein the chain of carbon atoms is a saturated hydrocarbon chain or can be substituted with up to 4 non-hydrogen substituents selected from alkyl, fused cycloalkyl, aryl, fused aryl, haloalkyl, nitro, halogen, alkoxy, alkylthio, haloalkoxy, sulfonyl, sulfinyl, carboxy, alkoxycarbonyl, or aminocarbonyl, or this group can also include connections through either R4 or R5 to produce non-aromatic fused cyclic ring structures;

or a pharmaceutically acceptable salt thereof.

14. The compound according to claim 13 further comprising a pharmaceutically acceptable carrier or excipient.

15. The compound according to claim 14, wherein said pharmaceutically acceptable carrier or excipient further comprises an additional antiviral compound.

16. The compound according to claim 13 formulated for oral, parenteral, or topical administration.

17. A compound of Formula V:

Formula V wherein:

A is C or N; and where A is C, Y is hydrogen, hydroxyl, alkyl, alkoxy, haloalkyl, haloalkoxy, haloalkoxysulfonyl, halogen, nitro, cyano, or NRR', where R and R' are independently selected from hydrogen, alkyl, acetyl, sulfonyl, and alkylsulfonyl;

Ar is, independently, an aryl or heteroaryl ring of 5-7 members, or a fused aryl or heteroaryl bicyclic ring system of 9-11 members, each ring optionally substituted with 0-3 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups;

W is a ring nitrogen in a non-aromatic heterocyclic ring of from 5-7 members having 0-1 additional heteroatom selected from N or O or a fused non-aromatic bicyclic ring system of from 6 to 10 members having 0-1 additional heteroatom selected from N or O; where said heterocyclic ring or said bicyclic ring has 0-3 substituents independently selected from alkyl, cycloalkyl, heterocycloalkyl, aryl, heteroaryl, haloalkyl, acetyl, arylcarbonyl, heteroarylcarbonyl, aralkyl, alkoxyalkyl, nitro, halogen, alkoxy, alkylthio, haloalkoxy, sulfonyl, or sulfinyl, and where a cycloalkyl, heterocycloalkyl, aryl, or heteroaryl substituent may optionally be fused with one or more aromatic, heteroaromatic, cycloalkyl, or heterocycloalkyl rings; or W is NRR', where R is hydrogen or alkyl, and R' is alkyl, alkenyl, aminoalkyl, or aminoalkenyl, cycloalkyl, heterocycloalkyl, aryl, and heteroaryl, which R' group may optionally be further substituted with up to three substituents selected from alkyl, haloalkyl, nitro, halogen, alkoxy, alkylthio, haloalkoxy, sulfonyl, sulfinyl, carboxy, alkoxycarbonyl, or aminocarbonyl groups;

R1 and R2 are, independently, hydrogen, straight-chain or branched alkyl, cycloalkyl, haloalkyl, nitro, halogen, alkoxy, alkylthio, haloalkoxy, sulfonyl, sulfinyl, carboxy, alkoxycarbonyl, or aminocarbonyl groups; and wherein R2 can independently be Ar as defined above;

R4, R5, and R6 are independently selected from hydrogen, alkyl, haloalkyl, nitro, halogen, cyano, alkoxy, alkylthio, haloalkoxy, sulfonyl, sulfinyl, carboxy, alkoxycarbonyl, or aminocarbonyl groups;

or a pharmaceutically acceptable salt thereof.

18. The compound according to claim 17 further comprising a pharmaceutically acceptable carrier or excipient.

19. The compound according to claim 18, wherein said pharmaceutically acceptable carrier or excipient further comprises an additional antiviral compound.

20. The compound according to claim 17 formulated for oral, parenteral, or topical administration.

21. A method of inhibiting Filovirus infection in a mammal comprising administering to a mammal in need thereof an effective amount of a composition comprising a compound of Formula I:

Formula I wherein:

X is hydrogen, C or N;

wherein, if X is other than hydrogen,

X and Y are connected by a double bond to form a 5-membered heteroaromatic ring; Y is C or N, with the proviso that at least one of X and Y is N; A is C; the ring atoms U, V and Z are C or N atoms in one of the following configurations, taken in order UVZ: CCC, CCN, CNC, NCC, NCN, CNN, or NNN;

R1 is hydrogen, a straight-chain or branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl groups; or R1 is an aryl ring of 5-7 members wherein said aryl is optionally substituted with 0-5 substituents independently selected from alkyl, alkoxy, hydroxyl, carbonyl, carboxy, halogen, haloalkyl, nitro, haloalkoxy, alkylthio, sulfonyl, sulfinyl, alkoxyalkyl, alkoxycarbonyl, or aminocarbonyl groups; or R1 is a heteroaryl, fused aryl ring system or heteroaryl bicyclic ring system of 9-11 members wherein said ring system is optionally substituted with 0-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups, with the proviso that if R1 is an aryl group, it must have at least one substituent;

R2 and R3 are independently selected from straight-chain or branched aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring, wherein the ring has 1-4 carbon substituents and 0-1 substituents on any present ring nitrogen, which are independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, substituted aryl, or substituted or unsubstituted heteroaryl rings, wherein substituted aryl or heteroaryl rings have 1-4 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein, if R1 is other than hydrogen, then R2 and R3 can independently be alkyl; cycloalkyl; heterocycloalkyl; aryl; heteroaryl; haloalkyl; nitro; halogen; alkoxy; alkylthio; haloalkoxy; sulfonyl; sulfinyl; carboxy; alkoxycarbonyl; or aminocarbonyl groups;

R4, R5 and R6 are independently selected from hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms, 0-1 oxygen atoms and bearing 0-3 substituents (in addition to the bond between W and the ring carbon in the formula) selected from alkyl, cycloalkyl, aryl, heteroaryl, haloalkyl, nitro, halogen, alkoxy, alkylthio, haloalkoxy, sulfonyl, or sulfinyl, optionally fused with one or more aromatic, heteroaromatic, cycloalkyl, or heterocycloalkyl rings, wherein said 0-3 substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and additionally W can be either a nitrogen or a saturated carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups, which optional substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl, which non-hydrogen substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; or, wherein, if X is hydrogen, A is C or N; and where A is C, Y is hydrogen, hydroxyl, alkyl, alkoxy, haloalkyl, haloalkoxy, haloalkoxysulfonyl, halogen, nitro, cyano, or NRR', where R and R' are independently selected from hydrogen, alkyl, acetyl, sulfonyl, and alkylsulfonyl; the ring atoms U, V and Z are C or N atoms;

R1 is an aryl or heteroaryl ring of 5-7 members, or a fused aryl or heteroaryl bicyclic ring system of 9-11 members, which R1 aryl or heteroaryl ring or ring system is substituted with 0-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups, with the proviso that if R1 is an aryl group, it must have at least one substituent;

R2 and R3 are independently selected from branched aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring, wherein the ring has 1-4 carbon substituents and 0-1 substituents on any present ring nitrogen, which are independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, substituted aryl, or substituted or unsubstituted heteroaryl rings, wherein substituted aryl or heteroaryl rings have 1-4 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl;

R4, R5 and R6 are independently selected from hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a heterocyclic ring system containing 0-3 degrees of unsaturation and between 5-7 members and containing 1-2 nitrogen atoms, 0-1 oxygen atoms and bearing 0-3 substituents (in addition to the bond linking W and the ring carbon in the formula) including alkyl, cycloalkyl, heterocycloalkyl, aryl, heteroaryl, haloalkyl, acetyl, arylcarbonyl, heteroarylcarbonyl, aralkyl, alkoxyalkyl, nitro, halogen, alkoxy, alkylthio, haloalkoxy, sulfonyl, or sulfinyl, optionally fused with one or more aromatic, heteroaromatic, cycloalkyl, or heterocycloalkyl rings, wherein said 0-3 substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and additionally W can be either a nitrogen or a saturated carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups, which optional substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl, which non-hydrogen substituents may, together with either R4 or R5, form a fused substituted or unsubstituted non-aromatic ring bearing 0-2 substituents selected from alkyl, cycloalkyl, hydroxyl, amino, alkylamino, aryl, heteroaryl, haloalkyl, nitro, halogen, alkoxy, alkylthio, haloalkoxy, sulfonyl, or sulfinyl;

or a pharmaceutically acceptable salt thereof.

22. The method according to claim 21, wherein the filovirus is selected from Ebola virus, Sudan virus, Reston virus, Bundibugyo virus, Taï virus, Marburg virus, and Ravn virus.

23. The method according to claim 21, wherein the composition is formulated for administration in a pharmaceutically acceptable carrier or excipient.

24. The method according to claim 21, wherein the mammal is a human.

25. A method of inhibiting filovirus infection in a mammal comprising administering to a mammal in need thereof an effective amount of a composition comprising a compound according to Formula II:

Formula II wherein:
X is C or N; Y is C or N; and at least one of X and Y is N;

R1 is hydrogen, a straight-chain or branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl groups; or R1 is an aryl or heteroaryl ring of 5-7 members, or a fused aryl or heteroaryl bicyclic ring system of 9-11 members, each ring substituted with 1-5 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups;

R2 and R3 can independently be branched-chain aliphatic groups, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl groups, aryl, or heteroaryl; or R2 and R3 can be linked together to form a substituted aliphatic or heterocyclic ring bearing 1-4 carbon substituents and 0-1 nitrogen substituents which may be independently selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl, or heteroaryl rings; and wherein, if R1 is other than hydrogen, then R2 and R3 can independently be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5 and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms and bearing 0-3 substituents including alkyl, cycloalkyl, aryl, heteroaryl, haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; and additionally W can be either a nitrogen, a saturated carbon, or an olefinic carbon that is linked via a chain of 1-4 carbon atoms to a basic nitrogen bearing, independently, hydrogen or aliphatic groups of less than nine carbon atoms that can be optionally substituted with groups selected from haloalkyl, nitro, halogen, alkoxy, alkylthio, haloalkoxy, sulfonyl, sulfinyl, carboxy, alkoxycarbonyl, or aminocarbonyl groups; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl; or alternatively, W may be linked with R4 or R5 to produce fused cyclic structures;

or a pharmaceutically acceptable salt thereof.

26. The method according to claim 25, wherein the filovirus is selected from Ebola virus, Sudan virus, Reston virus, Bundibugyo virus, Taï virus, Marburg virus, and Ravn virus.

27. The method according to claim 25, wherein the composition is formulated for administration in a pharmaceutically acceptable carrier or excipient.

28. The method according to claim 25, wherein the mammal is a human.

29. A method of inhibiting filovirus infection in a mammal comprising administering to a mammal in need thereof an effective amount of a composition comprising a compound according to Formula III:

Formula III wherein:
X is C or N; Y is C or N; and at least one of X and Y is N;
Ar is where each R3 can independently be hydrogen, alkyl, haloalkyl, haloalkyl, nitro, halogen, alkoxy, alkylthio, haloalkoxy, sulfonyl, sulfinyl, carboxy, alkoxycarbonyl, or aminocarbonyl;

R1 is hydrogen, a straight-chain aliphatic group, a branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group;

R2 can independently be a branched chain aliphatic group, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl group, aryl, or heteroaryl; or R1 and R2 can be linked together to form a substituted aliphatic or heterocyclic ring bearing 1-4 substituents selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl or heteroaryl rings; and, additionally, if R1 is straight-chain aliphatic group, branched aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group, then R2 can be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5 and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups; and W can be either a nitrogen or a carbon that is part of a non-aromatic heterocyclic ring system of between 5-7 members and containing 1-2 nitrogen atoms, 0-1 oxygen atoms, and bearing 0-3 substituents including alkyl, cycloalkyl, aryl, heteroaryl haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; and additionally, W can be either a nitrogen, a saturated carbon, or an olefinic carbon that is linked via a chain of 1-4 carbons to a basic nitrogen bearing independently hydrogen or aliphatic groups of less than nine carbon atoms that can be optionally substituted with haloalkyl, nitro, halogen, alkoxy, alkylthio, haloalkoxy, sulfonyl, sulfinyl, carboxy, alkoxycarbonyl, or aminocarbonyl groups; and wherein the chain of 1-4 carbon atoms is a saturated hydrocarbon chain or can be substituted with up to 4 non-hydrogen substituents selected from alkyl, fused cycloalkyl, aryl, haloalkyl, nitro, halogen, alkoxy, alkylthio, haloalkoxy, sulfonyl, sulfinyl, carboxy, alkoxycarbonyl, or aminocarbonyl; or alternatively, W may be linked with R4 or R5 to produce fused cyclic structures; or W can be a nitrogen that is part of an aromatic heterocyclic ring system of between 5-7 members and containing 1-2 nitrogen atoms that may be unsubstituted or substituted and may optionally be fused with one or more aromatic, heteroaromatic, cycloalkyl, or heterocycloalkyl rings, and this group can also include connections through either R4 or R5 to produce fused bicyclic structures;

or a pharmaceutically acceptable salt thereof.

30. The method according to claim 29, wherein the filovirus is selected from Ebola virus, Sudan virus, Reston virus, Bundibugyo virus, Taï virus, Marburg virus, and Ravn virus.

31. The method according to claim 29, wherein the composition is formulated for administration in a pharmaceutically acceptable carrier or excipient.

32. The method according to claim 29, wherein the mammal is a human.

33. A method of inhibiting filovirus infection in a mammal comprising administering to a mammal in need thereof an effective amount of a composition comprising a compound according to Formula IV:

Formula IV wherein:
X can be carbon or nitrogen and Y can be a carbon or nitrogen, and at least one of X and Y is nitrogen, and wherein X and Y can be independently unsubstituted or substituted with a hydrogen, alkyl, halogen, hydroxy, carbonyl, thiol, amino, alkylamino, alkylthio, alkoxy, aryl, haloalkyl, nitro, halogen, alkoxy, alkylthio, haloalkoxy, sulfonyl, sulfinyl, carboxy, alkoxycarbonyl, or aminocarbonyl group;
Ar is where each R3 can independently be hydrogen, alkyl, haloalkyl, nitro, halogen, alkoxy, alkylthio, haloalkoxy, sulfonyl, sulfinyl, carboxy, alkoxycarbonyl, or an aminocarbonyl group;

R1 is a hydrogen, straight-chain aliphatic group, branched chain aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group;

R2 can independently be a branched chain aliphatic group, cycloalkyl, heterocycloalkyl, haloalkyl, nitro, halogen, alkoxy, alkylthio, haloalkoxy, sulfonyl, sulfinyl, carboxy, alkoxycarbonyl, aminocarbonyl group, aryl, or heteroaryl; or R1 and R2 can be linked together to form a substituted aliphatic or heterocyclic ring bearing 1-4 substituents selected from alkyl, haloalkyl, nitro, halogen, alkoxy, alkylthio, haloalkoxy, sulfonyl, sulfinyl, carboxy, alkoxycarbonyl, or aminocarbonyl groups and/or additional fused cycloalkyl, heterocycloalkyl, aryl or heteroaryl rings; and additionally, if R1 is a straight-chain aliphatic group, branched chain aliphatic group, cycloalkyl, haloalkyl, nitro, halogen, alkoxy, alkylthio, haloalkoxy, sulfonyl, sulfinyl, carboxy, alkoxycarbonyl, or aminocarbonyl group, then R2 can be alkyl, cycloalkyl, heterocycloalkyl, aryl, heteroaryl, haloalkyl, nitro, halogen, alkoxy, alkylthio, haloalkoxy, sulfonyl, sulfinyl, carboxy, alkoxycarbonyl, or aminocarbonyl groups;

R4, R5, and R6 can independently be hydrogen, alkyl, haloalkyl, nitro, halogen, alkoxy, alkylthio, haloalkoxy, sulfonyl, sulfinyl, carboxy, alkoxycarbonyl, or aminocarbonyl groups, W can be a nitrogen that is part of an aromatic or non-aromatic heterocyclic ring system of between 5-7 members, containing 1-2 nitrogen atoms, 0-1 oxygen atoms, and bearing 0-3 substituents selected from alkyl, cycloalkyl, aryl, heteroaryl haloalkyl, nitro, halogen, alkoxy, alkylthio, haloalkoxy, sulfonyl, or sulfinyl, and may optionally be fused with one or more aromatic, heteroaromatic, cycloalkyl, or heterocycloalkyl rings; or W can be a nitrogen that is linked via a chain of 1-4 carbon atoms to a basic nitrogen bearing independently hydrogen or aliphatic groups of less than nine carbon atoms that can be optionally substituted with haloalkyl, nitro, halogen, alkoxy, alkylthio, haloalkoxy, sulfonyl, sulfinyl, carboxy, alkoxycarbonyl, or aminocarbonyl groups; wherein the chain of carbon atoms is a saturated hydrocarbon chain or can be substituted with up to 4 non-hydrogen substituents selected from alkyl, fused cycloalkyl, aryl, fused aryl, haloalkyl, nitro, halogen, alkoxy, alkylthio, haloalkoxy, sulfonyl, sulfinyl, carboxy, alkoxycarbonyl, or aminocarbonyl, or this group can also include connections through either R4 or R5 to produce non-aromatic fused cyclic ring structures;

or a pharmaceutically acceptable salt thereof.

34. The method according to claim 33, wherein the filovirus is selected from Ebola virus, Sudan virus, Reston virus, Bundibugyo virus, Taï virus, Marburg virus, and Ravn virus.

35. The method according to claim 33, wherein the composition is formulated for administration in a pharmaceutically acceptable carrier or excipient.

36. The method according to claim 33, wherein the mammal is a human.

37. A method of inhibiting filovirus infection in a mammal comprising administering to a mammal in need thereof an effective amount of a composition comprising a compound according to Formula V:

Formula V 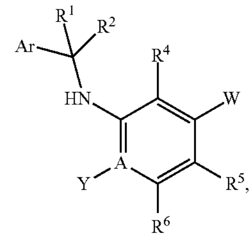 wherein:

A is C or N; and where A is C, Y is hydrogen, hydroxyl, alkyl, alkoxy, haloalkyl, haloalkoxy, haloalkoxysulfonyl, halogen, nitro, cyano, or NRR', where R and R' are independently selected from hydrogen, alkyl, acetyl, sulfonyl, and alkylsulfonyl;

Ar is, independently, an aryl or heteroaryl ring of 5-7 members, or a fused aryl or heteroaryl bicyclic ring system of 9-11 members, each ring optionally substituted with 0-3 substituents independently selected from alkyl, alkoxy, hydroxyl, carbonyl, carboxy, halogen, haloalkyl, haloalkoxy, alkylthio, sulfonyl, sulfinyl, alkoxyalkyl, alkoxycarbonyl, or aminocarbonyl groups;

W is a ring nitrogen in a non-aromatic heterocyclic ring of from 5-7 members having 0-1 additional heteroatom selected from N or O or a fused non-aromatic bicyclic ring system of from 6 to 10 members having 0-1 additional heteroatom selected from N or O; where said heterocyclic ring or said bicyclic ring has 0-3 substituents independently selected from alkyl, cycloalkyl, heterocycloalkyl, aryl, heteroaryl, haloalkyl, acetyl, arylcarbonyl, heteroarylcarbonyl, aralkyl, alkoxyalkyl, nitro, halogen, alkoxy, alkylthio, haloalkoxy, sulfonyl, or sulfinyl, and where a cycloalkyl, heterocycloalkyl, aryl, or heteroaryl substituent may optionally be fused with one or more aromatic, heteroaromatic, cycloalkyl, or heterocycloalkyl rings; or W is NRR', where R is hydrogen or alkyl, and R' is alkyl, alkenyl, aminoalkyl, or aminoalkenyl, cycloalkyl, heterocycloalkyl, aryl, and heteroaryl, which R' group may optionally be further substituted with up to three substituents selected from alkyl, haloalkyl, nitro, halogen, alkoxy, alkylthio, haloalkoxy, sulfonyl, sulfinyl, carboxy, alkoxycarbonyl, or aminocarbonyl groups;

R1 and R2 are, independently, hydrogen, straight-chain or branched alkyl, cycloalkyl, haloalkyl, nitro, halogen, alkoxy, alkylthio, haloalkoxy, sulfonyl, sulfinyl, carboxy, alkoxycarbonyl, or aminocarbonyl groups; and wherein R2 can independently be Ar as defined above;

R4, R5, and R6 are independently selected from hydrogen, alkyl, haloalkyl, nitro, halogen, cyano, alkoxy, alkylthio, haloalkoxy, sulfonyl, sulfinyl, carboxy, alkoxycarbonyl, or aminocarbonyl groups;

or a pharmaceutically acceptable salt thereof.

38. The method according to claim 37, wherein the filovirus is selected from Ebola virus, Sudan virus, Reston virus, Bundibugyo virus, Taï virus, Marburg virus, and Ravn virus.

39. The method according to claim 37, wherein the composition is formulated for administration in a pharmaceutically acceptable carrier or excipient.

40. The method according to claim 37, wherein the mammal is a human.

41. A filovirus inhibitor compound selected from the group consisting of:

1-benzhydryl-6-(4-benzylhomopiperazin-1-yl)-1H-benzo[d]imidazole;
1-benzhydryl-6-(4-benzylpiperazin-1-yl)-1H-benzo[d]imidazole;
1-benzhydryl-6-(4-but-2-enylpiperazin-1-yl)-1H-benzo[d]imidazole;
1-benzhydryl-6-(4-butylhomopiperazin-1-yl)-1H-benzo[d]imidazole;
1-benzhydryl-6-(4-butylpiperazin-1-yl)-1H-benzo[d]imidazole;
1-benzhydryl-6-(4-cyclobutylpiperazin-1-yl)-1H-benzo[d]imidazole;
1-benzhydryl-6-(4-cyclohexylpiperazin-1-yl)-1H-benzo[d]imidazole;
1-benzhydryl-6-(4-cyclopentylpiperazin-1-yl)-1H-benzo[d]imidazole;
1-benzhydryl-6-(4-cyclopropylmethylpiperazin-1-yl)-1H-benzo[d]imidazole;
1-benzhydryl-6-(4-decylpiperazin-1-yl)-1H-benzo[d]imidazole;
1-benzhydryl-6-(4-fluoroethylhomopiperazin-1-yl)-1H-benzo[d]imidazole;
1-benzhydryl-6-(4-fluoroethylpiperazin-1-yl)-1H-benzo[d]imidazole;
1-benzhydryl-6-(4-furan-2-ylmethylpiperazin-1-yl)-1H-benzo[d]imidazole;
1-benzhydryl-6-(4-furan-3-ylmethylpiperazin-1-yl)-1H-benzo[d]imidazole;
1-benzhydryl-6-(4-hexylpiperazin-1-yl)-1H-benzo[d]imidazole;
1-benzhydryl-6-(4-hydroxyethylhomopiperazin-1-yl)-1H-benzo[d]imidazole;
1-benzhydryl-6-(4-hydroxyethylpiperazin-1-yl)-1H-benzo[d]imidazole;
1-benzhydryl-6-(4-isopropylhomopiperazin-1-yl)-1H-benzo[d]imidazole;
1-benzhydryl-6-(4-isopropylpiperazin-1-yl)-1H-benzo[d]imidazole;
1-benzhydryl-6-(4-methoxyethylhomopiperazin-1-yl)-1H-benzo[d]imidazole;
1-benzhydryl-6-(4-methoxyethylpiperazin-1-yl)-1H-benzo[d]imidazole;
1-benzhydryl-6-(4-methylhomopiperazin-1-yl)-1H-benzo[d]imidazole;
1-benzhydryl-6-(4-methylpiperazin-1-yl)-1H-benzo[d]imidazole;
1-benzhydryl-6-(4-ethylpiperazin-1-yl)-1H-benzo[d]imidazole;
1-benzhydryl-6-(4-octylpiperazin-1-yl)-1H-benzo[d]imidazole;
1-benzhydryl-6-(4-pentyllpiperazin-1-yl)-1H-benzo[d]imidazole;
1-benzhydryl-6-(4-phenethylpiperazin-1-yl)-1H-benzo[d]imidazole;
1-benzhydryl-6-(4-propylpiperazin-1-yl)-1H-benzo[d]imidazole;
1-benzhydryl-6-(4-pyridine-2-ylmethylpiperazin-1-yl)-1H-benzo[d]imidazole;
1-benzhydryl-6-(4-pyridine-3-ylmethylpiperazin-1-yl)-1H-benzo[d]imidazole;
1-benzhydryl-6-(4-pyridine-4-ylmethylpiperazin-1-yl)-1H-benzo[d]imidazole;
1-benzhydryl-6-(4-t-butylhomopiperazin-1-yl)-1H-benzo[d]imidazole;
1-benzhydryl-6-(4-t-butylpiperazin-1-yl)-1H-benzo[d]imidazole;
1-benzhydryl-6-(4-trifluoromethylpiperazin-1-yl)-1H-benzo[d]imidazole;
1-benzhydryl-6-[4-(2,3-dihydro-1H-inden-2-yl)piperazin-1-yl]-1H-benzo[d]imidazole;
1-benzhydryl-6-[4-(2-cyanoethyl)piperazin-1-yl]-1H-benzo[d]imidazole;
1-benzhydryl-6-[4-(2-fluoroethyl)piperazin-1-yl]-1H-benzo[d]imidazole;
1-benzhydryl-6-[4-(2-methanesulfonylethyl)piperazin-1-yl]-1H-benzo[d]imidazole;
1-benzhydryl-6-[4-(2-methoxyethyl)piperazin-1-yl]-1H-benzo[d]imidazole;
1-benzhydryl-6-[4-(3-hydroxypropyl)piperazin-1-yl]-1H-benzo[d]imidazole;
1-benzhydryl-6-[4-(3-methanesulfonylaminopropyl)piperazin-1-yl]-1H-benzo[d]imidazole;
1-benzhydryl-6-[4-(3-methoxypropyl)piperazin-1-yl]-1H-benzo[d]imidazole;
1-benzhydryl-6-[4-(3-morpholinocarbonylpropyl)piperazin-1-yl]-1H-benzo[d]imidazole;
1-benzhydryl-6-[4-(dimethylaminocarbonylmethyl)piperazin-1-yl]-1H-benzo[d]imidazole;
1-benzhydryl-6-[4-(ethoxycarbonylmethyl)piperazin-1-yl]-1H-benzo[d]imidazole;
1-benzhydryl-6-[4-(pyrrolodinocarbonylmethyl)piperazin-1-yl]-1H-benzo[d]imidazole;
1-benzhydryl-6-{4-[2-(2-oxoimidazolidin-1-yl)ethyl]piperazin-1-yl}-1H-benzo[d]imidazole;
1-(benzhydrylamino)-5-(piperazin-1-yl)-2-cyanobenzene;
1-(benzhydrylamino)-5-(piperazin-1-yl)-2-fluorobenzene;
1-(benzhydrylamino)-5-(piperazin-1-yl)-2-methanesulfonylbenzene;
1-(benzhydrylamino)-5-(piperazin-1-yl)-2-nitrobenzene;
1-(benzhydrylamino)-5-(piperazin-1-yl)-2-trifluoromethoxybenzene;
1-(benzhydrylamino)-5-(piperazin-1-yl)-2-trifluoromethylbenzene;
1-(benzhydrylamino)-5-(piperazin-1-yl)benzene;
1-benzhydryl-6-(piperazin-1-yl)-1H-benzo[d]imidazole;
1-(benzhydrylamino)-5-(homopiperazin-1-yl)-2-cyanobenzene;
1-(benzhydrylamino)-5-(homopiperazin-1-yl)-2-fluorobenzene;
1-(benzhydrylamino)-5-(homopiperazin-1-yl)-2-methanesulfonylbenzene;
1-(benzhydrylamino)-5-(homopiperazin-1-yl)-2-nitrobenzene;
1-(benzhydrylamino)-5-(homopiperazin-1-yl)-2-trifluoromethoxybenzene;
1-(benzhydrylamino)-5-(homopiperazin-1-yl)-2-trifluoromethylbenzene;
1-(benzhydrylamino)-5-(homopiperazin-1-yl) benzene;
1-benzhydryl-6-(homopiperazin-1-yl)-1H-benzo[d]imidazole;
1-benzhydryl-6-(hexahydropyrrolo[1,2-a]pyrazin-2(1H)-yl)-1H-benzo[d]imidazole;
2-(1-benzhydryl-1H-benzo[d]imidazol-6-yl)octahydro-1H-pyrido[1,2-a]pyrazine;
1-benzhydryl-6-(3,4-dimethylpiperazin-1-yl)-1H-benzo[d]imidazole;

3-benzhydryl-5-(piperazin-1-yl)-3H-imidazo[4,5-c]pyridine;
6-(4-methylpiperazin-1-yl)-1-(2-phenylpropan-2-yl)-1H-benzo[d]imidazole
1-(cyclohexyl(phenyl)methyl)-6-(4-methylpiperazin-1-yl)-1H-benzo[d]imidazole;
1-(2,2-dimethyl-1-phenylpropyl)-6-(4-methylpiperazin-1-yl)-1H-benzo[d]imidazole;
1-(2-cyclopropyl-1-phenethyl)-6-(4-methylpiperazin-1-yl)-1H-benzo[d]imidazole;
1-benzhydryl-5-methyl-6-(4-methylpiperazin-1-yl)-1H-benzo[d]imidazole;
3-((2-nitro-5-(piperazin-1-yl)phenyl)amino)-3-phenyl-propanoic acid;
3-((2-nitro-5-(4-methylpiperazin-1-yl)phenyl)amino)-3-phenylpropanoic acid;
ethyl 2-((5-(4-methylpiperazin-1-yl)-2-nitrophenyl)amino)-2-phenylacetate;
ethyl 2-((5-(piperazin-1-yl)-2-nitrophenyl)amino)-2-phenylacetate;
1-benzhydryl-6-[4-(thiophen-2-ylmethyl)piperazin-1-yl]-1H-benzo[d]imidazole;
1-(1-benzhydryl-1H-benzo[d]imidazol-6-yl)-N,N-dimethylpiperidin-4-amine;
1-benzhydryl-7-fluoro-6-[4-methylpiperazin-1-yl]-1H-benzo[d]imidazole;
6-([1,4'-bipiperidin]-1'-yl)-1-benzhydryl-1H-benzo[d]imidazole;
1-(benzhydrylamino)-5-(4-methylpiperazin-1-yl)benzene;
1-(benzhydrylamino)-5-(4-trifluoromethylpiperazin-1-yl)benzene;
1-(benzhydrylamino)-5-(4-isopropylpiperazin-1-yl)benzene;
1-(benzhydrylamino)-5-(4-t-butylpiperazin-1-yl)benzene;
1-(benzhydrylamino)-5-(4-hydroxyethylpiperazin-1-yl)benzene;
1-(benzhydrylamino)-5-(4-methoxyethylpiperazin-1-yl)benzene;
1-(benzhydrylamino)-5-(4-fluoroethylpiperazin-1-yl)benzene;
1-(benzhydrylamino)-5-(4-furan-2-ylmethylpiperazin-1-yl)benzene;
1-(benzhydrylamino)-5-(4-furan-3-ylmethylpiperazin-1-yl)benzene;
1-(benzhydrylamino)-5-(4-t-butylhomopiperazin-l-yl)benzene;
1-(benzhydrylamino)-5-(4-trifluoromethylpiperazin-1-yl)-2-nitrobenzene;
1-(benzhydrylamino)-5-(4-propylpiperazin-1-yl)-2-nitrobenzene;
1-(benzhydrylamino)-5-(4-isopropylpiperazin-1-yl)-2-nitrobenzene;
1-(benzhydrylamino)-5-(4-butylpiperazin-1-yl)-2-nitrobenzene;
1-(benzhydrylamino)-5-(4-but-2-enylpiperazin-1-yl)-2-nitrobenzene;
1-(benzhydrylamino)-5-(4-cyclopropylmethylpiperazin-1-yl)-2-nitrobenzene;
1-(benzhydrylamino)-5-(4-t-butylpiperazin-1-yl)-2-nitrobenzene;
1-(benzhydrylamino)-5-(4-methylpiperazin-1-yl)-3-cyano-2-nitrobenzene;
1-(benzhydrylamino)-5-(4-cyclobutylpiperazin-1-yl)-2-nitrobenzene;
1-(benzhydrylamino)-5-(4-pentyllpiperazin-1-yl)-2-nitrobenzene;
1-(benzhydrylamino)-5-(4-cyclopentylpiperazin-1-yl)-2-nitrobenzene;
1-(benzhydrylamino)-5-(4-hexylpiperazin-1-yl)-2-nitrobenzene;
1-(benzhydrylamino)-5-(4-cyclohexylpiperazin-1-yl)-2-nitrobenzene;
1-(benzhydrylamino)-5-(4-octylpiperazin-1-yl)-2-nitrobenzene;
1-(benzhydrylamino)-5-(4-decylpiperazin-1-yl)-2-nitrobenzene;
1-(benzhydrylamino)-5-(4-benzylpiperazin-1-yl)-2-nitrobenzene;
1-(benzhydrylamino)-5-(4-phenethylpiperazin-1-yl)-2-nitrobenzene;
1-(benzhydrylamino)-5-(4-pyridine-2-ylmethylpiperazin-1-yl)-2-nitrobenzene;
1-(benzhydrylamino)-5-(4-pyridine-3-ylmethylpiperazin-1-yl)-2-nitrobenzene;
1-(benzhydrylamino)-5-(4-pyridine-4-ylmethylpiperazin-1-yl)-2-nitrobenzene;
1-(benzhydrylamino)-5-(4-furan-2-ylmethylpiperazin-1-yl)-2-nitrobenzene;
1-(benzhydrylamino)-5-(4-furan-3-ylmethylpiperazin-1-yl)-2-nitrobenzene;
1-(benzhydrylamino)-5-[4-(2,3-dihydro-1H-inden-2-yl)piperazin-1-yl]-2-nitrobenzene;
1-(benzhydrylamino)-5-[4-(ethoxycarbonylmethyl)piperazin-1-yl]-2-nitrobenzene;
1-(benzhydrylamino)-5-[4-(dimethylaminocarbonylmethyl)piperazin-1-yl]-2-nitrobenzene;
1-(benzhydrylamino)-5-[4-(pyrrolodinocarbonylmethyl)piperazin-1-yl]-2-nitrobenzene;
1-(benzhydrylamino)-5-[4-(2-methyoxyethyl)piperazin-1-yl]-2-nitrobenzene;
1-(benzhydrylamino)-5-[4-(2-cyanoethyl)piperazin-1-yl]-2-nitrobenzene;
1-(benzhydrylamino)-5-[4-(2-fluoroethyl)piperazin-1-yl]-2-nitrobenzene;
1-(benzhydrylamino)-5-[4-(2-methanesulfonylethyl)piperazin-1-yl]-2-nitrobenzene;
1-(benzhydrylamino)-5-{4-[2-(2-oxoimidazolidin-1-yl)ethyl]piperazin-1-yl}-2-nitrobenzene;
1-(benzhydrylamino)-5-[4-(3-hydroxypropyl)piperazin-1-yl]-2-nitrobenzene;
1-(benzhydrylamino)-5-[4-(3-methoxypropyl)piperazin-1-yl]-2-nitrobenzene;
1-(benzhydrylamino)-5-[4-(3-morpholinocarbonylpropyl)piperazin-1-yl]-2-nitrobenzene;
1-(benzhydrylamino)-5-[4-(3-methanesulfonylaminopropyl)piperazin-1-yl]-2-nitrobenzene;
1-(benzhydrylamino)-5-(4-methylhomopiperazin-1-yl)-2-nitrobenzene;
1-(benzhydrylamino)-5-(4-isopropylhomopiperazin-1-yl)-2-nitrobenzene;
1-(benzhydrylamino)-5-(4-butylhomopiperazin-1-yl)-2-nitrobenzene;
1-(benzhydrylamino)-5-(4-t-butylhomopiperazin-1-yl)-2-nitrobenzene;
1-(benzhydrylamino)-5-(4-benzylhomopiperazin-1-yl)-2-nitrobenzene;
1-(benzhydrylamino)-5-(4-hydroxyethylhomopiperazin-1-yl)-2-nitrobenzene;
1-(benzhydrylamino)-5-(4-methoxyethylhomopiperazin-1-yl)-2-nitrobenzene;

1-(benzhydrylamino)-5-(4-fluoroethylhomopiperazin-1-yl)-2-nitrobenzene;
1-(benzhydrylamino)-5-(4-methylpiperazin-1-yl)-2-trifluoromethylbenzene;
1-(benzhydrylamino)-5-(4-trifluoromethylpiperazin-1-yl)-2-trifluoromethylbenzene;
1-(benzhydrylamino)-5-(4-isopropylpiperazin-1-yl)-2-trifluoromethylbenzene;
1-(benzhydrylamino)-5-(4-t-butylpiperazin-1-yl)-2-trifluoromethylbenzene;
1-(benzhydrylamino)-5-(4-hydroxyethylpiperazin-1-yl)-2-trifluoromethylbenzene;
1-(benzhydrylamino)-5-(4-methoxyethylpiperazin-1-yl)-2-trifluoromethylbenzene;
1-(benzhydrylamino)-5-(4-fluoroethylpiperazin-1-yl)-2-trifluoromethylbenzene;
1-(benzhydrylamino)-5-(4-furan-2-ylmethylpiperazin-1-yl)-2-trifluoromethylbenzene;
1-(benzhydrylamino)-5-(4-furan-3-ylmethylpiperazin-1-yl)-2-trifluoromethylbenzene;
1-(benzhydrylamino)-5-(4-t-butylhomopiperazin-1-yl)-2-trifluoromethylbenzene;
1-(benzhydrylamino)-5-(4-methylpiperazin-1-yl)-2-fluorobenzene;
1-(benzhydrylamino)-5-(4-trifluoromethylpiperazin-1-yl)-2-fluorobenzene;
1-(benzhydrylamino)-5-(4-isopropylpiperazin-1-yl)-2-fluorobenzene;
1-(benzhydrylamino)-5-(4-t-butylpiperazin-1-yl)-2-fluorobenzene;
1-(benzhydrylamino)-5-(4-hydroxyethylpiperazin-1-yl)-2-fluorobenzene;
1-(benzhydrylamino)-5-(4-methoxyethylpiperazin-1-yl)-2-fluorobenzene;
1-(benzhydrylamino)-5-(4-fluoroethylpiperazin-1-yl)-2-fluorobenzene;
1-(benzhydrylamino)-5-(4-furan-2-ylmethylpiperazin-1-yl)-2-fluorobenzene;
1-(benzhydrylamino)-5-(4-furan-3-ylmethylpiperazin-1-yl)-2-fluorobenzene;
1-(benzhydrylamino)-5-(4-t-butylhomopiperazin-1-yl)-2-fluorobenzene;
1-(benzhydrylamino)-5-(4-methylpiperazin-1-yl)-2-cyanobenzene;
1-(benzhydrylamino)-5-(4-trifluoromethylpiperazin-1-yl)-2-cyanobenzene;
1-(benzhydrylamino)-5-(4-isopropylpiperazin-1-yl)-2-cyanobenzene;
1-(benzhydrylamino)-5-(4-t-butylpiperazin-1-yl)-2-cyanobenzene;
1-(benzhydrylamino)-5-(4-hydroxyethylpiperazin-1-yl)-2-cyanobenzene;
1-(benzhydrylamino)-5-(4-methoxyethylpiperazin-1-yl)-2-cyanobenzene;
1-(benzhydrylamino)-5-(4-fluoroethylpiperazin-1-yl)-2-cyanobenzene;
1-(benzhydrylamino)-5-(4-furan-2-ylmethylpiperazin-1-yl)-2-cyanobenzene;
1-(benzhydrylamino)-5-(4-furan-3-ylmethylpiperazin-1-yl)-2-cyanobenzene;
1-(benzhydrylamino)-5-(4-t-butylhomopiperazin-1-yl)-2-cyanobenzene;
1-(benzhydrylamino)-5-(4-methylpiperazin-1-yl)-2-trifluoromethoxybenzene;
1-(benzhydrylamino)-5-(4-trifluoromethylpiperazin-1-yl)-2-trifluoromethoxybenzene;
1-(benzhydrylamino)-5-(4-isopropylpiperazin-1-yl)-2-trifluoromethoxybenzene;
1-(benzhydrylamino)-5-(4-t-butylpiperazin-1-yl)-2-trifluoromethoxybenzene;
1-(benzhydrylamino)-5-(4-hydroxyethylpiperazin-1-yl)-2-trifluoromethoxybenzene;
1-(benzhydrylamino)-5-(4-methoxyethylpiperazin-1-yl)-2-trifluoromethoxybenzene;
1-(benzhydrylamino)-5-(4-trifluoromethylethylpiperazin-1-yl)-2-trifluoromethoxybenzene;
1-(benzhydrylamino)-5-(4-furan-2-ylmethylpiperazin-1-yl)-2-trifluoromethoxybenzene;
1-(benzhydrylamino)-5-(4-furan-3-ylmethylpiperazin-1-yl)-2-trifluoromethoxybenzene;
1-(benzhydrylamino)-5-(4-t-butylhomopiperazin-1-yl)-2-trifluoromethoxybenzene;
1-(benzhydrylamino)-5-(4-methylpiperazin-1-yl)-2-methanesulfonylbenzene;
1-(benzhydrylamino)-5-(4-trifluoromethylpiperazin-1-yl)-2-methanesulfonylbenzene;
1-(benzhydrylamino)-5-(4-isopropylpiperazin-1-yl)-2-methanesulfonylbenzene;
1-(benzhydrylamino)-5-(4-t-butylpiperazin-1-yl)-2-methanesulfonylbenzene;
1-(benzhydrylamino)-5-(4-hydroxyethylpiperazin-1-yl)-2-methanesulfonylbenzene;
1-(benzhydrylamino)-5-(4-methoxyethylpiperazin-1-yl)-2-methanesulfonylbenzene;
1-(benzhydrylamino)-5-(4-trifluoromethylethylpiperazin-1-yl)-2-methanesulfonylbenzene;
1-(benzhydrylamino)-5-(4-furan-2-ylmethylpiperazin-1-yl)-2-methanesulfonylbenzene;
1-(benzhydrylamino)-5-(4-furan-3-ylmethylpiperazin-1-yl)-2-methanesulfonylbenzene;
1-(benzhydrylamino)-5-(4-t-butylhomopiperazin-1-yl)-2-methanesulfonylbenzene;
1-(benzhydrylamino)-5-(4-methylpiperazin-1-yl)-2-aminosulfonylbenzene;
1-(benzhydrylamino)-5-(4-trifluoromethylpiperazin-1-yl)-2-aminosulfonylbenzene;
1-(benzhydrylamino)-5-(4-isopropylpiperazin-1-yl)-2-aminosulfonylbenzene;
1-(benzhydrylamino)-5-(4-t-butylpiperazin-1-yl)-2-aminosulfonylbenzene;
1-(benzhydrylamino)-5-(4-hydroxyethylpiperazin-1-yl)-2-aminosulfonylbenzene;
1-(benzhydrylamino)-5-(4-methoxyethylpiperazin-1-yl)-2-aminosulfonylbenzene;
1-(benzhydrylamino)-5-(4-trifluoromethylethylpiperazin-1-yl)-2-aminosulfonylbenzene;
1-(benzhydrylamino)-5-(4-furan-2-ylmethylpiperazin-1-yl)-2-aminosulfonylbenzene;
1-(benzhydrylamino)-5-(4-furan-3-ylmethylpiperazin-1-yl)-2-aminosulfonylbenzene; and
1-(benzhydrylamino)-5-(4-t-butylhomopiperazin-1-yl)-2-aminosulfonylbenzene;
and pharmaceutically acceptable salts thereof.

* * * * *